US012754745B2

(12) United States Patent
Xiong et al.

(10) Patent No.: US 12,754,745 B2
(45) Date of Patent: Oct. 6, 2026

(54) USER INTERFACE IMPLEMENTATION METHOD AND APPARATUS

(71) Applicant: Huawei Technologies Co., Ltd., Shenzhen (CN)

(72) Inventors: Shiyi Xiong, Wuhan (CN); Bo Tang, Shanghai (CN); Xiaoxiao Chen, Nanjing (CN); Zhihua Yin, Shanghai (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 326 days.

(21) Appl. No.: 18/042,929

(22) PCT Filed: Jul. 23, 2021

(86) PCT No.: PCT/CN2021/108273

§ 371 (c)(1),
(2) Date: Feb. 24, 2023

(87) PCT Pub. No.: WO2022/042162

PCT Pub. Date: Mar. 3, 2022

(65) Prior Publication Data

US 2023/0325209 A1 Oct. 12, 2023

(30) Foreign Application Priority Data

Aug. 25, 2020 (CN) ......................... 202010862489.9
Sep. 30, 2020 (CN) ......................... 202011064544.6
(Continued)

(51) Int. Cl.
*G06F 9/451* (2018.01)
*A61B 5/00* (2006.01)
(Continued)

(52) U.S. Cl.
CPC ................ *G06F 9/451* (2018.02); *G06F 8/38* (2013.01); *A61B 5/7435* (2013.01); *A61B 8/465* (2013.01);
(Continued)

(58) Field of Classification Search
CPC .. G06F 9/451; G06F 8/38; G06F 8/61; H04N 2201/0046; G05B 2219/36136;
(Continued)

(56) References Cited

U.S. PATENT DOCUMENTS

2007/0192682 A1 8/2007 Neil et al.
2013/0097521 A1 4/2013 Lewin et al.
(Continued)

FOREIGN PATENT DOCUMENTS

CN 110381195 A 10/2019
CN 110597512 A 12/2019
WO WO-2016036605 A1 * 3/2016 ............... G06F 8/61

OTHER PUBLICATIONS

Minhong Yun et al: "Downloadable User Interface for Mobile Devices." Sep. 12, 2008. total 4 pages.

*Primary Examiner* — Quoc A Tran
(74) *Attorney, Agent, or Firm* — Slater Matsil, LLP

(57) ABSTRACT

An application installation package of a first application includes a first description file and a second description file that are used to perform interface description and interface behavior definition on a UI of the first application. The first description file and the second description file use different interface description languages. The first description file uses a first interface description language, and the second description file uses a second interface description language. When an electronic device runs the first application, a first UI engine reads, parses, and executes the first description file, to generate a first part of a first UI; and a second UI
(Continued)

engine reads, parses, and executes the second description file, to generate a second part of the first UI.

17 Claims, 78 Drawing Sheets

(30) Foreign Application Priority Data

| | | | |
|---|---|---|---|
| Oct. 22, 2020 | (CN) | ......................... | 202011141010.9 |
| Oct. 22, 2020 | (CN) | ......................... | 202011142718.6 |
| Nov. 30, 2020 | (CN) | ......................... | 202011381146.7 |
| Nov. 30, 2020 | (CN) | ......................... | 202011384490.1 |
| Dec. 14, 2020 | (CN) | ......................... | 202011475517.8 |

(51) Int. Cl.

| | |
|---|---|
| ***A61B 8/00*** | (2006.01) |
| ***A61M 60/585*** | (2021.01) |
| ***G06F 8/38*** | (2018.01) |
| ***G06F 8/61*** | (2018.01) |

(52) U.S. Cl.
CPC . *A61M 60/585* (2021.01); *G05B 2219/32178* (2013.01); *G05B 2219/36136* (2013.01); *G06F 8/61* (2013.01); *H04N 2201/0046* (2013.01)

(58) Field of Classification Search
CPC ....... G05B 2219/32178; A61M 60/585; A61B 5/7435; A61B 8/465
See application file for complete search history.

(56) References Cited

U.S. PATENT DOCUMENTS

| | | | | |
|---|---|---|---|---|
| 2013/0339928 | A1 | 12/2013 | Trofin et al. | |
| 2014/0035945 | A1 | 2/2014 | Anglin et al. | |
| 2016/0378439 | A1* | 12/2016 | Straub ........................ | G06F 8/61 717/107 |
| 2017/0091159 | A1 | 3/2017 | Su et al. | |
| 2018/0307465 | A1 | 10/2018 | He et al. | |
| 2018/0349111 | A1* | 12/2018 | Totale ........................ | G06F 8/38 |
| 2019/0310882 | A1* | 10/2019 | Wei ........................ | G06F 9/4881 |
| 2025/0068300 | A1* | 2/2025 | Wohlstadter .......... | G06F 3/0482 |

* cited by examiner

FIG. 8
app
build
libs
src
androidTest
main
assets
huawei_dsl.json
java
res
AndroidManifest.xml

710

```
{
  "meta-data": {
   "version": "10.0.1008"
 }
 "import": {
  "UserInfo": "com.myapp.UserInfo",
  "Context": "com.myapp.TestActivity"
 },
 "model": {
  "user": "UserInfo",
  "context": "Context"
 },
 "layout-data-common": {
   "Column()": {
    "ImageView(id:photo)": {
     "imageUri": "$user.photo"
    },
    "Row(id:name)": {
     "TextView(text:@string/text_name)": {
      "style":"$style.myTextStyle"
     },
     "EditText(hint:@string/text_hint, text:$user.name)": {}
    },
    "Row(id:age)": {
     "TextView(text:@string/text_age)": {
      "style":"$style.myTextStyle"
     },
     "EditText(hint:18, text:$user.age)": {}
    },
    "Button(text:submit, id:btn_commit, style:$style.myTextStyle)": {
     "onClick": "$context::handleClick"
    },
    "TextView (id:text_commit, text:submitted, visible:$user::hasName)": {},
    "Row(id:commit_name)": {
     "TextView(text:@string/text_name)": {},
     "TextView(text:$user.name)": {}
    },
    "Row(id:commit_age)": {
     "TextView(text:@string/text_age)": {},
     "TextView(text:$user.age)": {}
    }
   }
 },
```

711, 7111, 7112, 7113, 7114, 7115

TO FIG. 16C

TO FIG. 16B

TO FIG. 16B

FIG. 16A

CONT. FROM FIG. 27A

TO FIG. 38A-2

CONT. FROM FIG. 40C-1

TO FIG. 40C-3

CONT. FROM FIG. 40C-2

TO FIG. 42A-2

USER INTERFACE IMPLEMENTATION METHOD AND APPARATUS

CROSS-REFERENCE TO RELATED APPLICATIONS

This application is a National Stage of International Application No. PCT/CN2021/108273, filed on Jul. 23, 2021, which claims priority to Chinese Patent Application No. 202011475517.8, filed on Dec. 14, 2020, and Chinese Patent Application No. 202010862489.9, filed on Aug. 25, 2020 and Chinese Patent Application No. 202011064544.6, filed on Sep. 30, 2020 and Chinese Patent Application No. 202011381146.7, filed on Nov. 30, 2020 and Chinese Patent Application No. 202011141010.9, filed on Oct. 22, 2020 and Chinese Patent Application No. 202011384490.1, filed on Nov. 30, 2020 and Chinese Patent Application No. 202011142718.6, filed on Oct. 22, 2020. The disclosures of the aforementioned applications are hereby incorporated by reference in their entireties.

TECHNICAL FIELD

This application relates to the field of terminal technologies, and in particular, to a user interface implementation method and an apparatus.

BACKGROUND

Developers usually develop an application (app) based on an operating system (OS) platform. During app development, an important task is to develop a user interface (user interface, UI) of the app. Usually, the developers use a software development kit (software development kit, SDK) provided by the OS platform to develop the UI of the app. UI development mainly includes interface description and interface behavior definition. The interface description means using an interface description language to describe a UI layout (layout), a used view, and visual styles of the layout and the view. The interface behavior definition refers to defining interface behavior by using the interface description language. The interface behavior includes a dynamic change of the UI and a response of an electronic device to the dynamic change of the UI (for example, a response to an operation of a user on the UI). Each OS platform has a corresponding interface description language. For example, Android® uses an extensible markup language (extensible markup language, xml) format, and iOS® uses an embedded domain-specific language (embedded domain-specific language, EDSL) built by swift to perform interface description and interface behavior definition. A UI engine provided by the OS platform may interpret the interface description language for executing the UI, render the UI, and present the UI to the user. In addition, each OS platform has a corresponding programming language used to implement interface behavior, implement the dynamic change of the UI, and respond to the operation of the user on the UI. For example, Android® uses JAVA, and iOS® uses a swift programming language to implement interface behavior.

How to provide convenience for the developers and help the developers to develop a UI that adapts to the operating system and provides rich functions is a to-be-solved problem.

SUMMARY

Embodiments of this application provide a user interface implementation method and an apparatus, to provide rich UI programming capabilities, and provide convenience for developers to develop a UI that adapts to an operating system and provides rich functions. To achieve the foregoing objectives, the following technical solutions are used in this application:

According to a first aspect, this application provides a user interface implementation method, including: An electronic device installs an application installation package of a first application. The application installation package includes a first description file and a second description file, the first description file and the second description file are used to perform interface description and interface behavior definition on a first user interface UI of the first application, the first description file uses a first interface description language, the second description file uses a second interface description language, and the first interface description language is different from the second interface description language. The electronic device runs the first application. A first UI engine of the electronic device reads, parses, and executes the first description file to generate a first part of the first UI. A second UI engine of the electronic device reads, parses, and executes the second description file to generate a second part of the first UI. The electronic device displays the first UI.

In this method, two different interface description languages can be used to jointly develop a UI. An operating system of the electronic device includes two UI engines, which respectively parse and execute two different interface description languages. One UI engine may be a UI engine of a general-purpose OS (for example, Android®), and may parse a common interface description language. The other UI engine is an extended UI engine not related to an OS platform, and may parse a DSL. In this way, developers can use a basic interface description language to describe a UI layout and included views. In addition, the developers can selectively use the DSL to apply a customized UI programming capability to some views and add some animations to the UI. The extended UI engine provided in this embodiment of this application is not related to the OS platform. Therefore, the extended UI engine can adapt to a plurality of OS platforms, has low technical implementation difficulty, and facilitates use by the developers.

In a possible implementation, that the first UI engine of the electronic device generates the first part of the first UI includes: The first UI engine of the electronic device generates one or more first views on the first UI based on the first description file. The one or more first views have a first UI programming capability.

The first view is a view generated by the general-purpose OS (for example, Android®). The first UI programming capability is a UI programming capability supported by the general-purpose OS (for example, Android®), for example, including setting a length, width, height, spacing, and color of a view, selecting a view, and entering text on the view.

In a possible implementation, that the second UI engine of the electronic device generates the second part of the first UI includes: The second UI engine of the electronic device applies a second UI programming capability to the one or more first views based on the second description file. In other words, the developers may apply, in the second description file by using a customized interface description language, the customized UI programming capability to the view generated by the general-purpose OS, to extend a capability of the general-purpose OS view, and enrich use effects of the general-purpose OS view.

In a possible implementation, that the second UI engine of the electronic device generates the second part of the first UI includes: The second UI engine of the electronic device generates one or more second views on the first UI based on the second description file. The one or more second views have a second UI programming capability.

The second view is a customized view provided by an OEM OS in this embodiment of this application, supports a customized second UI programming capability, and supports rich view effects.

In a possible implementation, the second UI programming capability includes at least one of a visual property capability, a layout capability, a unified interaction capability, and an animation capability.

The layout capability is used to describe a layout of a view on a UI, for example, a shape, a position, and a size of a view. The visual property capability is used to describe a visual property of a view, for example, visual effects such as a color and grayscale of a view. The unified interaction capability is used to provide a view response based on user behavior, for example, perform a search based on "confirm" behavior of a user. The animation capability is used to display an animation effect on a view, for example, display a click-rebound animation on a view.

In a possible implementation, the layout capability includes at least one of stretching, hiding, wrapping, equalization, proportion, and extension. Stretching is a display capability of zooming in or zooming out a width and height of a view according to different proportions; hiding is a display capability of the view visible or gone on a display interface; wrapping is a display capability of displaying content in the view through one or more lines on the display interface; equalization is a display capability of the view evenly distributed on the display interface; proportion is a capability of the view to occupy a total layout according to a specified percentage in a specified direction; and extension is a capability of the view to be displayed in one direction on the UI.

In a possible implementation, if the second UI engine determines that the second description file exists, the second UI engine triggers the first UI engine to read the first description file and the second UI engine to read the second description file. In other words, the second UI engine controls a distribution procedure, and triggers the first UI engine and the second UI engine to parse and execute the description file.

In a possible implementation, the first description file and the second description file are in different paths in the application installation package. The first UI engine and the second UI engine respectively read description files in different paths according to a preset rule.

In a possible implementation, different tags are preset in the first description file and the second description file. The first UI engine and the second UI engine respectively read corresponding description files based on the preset tags.

In a possible implementation, the second UI engine further performs syntax check on the second interface description language; and if the syntax check succeeds, the second UI engine parses and executes the second description file.

In a possible implementation, the second UI engine of the electronic device implements mapping between a component event and user behavior in the second description file; and in response to the component event, executes a view action corresponding to the user behavior in the second description file. In other words, the OEM OS may map events triggered by electronic devices in different forms to same user behavior (for example, map a mouse double-click event on a PC to "confirm" behavior, and map a finger tap event on a mobile phone to "confirm" behavior). This prevents the developers from defining a correspondence between a component event and user behavior for electronic devices in different forms, causing repeated work. In this way, a same description file is applicable to electronic devices in a plurality of forms, reducing development difficulty and bringing convenience to the developers.

In a possible implementation, the second UI engine includes a syntactic and semantic specification set of fields in the second description file. In this way, the developers can develop the UI on an OEM OS platform according to syntactic and semantic specifications of the OEM OS.

In a possible implementation, the first interface description language is an extensible markup language xml language, and the second interface description language is a domain-specific language DSL.

According to a second aspect, this application provides a user interface implementation method, including: displaying a development interface of a first application, where the development interface of the first application includes a first description file and a second description file, the first description file and the second description file are used to perform interface description and interface behavior definition on a first user interface UI of the first application, the first description file uses a first interface description language, the second description file uses a second interface description language, and the first interface description language is different from the second interface description language; adding a description about a first part of the first UI to the first description file in response to a first operation entered by a user; adding a description about a second part of the first UI to the second description file in response to a second operation entered by the user; and generating an application installation package of the first application based on the first description file and the second description file.

In this method, developers can use two different interface description languages to jointly develop a UI. One language is a basic interface description language supported by a general-purpose OS (for example, Android®), and the other language is a customized interface description language. The developers can use the basic interface description language to describe a UI layout and included views, and selectively use a DSL to apply a customized UI programming capability to some views and add some animations to the UI. The customized interface description language is not related to an OS platform. Therefore, the customized interface description language can adapt to a plurality of OS platforms, has low technical implementation difficulty, and facilitates use by the developers.

In a possible implementation, the adding a description about a first part of the first UI to the first description file includes: adding a description about one or more first views on the first UI to the first description file; and applying a first UI programming capability to the one or more first views.

The first view is a view supported by the general-purpose OS (for example, Android®). The first UI programming capability is a UI programming capability supported by the general-purpose OS (for example, Android®), for example, including setting a length, width, height, spacing, and color of a view, selecting a view, and entering text on the view.

In a possible implementation, the adding a description about a second part of the first UI to the second description file includes: adding the description about the one or more first views to the second description file; and applying a second UI programming capability to the one or more first views.

In other words, the developers may apply, in the second description file by using a customized interface description language, the customized UI programming capability to the view generated by the general-purpose OS, to extend a capability of the general-purpose OS view, and enrich use effects of the general-purpose OS view.

In a possible implementation, the adding a description about a second part of the first UI to the second description file includes: adding a description about one or more second views to the second description file; and applying the second UI programming capability to the one or more second views. The second view is a customized view provided by an OEM OS in this embodiment of this application, supports a customized second UI programming capability, and supports rich view effects.

In a possible implementation, the second UI programming capability includes at least one of a visual property capability, a layout capability, a unified interaction capability, and an animation capability.

In a possible implementation, the layout capability includes at least one of stretching, hiding, wrapping, equalization, proportion, and extension.

In a possible implementation, the first description file and the second description file are in different paths in the application installation package. In this way, the first UI engine and the second UI engine of the OEM OS may respectively read files in different paths according to a preset rule, to obtain corresponding description files.

In a possible implementation, different tags are preset in the first description file and the second description file. In this way, the first UI engine and the second UI engine of the OEM OS may respectively read corresponding description files based on the preset tags.

According to a third aspect, this application provides a computer-readable storage medium, including computer instructions. The computer instructions are used to perform interface description and interface behavior definition on a first user interface UI of a first application. The computer instructions include a first instruction stored in a first description file and a second instruction stored in a second description file. The first description file uses a first interface description language, the second description file uses a second interface description language, and the first interface description language is different from the second interface description language. The first instruction is used to describe a first part of the first UI, and the second instruction is used to describe a second part of the first UI.

In this method, developers use two different interface description languages to jointly develop a UI. One interface description language is a basic interface description language supported by a general-purpose OS (for example, Android®), and the other interface description language is a customized interface description language. The developers use the basic interface description language to describe a UI layout and included views, and selectively use a DSL to apply a customized UI programming capability to some views and add some animations to the UI. The customized interface description language is not related to an OS platform. Therefore, the customized interface description language can adapt to a plurality of OS platforms, has low technical implementation difficulty, and facilitates use by the developers.

In a possible implementation, the first instruction is specifically used to: describe one or more first views on the first UI, and apply a first UI programming capability to the one or more first views.

The first view is a view supported by the general-purpose OS (for example, Android®). The first UI programming capability is a UI programming capability supported by the general-purpose OS (for example, Android®), for example, including setting a length, width, height, spacing, and color of a view, selecting a view, and entering text on the view.

In a possible implementation, the second instruction is specifically used to: apply a second UI programming capability to the one or more first views. In another possible implementation, the second instruction is specifically used to: describe one or more second views on the first UI, and apply the second UI programming capability to the one or more second views.

In other words, the developers may apply, in the second description file by using the customized interface description language, the customized UI programming capability to the view generated by the general-purpose OS, to extend a capability of the general-purpose OS view; or may add a customized view having rich view effects.

In a possible implementation, the second UI programming capability includes at least one of a visual property capability, a layout capability, a unified interaction capability, and an animation capability. The layout capability includes at least one of stretching, hiding, wrapping, equalization, proportion, and extension.

In a possible implementation, the first description file and the second description file are in different paths in the computer-readable storage medium. In this way, a first UI engine and a second UI engine of an OEM OS may respectively read files in different paths according to a preset rule, to obtain corresponding description files.

In a possible implementation, different tags are preset in the first description file and the second description file. In this way, the first UI engine and the second UI engine of the OEM OS may respectively read corresponding description files based on the preset tags.

According to a fourth aspect, this application provides a computer-readable storage medium, for example, an application development tool. The application development tool may specifically include computer instructions. When the computer instructions are run on the foregoing electronic device, the electronic device is enabled to perform the method according to any one of the first aspect.

According to a fifth aspect, this application provides an electronic device, including a display, an input device, one or more processors, one or more memories, and one or more computer programs. The processor is coupled to the input device, the display, and the memory. The one or more computer programs are stored in the memory. When the electronic device runs, the processor may execute the one or more computer programs stored in the memory, so that the electronic device performs the method according to any one of the first aspect.

According to a sixth aspect, this application provides an electronic device, including a display, one or more processors, one or more memories, and one or more computer programs. The processor is coupled to both the display and the memory. The one or more computer programs are stored in the memory. When the electronic device runs the foregoing first application, the processor may execute the one or more computer programs stored in the memory, so that the electronic device performs the method according to any one of the second aspect.

Embodiments of this application provide a user interface implementation method and an apparatus, to implement one-time development and multi-device deployment, that is, develop a set of interface description files that are applicable to various different types of electronic devices, to reduce development difficulty for developers. To achieve the foregoing objective, the following technical solutions are used in this application.

According to a seventh aspect, this application provides a user interface implementation method, including: A first electronic device and a second electronic device separately download an application installation package of a first application from a server; and separately install the application installation package. The application installation package includes a description file and a resource file. The description file is used to perform interface description and interface behavior definition on a first UI of the first application. The resource file includes resources used to generate a UI of the first application. The first electronic device reads first code that is in the description file and corresponding to a device type of the first electronic device, and generates, based on a definition of the first code, a first UI of the first electronic device by using the resources in the resource file. The second electronic device reads second code that is in the description file and corresponding to a device type of the second electronic device, and generates, based on a definition of the second code, a first UI of the second electronic device by using the resources in the resource file. The device type of the first electronic device is different from the device type of the second electronic device. Device types of an electronic device may include a mobile phone, a smart television, a smartwatch, a tablet computer, a notebook computer, a netbook, a large screen, a vehicle-mounted computer, and the like.

In the method, different types of electronic devices present different UI layouts by reading a same description file of a same UI. A set of description files that are applicable to various different types of electronic devices can be developed, to reduce development difficulty for developers.

With reference to the seventh aspect, in a possible implementation, the method further includes: The first electronic device generates a first view on the first UI of the first electronic device based on a definition of third code in the description file. The first view on the first UI of the first electronic device has a customized view property of an operating system of the first electronic device. A third electronic device generates a first view on a first UI of the third electronic device based on the definition of the third code in the description file. The first view on the first UI of the third electronic device has a view property of a general-purpose operating system. The third code is a part or all of the first code.

In the method, it is defined in the description file that the first view supports the customized view property of the operating system. The operating system of the first electronic device provides the customized view property, and the first view on the first UI of the first electronic device has the customized view property of the operating system of the first electronic device. The third electronic device supports a view property of a general-purpose operating system (for example, Android®), and the first view on the first UI of the third electronic device has the view property of the general-purpose operating system. In this way, a same description file can be successfully run in different operating systems. This implements running across operating system platforms and reduces development difficulty for the developers.

According to an eighth aspect, this application provides a user interface implementation method, including: A first electronic device downloads an application installation package of a first application and installs the application installation package. The application installation package includes a description file and a resource file, the description file is used to perform interface description and interface behavior definition on a first user interface UI of the first application, and the resource file includes resources used to generate a UI of the first application. The first electronic device reads first code that is in the description file and corresponding to a device type of the first electronic device, and generates, based on a definition of the first code, a first UI of the first electronic device by using the resources in the resource file.

In the method, an electronic device reads code corresponding to a device type of the electronic device in the description file. In this way, different electronic devices may present different UI layouts by reading a same description file. A set of description files that are applicable to various different types of electronic devices can be developed, to reduce development difficulty for developers.

With reference to the eighth aspect, in a possible implementation, the first electronic device generates a first view on the first UI of the first electronic device based on a definition of third code in the description file. The first view on the first UI of the first electronic device has a customized view property of an operating system of the first electronic device. The third code is a part or all of the first code.

In the method, it is defined in the description file that the first view supports the customized view property of the operating system. The operating system of the first electronic device provides the customized view property, and the first view on the first UI of the first electronic device has the customized view property of the operating system of the first electronic device.

With reference to the seventh aspect or the eighth aspect, in a possible implementation, the operating system of the first electronic device includes a customized UI programming capability, and the customized UI programming capability is used to provide the customized view property of the operating system of the first electronic device.

With reference to the seventh aspect or the eighth aspect, in a possible implementation, the customized view property includes at least one of a visual property, a layout property, an interaction property, an animation property, and a software and hardware dependency property.

With reference to the seventh aspect or the eighth aspect, in a possible implementation, the layout property includes at least one of stretching, hiding, wrapping, equalization, proportion, and extension.

With reference to the seventh aspect or the eighth aspect, in a possible implementation, the first UI of the first electronic device includes a second view, and the second view has the view property of the general-purpose operating system. In other words, the first UI generated by the first electronic device based on the description file may include a view having the customized view property of the operating system of the first electronic device, or may include a view having the view property of the general-purpose operating system. This provides views in more forms.

With reference to the seventh aspect or the eighth aspect, in a possible implementation, the first UI of the first electronic device includes a third view, and the third view has the customized view property of the first application. In the method, the developers may customize, in a file of the installation package, a view property that belongs to the first application, to enrich the UI.

With reference to the seventh aspect or the eighth aspect, in a possible implementation, the description file includes fourth code, and the fourth code is used to define a correspondence between a view property of a fourth view on the first UI of the first electronic device and first data in the operating system of the first electronic device. The method further includes: The first electronic device receives a first input of a user on the fourth view; and modifies a value of the first data based on the first input.

In the method, the developers define, in the description file, a correspondence between a view property of a view and background data in an operating system; and a UI engine of an electronic device implements a function of modifying the background data based on a user input. This prevents the developers from describing, in the description file, an implementation of modifying the background data based on a user input, and reduces development difficulty for the developers.

With reference to the seventh aspect or the eighth aspect, in a possible implementation, the method further includes: The view property of the fourth view on the first UI of the first electronic device varies with the first data in the operating system of the first electronic device.

In the method, the developers define, in the description file, a correspondence between a view property of a view and background data in an operating system; and a UI engine of an electronic device implements that the view property of the view varies with the background data in the operating system of the electronic device. A view on the UI may vary with a parameter of the electronic device. In addition, this prevents the developers from describing, in the description file, an implementation that the view property of the view varies with the parameter of the electronic device, and reduces development difficulty for the developers.

According to a ninth aspect, this application provides a user interface implementation method, including: displaying a development interface of a first application, where the development interface of the first application includes a description file, used to perform interface description and interface behavior definition on a first user interface UI of the first application; in response to a first operation entered by a user, adding first code corresponding to a device type of a first electronic device to the description file; in response to a second operation entered by the user, adding second code corresponding to a device type of a second electronic device to the description file; and generating an application installation package of the first application based on the description file. The device type of the first electronic device is different from the device type of the second electronic device. Device types of an electronic device may include a mobile phone, a smart television, a smartwatch, a tablet computer, a notebook computer, a netbook, a large screen, a vehicle-mounted computer, and the like.

In the method, one description file includes code corresponding to different types of electronic devices. Different types of electronic devices may present different UI layouts by reading a same description file of a same UI. A set of description files that are applicable to various different types of electronic devices can be developed, to reduce development difficulty for developers.

With reference to the ninth aspect, in a possible implementation, the application installation package of the first application further includes a resource file, and the resource file includes resources used to generate a UI of the first application.

With reference to the ninth aspect, in a possible implementation, the description file includes: third code defining that a first view has a customized view property of an operating system of the first electronic device, and fourth code defining that a second view has a view property of a general-purpose operating system. In other words, the first UI generated by the electronic device based on the description file may include a view having the customized view property of the operating system of the first electronic device, or may include a view having the view property of the general-purpose operating system. This provides views in more forms.

With reference to the ninth aspect, in a possible implementation, the customized view property of the operating system of the first electronic device includes at least one of a visual property, a layout property, an interaction property, an animation property, and a software and hardware dependency property.

With reference to the ninth aspect, in a possible implementation, the layout property includes at least one of stretching, hiding, wrapping, equalization, proportion, and extension.

According to a tenth aspect, this application provides a computer-readable storage medium, for example, an application development tool. The application development tool may specifically include computer instructions. When the computer instructions are run on the foregoing electronic device, the electronic device is enabled to perform the method according to any one of the ninth aspect.

According to an eleventh aspect, this application provides a computer-readable storage medium, including computer instructions. The computer instructions are used to perform interface description and interface behavior definition on a first user interface UI of a first application. The computer instructions include first code corresponding to a device type of a first electronic device and second code corresponding to a device type of a second electronic device. The device type of the first electronic device is different from the device type of the second electronic device. Device types of an electronic device may include a mobile phone, a smart television, a smartwatch, a tablet computer, a notebook computer, a netbook, a large screen, a vehicle-mounted computer, and the like.

With reference to the eleventh aspect, in a possible implementation, the computer instructions further include resources used to generate a UI of the first application.

With reference to the eleventh aspect, in a possible implementation, the computer instructions further include: third code defining that a first view has a customized view property of an operating system of the first electronic device, and fourth code defining that a second view has a view property of a general-purpose operating system.

According to a twelfth aspect, this application provides an electronic device, including a display, an input device, one or more processors, one or more memories, and one or more computer programs. The processor is coupled to the input device, the display, and the memory. The one or more computer programs are stored in the memory. When the electronic device runs, the processor may execute the one or more computer programs stored in the memory, so that the electronic device performs the method according to any one of the eighth aspect.

According to a thirteenth aspect, this application provides an electronic device, including a display, one or more processors, one or more memories, and one or more computer programs. The processor is coupled to both the display and the memory. The one or more computer programs are stored in the memory. When the electronic device runs the foregoing first application, the processor may execute the one or more computer programs stored in the memory, so that the electronic device performs the method according to any one of the ninth aspect.

Embodiments of this application provide a user interface implementation method and an apparatus, to support display of various layout manners and view types on a UI of an application widget, thereby facilitating use of the application widget by a user and improving user experience. To achieve the foregoing objective, the following technical solutions are used in this application.

According to a fourteenth aspect, this application provides a user interface implementation method, including: A first application process of an electronic device reads a widget interface description file, generates first widget UI data based on the widget interface description file, and binds a view in the first widget UI data to background data in an operating system of the electronic device. The widget interface description file is used to perform interface description and interface behavior definition on a first UI of an application widget of a first application. Then, the first application process sends first data to an application widget process. The application widget process receives the first data, obtains the first widget UI data based on the first data, and displays the first UI of the application widget based on the first widget UI data.

In the method, both an application process and the application widget process generate widget UI data based on the widget interface description file. The application process binds a view in the widget UI data to the background data, and the application widget process displays the widget UI data as a UI of an application widget. In this way, developers may define various types of views in the widget interface description file, so that the UI of the application widget supports the various types of views. When a user performs an operation on the UI of the application widget, the application process may execute corresponding service logic based on a correspondence between the view in the widget UI data and the background data.

In a possible implementation, the first application process sends the widget interface description file to the application widget process. The application widget process receives the widget interface description file, generates the first widget UI data based on the widget interface description file, and displays the first UI of the application widget based on the first widget UI data.

In a possible implementation, the first application process sends the first widget UI data to the application widget process. The application widget process receives the first widget UI data, and displays the first UI of the application widget based on the first widget UI data.

With reference to the fourteenth aspect, in a possible implementation, the method further includes: The first application process generates a first view in the first widget UI data based on a definition of first code in the widget interface description file. The first view has a native view property of the operating system of the electronic device. Native views of the operating system include: a text box, a check box, a picker, a scroll view, a radio button, a rating bar, a search box, a seekbar, a switch, or the like.

In other words, the developers may define various native view properties of the operating system in the widget interface description file, so that the UI of the application widget supports various native views of the operating system.

With reference to the fourteenth aspect, in a possible implementation, the method further includes: The first application process generates a second view in the first widget UI data based on a definition of second code in the widget interface description file. The second view has a customized view property of the operating system of the electronic device. The customized view property includes at least one of a visual property, a layout property, an interaction property, an animation property, and a software and hardware dependency property. The layout property includes at least one of stretching, hiding, wrapping, equalization, proportion, and extension.

In other words, the developers may define various customized view properties of the operating system in the widget interface description file, so that the UI of the application widget supports various customized views of the operating system.

With reference to the fourteenth aspect, in a possible implementation, the widget interface description file includes third code, used to define a correspondence between a view property of a third view on the first UI of the application widget and the first data in the operating system of the electronic device. The method further includes: The electronic device receives a first input of a user on the third view; and modifies a value of the first data based on the first input.

With reference to the fourteenth aspect, in a possible implementation, the view property of the third view on the first UI of the application widget varies with the first data in the operating system of the electronic device.

With reference to the fourteenth aspect, in a possible implementation, the method further includes: The electronic device downloads an application installation package of the first application from a server. The application installation package includes the widget interface description file. The electronic device installs the first application by using the application installation package.

In the method, the widget interface description file is obtained from the application installation package.

According to a fifteenth aspect, this application provides a user interface implementation method, including: displaying a development interface of a first application, where the development interface of the first application includes a widget interface description file, and the widget interface description file is used to perform interface description and interface behavior definition on a first UI of an application widget of the first application; in response to a first operation entered by a user, adding, to the widget interface description file, first code for defining a first view on a first widget UI, where the first view has a native view property of an operating system, and native views of the operating system include: a text box, a check box, a picker, a scroll view, a radio button, a rating bar, a search box, a seekbar, a switch, or the like; and generating an application installation package of the first application based on the widget interface description file.

In the method, developers may define, in the widget interface description file, that a view has the native view property of the operating system. Therefore, a UI of the application widget running on the electronic device includes various views that have the native view property of the operating system.

With reference to the fifteenth aspect, in a possible implementation, the method further includes: in response to a second operation entered by the user, adding, to the widget interface description file, second code for defining a second view on the first widget UI, where the second view has a customized view property of the operating system, and the customized view property includes at least one of a visual property, a layout property, an interaction property, an animation property, and a software and hardware dependency property. The layout property includes at least one of stretching, hiding, wrapping, equalization, proportion, and extension.

In the method, the developers may define, in the widget interface description file, that a view has the customized view property of the operating system. Therefore, the UI of the application widget running on the electronic device includes various views that have the customized view property of the operating system.

According to a sixteenth aspect, this application provides a computer-readable storage medium, for example, an application development tool. The application development tool may specifically include computer instructions. When the computer instructions are run on the foregoing electronic device, the electronic device is enabled to perform the method according to any one of the fifteenth aspect.

According to a seventeenth aspect, this application provides a computer-readable storage medium, including computer instructions. The computer instructions are used to perform interface description and interface behavior definition on a first user interface UI of an application widget of a first application. The computer instructions include first code for generating a first view on a first widget UI. The first view has a native view property of an operating system. Native views of the operating system include: a text box, a check box, a picker, a scroll view, a radio button, a rating bar, a search box, a seekbar, a switch, or the like.

With reference to the seventeenth aspect, in a possible implementation, the computer instructions further include second code for generating a second view on the first widget UI. The second view has a customized view property of the operating system, and the customized view property includes at least one of a visual property, a layout property, an interaction property, an animation property, and a software and hardware dependency property. The layout property includes at least one of stretching, hiding, wrapping, equalization, proportion, and extension.

According to an eighteenth aspect, this application provides a computer-readable storage medium. The computer-readable storage medium includes a computer program, and when the computer program is run on an electronic device, the electronic device is enabled to perform the method according to any one of the fourteenth aspect.

According to a nineteenth aspect, this application provides an electronic device, including a display, an input device, one or more processors, one or more memories, and one or more computer programs. The processor is coupled to the input device, the display, and the memory. The one or more computer programs are stored in the memory. When the electronic device runs, the processor may execute the one or more computer programs stored in the memory, so that the electronic device performs the method according to any one of the fourteenth aspect or the fifteenth aspect.

Embodiments of this application provide a user interface implementation method and an apparatus, to support projection of various UIs on a control device to an IoT device for playing, thereby improving user experience. To achieve the foregoing objective, the following technical solutions are used in this application.

According to a twentieth aspect, this application provides a user interface implementation method, including: A first electronic device reads a first playback end interface description file of a first application, generates first playback end UI data based on the first playback end interface description file, and binds a view in the first playback end UI data to background data in an operating system of the first electronic device. The first playback end interface description file is used to perform interface description and interface behavior definition on a first playback end user interface UI that plays the first application on a second electronic device. The first electronic device sends first data to the second electronic device. The second electronic device receives the first data, obtains the first playback end UI data based on the first data, and displays the first playback end UI based on the first playback end UI data.

In the method, both a control device and a playback end generate playback end UI data based on a playback end interface description file. The control device binds a view in the playback end UI data to background data, and the playback end displays the playback end UI data as a playback end UI. In this way, developers may define various UIs in the playback end interface description file to enrich playback end UIs. Different UI layouts may be further defined for playback ends of different device types, so that a size and a form of a playback end UI match a size and a form of a playback end screen. When a user performs an operation on the playback end UI, the control device may execute corresponding service logic based on a correspondence between the view in the playback end UI data and the background data.

In a possible implementation, the first electronic device sends the first playback end interface description file to the second electronic device, and the second electronic device generates the first playback end UI data based on the first playback end interface description file, and displays the first playback end UI based on the first playback end UI data.

In a possible implementation, the first electronic device sends the first playback end UI data to the second electronic device, and the second electronic device receives the first playback end UI data, and displays the first playback end UI based on the first playback end UI data.

With reference to the twentieth aspect, in a possible implementation, the method further includes: The second electronic device receives a first operation of the user on the first playback end UI. The second electronic device sends a first instruction to the first electronic device in response to the first operation of the user on the first playback end UI. The first electronic device receives the first instruction, reads a second playback end interface description file, generates second playback end UI data based on the second playback end interface description file, and binds a view in the second playback end UI data to the background data in the operating system of the first electronic device. The second playback end interface description file is used to perform interface description and interface behavior definition on a second playback end UI that plays the first application on the second electronic device. The first electronic device sends the second playback end interface description file to the second electronic device. The second electronic device receives the second playback end interface description file, generates the second playback end UI data based on the second playback end interface description file, and displays the second playback end UI based on the second playback end UI data.

In the method, the user may directly perform an operation on the playback end UI on the playback device. The control device executes service logic corresponding to the operation, and sends, to the playback device, an updated playback end interface description file corresponding to the playback end UI. The playback device generates an updated playback end UI based on the updated playback end interface description file. Therefore, an operation can be directly performed on the playback end UI on the playback device, and the playback end UI can be successfully switched.

With reference to the twentieth aspect, in a possible implementation, the method further includes: The second electronic device receives a first operation of the user on the first playback end UI. The second electronic device sends a first instruction to the first electronic device in response to the first operation of the user on the first playback end UI.

The first electronic device receives the first instruction, and reads a second playback end interface description file. The second playback end interface description file is used to perform interface description and interface behavior definition on a second playback end UI that plays the first application on the second electronic device. The first electronic device generates second playback end UI data based on the second playback end interface description file, and binds a view in the second playback end UI data to the background data in the operating system of the first electronic device. The first electronic device sends the second playback end UI data to the second electronic device. The second electronic device receives the second playback end UI data, and displays the second playback end UI based on the second playback end UI data.

In the method, the user may directly perform an operation on the playback end UI on the playback device. The control device executes service logic corresponding to the operation, and sends updated playback end UI data to the playback device. The playback device updates the playback end UI based on the updated playback end UI data. Therefore, an operation can be directly performed on the playback end UI on the playback device, and the playback end UI can be successfully switched.

With reference to the twentieth aspect, in a possible implementation, the method further includes: The first electronic device downloads an application installation package of the first application from a server. The application installation package includes the first playback end interface description file and a resource file, and the resource file includes resources used to generate a playback end UI of the first application. The first electronic device installs the first application by using the application installation package.

With reference to the twentieth aspect, in a possible implementation, the method further includes: The first electronic device reads first code that is in the first playback end interface description file and corresponding to a device type of a third electronic device, and generates, based on a definition of the first code, third playback end UI data by using the resources in the resource file. The first electronic device reads second code that is in the first playback end interface description file and corresponding to a device type of a fourth electronic device, and generates, based on a definition of the second code, fourth playback end UI data by using the resources in the resource file. The device type of the fourth electronic device is different from the device type of the third electronic device. The first electronic device separately sends the first playback end interface description file and the resource file to the third electronic device and the fourth electronic device. The third electronic device generates the third playback end UI data based on the definition of the first code that is in the first playback end interface description file and corresponding to the device type of the third electronic device by using the resources in the resource file, and displays the first playback end UI based on the third playback end UI data. The fourth electronic device generates the fourth playback end UI data based on the definition of the second code that is in the first playback end interface description file and corresponding to the device type of the fourth electronic device by using the resources in the resource file, and displays the first playback end UI based on the fourth playback end UI data.

In the method, playback devices of different types present different playback end UI layouts by reading a same playback end interface description file of a same UI. A set of playback end interface description files that are applicable to various different types of playback devices can be developed, to reduce development difficulty for developers.

With reference to the twentieth aspect, in a possible implementation, the method further includes: The first electronic device reads first code that is in the first playback end interface description file and corresponding to a device type of a third electronic device, and generates, based on a definition of the first code, third playback end UI data by using the resources in the resource file. The first electronic device reads second code that is in the first playback end interface description file and corresponding to a device type of a fourth electronic device, and generates, based on a definition of the second code, fourth playback end UI data by using the resources in the resource file. The device type of the fourth electronic device is different from the device type of the third electronic device. The first electronic device sends the third playback end UI data to the third electronic device. The third electronic device displays the first playback end UI based on the third playback end UI data. The first electronic device sends the fourth playback end UI data to the fourth electronic device. The fourth electronic device displays the first playback end UI based on the fourth playback end UI data.

In the method, playback devices of different types present different playback end UI layouts based on a same playback end interface description file of a same UI. A set of playback end interface description files that are applicable to various different types of playback devices can be developed, to reduce development difficulty for developers.

With reference to the twentieth aspect, in a possible implementation, the method further includes: The first electronic device generates a first view on the first playback end UI based on a definition of third code in the first playback end interface description file. The first view has a customized view property of the operating system of the first electronic device. The customized view property of the operating system of the first electronic device includes at least one of a visual property, a layout property, an interaction property, an animation property, and a software and hardware dependency property. The layout property includes at least one of stretching, hiding, wrapping, equalization, proportion, and extension.

With reference to the twentieth aspect, in a possible implementation, the method further includes: The first electronic device displays the first playback end UI based on the first playback end UI data. In the method, the control device and the playback device synchronously play the playback end UI, so that mirror projection can be implemented, and the control device and the playback device work cooperatively.

According to a twenty-first aspect, this application provides a user interface implementation method, including: displaying a development interface of a first application, where the development interface of the first application includes a playback end interface description file, and the playback end interface description file is used to perform interface description and interface behavior definition on a playback end user interface UI that plays the first application on a playback end; in response to a first input of a user, adding first code corresponding to a device type of a first electronic device to the playback end interface description file; in response to a second input of the user, adding second code corresponding to a device type of a second electronic device to the playback end interface description file, where the device type of the first electronic device is different from the device type of the second electronic device; and generating an application installation package of the first application based on the playback end interface description file.

In the method, one playback end interface description file includes code corresponding to playback devices of different types. Playback devices of different types may present different playback end UI layouts by reading a same playback end interface description file of a same UI. A set of playback end interface description files that are applicable to various different types of playback devices can be developed, to reduce development difficulty for developers.

With reference to the twenty-first aspect, in a possible implementation, the application installation package of the first application further includes a resource file, and the resource file includes resources used to generate the playback end UI of the first application.

With reference to the twenty-first aspect, in a possible implementation, the playback end interface description file includes third code defining that a first view on a first playback end UI has a customized view property of an operating system of the first electronic device. The customized view property of the operating system of the first electronic device includes at least one of a visual property, a layout property, an interaction property, an animation property, and a software and hardware dependency property. The layout property includes at least one of stretching, hiding, wrapping, equalization, proportion, and extension.

According to a twenty-second aspect, this application provides a computer-readable storage medium, for example, an application development tool. The application development tool may specifically include computer instructions. When the computer instructions are run on the foregoing electronic device, the electronic device is enabled to perform the method according to any one of the twenty-first aspect.

According to a twenty-third aspect, this application provides a computer-readable storage medium, including computer instructions. The computer instructions are used to perform interface description and interface behavior definition on a first playback end UI of a first application. The computer instructions include first code corresponding to a device type of a first electronic device and second code corresponding to a device type of a second electronic device. The device type of the first electronic device is different from the device type of the second electronic device. Device types of an electronic device may include a mobile phone, a smart television, a smartwatch, a tablet computer, a notebook computer, a netbook, a large screen, a vehicle-mounted computer, and the like.

With reference to the twenty-third aspect, in a possible implementation, the computer instructions further include resources used to generate a playback end UI of the first application.

With reference to the twenty-third aspect, in a possible implementation, the computer instructions further include third code defining that a first view on the first playback end UI has a customized view property of an operating system of the first electronic device. The customized view property of the operating system of the first electronic device includes at least one of a visual property, a layout property, an interaction property, an animation property, and a software and hardware dependency property. The layout property includes at least one of stretching, hiding, wrapping, equalization, proportion, and extension.

According to a twenty-fourth aspect, this application provides a computer-readable storage medium. The computer-readable storage medium includes a computer program, and when the computer program is run on an electronic device, the electronic device is enabled to perform the method according to any one of the twentieth aspect.

According to a twenty-fifth aspect, this application provides an electronic device, including a display, an input device, one or more processors, one or more memories, and one or more computer programs. The processor is coupled to the input device, the display, and the memory. The one or more computer programs are stored in the memory. When the electronic device runs, the processor may execute the one or more computer programs stored in the memory, so that the electronic device performs the method according to any one of the twentieth aspect or the twenty-first aspect.

It can be understood that the electronic device and the computer-readable storage medium provided in the foregoing aspects are all applied to the corresponding methods provided above. Therefore, for beneficial effects that can be achieved by the electronic device and the computer-readable storage medium, refer to the beneficial effects in the corresponding methods provided above. Details are not described herein again.

BRIEF DESCRIPTION OF THE DRAWINGS

FIG. 16A to FIG. 16D are a schematic diagram of a scenario example of a user interface implementation method according to an embodiment of this application;

FIG. 37A-1 and FIG. 37A-2 are a schematic diagram of a user interface implementation method according to an embodiment of this application;

FIG. 38A-1 and FIG. 38A-2 are a schematic diagram of a scenario example of a user interface implementation method according to an embodiment of this application;

FIG. 39A-1 to FIG. 39A-3 are a schematic diagram of a scenario example of a user interface implementation method according to an embodiment of this application;

FIG. 39B-1 and FIG. 39B-2 are a schematic diagram of a user interface implementation method according to an embodiment of this application;

FIG. 40C-1 to FIG. 40C-3 are a schematic diagram of a scenario example of a user interface implementation method according to an embodiment of this application;

FIG. 40D-1 and FIG. 40D-2 are a schematic diagram of a user interface implementation method according to an embodiment of this application;

FIG. 41A-1 and FIG. 41A-2 are a schematic flowchart of a user interface implementation method according to an embodiment of this application;

FIG. 42A-1 and FIG. 42A-2 are a schematic diagram of a scenario example of a user interface implementation method according to an embodiment of this application;

DETAILED DESCRIPTION OF ILLUSTRATIVE EMBODIMENTS

Terms used in the following embodiments are merely intended to describe specific embodiments, but are not intended to limit this application. Terms "one", "a", "the", "the foregoing", "this", and "the one" of singular forms used in this specification and the appended claims of this application are also intended to include plural forms like "one or more", unless otherwise specified in the context clearly. It should be further understood that in the following embodiments of this application, "at least one" and "one or more" refer to one, two, or more. The term "and/or" describes an association relationship between associated objects and represents that three relationships may exist. For example, A and/or B may represent the following cases: Only A exists, both A and B exist, and only B exists, where A and B may be singular or plural. The character "/" generally represents an "or" relationship between the associated objects.

Reference to "an embodiment", "some embodiments", or the like described in this specification indicates that one or more embodiments of this application include a specific feature, structure, or characteristic described with reference to embodiments. Therefore, in this specification, statements such as "in an embodiment", "in some embodiments", "in some other embodiments", and "in other embodiments", that appear at different places do not necessarily mean referring to a same embodiment, instead, the statements mean referring to "one or more but not all of embodiments", unless otherwise specifically emphasized in other ways. The terms "include", "contain", "have", and their variants all mean "include but are not limited to", unless otherwise specifically emphasized. The term "connection" includes direct connection and indirect connection, unless otherwise specified.

Figure 1:
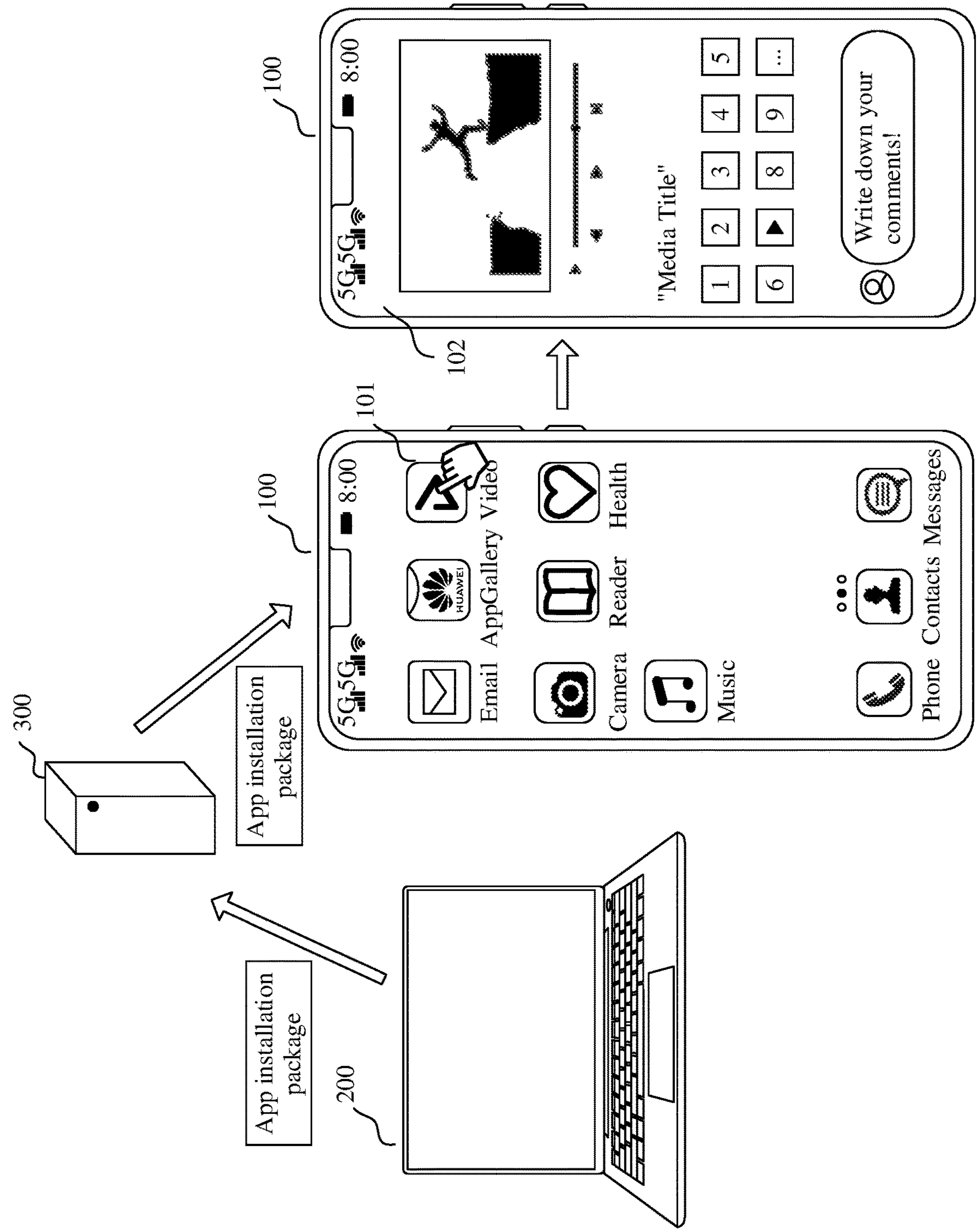
FIG. 1 is a schematic diagram of a scenario of a user interface implementation method according to an embodiment of this application.

Refer to FIG. 1. An application development tool (for example, Android Studio or DevEco Studio) is installed on an electronic device 200. Usually, developers use an interface description language to develop a UI in the application development tool, to form an interface description file. The electronic device 200 in this application may also be referred to as a developer device. The interface description file may also be referred to as a description file.

UI development mainly includes interface description and interface behavior definition. The interface description refers to using an interface description language to describe a UI layout (layout), used views, and visual style of the layout and views. The interface behavior definition refers to defining interface behavior by using the interface description language. The interface behavior includes a dynamic change of the UI and a response of an electronic device to the dynamic change of the UI (for example, a response to an operation of a user on the UI). Each OS platform has a corresponding interface description language. For example, Android® uses an extensible markup language (extensible markup language, xml) format, and iOS® uses an embedded domain-specific language (embedded domain-specific language, EDSL) built by swift to perform interface description and interface behavior definition.

The developers pack the interface description file into an installation package of an app, and release the app in an AppGallery provided by a server 300. The AppGallery may provide an installation package of each app for a user to download. For example, the installation package may be an Android® application package (Android application package, APK) file.

For example, a mobile phone is an electronic device 100. The user may download an installation package of an app from the AppGallery by using the mobile phone. A video app is used as an example. After the mobile phone downloads an installation package of the video app, the video app may be installed on the mobile phone by running the installation package. In this way, the mobile phone also obtains an interface description file in the installation package. The mobile phone may build a UI based on the interface description file. A UI engine provided by the OS platform of the mobile phone interprets and executes the interface description language, render a UI, and present the UI to the user. The built UI is presented on a display apparatus (for example, a display) of the mobile phone. The OS platform of the mobile phone further executes a programming language for implementing interface behavior, to implement a dynamic change of the UI and respond to an operation performed by the user on the UI.

For example, developers develop, on the electronic device 200, a UI of the video app by using an interface description language supported by the OS platform, and release the video app. The user installs the video app on the mobile phone by using the installation package of the video app, and a "Video" icon 101 is generated on a desktop of the mobile phone. The user may tap the "Video" icon 101 to open the video app. In response to a tap operation performed by the user on the "Video" icon 101, the mobile phone runs the video app. The OS platform is installed on the mobile phone. The OS platform reads the interface description file, parses and executes the interface description language, renders the UI of the video app based on the interface description in the interface description file, and presents the UI 102 of the video app on the display. Further, the interface description file may further include a definition of interface behavior. The mobile phone may perform, in response to an operation performed by the user on the UI 102, a corresponding interface action based on interface behavior defined in the interface description file, to implement the interface behavior. Generally, the OS platform has a corresponding programming language used to implement interface behavior, implement a dynamic change of the UI 102, and respond to the operation of the user on the UI 102. For example, Android® uses JAVA, and iOS® uses a swift programming language to implement interface behavior.

It may be understood that, in some embodiments, developers may directly develop a UI of an app on the electronic device 100, and run the app on the electronic device 100. In other words, the electronic device 200 and the electronic device 100 may be a same electronic device. This is not limited in embodiments of this application.

The electronic device 100 may include a portable computer (such as a mobile phone), a handheld computer, a tablet computer, a notebook computer, a netbook, a personal computer (personal computer, PC), a smart home device (such as a smart television, a smart screen, a large screen, or a smart speaker), a personal digital assistant (personal digital assistant, PDA), a wearable device (such as a smartwatch or a smart band), an augmented reality (augmented reality, AR)\virtual reality (virtual reality, VR) device, a vehicle-mounted computer, or the like. This is not limited in embodiments of this application. An example embodiment of the electronic device 100 includes but is not limited to a portable electronic device using Android®, iOS®, or another operating system. It may be understood that in some other embodiments, the electronic device 100 may not be a portable electronic device, but a desktop computer.

Figure 2:
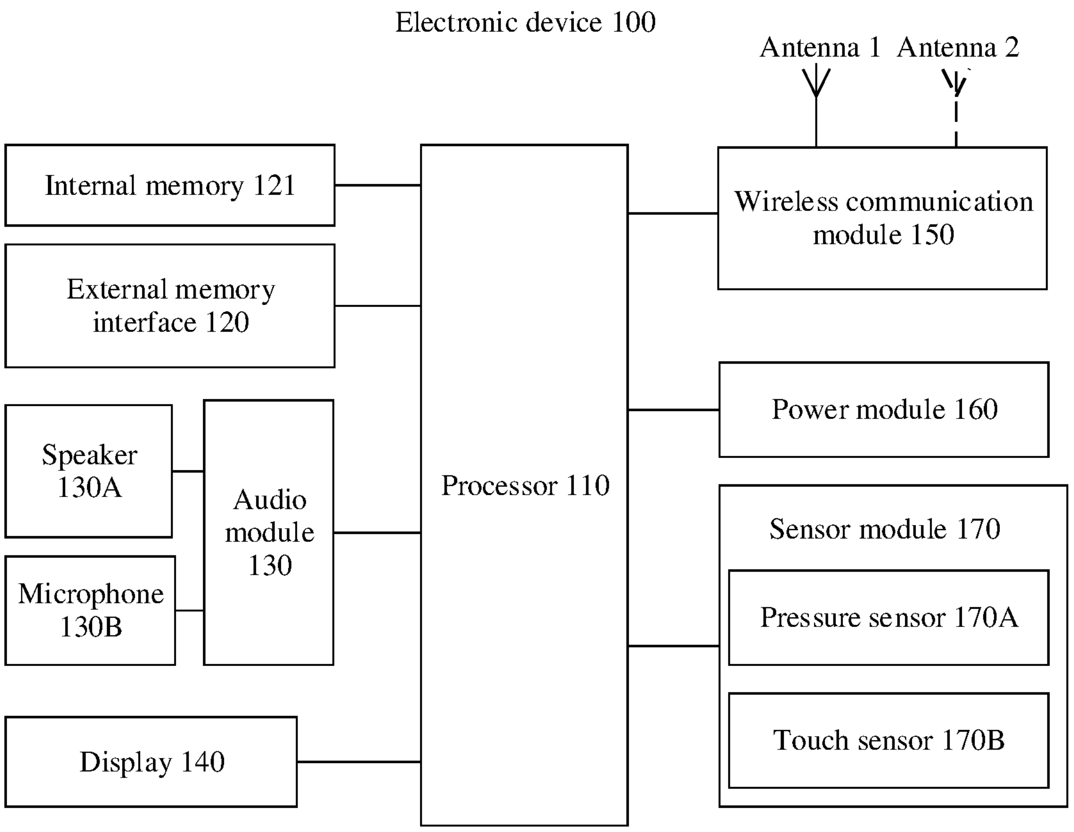
FIG. 2 is a schematic diagram of a hardware structure of an electronic device according to an embodiment of this application.

For example, FIG. 2 is a schematic diagram of a structure of the electronic device 100. The electronic device 100 may include a processor 11o, an external memory interface 120, an internal memory 121, an audio module 130, a speaker 130A, a microphone 130B, a display 140, a wireless communication module 150, a power module 160, and the like.

It may be understood that the structure shown in this embodiment of this application does not constitute a specific limitation on the electronic device 100. In some other embodiments of this application, the electronic device 100 may include more or fewer components than those shown in the figure, or some components may be combined, or some components may be split, or different component arrangements may be used. The components shown in the figure may be implemented by using hardware, software, or a combination of software and hardware.

The processor 110 may include one or more processing units. For example, the processor 110 may include an application processor (application processor, AP), a modem processor, a graphics processing unit (graphics processing unit, GPU), an image signal processor (image signal processor, ISP), a controller, a video codec, a digital signal processor (digital signal processor, DSP), a baseband processor, a neural-network processing unit (neural-network processing unit, NPU), and/or the like. Different processing units may be independent components, or may be integrated into one or more processors. In some embodiments, the electronic device 100 may also include one or more processors 110.

The controller is a nerve center and a command center of the electronic device 100. The controller may generate an operation control signal based on instruction operation code and a time sequence signal, to complete control of instruction reading and instruction execution.

An operating system of the electronic device 100 may run on the application processor, and is configured to manage hardware and software resources of the electronic device 100, for example, manage and configure memory, determine priorities of system resource supply and demand, control input and output devices, operate networks, manage file systems, and manage drivers. The operating system may also be configured to provide an operation interface for a user to interact with the system. Various types of software, such as a driver and an application (application, app), may be installed in the operating system.

A memory may be further disposed in the processor 11o, and is configured to store instructions and data. In some embodiments, the memory in the processor 110 is a cache. The memory may store instructions or data just used or cyclically used by the processor 110. If the processor 110 needs to use the instructions or the data again, the processor 110 may directly invoke the instructions or the data from the memory. This avoids repeated access, reduces waiting time of the processor 110, and improves system efficiency.

In some embodiments, the processor 110 may include one or more interfaces. The interface may include an inter-integrated circuit (inter-integrated circuit, I2C) interface, an inter-integrated circuit sound (inter-integrated circuit sound, I2S) interface, a pulse code modulation (pulse code modulation, PCM) interface, a universal asynchronous receiver/transmitter (universal asynchronous receiver/transmitter, UART) interface, a mobile industry processor interface (mobile industry processor interface, MIPI), a general-purpose input/output (general-purpose input/output, GPIO) interface, a SIM card interface, a USB interface, and/or the like.

It may be understood that an interface connection relationship between modules illustrated in this embodiment of this application is merely an example for description, and does not constitute a limitation on the structure of the electronic device 100. In some other embodiments of this application, the electronic device 100 may alternatively use an interface connection manner different from that in the foregoing embodiment, or a combination of a plurality of interface connection manners.

The external memory interface 120 may be configured to connect to an external memory card, for example, a micro SD card, to extend a storage capability of the electronic device 100. The external storage card communicates with the processor 110 through the external memory interface 120, to implement a data storage function. For example, files such as music and videos are stored in the external storage card.

The internal memory 121 may be configured to store one or more computer programs, and the one or more computer programs include instructions. The processor 110 may run the instructions stored in the internal memory 121, so that the electronic device 100 performs the user interface implementation method, various applications, data processing, and the like that are provided in some embodiments of this application. The internal memory 121 may include a code storage area and a data storage area. The data storage area may store data created during use of the electronic device 100, and the like. In addition, the internal memory 121 may include a high-speed random access memory, or may include a nonvolatile memory, for example, one or more magnetic disk storage devices, a flash memory device, or a universal flash storage (universal flash storage, UFS). In some embodiments, the processor 110 may run the instructions stored in the internal memory 121 and/or the instructions stored in the memory that is disposed in the processor 110, to enable the electronic device 100 to perform the user interface implementation method, other applications, and data processing that are provided in embodiments of this application.

The electronic device 100 may implement an audio function such as music playing or recording by using the audio module 130, the speaker 130A, the microphone 130B, the application processor, and the like. The audio module 130 is configured to convert digital audio information into an analog audio signal for output, and is also configured to convert an analog audio input into a digital audio signal. The audio module 130 may be further configured to code and decode an audio signal. In some embodiments, the audio module 130 may be disposed in the processor 110, or some function modules in the audio module 130 are disposed in the processor 110.

The speaker 130A, also referred to as a "loudspeaker", is configured to convert an audio electrical signal into a sound signal.

The microphone 130B, also referred to as a "mike" or a "mic", is configured to convert a sound signal into an electrical signal. The user may make a sound by moving a human mouth close to the microphone 130B, to input the sound signal to the microphone 130B.

A wireless communication function of the electronic device 100 may be implemented by using the antenna 1, the antenna 2, the wireless communication module 150, or the like.

The wireless communication module 150 may provide a wireless communication solution that is applied to the electronic device 100 and that includes Wi-Fi, Bluetooth (Bluetooth, BT), and a wireless data transmission module (for example, 433 MHz, 868 MHz, or 915 MHz). The wireless communication module 150 may be one or more components integrating at least one communication processing module. The wireless communication module 150 receives an electromagnetic wave through the antenna 1 or the antenna 2, performs frequency filtering and modulation processing on an electromagnetic wave signal, and sends a processed signal to the processor 11*o*. The wireless communication module 150 may further receive a to-be-sent signal from the processor 11*o*, perform frequency modulation and amplification on the signal, and convert the signal into an electromagnetic wave for radiation through the antenna 1 or the antenna 2.

The electronic device 100 implements a display function by using the GPU, the display 140, the application processor, and the like. The GPU is a microprocessor for image processing, and is connected to the display 140 and the application processor. The GPU is configured to perform mathematical and geometric calculation, and render an image. The processor 110 may include one or more GPUs, which execute program instructions to generate or change display information.

The display 140 is configured to display an image, a video, and the like. The display 140 includes a display panel. The display panel may be a liquid crystal display (liquid crystal display, LCD), an organic light-emitting diode (organic light-emitting diode, OLED), an active-matrix organic light-emitting diode (active-matrix organic light-emitting diode, AMOLED), a flexible light-emitting diode (flexible light-emitting diode, FLED), a mini LED, a micro LED, a micro OLED, a quantum dot light-emitting diode (quantum dot light-emitting diode, QLED), or the like. In some embodiments, the electronic device 100 may include one or N displays 140, where N is a positive integer greater than 1. In this embodiment of this application, the display 140 may be configured to display a UI and receive an operation performed by the user on the UI.

In some embodiments, a pressure sensor 170A, a touch sensor 170B, and the like are disposed on the display 140. The pressure sensor 170A is configured to sense a pressure signal, and may convert the pressure signal into an electrical signal. When a touch operation is performed on the display 140, the electronic device 100 detects intensity of the touch operation by using the pressure sensor 170A. The electronic device 100 may also calculate a touch location based on a detection signal of the pressure sensor 170A. The touch sensor 170B, also referred to as a "touch panel", may form a touchscreen, also referred to as a "touch screen", with the display 140. The touch sensor 170B is configured to detect a touch operation on or near the touch sensor 170B. The touch sensor may transfer the detected touch operation to the application processor, to determine a type of a touch event. A visual output related to the touch operation may be further provided through the display 140.

The power module 160 may be configured to supply power to components included in the electronic device 100. In some embodiments, the power module 160 may be a battery, for example, a rechargeable battery.

A software system of the electronic device 100 may use a layered architecture, an event-driven architecture, a micro-kernel architecture, a microservice architecture, or a cloud architecture. In this embodiment of the present invention, an Android® system of the layered architecture is used as an example to describe the software structure of the electronic device 100.

Figure 3:
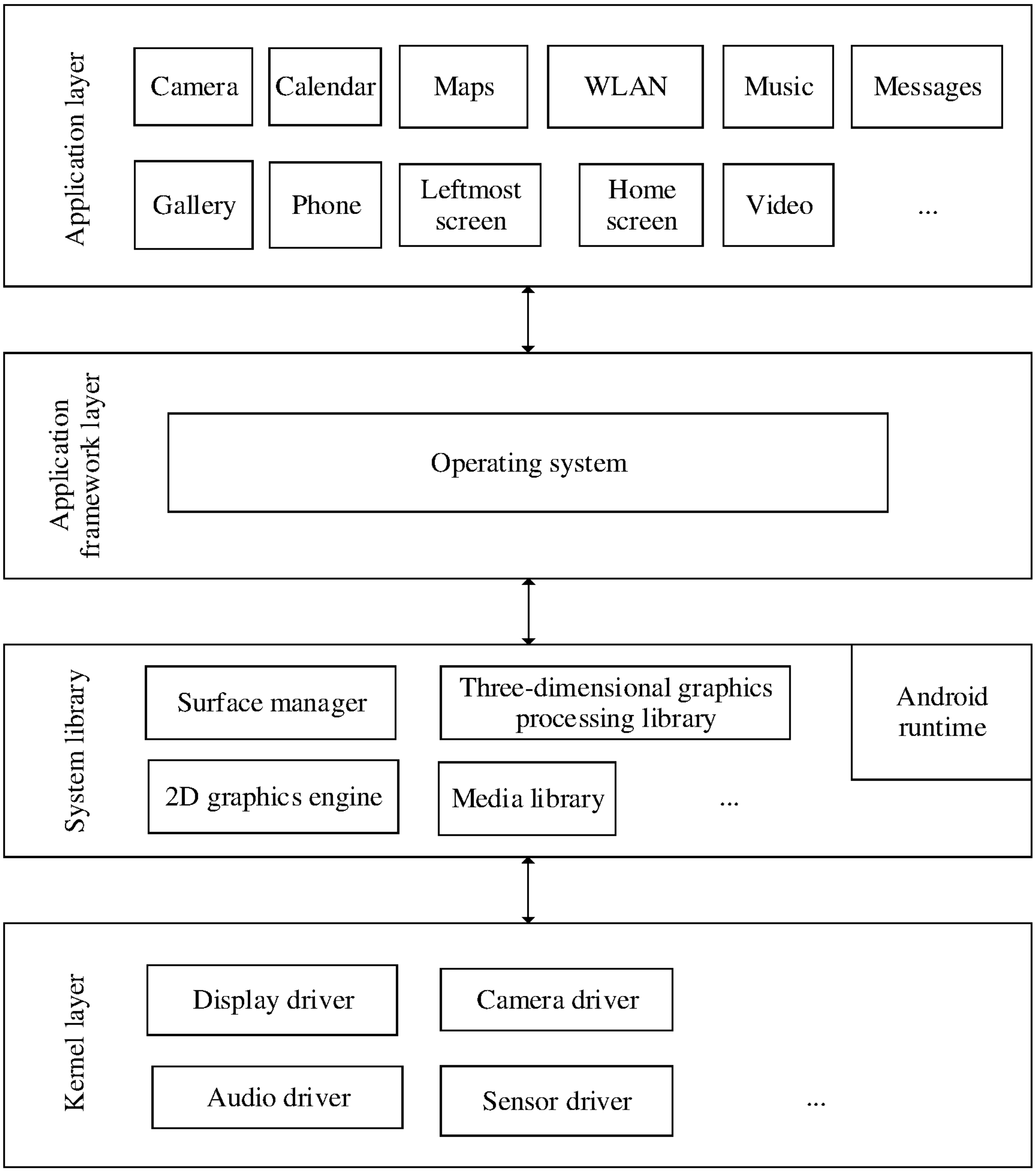
FIG. 3 is a schematic diagram of a software architecture of an electronic device according to an embodiment of this application.

FIG. 3 is a block diagram of a software structure of the electronic device 100 according to an embodiment of the present invention.

In a layered architecture, software is divided into several layers, and each layer has a clear role and task. The layers communicate with each other through a software interface. In some embodiments, the software system is divided into four layers: an application layer, an application framework layer, an Android runtime (Android runtime) and system library, and a kernel layer from top to bottom.

The application layer may include a series of application packages.

As shown in FIG. 3, the application packages may include applications such as Camera, Gallery, Calendar, Phone, Maps, Leftmost screen, WLAN, Home screen, Music, Videos, and Messages.

The application framework layer includes an OS, and provides an application programming interface (application programming interface, API) and a programming framework for an application at the application layer. The application framework layer includes some predefined functions, to implement predefined functions, for example, obtain a size of a display, determine whether there is a status bar, lock a screen, and capture a screen; provide data accessed by an application; and provide various resources for the application, such as a localized character string, an icon, an image, an interface description file, and a video file. A view system of the OS includes visual views, such as a view for displaying a text and a view for displaying an image. The view system may be configured to build an application. A display interface may include one or more views. For example, a display interface including an SMS notification icon may include a text display view and an image display view. The OS may further enable the application to display notification information in the status bar, and may be used to convey a notification message, which may automatically disappear after a short pause without user interaction. Alternatively, a notification may appear in the status bar on the top of the system in a form of a chart or a scroll bar text, for example, a notification of an application running in the background. Alternatively, a notification may appear on the screen in a form of a dialog window. For example, text information is prompted in the status bar, a prompt tone is produced, the electronic device vibrates, or an indicator light blinks.

The Android runtime includes a kernel library and a virtual machine. The Android runtime is responsible for scheduling and management of the Android system.

The kernel library includes two parts: One part is a function that needs to be invoked by a Java language, and the other part is a kernel library of Android.

The application layer and the application framework layer run on the virtual machine. The virtual machine executes Java files of the application layer and the application framework layer as binary files. The virtual machine is configured to implement functions such as object lifecycle management, stack management, thread management, security and exception management, and garbage collection.

The system library may include a plurality of function modules, for example, a surface manager (surface manager), a media library (Media Library), a three-dimensional graphics processing library (for example, OpenGL ES), and a 2D graphics engine (for example, SGL).

The surface manager is configured to manage a display subsystem and provide fusion of 2D and 3D layers for a plurality of applications.

The media library supports playback and recording in a plurality of commonly used audio and video formats, a static image file, and the like. The media library may support a plurality of audio and video coding formats, such as MPEG-4, H.264, MP3, AAC, AMR, JPG, and PNG.

The three-dimensional graphics processing library is configured to implement three-dimensional graphics drawing, image rendering, compositing, layer processing, and the like.

The 2D graphics engine is a drawing engine for 2D drawing.

The kernel layer is a layer between hardware and software. The kernel layer includes at least a display driver, a camera driver, an audio driver, and a sensor driver.

As an open-source OS, Android® is widely used on portable electronic devices. At the same time, many vendors have launched their own enhanced systems (OEM OS). For example, Huawei EMUI is built based on Android®. The OEM OS can provide a more optimized and enhanced SDK than a basic OS (such as Android®), and provide a vendor-defined UI programming capability.

Figure 4:
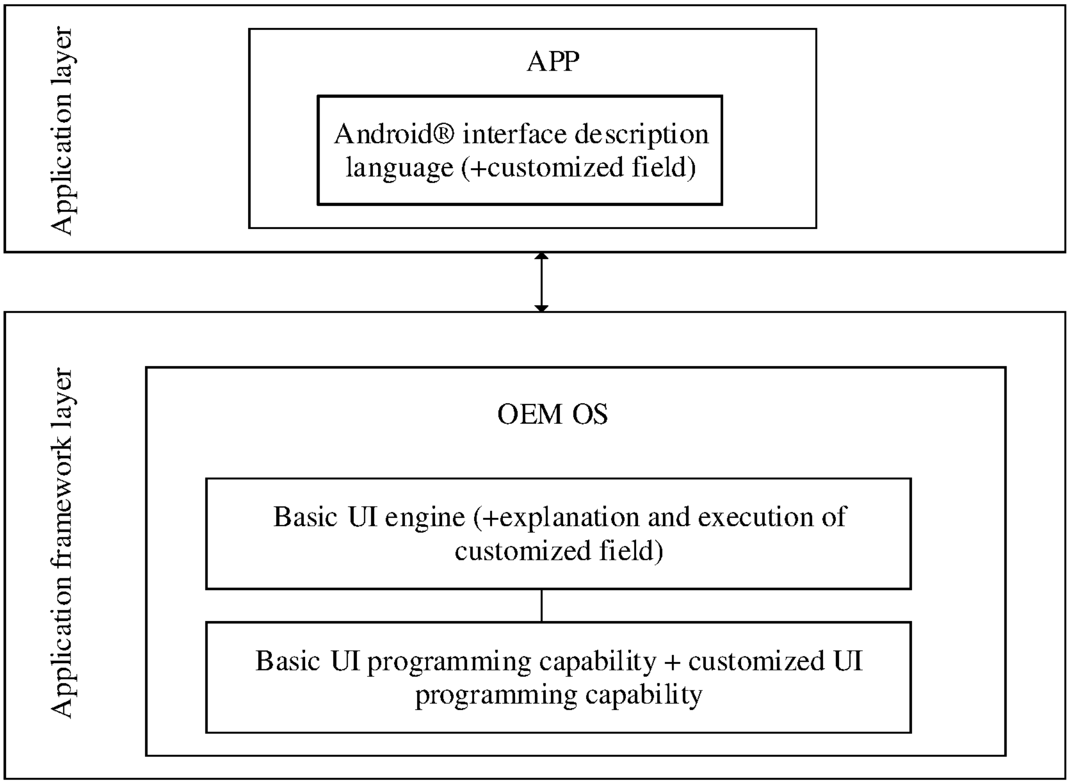
FIG. 4 is a schematic diagram of a user interface implementation method.

In an implementation method, an OEM OS released by a vendor supports an interface description language (for example, xml) of Android®, and can provide a basic UI programming capability of Android® and a vendor-defined UI programming capability. Refer to FIG. 4. A UI development language of an app is an interface description language (for example, xml) applicable to Android®, and is used to declare the basic UI programming capability provided by Android®. A vendor-defined field is added to the interface description language (for example, xml) of Android® to declare the vendor-defined UI programming capability. An OEM OS platform interprets and executes the interface description language based on a basic UI engine provided by Android®. The basic UI engine interprets and executes the vendor-defined field. The OEM OS supports the basic UI programming capability provided by Android® and provides the vendor-defined UI programming capability. In this method, an Android® native development interface, interface description language, and UI engine are used, and a customized field is added to the Android® native interface description language and UI engine to provide the vendor-defined UI programming capability.

Figure 5:
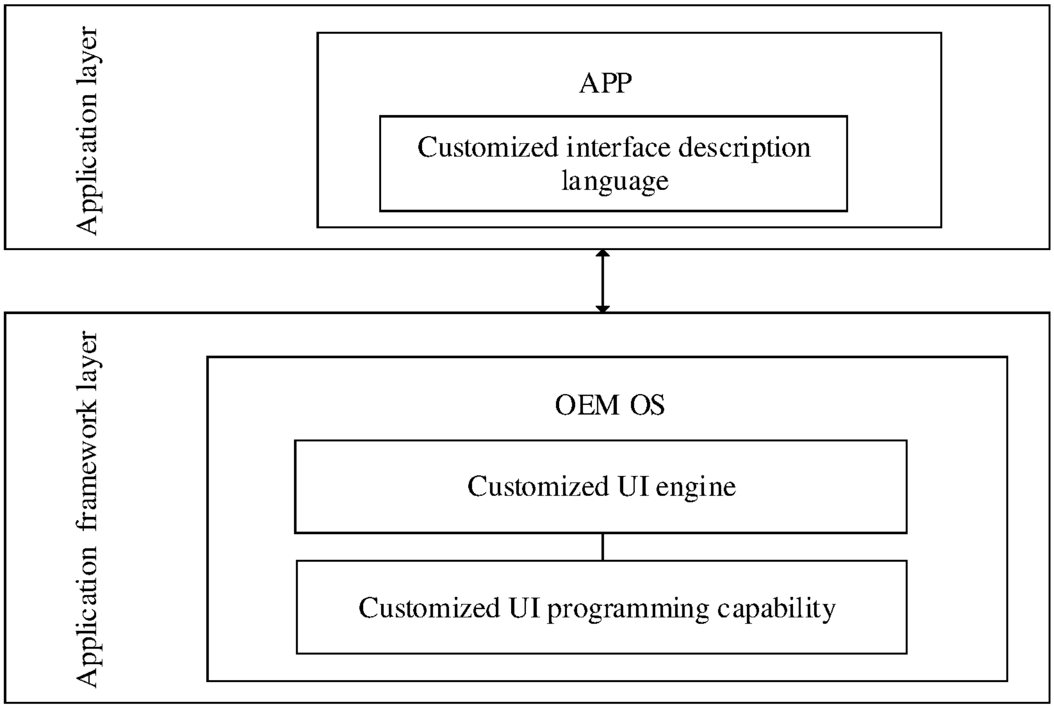
FIG. 5 is a schematic diagram of a user interface implementation method.

In another implementation method, an OEM OS released by a vendor is independent of a general-purpose OS platform (for example, Android®), and provides a vendor-defined UI programming capability. Refer to FIG. 5. A UI development language of an app is a vendor-defined interface description language. An OEM OS platform provides a customized UI engine to parse and execute a customized interface description language, and provides the vendor-defined UI programming capability. In this method, the vendor customizes a complete UI programming framework that is independent of the general-purpose OS platform to meet developers' requirements for cross-platform app development and running.

Embodiments of this application provide a user interface implementation method and an apparatus, to provide rich UI programming capabilities, adapt to a plurality of OS platforms, reduce technical implementation difficulty, and facilitate use by developers.

Figure 6:
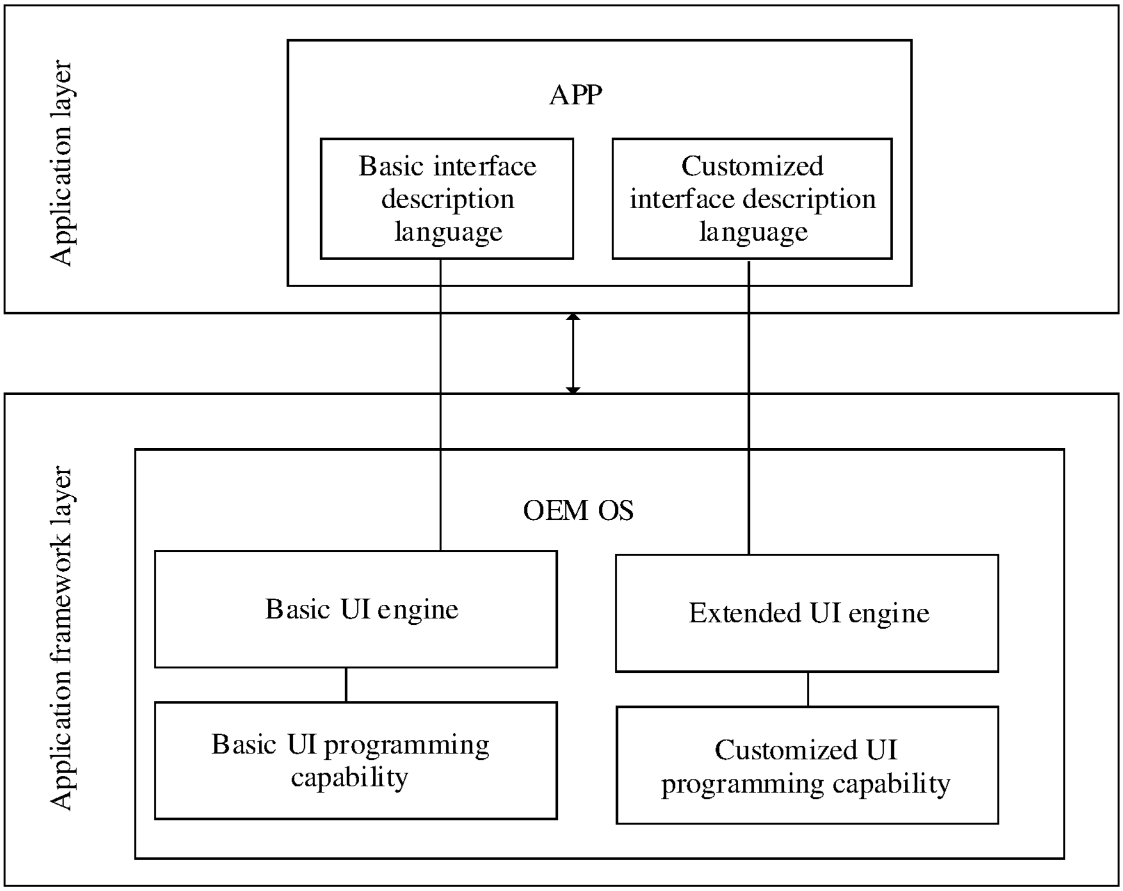
FIG. 6 is a schematic diagram of a user interface implementation method according to an embodiment of this application.

Refer to FIG. 6. An OEM OS platform provided in this embodiment of this application supports a basic interface description language and a customized interface description language. The basic interface description language is supported by a general-purpose OS platform, for example, xml of Android®, and swift of iOS®. In this embodiment of this application, the customized interface description language is a domain-specific language (domain-specific language, DSL), and the customized interface description language is not related to the general-purpose OS platform. In the following embodiments of this application, the customized interface description language is referred to as the DSL. Developers can use the basic interface description language and the DSL to jointly develop a UI of an app. For example, the developers use the basic interface description language to describe a UI layout and included views, and selectively use a DSL to apply a customized UI programming capability to some views and add some animations to the UI. For example, the customized UI programming capability may include a layout capability, a visual property capability, a unified interaction capability, an animation capability, and the like. The layout capability is used to describe a layout of a view on a UI, for example, a shape, a position, and a size of a view. The visual property capability is used to describe a visual property of a view, for example, visual effects such as a color and grayscale of a view. The unified interaction capability is used to provide a view response based on user behavior, for example, perform a search based on "confirm" behavior of a user. The animation capability is used to display an animation effect on a view, for example, display a click-rebound animation on a view.

An OEM OS provided in this embodiment of this application can implement not only a basic UI programming capability provided by the general-purpose OS platform, but also the customized UI programming capability extended relative to the OS platform. The OEM OS platform includes a basic UI engine and an extended UI engine. When an electronic device builds a UI, the basic UI engine is configured to interpret and execute the basic interface description language, to generate a basic UI (with the basic UI programming capability); and the extended UI engine is configured to interpret and execute the DSL, to superimpose the customized UI programming capability on the basic UI.

According to the user interface implementation method provided in this embodiment of this application, the customized interface description language and the extended UI engine only need to cover the customized UI programming capability. Therefore, release difficulty for a vendor is low, and extension is easy. In addition, an access threshold for developers is low. The customized interface description language and the extended UI engine are not related to the general-purpose OS platform. The general-purpose OS platform may be Android® or another general-purpose OS platform. The customized interface description language and the extended UI engine can be easily applied to a plurality of general-purpose OS platforms.

Figure 7:
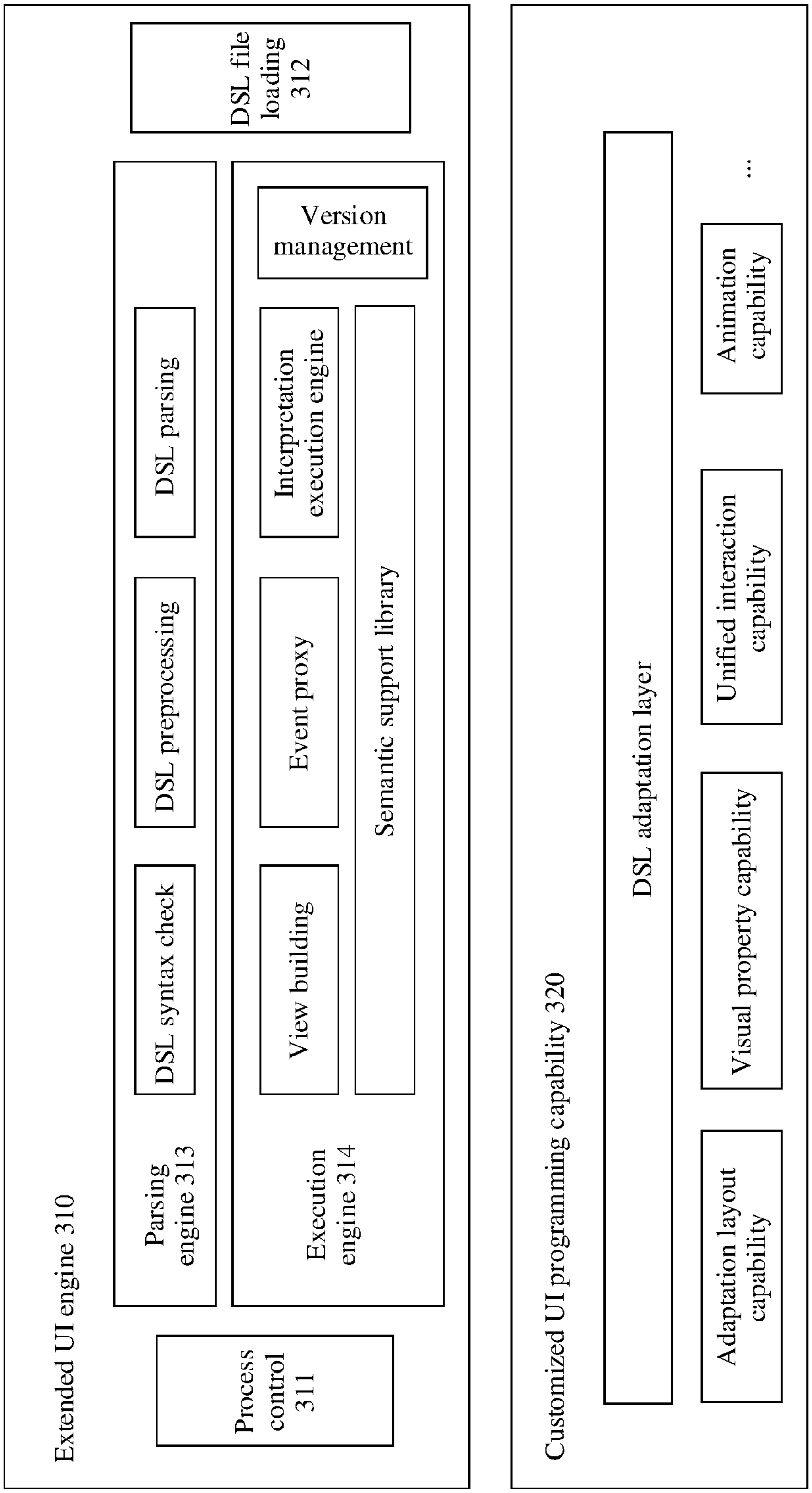
FIG. 7 is a schematic diagram of an architecture of a user interface implementation method according to an embodiment of this application.

The developers use the basic interface description language and the customized interface description language to develop the app. When the app runs on the electronic device, a UI engine of the OEM OS on the electronic device parses and executes an interface description language (the basic interface description language and the customized interface description language), to generate the UI. The basic UI engine is configured to interpret and execute the basic interface description language. The extended UI engine provided by the OEM OS in this embodiment of this application is configured to parse and execute the customized interface description language. Refer to FIG. 7. In an example, an extended UI engine 310 includes modules such as process control 311, DSL file loading 312, parsing engine 313, and execution engine 314. The process control 311 is configured to control an execution process of each module in the extended UI engine 310, an interaction process between the extended UI engine 310 and another module in the OEM OS, and the like. The DSL file loading 312 is configured to read a DSL file. The parsing engine 313 includes a DSL syntax check submodule, a DSL parsing submodule, and the like. The DSL syntax check submodule is configured to perform syntax check on content in the DSL file. The DSL parsing submodule is configured to parse the DSL file, and convert the content in the DSL file into a data format that matches the execution engine. In an implementation, if the syntax check performed by the DSL syntax check submodule on the DSL file succeeds, the DSL parsing submodule parses the DSL file; or if the syntax check performed by the DSL syntax check submodule on the DSL file fails, the DSL parsing submodule does not parse the DSL file. The parsing engine 313 may further include a submodule such as DSL preprocessing. For example, the DSL preprocessing submodule is configured to precompile the DSL file. The execution engine 314 includes submodules such as version management, view building, event proxy, interpretation execution engine, and semantic support library. The version management submodule is configured to match a version of the extended UI engine 310 with a version of a DSL file in an app. The version of the extended UI engine 310 needs to be consistent with the version of the DSL file or later than the version of the DSL file, so that the extended UI engine 310 can run normally. The view building submodule is configured to build a view of a UI based on the content in the DSL file. The event proxy submodule is configured to implement mapping between a component event and user behavior. For example, both a mouse double-click event and a finger tap event on a display may be mapped to "confirm" behavior of a user on the electronic device. The interpretation execution engine is configured to interpret and execute code in the DSL file, and in response to the user behavior, execute an action corresponding to the user behavior defined in the DSL file. The semantic support library includes a syntactic and semantic specification set of all fields in the DSL file, for example, definitions and syntax of fields such as an environment variable interface, a public field, a layout template property, a visual property, a layout property, an interaction property, and an animation property.

Still refer to FIG. 7. An OEM OS in this embodiment of this application further includes a customized UI programming capability 320. The customized UI programming capability 320 includes a DSL adaptation layer, configured to provide an adaptation interface of the customized UI programming capability for the extended UI engine 310. The customized UI programming capability 320 further provides implementation of customized UI programming capabilities such as a visual property capability, a layout capability, a unified interaction capability, and an animation capability. For example, the DSL file declares that a view enables a vertical stretching capability, and implementation of the customized UI programming capability (vertical stretching capability) is completed by the customized UI programming capability 320. That is, when a display window of the view changes, the customized UI programming capability 320 implements vertical stretching of the view, and developers do not need to implement vertical stretching of the view in a DSL.

The developers can use a basic interface description language and the DSL to jointly develop the app. A syntax rule and a development tool of the basic interface description language can follow the conventional technology. This embodiment of this application further provides a syntax rule and a development tool of the DSL. In an example, this embodiment of this application provides a development tool, to support syntax rules of the basic interface description language and the DSL, and provide an editing and compilation environment of the basic interface description language and the DSL.

In some embodiments, this embodiment of this application provides a development tool. A development interface of the development tool includes the basic interface description language file and the DSL file. For example, the developers open the development interface of the development tool. The development interface includes an initial version of the basic interface description language file and an initial version of the DSL file. Further, the developers may add a view description in the initial version of the basic interface description language file by using the basic interface description language, or may add a view description in the initial version of the DSL file by using the DSL. It may be understood that the initial version of the DSL file may be preset in the development tool, or may be added by the developers in the development tool. In some instances, the development tool may further include a DSL template, a DSL syntax rule description file, an interface description example, and the like.

In some examples, the basic interface description language file is used to describe a native view, and apply a basic UI programming capability to the native view. The DSL file is used to declare the customized UI programming capability of the view. For example, the customized UI programming capability may be applied to the native view in the DSL file. For another example, a customized view may be declared in the DSL file, and the customized UI programming capability is applied to the customized view.

Figure 8:
FIG. 8 is a schematic diagram of a scenario example of a user interface implementation method according to an embodiment of this application.

In an implementation, the basic interface description language file and the DSL file are respectively set in different paths of a development tool folder. For example, the basic interface description language is borne by one or more files in an xml format, and the DSL is borne by one or more files in a json format. For example, as shown in FIG. 8, an Android® platform is used as a general-purpose OS platform, and developers create an app folder of an app in a development tool. An AndroidManifest.xml file is integrated in a res directory of the app folder. The developers can declare a used basic UI programming capability in the xml file. A huawei_dsl.json file is integrated in an assets directory of the app folder. The developers can declare a used customized UI programming capability in the DSL file in the json format.

It may be understood that the basic interface description language file and the DSL file are respectively set in different paths of the development tool folder, so that the UI engine of the OEM OS can distinguish the basic interface description language file from the DSL file. In an actual application, the basic interface description language file and the DSL file may also be distinguished in another manner. For example, different tags are preset for the basic interface description language file and the DSL file, and the UI engine of the OEM OS may separately obtain the basic interface description language file and the DSL file based on the preset tags. This is not limited in this embodiment of this application.

The developers develop an app in the development tool, compiles the app, and generates an app installation package. The basic interface description language file and the DSL file are integrated into the app installation package, so that the UI engine of the OEM OS can read the basic interface description language file and the DSL file. In an implementation, storage locations of the basic interface description language file and the DSL file in the app installation package are consistent with locations of the basic interface description language file and the DSL file in the app folder in the development tool.

In an example, the DSL file uses a standard json format. For example, the DSL file includes content such as a version, an app, and a layout.

The version indicates a version number of the DSL file. For example, a format of the version is x.y.z, where x indicates a product, y indicates a subsystem of the product, and z indicates a quantity of development times, for example, may be 101.1.003.

The app content block is used to declare a customized UI programming capability of an app global view in the app installation package where the DSL file is located. For example, a format of the app content block is as follows:

```
{
  "feature_name1": "value"
  "feature_name2": "value"
}
```

The feature_name indicates a property of the customized UI programming capability, and the value is a property value of the customized UI programming capability.

The layout content block is used to declare a customized UI programming capability of a view in a layout (layout). For example, a format of the layout content block is as follows:

```
{
  "layoutId": {
    "widgetId": {
      "prop_name1": "value"
      "prop_name2": "value"
      ...
    }
  }
}
```

The layoutId is used to indicate a layout. For example, the layoutId is an identifier of a layout. The widgetId is used to indicate a view in the layout. For example, the widgetId is a view identifier. The prop_name is a property of the customized UI programming capability, and indicates a feature of the customized UI programming capability, for example, enabling of the customized UI programming capability, a priority of the customized UI programming capability, and a parameter of the customized UI programming capability. The value is a property value of the customized UI programming capability, and the property value is used to specify a value of the property. For example, the property is enabling of customized UI programming capability. Correspondingly, if the property value is true, it indicates that the customized UI programming capability is enabled, and if the property value is false, it indicates that the customized UI programming capability is disabled.

For example, the DSL file includes the following code segment:

```
version: 101.1.003
app: {
"zoom": "enable"
}
layout: {
"R. layout.mainpage": {
  "R.id.edit_text": {
    "onSearch": {com.app. Search$ onSearchPrice}
  }
}
}
```

The version number is 101.1.003. A property value of a customized zoom (zoom) UI programming capability is enabled, that is, the zoom (zoom) capability is enabled for the app global view. A view named R.id.edit_text in a layout named R. layout.mainpage in the app enables an onSearch (search) capability, a property value of onSearch is com.app. Search$onSearchPrice (that is, a specific execution action of the search function is defined in com.app. Search$onSearch-Price).

It may be understood that the DSL file may include fewer or more fields. For example, the DSL file may include the version and layout content blocks, but does not include the app content block. For another example, the layout content block may include description fields of a plurality of views. For another example, a plurality of customized UI programming capabilities can be enabled for a view. This is not limited in this embodiment of this application.

The customized UI programming capability in this embodiment of this application may include a visual property capability, a layout capability, a unified interaction capability, an animation capability, and the like. The developers can declare the customized UI programming capability in the DSL file to use the customized UI programming capability provided by the OEM OS.

For example, a visual property of a UI is embodied as a visual property of a view. The OEM OS defines a set of visual parameter variables for the view to describe the visual property of the view. The set of visual parameter variables can be used to switch visual properties of a plurality of brands or devices. When describing the visual property of the UI, the developers only need to use the visual parameter variable (a property value that matches a brand or an electronic device is dynamically obtained when the electronic device is running), and the developers do not need to specify a specific variable value. The visual parameter variable is declared in the DSL file, so that the view has a corresponding visual property capability.

The following is an example of using the visual property capability in the DSL file:

```
version: 101.0.100
layout: {
"R.layout.mainpage": {
"paddingStart": "defaultPaddingStart" //use a padding interface defined
by the OEM OS
    "R.id.textview": {
      "textColor": "emuiColor1" //use a color interface defined by the
      OEM OS
    }
    "R.id.image": {
      "foreground": "emui_color_bg" //use the color interface defined
by the OEM OS
    }
  }
}
```

In this example, a property value of the visual property textColor of the R.id.textview view is emuiColor1, and a property value of the visual property foreground of the R.id.image view is emui_color_bg. Herein, emuiColor1 and emui_color_bg are visual parameter variables, and are mapped to different color values on different brands or devices. A mapping relationship between visual parameter variables and color values of different brands or devices is preset in the OEM OS. This avoids repeated work of the developers to specify textColor and foreground property values on different brands or devices.

The OEM OS provides an adaptive layout capability to build a responsive UI, so that the UI layout can adapt to displays of different sizes and forms, and the developers do not need to perform different layouts for different devices. For example, the adaptive layout capability includes layout capabilities such as stretching, hiding, wrapping, equalization, proportion, and extension. In an example, the adaptive layout capability provided by the OEM OS is applicable to a LinearLayout layout and a view in the layout.

Several layout capabilities are shown below as examples.

1. Main switch of an adaptive layout capability, used to enable or disable an adaptive layout capability of a view. In an example, any one of the layout capabilities can be enabled only when the main switch of the adaptive layout capability is turned on.

1. Field definition

| Capability | Property | Field definition | Property category |
|---|---|---|---|
| Main switch | Enabling the adaptive layout capability | use__HwConstraintLayout | Layout |

The "capability" is used to indicate a customized UI programming capability. The "property" indicates a feature parameter of the customized UI programming capability. The "property category" indicates a category of a property function. For example, if a property category is a layout, the property is used for view layout. If a property category is a child element, the property is used for view description.

2. Automatic stretching capability. After the automatic stretching capability is enabled for a view, the view can be automatically stretched on a UI based on a window size to adapt to the window size.

1. Field definition

| Capability | Property | Field definition | Property category |
|---|---|---|---|
| Automatic stretching | Horizontal stretching enabling | hwHorizontalStrechEnabled | Layout |
| | Vertical stretching enabling | hwVerticalStrechEnabled | Layout |

2. An example of using the automatic stretching capability in the DSL file:

```
version: 101.0.100
layout: {
  "R.layout.linearlayout__vertical": {
    "user__HwConstraintLayout": "true" //enable the layout capability
    "hwVerticalStrechEnabled": "true" //enable the vertical stretching
    capability
  }
}
```

In this example, the vertical stretching capability of the view is enabled in the R.layout.linearlayout_vertical_layout. In this layout, when the display window changes, the view can be automatically stretched vertically to adapt to the display window size.

3. Hiding capability. If the hiding capability is enabled for a view, the view can be hidden on a UI.

1. Field definition

| Capability | Property | Field definition | Property category |
|---|---|---|---|
| Hiding | Horizontal hiding enabling | hwHtlHideEnabled | Layout |
| | Vertical hiding enabling | hwVtlHideEnabled | Layout |
| | Horizontal hiding priority | layout__hwHtlLayoutPriority | Child element |
| | Vertical hiding priority | layout__hwVtlLayoutPriority | Child element |

2. An example of using the hiding capability in the DSL file:

```
version: 101.0.100
layout: {
  "R.layout.mainpage": {
    "user__HwConstraintLayout": "true" //enable the layout capability
    "R.id.container": {
      "user__HwConstraintLayout": "true" //enable the layout capability
      "hwVtlHideEnabled": "true" //enable the vertical hiding capability
      "R.id.image1": {
        "layout__hwVtlLayoutPriority": "2" //the vertical hiding priority
        is 2
      }
```

-continued

```
      "R.id.image2": {
        "layout__hwVtlLayoutPriority": "1" //the vertical hiding priority
        is 1
      }
    }
  }
}
```

In this example, the vertical hiding capability is enabled for the R.id.container view in the R.layout.mainpage layout. In R.id.container, the vertical hiding priority of R.id.image1 is 2, and the vertical hiding priority of R.id.image2 is 1.

4. Wrapping capability. If the wrapping capability is enabled for a view, the view can be wrapped into a plurality of lines on a UI. In an example, a width limit of a wrapped line may be used to specify a maximum width of the view displayed in each line.

1. Field definition

| Capability | Property | Field definition | Property category |
|---|---|---|---|
| Wrapping | Wrapping capability enabling | hwFlexEnabled | Layout |
| | Width limit of a wrapped line | layout__hwReferenceSize | Layout |

2. An example of using the wrapping capability in the DSL file:

```
version: 101.0.100
layout: {
  "R.layout.mainpage": {
    "user__HwConstraintLayout": "true" //enable the layout capability
    "hwFlexEnabled": "true" //enable the wrapping capability
    "R.id.image1": {
      "layout__hwReferenceSize": "160dp" //the width limit of a
wrapped line is 160 dp
    }
    "R.id.image2": {
      "layout__hwReferenceSize": "160dp" //the width limit of a
wrapped line is 160 dp
    }
  }
}
```

In this example, the wrapping capability is enabled for the view in the R.layout.mainpage layout. The width limit of a wrapped line of R.id.image1 is 160 dp, and the width limit of a wrapped line of R.id.image2 is 160 dp. It indicates that the maximum width value of R.id.image1 displayed in each line is 160 dp, and the maximum width value of R.id.image2 displayed in each line is 160 dp.

5. Equalization capability. If the equalization capability is enabled for a view, the view can be evenly displayed on a UI.

1. Field definition

| Capability | Property | Field definition | Property category |
|---|---|---|---|
| Equalization | Equalization capability enabling | hwVtlSpreadEnabled | Layout |
| | Equalization type | hwSpreadType | Layout |

2. An example of using the equalization capability in the DSL file:

```
version: 101.0.100
layout: {
  "R.layout.mainpage": {
    "user__HwConstraintLayout": "true" //enable the layout capability
    "hwVtlSpreadEnabled": "true" //enable the equalization capability
    "R.id.image1": {
      "hwSpreadType": "spread" //the equalization type is spread
    }
  }
}
```

In this example, the equalization capability is enabled for the view in the R.layout.mainpage layout. The equalization type of R.id.image1 is spread.

6. Proportion capability. If the proportion capability is enabled for a view, the view can occupy a total layout size according to a specified percentage in a specified direction.

1. Field definition

| Capability | Property | Field definition | Property category |
|---|---|---|---|
| Proportion | Horizontal proportion enabling | hwHorizontalWeightEnabled | Layout |
| | Vertical proportion enabling | hwVerticalWeightEnabled | Layout |
| | Horizontal proportion value | layout__hwHorizonWeight | Layout |
| | Vertical proportion value | layout__hwVerticalWeight | Layout |

2. An example of using the proportion capability in the DSL file:

```
version: 101.0.100
layout: {
  "R.layout.mainpage": {
    "user__HwConstraintLayout": "true" //enable the layout capability
    "hwVerticalWeightEnabled": "true" //enable the vertical
proportion capability
    "R.id.image1": {
      "layout__hwVerticalWeight": "33.33%" //the vertical proportion
      is 33.33%
    }
  }
}
```

In this example, the vertical proportion capability is enabled for the view in the R.layout.mainpage layout. The vertical proportion of R.id.image1 is 33.33%.

7. Extension capability. If the extension capability is enabled for a view, the view can be extended and displayed on the UI based on the display size. In an example, a revealing value is used to specify a revealing feature, on the UI, of the last view that can be displayed on the UI.

1. Field definition

| Capability | Property | Field definition | Property category |
|---|---|---|---|
| Extension | Extension capability enabling | hwHorizonExtendEnabled | Layout |
| | Revealing feature enabling | hwHorizonExtendRevealEnabled | Layout |
| | Revealing value | hwHorizonRevealWidth | Layout |

2. An example of using the extension capability in the DSL file:

```
version: 101.0.100
layout: {
  "R.layout.mainpage": {
    "user__HwConstraintLayout": "true" //enable the layout capability
    "hwHorizonExtendEnabled": "true" //enable the extension capability
    "R.id.image1": {
      "hwHorizonExtendRevealEnabled": "true" //enable the revealing
      feature
      "hwHorizonRevealWidth": "40dp" //the revealing value is 40 dp
    }
  }
}
```

In this example, the extension capability is enabled for the view in the R.layout.mainpage layout. R.id.image1 enables the revealing feature capability, and the revealing value is 40 dp.

The OEM OS further provides the unified interaction capability and allows the developers to define a view response based on behavior. In an example, the unified interaction capability includes search, zoom, and the like. The developers can declare the unified interaction capability in the DSL file, so that the view has the search and zoom capabilities.

When the developers develop the UI based on the general-purpose OS platform, the developers define behavior corresponding to an event, for example, define a mouse double-click event corresponding to "confirm" behavior, define a finger tap event on the display corresponding to the "confirm" behavior, and define a correspondence between another event and the "confirm" behavior. The workload of the developers is heavy. The OEM OS provided in this embodiment of this application allows the developers to directly define a response to the "confirm" behavior (that is, define the unified interaction capability corresponding to the behavior), and the developers do not need to define an event corresponding to the "confirm" behavior. A mapping relationship between an event and behavior is completed by the OEM OS. The OEM OS maps events triggered by electronic devices in different forms to same behavior (for example, map a mouse double-click event on a PC to "confirm" behavior, and map a finger tap event on a mobile phone to "confirm" behavior). This prevents the developers from defining a correspondence between an event and behavior for electronic devices in different forms, causing repeated work.

The following is an example of using the search capability in the DSL file:

```
version: 101.0.100
layout: {
  "R.layout.mainpage": {
  "R.id.sample__text": {
    "onSearch": "com.sample.SearchImplSample$onSearchSample"}
}
}
```

In this example, the R.id.sample_text view has the onSearch (search) capability. The electronic device receives “confirm” behavior of the user on the R.id.sample_text view (for example, receives a mouse double-click R.id.sample_text event, or receives a finger tap R.id.sample_text event), and performs a search function defined in com.sample.SearchImplSample$onSearchSample.

The following is an example of using the zoom capability in the DSL file:

```
version: 101.0.100
layout: {
  “R.layout.mainpage”: {
  “R.id.sample_text”: {
    “onZoom”: “com.sample.ZoomImplSample$onZoomSample”}
}
}
```

In this example, the R.id.sample_text view has the onZoom (zoom) capability. The electronic device receives “confirm” behavior of the user on the R.id.sample_text view (for example, receives a mouse double-click R.id.sample_text event, or receives a finger tap R.id.sample_text event), and performs a zoom function defined in com.sample.ZoomImplSample$onZoomSample.

The OEM OS further provides an enhanced animation capability, so that an animation of a view is more expressive. The animation capability provided by the OEM OS applies to Button and subclasses of the Button, can globally enable the app, or can enable the view.

In an example, the animation capability includes a click-rebound subtle animation (field definition: reboundAnimation) of the Button view.

The following is an example of using the animation capability in the DSL file:

```
version: 101.0.100
app: {      //globally enable the app
  “reboutAnimation”: “true”
}
```

The reboundAnimation is declared in the app content block, to enable the click-rebound subtle animation for all views in the app.

```
version: 101.0.100
layout: {
  “R.layout.mainpage”: {
  “R.id.button”: {        //enable a single view
    “reboutAnimation”: “true”
  }
}
}
```

The reboundAnimation is declared in the layout content block, to enable the click-rebound subtle animation for a target view.

Figure 9:
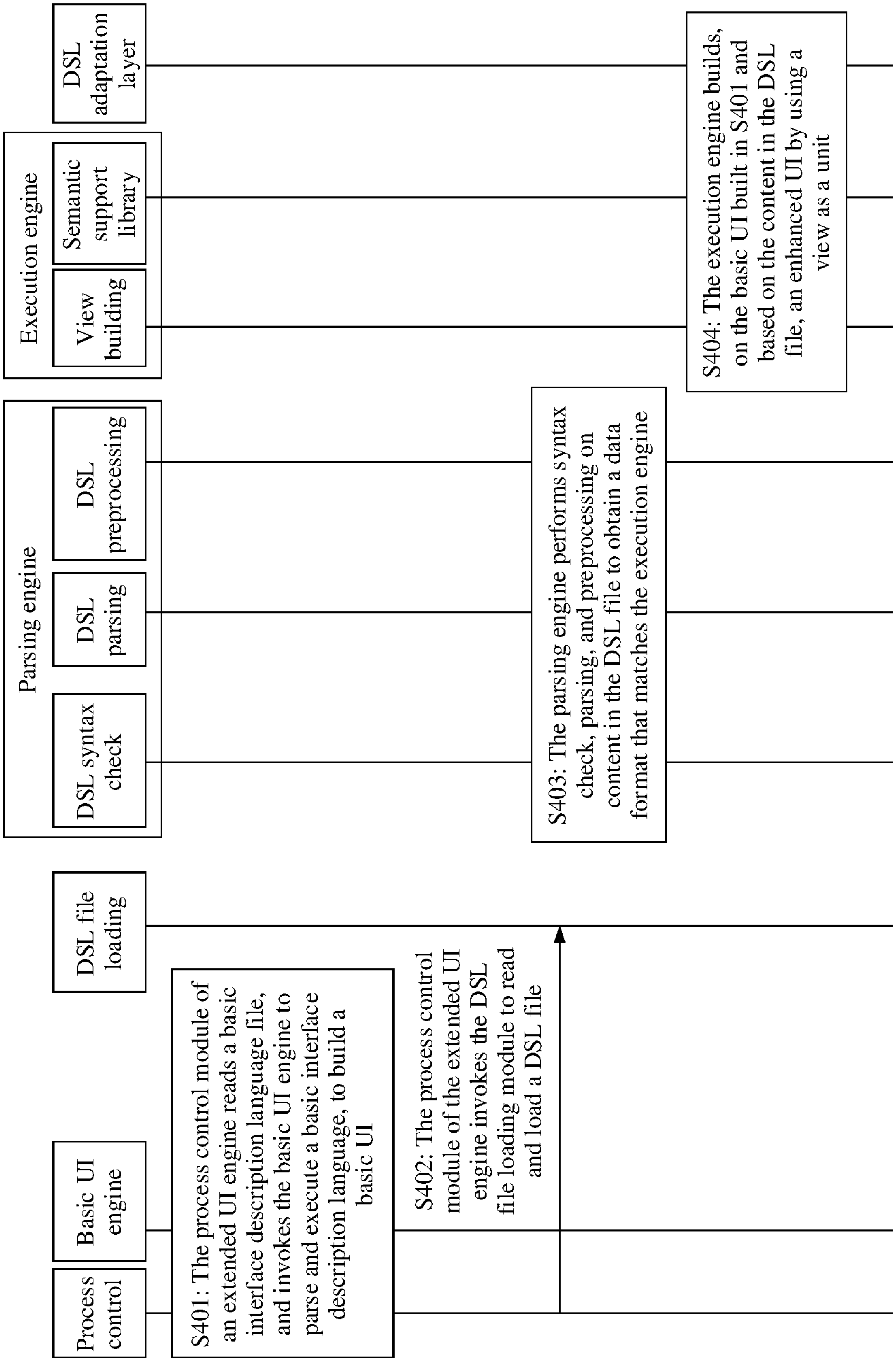
FIG. 9 is a schematic flowchart of a user interface implementation method according to an embodiment of this application.

For example, FIG. 9 is a schematic flowchart of generating a UI when an app runs.

S401: A process control module of an extended UI engine reads a basic interface description language file, and invokes a basic UI engine to parse and execute a basic interface description language, to build a basic UI.

A basic UI programming capability is used for a view on the basic UI.

S402: The process control module of the extended UI engine invokes a DSL file loading module to read and load a DSL file.

S403: A parsing engine performs syntax check, parsing, and preprocessing on content in the DSL file to obtain a data format that matches an execution engine.

In an example, a DSL syntax check submodule performs syntax check on content in the DSL file, and if the check succeeds, a DSL parsing submodule parses fields in the DSL file. Further, a DSL preprocessing submodule preprocesses the DSL file to obtain the data format that matches the execution engine.

S404: The execution engine builds, on the basic UI built in S401 and based on the content in the DSL file, an enhanced UI by using a view as a unit.

In an implementation, a view building submodule sequentially obtains, from a semantic support library, semantic processing components corresponding to the fields in the DSL file, for example, obtains a semantic processing component SearchHandler of an “onSearch” field from the semantic support library. Further, the view building submodule applies a customized UI programming capability to a view by using a DSL adaptation layer, to build the enhanced UI.

Figure 10:
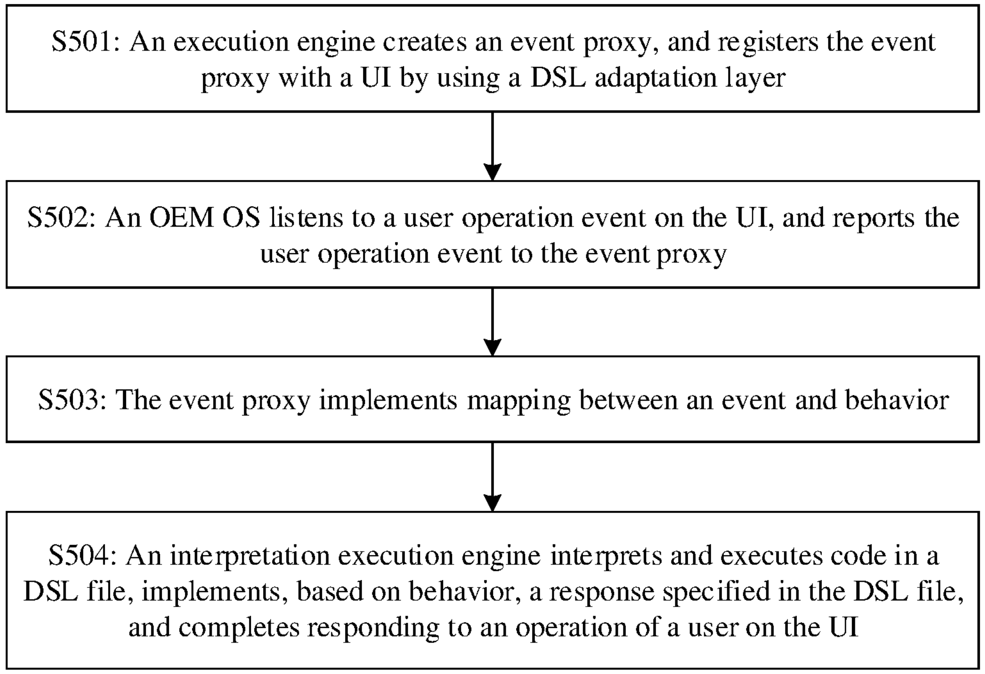
FIG. 10 is a schematic flowchart of a user interface implementation method according to an embodiment of this application.

For example, FIG. 10 is a schematic flowchart of responding by an electronic device to an operation of a user on a UI.

S501: An execution engine creates an event proxy, and registers the event proxy with a UI by using a DSL adaptation layer.

S502: An OEM OS listens to a user operation event on the UI, and reports the user operation event to the event proxy.

S503: The event proxy implements mapping between an event and behavior.

S504: An interpretation execution engine interprets and executes code in a DSL file, implements, based on behavior, a response specified in the DSL file, and completes responding to the operation of the user on the UI.

According to the user interface implementation method provided in this embodiment of this application, an app can include a native view and a customized view, and a customized UI programming capability can be applied to the native view. The native view is a view supported by a general-purpose OS (for example, Android®), and the general-purpose OS provides a basic UI programming capability for the native view. The customized view is a view supported by the OEM OS but not supported by the general-purpose OS, and the OEM OS provides the customized UI programming capability for the customized view.

Figure 11:
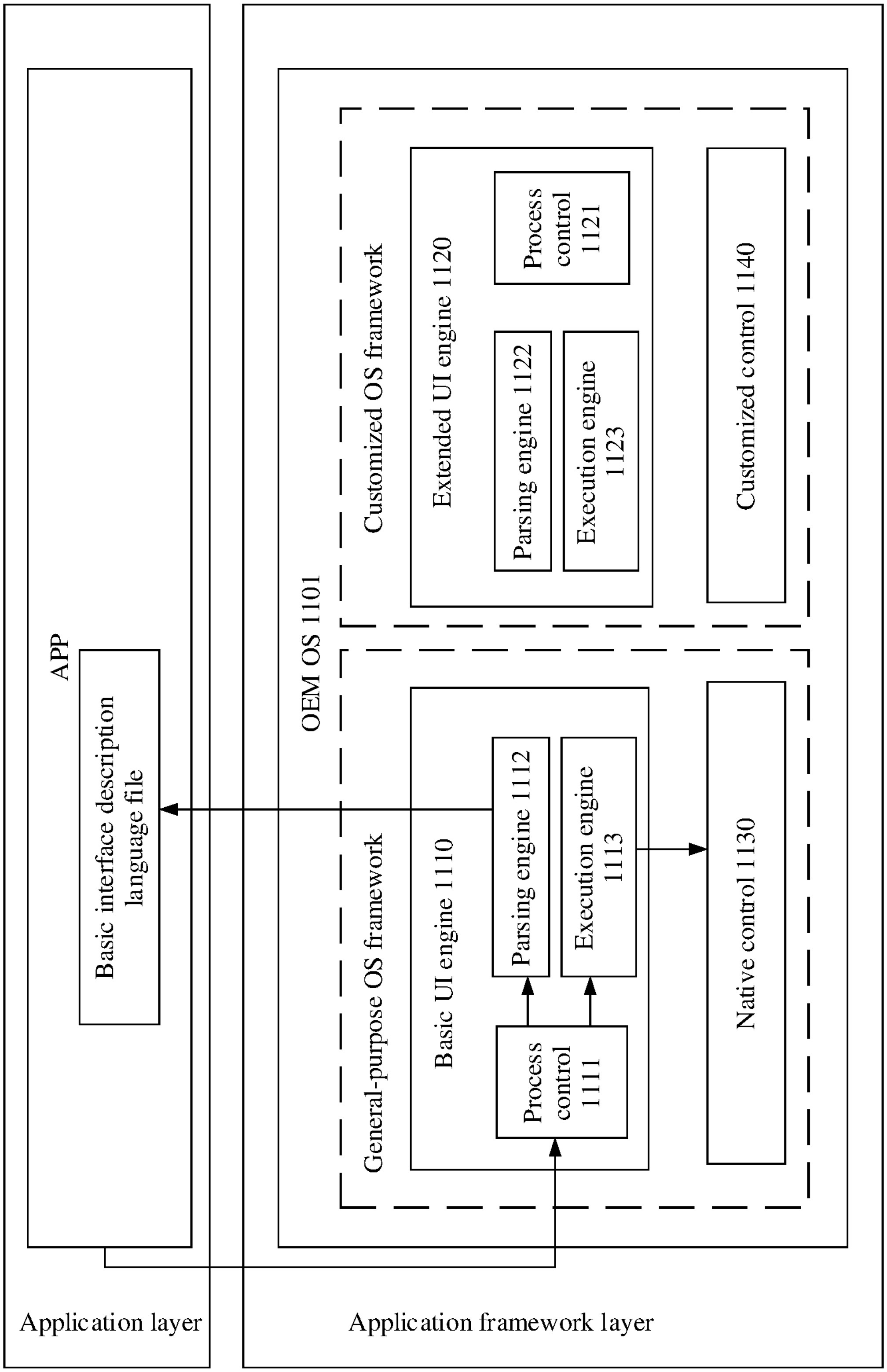
FIG. 11 is a schematic diagram of a scenario example of a user interface implementation method according to an embodiment of this application.

FIG. 11 is a schematic flowchart of building a native view by an OEM OS. An app development kit of an OEM OS 1101 includes a basic interface description language file, and a process control 1111 of a basic UI engine 1110 indicates a parsing engine 1112 to process the basic interface description language file. The parsing engine 1112 reads and loads the basic interface description language file, and converts the basic interface description language file into a data format that matches an execution engine 1113. The execution engine 1113 builds a basic UI based on content of the basic interface description language file, and generates a native view 1130.

Figure 12:
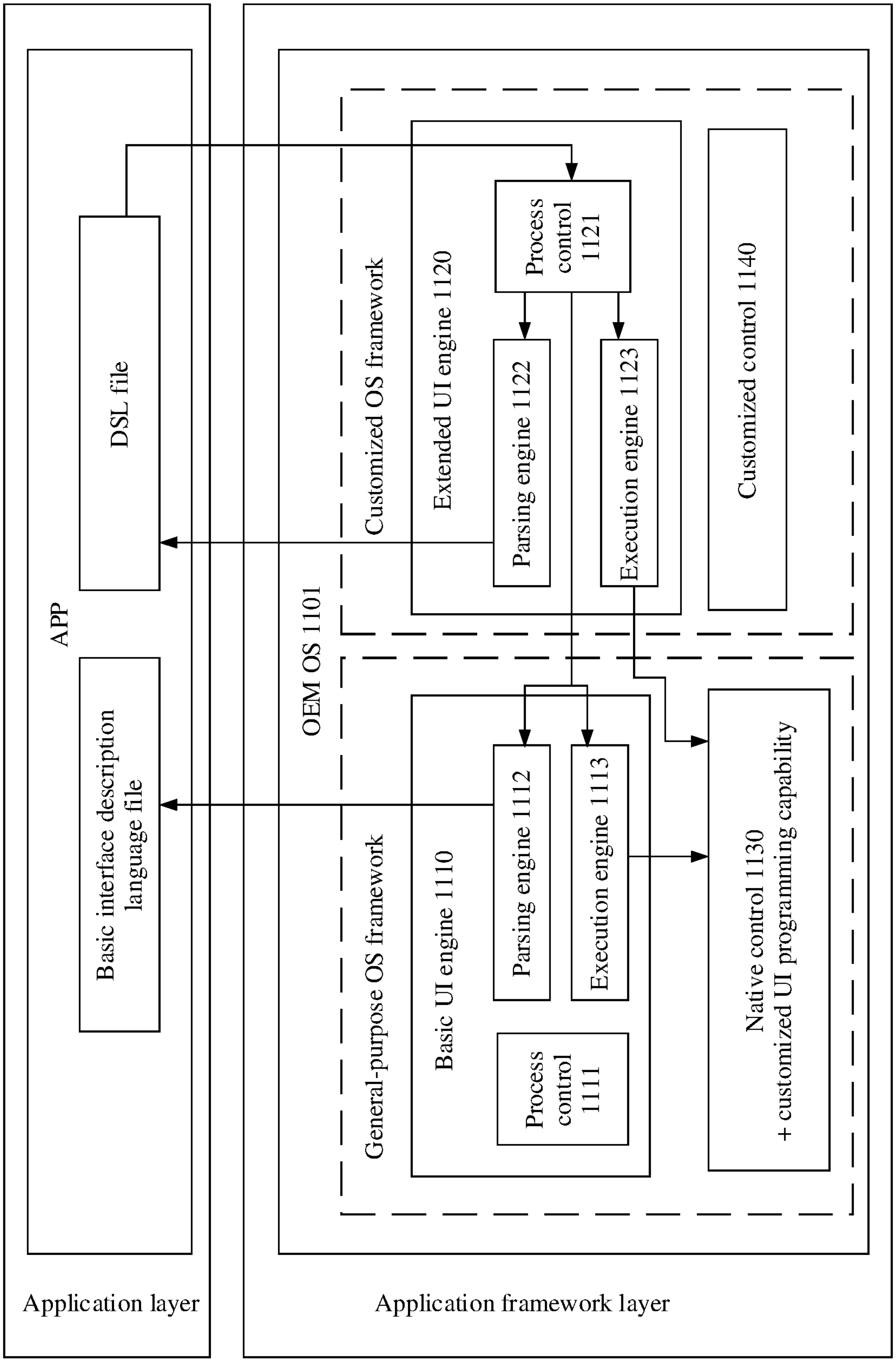
FIG. 12 is a schematic diagram of a scenario example of a user interface implementation method according to an embodiment of this application.

FIG. 12 is a schematic flowchart of applying a customized UI programming capability to a native view by an OEM OS. An app development kit of the OEM OS 1101 includes a basic interface description language file and a DSL file. A process control 1121 of an extended UI engine 1120 indicates the parsing engine 1112 in the basic UI engine 1110 to process the basic interface description language file. The parsing engine 1112 reads and loads the basic interface description language file, and converts the basic interface description language file into a data format that matches the execution engine 1113. The execution engine 1113 builds a basic UI based on content of the basic interface description language file, and generates a native view 1130. The process control 1121 indicates a parsing engine 1122 in the extended UI engine 1120 to process the DSL file. The parsing engine 1122 reads and loads the DSL file, and converts the DSL file into a data format that matches an execution engine 1123. The execution engine 1123 applies the customized UI programming capability to the native view 1130 based on the DSL file.

Figure 13:
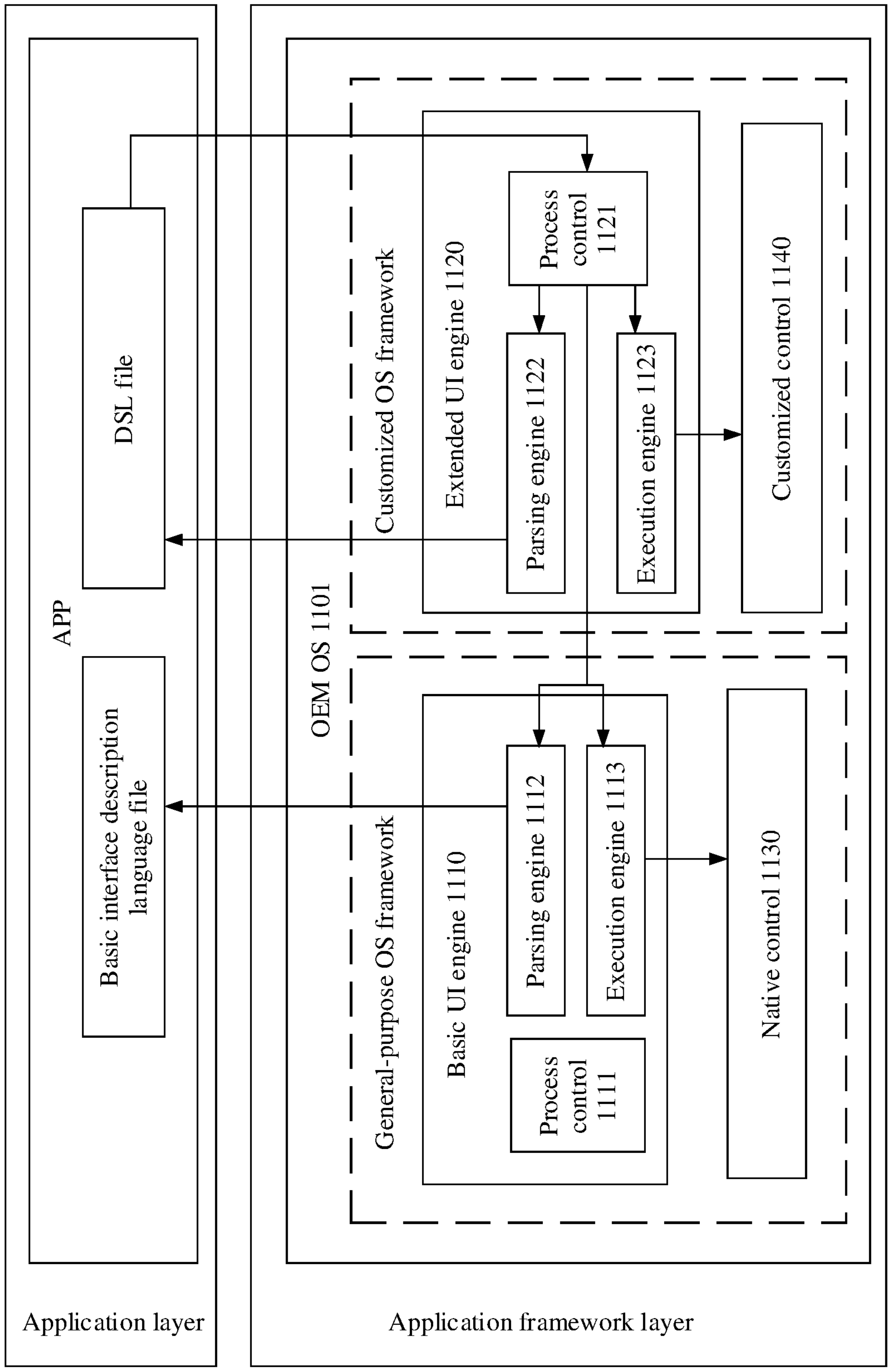
FIG. 13 is a schematic diagram of a scenario example of a user interface implementation method according to an embodiment of this application.

FIG. 13 is a schematic flowchart of building a customized view by an OEM OS. An app development kit of the OEM OS 1101 includes a basic interface description language file and a DSL file. A process control 1121 of an extended UI engine 1120 indicates the parsing engine 1112 in the basic UI engine 1110 to process the basic interface description language file. The parsing engine 1112 reads and loads the basic interface description language file, and converts the basic interface description language file into a data format that matches the execution engine 1113. The execution engine 1113 builds a basic UI based on content of the basic interface description language file, and generates a native view 1130. The process control 1121 indicates a parsing engine 1122 in the extended UI engine 1120 to process the DSL file. The parsing engine 1122 reads and loads the DSL file, and converts the DSL file into a data format that matches the execution engine 1123. The execution engine 1123 generates a customized view 1140 on the base UI based on the DSL file.

The OEM OS provided in this embodiment of this application includes a basic UI engine and an extended UI engine. When an electronic device builds a UI, the basic UI engine is configured to interpret and execute the basic interface description language, to generate a basic UI (with the basic UI programming capability); and the extended UI engine is configured to interpret and execute the DSL, to superimpose the customized UI programming capability on the basic UI. The user interface implementation method provided in this embodiment of this application can adapt to a plurality of OS platforms, provides rich UI programming capabilities, has low technical implementation difficulty, and facilitates use by developers.

An embodiment of this application further provides a user interface implementation method, which has low implementation difficulty and facilitates use by developers.

With the rapid development of the Internet of Things (Internet of Things, IoT), both the type and quantity of IoT devices increase rapidly. Different IoT devices have different screen sizes and user interaction modes. For example, a screen size of a mobile phone is mostly about 4 to 6 inches, and a user interaction mode is mainly touching or tapping a display. A screen size of a television may reach 50 inches or larger, and a user interaction mode is usually a remote view operation. A device such as a head unit has a wider screen form and user interaction mode. Currently, a development manner supported by a general-purpose OS platform (for example, Android®) is that for a same UI in a same app, developers design a different interface description file for each type of electronic device. It is clear that using this method to develop differentiated UIs for various devices has heavy workload and high development difficulty. Embodiments of this application provide a user interface implementation method and an apparatus, to implement one-time development and multi-device deployment, that is, develop a set of interface description files that are applicable to various different types of electronic devices, to reduce development difficulty for developers.

For example, Android®, as an open-source OS, is widely used on portable electronic devices. When a UI of an app is developed based on Android®, for a same UI in a same app, the developers design different interface description files for each type of electronic device, to develop differentiated UIs for different types of electronic devices. Android® supports to set layout folders for each type of electronic device to implement independent UI development for a plurality of types of devices. For example, a suffix is added to a name of a layout folder to distinguish different layout folders. In this way, for a same UI, different types of electronic devices read interface description files in different layout folders, to present different UI display effects. If the app needs to be installed on another type of electronic device, a corresponding interface description file needs to be independently developed for the type of electronic device (an independent layout folder is added). In such a development manner, the developers need to separately develop corresponding interface description files for different types of electronic devices, resulting in heavy development workload and high difficulty.

Some vendors provide some complete UI programming frameworks that are independent of Android®, such as Flutter, ReacNative, and Weex. This UI programming framework includes a UI description language and a corresponding parsing and execution engine, and provides an independent UI view library, a layout engine, a rendering engine, and the like. The UI programming framework can run across devices, but has poor compatibility.

Figure 14:
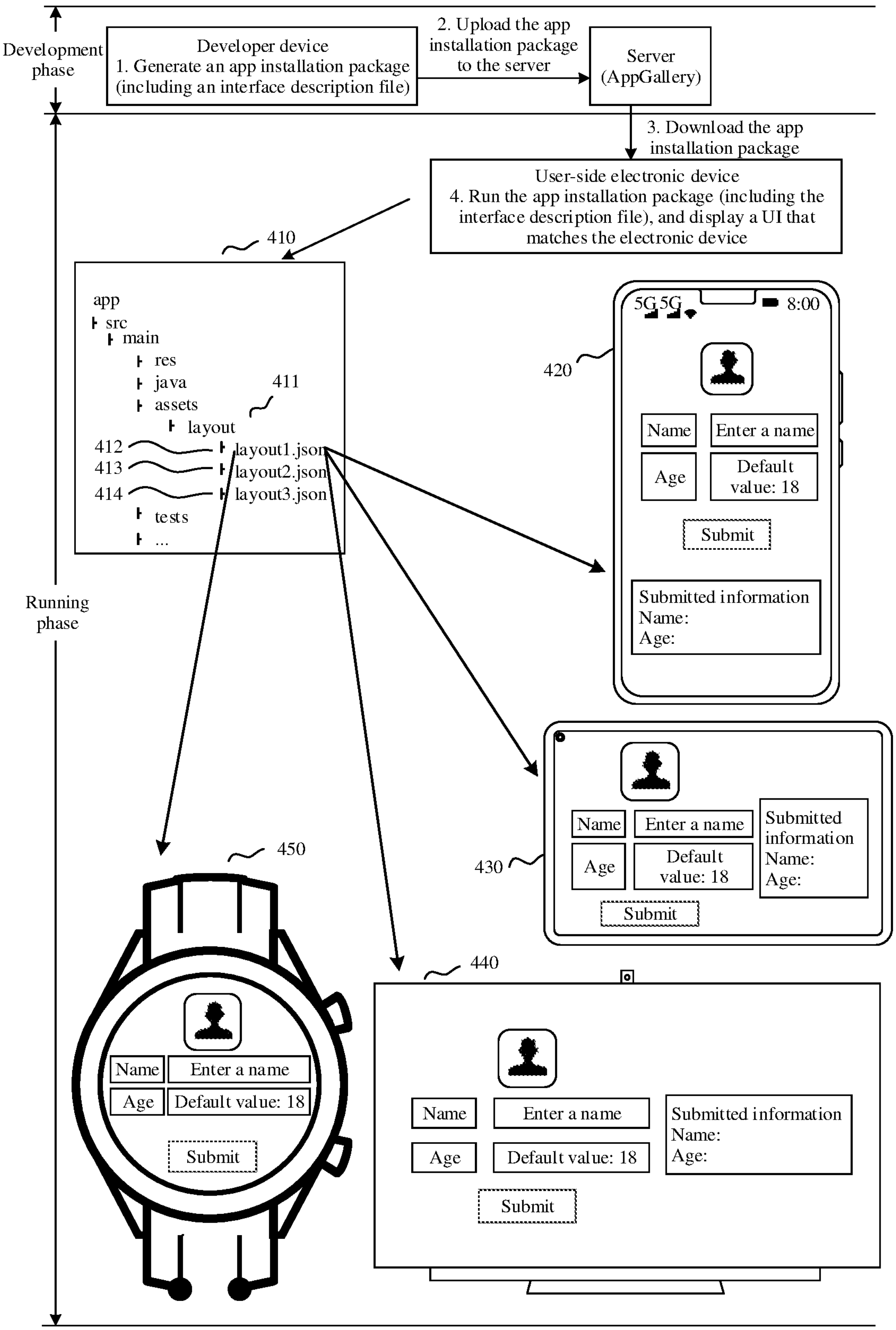
FIG. 14 is a schematic diagram of a user interface implementation method according to an embodiment of this application.

Embodiments of this application provide a user interface implementation method and an apparatus. Refer to FIG. 14. Developers open a development tool (for example, DevEco Studio) in an electronic device 200 (developer device), and generate an interface description file on a development interface of the development tool. For example, the developers open the development interface of the development tool. The development interface includes an initial version of the interface description file. The initial version of the interface description file may be a blank file or contain a simple example. It may be understood that the initial version of the interface description file may be preset in the development tool, or may be added by the developers in the development tool. In some examples, the development tool may further include an interface description language template, an interface description language syntax rule description file, and an interface description example. Details are not described in this embodiment of this application.

Further, the developers may add an interface description and an interface behavior definition in the initial version of the interface description file by using an interface description language, to form an interface description file for release. In an implementation, the developers generate one interface description file for each UI in the app. For example, a plurality of interface description files may be generated in one folder, and each interface description file corresponds to one UI.

An app installation package is generated on the developer device, including the interface description file. The app installation package is uploaded to a server, and the app is released in an AppGallery provided by the server. A user may download the app installation package in the AppGallery by using a user-side electronic device (the electronic device 100). After running the app installation package, the user-side electronic device obtains the interface description file in the installation package. When running the app, the user-side electronic device displays, on the display based on the interface description file, a UI that matches the electronic device.

In an example, the interface description file is in a json format. For example, as shown in FIG. 14, the app installation package includes a folder "app" 410. A src\main\assets directory of the folder "app" 410 includes a layout folder "layout" 411. The layout folder "layout" 411 includes interface description files layout1.json 412, layout2.json 413, layout3.json 414, and the like. Each interface description file corresponds to a UI of the app. Different types of user-side electronic devices such as a mobile phone 420, a head unit 430, a television 440, and a watch 450 all run a same interface description file in the "layout" 411, and separately display different display effects of a same UI. For example, the mobile phone 420, the head unit 430, the television 440, and the watch 450 all parse and execute layout1.json 512, and separately display different display effects of UIs corresponding to layout1.json 512.

In this embodiment of this application, for a same UI in a same app, the developers can develop differentiated UIs for different types of electronic devices by developing a set of code in an interface description file. Different types of electronic devices may present different UI display effects by reading a same interface description file of a same UI. A set of interface description files that are applicable to various different types of electronic devices can be developed, to reduce development difficulty for the developers.

According to the user interface implementation method provided in this embodiment of this application, a native UI programming capability of Android® and a customized UI programming capability of an operating system can be used in an interface description file. The native UI programming capability of Android® enables a view to have a native view property of Android®. The customized UI programming capability of the operating system enables a view to have a visual property, a layout property, an interaction property, an animation property, and a software and hardware dependency property that are extended. After the electronic device runs the app installation package and obtains the interface description file in the installation package, when the user runs the app on the electronic device, the electronic device may present a corresponding UI on the display based on the interface description file. A view on the UI may include the native view property of Android®, and may further include an extended view property. The customized UI engine provided in this embodiment of this application supports parsing and execution of the native view property of Android® and all extended view properties in the operating system.

Figure 15:
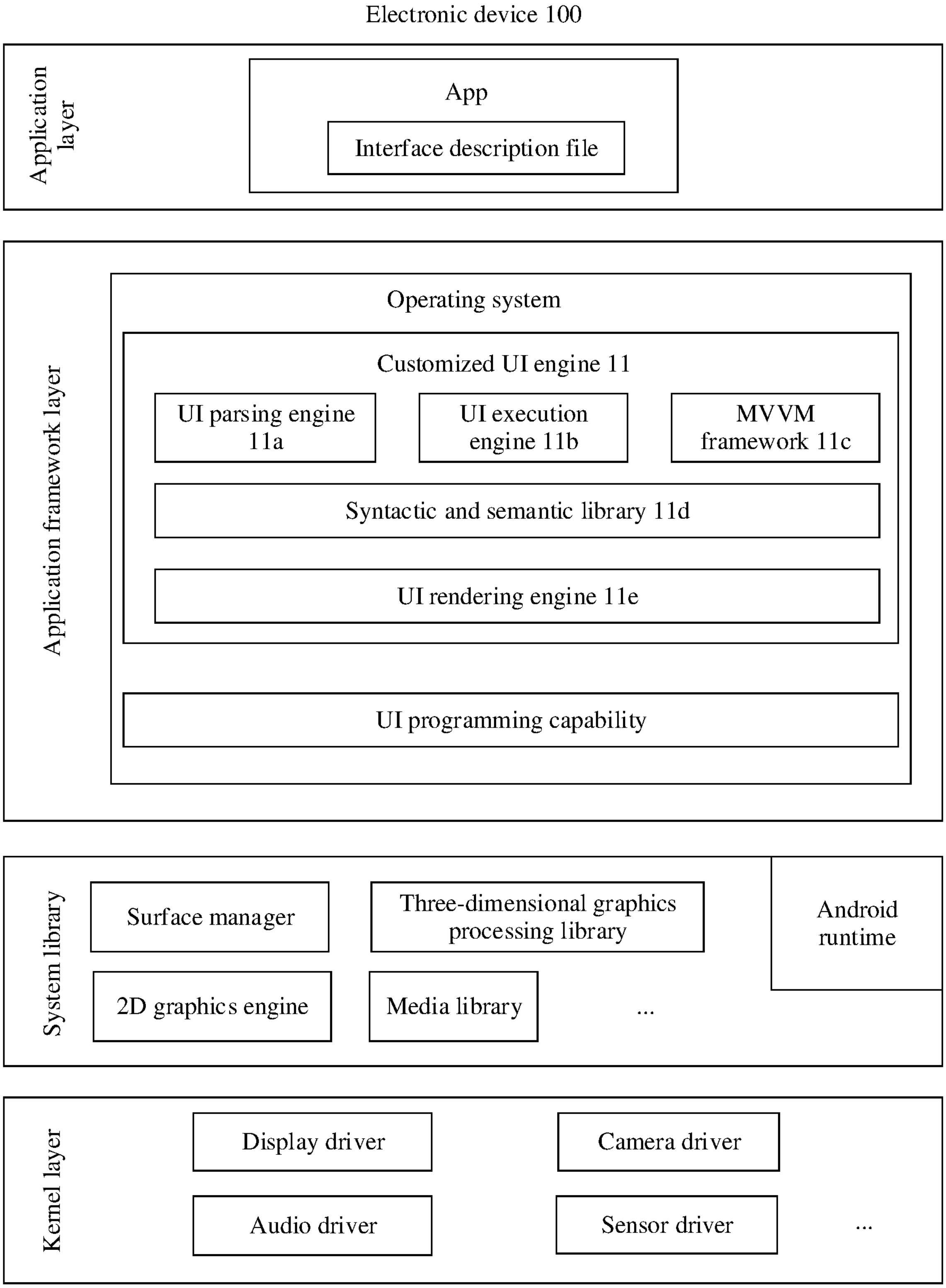
FIG. 15 is a schematic diagram of a software architecture of an electronic device according to an embodiment of this application.
Figure 16B:
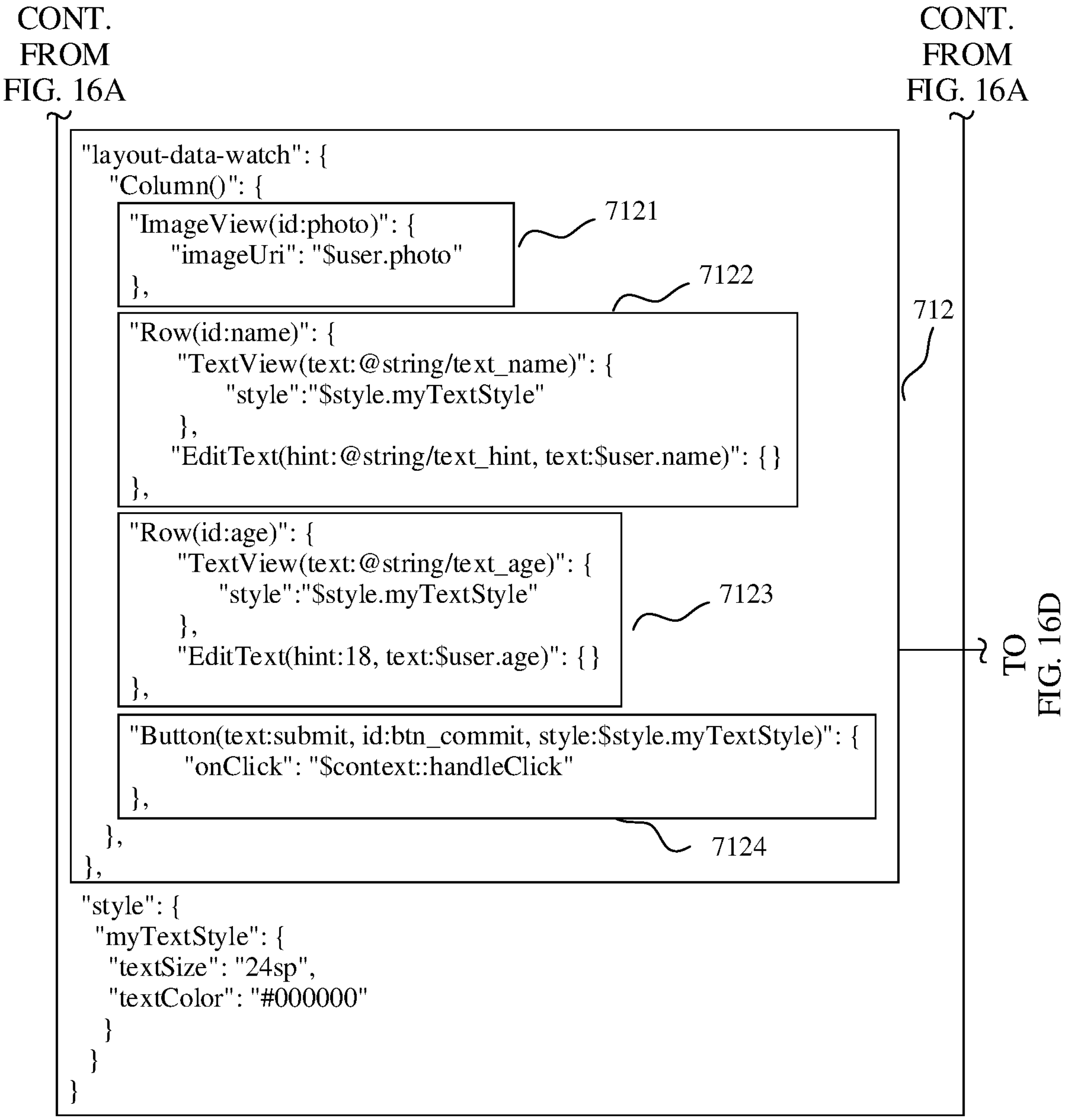
Figure 16C:
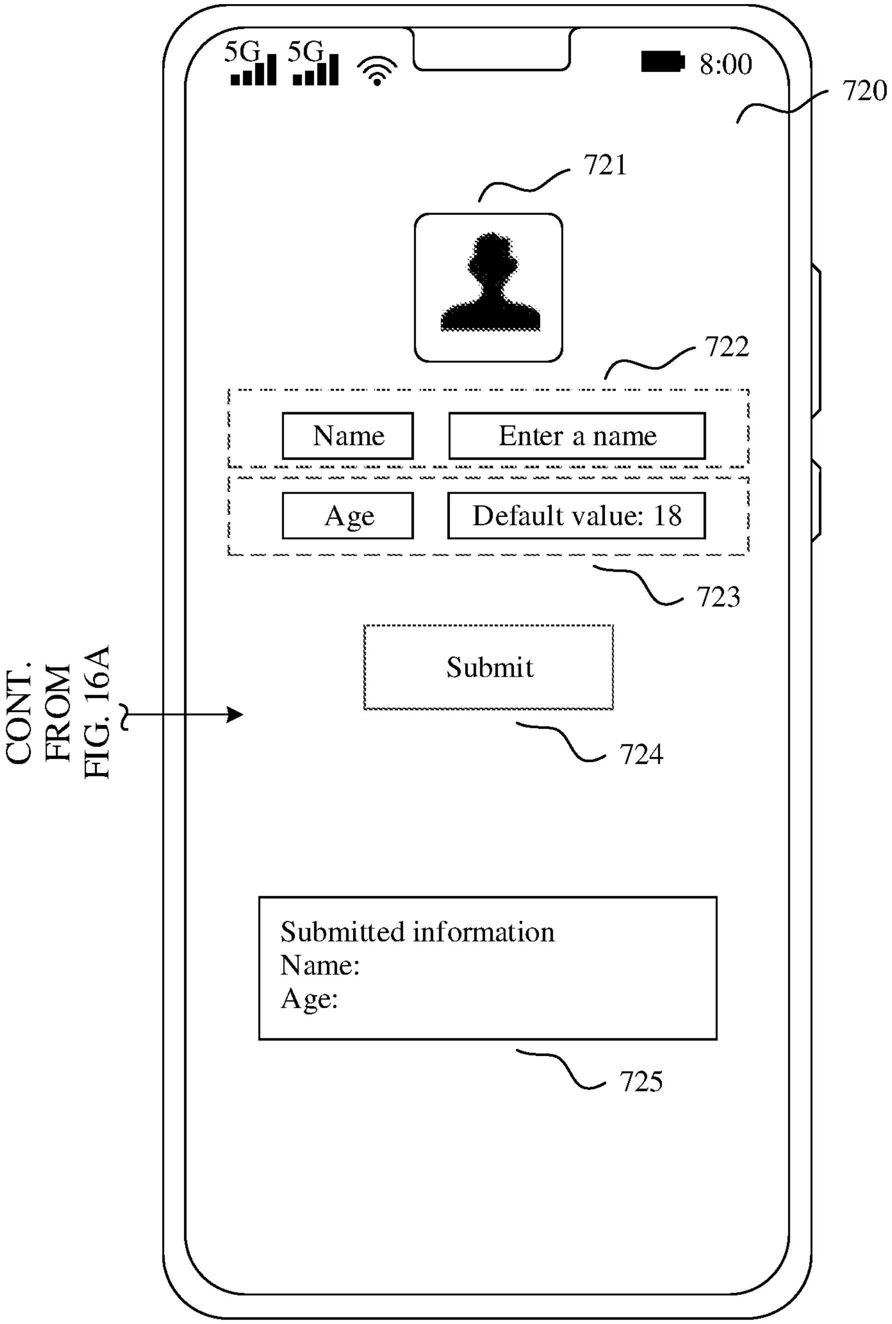
Figure 16D:
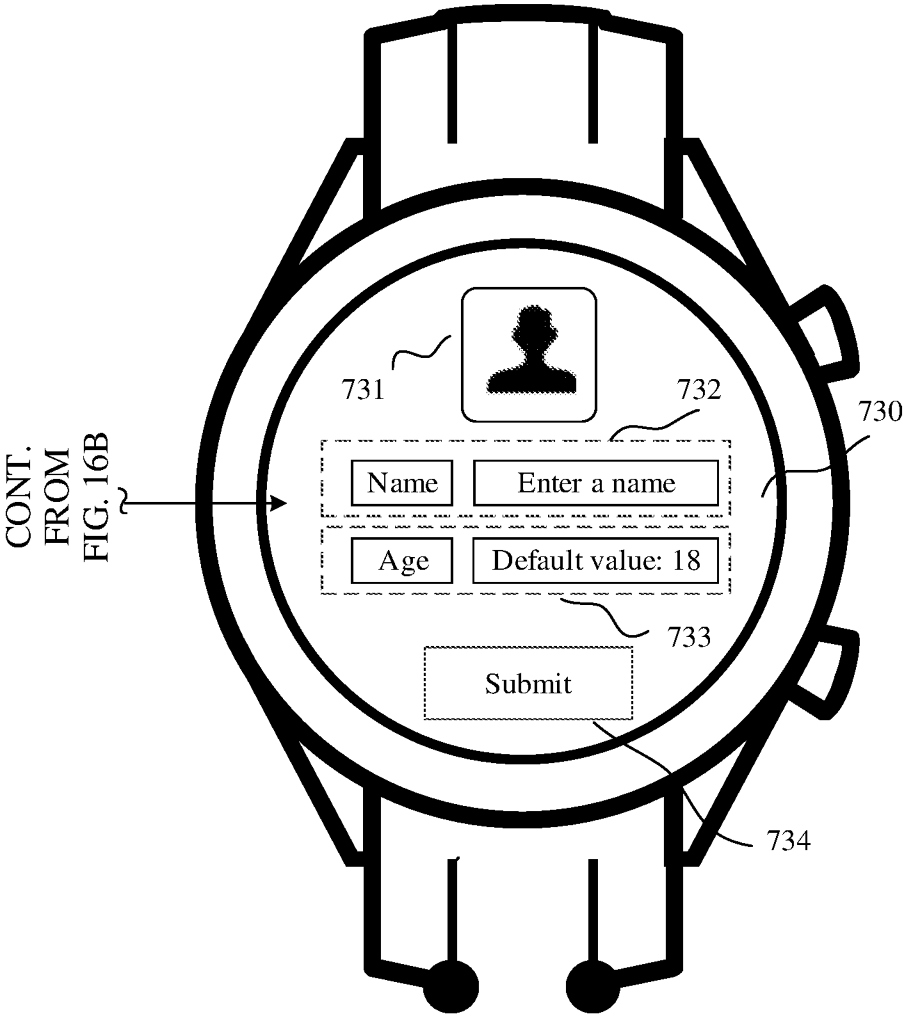
Figure 17A:
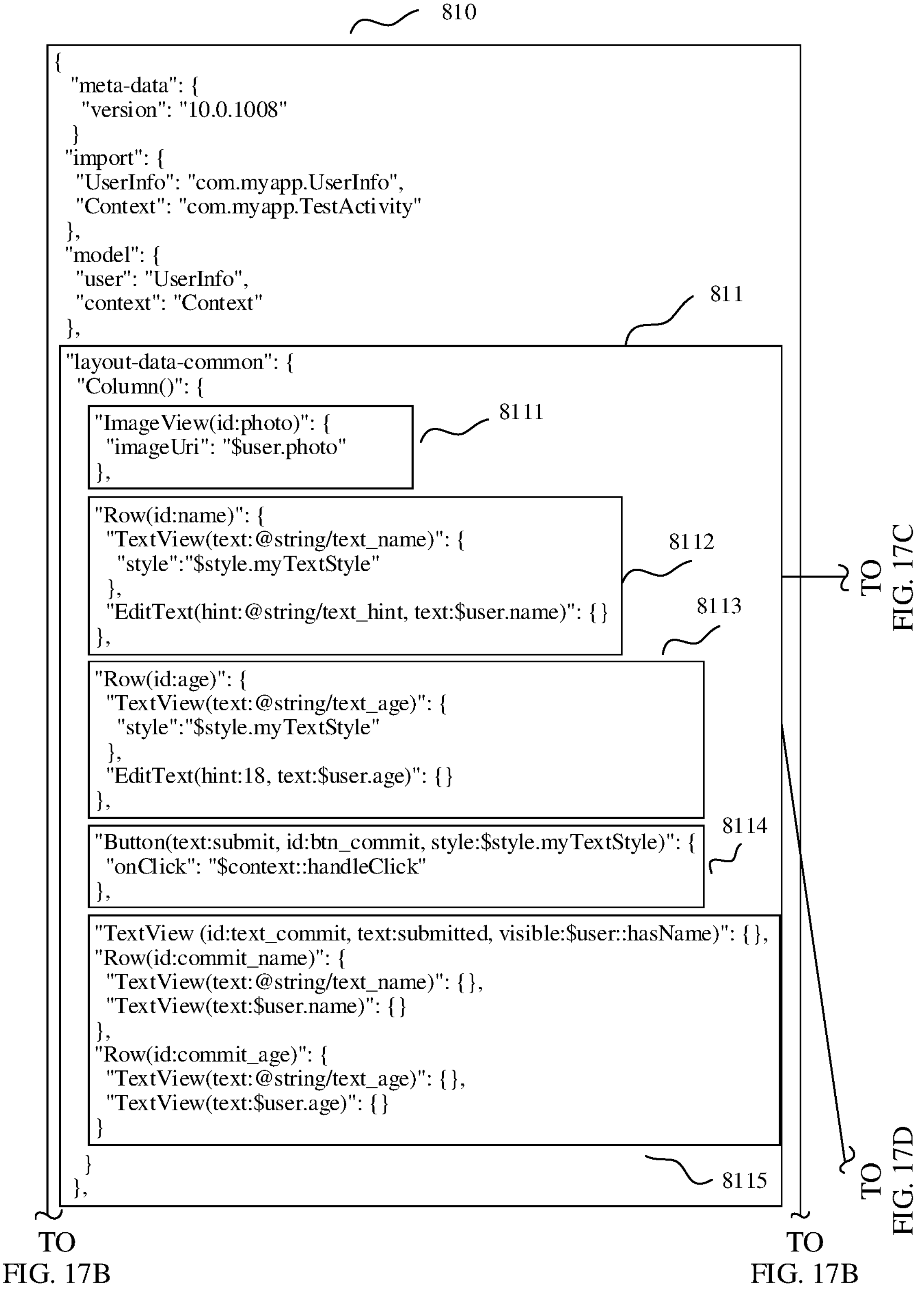
FIG. 17A to FIG. 17D are a schematic diagram of a scenario example of a user interface implementation method according to an embodiment of this application.
Figure 17B:
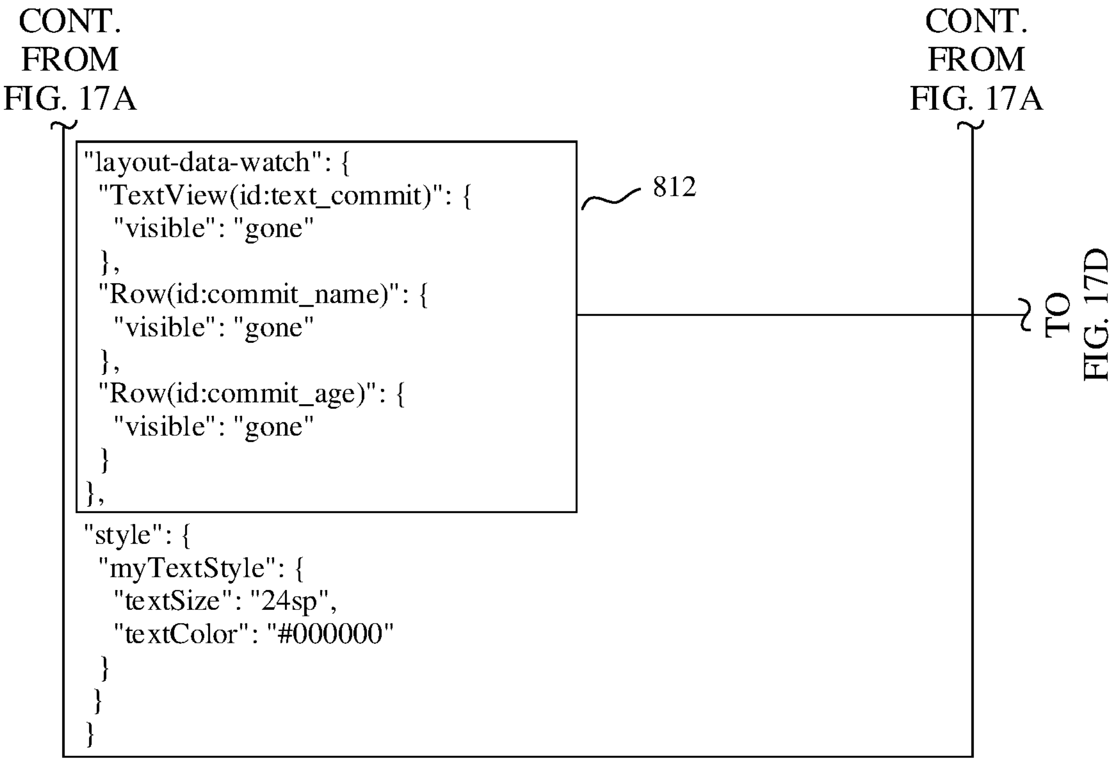
Figure 17C:
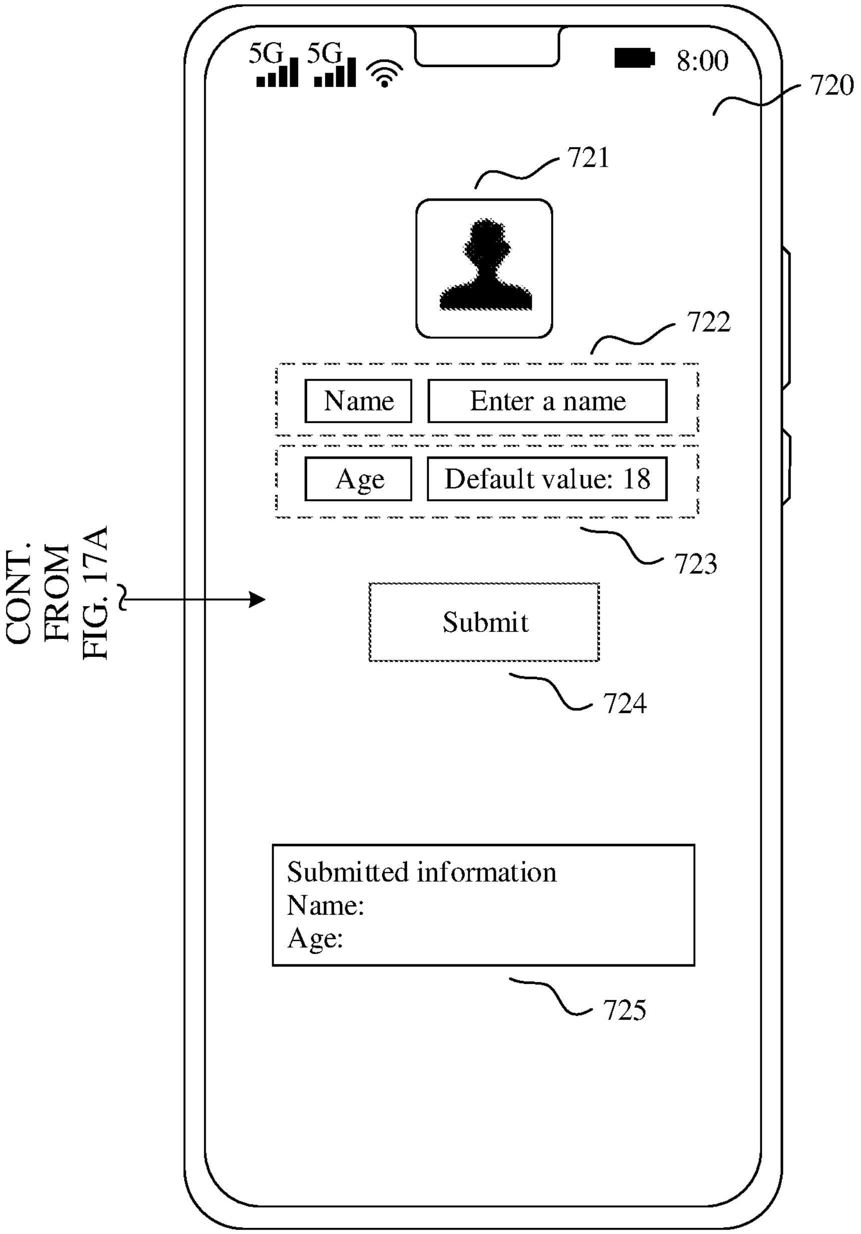
Figure 17D:
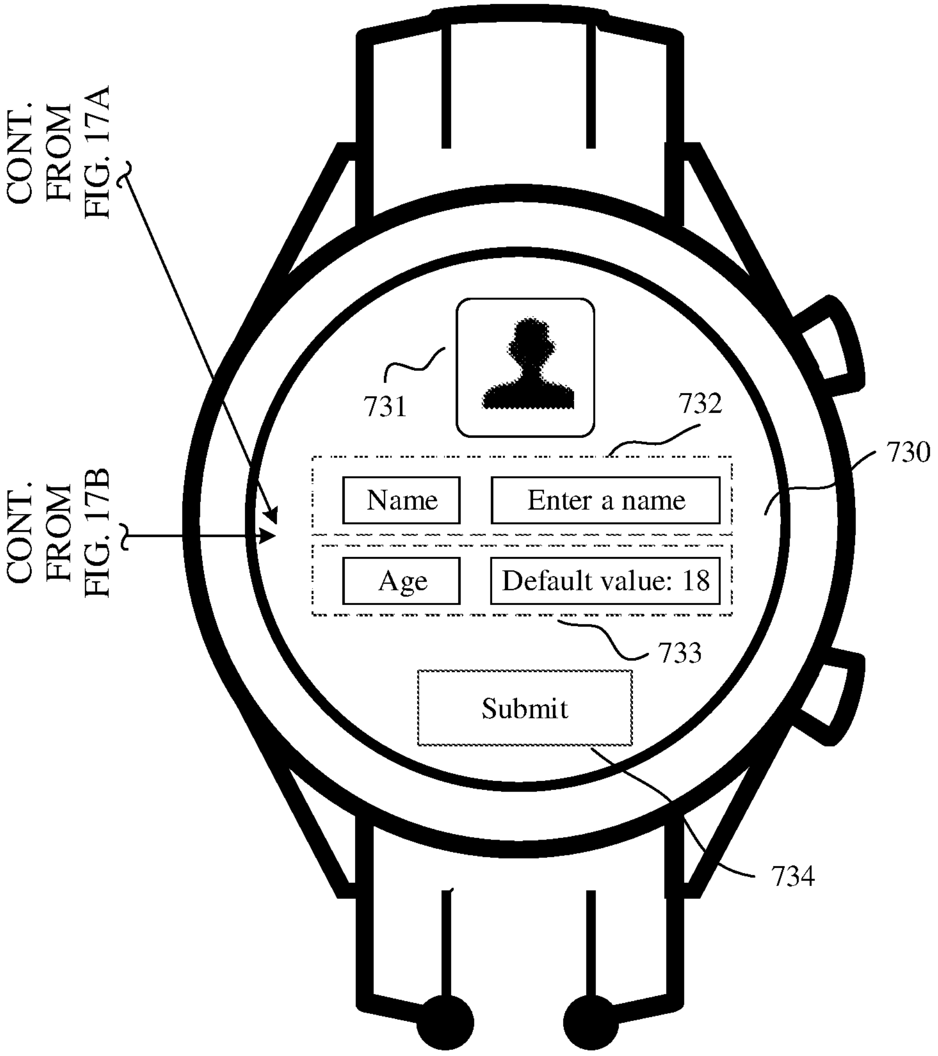

In an example, FIG. 15 shows a software architecture of the electronic device 100. As shown in FIG. 15, a software system of the electronic device 100 may include an application layer, an application framework layer, an Android runtime (Android runtime) and system library, and a kernel layer. In an example, for the application layer, the Android runtime (Android runtime) and system library, and the kernel layer, refer to corresponding descriptions in the Android® software architecture in FIG. 3. Details are not described herein again. The software system of the electronic device 100 provided in this embodiment of this application partially reuses a UI programming framework in the conventional technology, which is easy to learn, and reduces development difficulty of developers.

An operating system of the application framework layer includes a customized UI engine 11. The customized UI engine 11 is configured to parse and execute an interface description file of an app, to generate a UI of the app. The customized UI engine 11 may include a UI parsing engine 11*a*, a UI execution engine 11*b*, an MVVM (model-view-viewmodel) framework 11*c*, a syntactic and semantic library 11*d*, and a UI rendering engine lie. It may be understood that the application framework layer may further include more modules. Refer to the conventional technology. This is not limited in this embodiment of this application.

The following describes the foregoing modules in detail with reference to the accompanying drawings.

The syntactic and semantic library 11*d* includes a syntactic and semantic specification set of all fields in the interface description file, for example, definitions and syntax of fields such as a variable interface, a common field, a visual property, a layout property, an interaction property, an animation property, and a software and hardware dependency property. The layout property refers to a layout of each view on a UI, for example, a shape, a position, and a size of the view. The visual property refers to visual effects such as a color and grayscale of a view. The interaction property refers to a capability of providing a view response based on user behavior, for example, performing a search based on "confirm" behavior of a user. The animation property refers to displaying an animation effect on a view, for example, displaying a click-rebound animation on a view. The software and hardware dependency property refers to software and hardware parameters of a view dependency device.

The developers need to add code to the interface description file based on the syntactic and semantic specifications defined in the syntactic and semantic library 11*d* to develop the UI. The following describes the syntactic and semantic specifications defined in the syntactic and semantic library 11*d* from aspects such as layout orchestration, data & interface binding, interaction behavior orchestration, and differentiation description.

For example, the interface description file is in a json format. For example, the interface description file may include the following structure:

```
{
  "meta-data": { },
  "import": { },
  "model": { },
  "layout-data-common": { },
  "layout-data-uimode": { },
  "styles": { }
}
```

The meta-data includes information such as a version number. The following is an example:

```
"meta-data": {
  "version": "10.0.1008"
}
```

The version indicates a version number of the interface description file. For example, a format of the version is x.y.z, where x indicates a product, y indicates a subsystem of the product, and z indicates a quantity of development times. A version of the interface description file needs to match a version of the customized UI engine. For example, the version of the customized UI engine needs to be the same as or later than the version of the interface description file, so that the interface description file can be successfully parsed.

Import is used to import an object, and model is used to declare the object. The following is an example:

```
"import": {
  "UserInfo": "com.myapp.UserInfo",
  "Context": "com.myapp.TestActivity"
},
"model": {
  "user": "UserInfo",
  "context": "Context"
},
```

The complete path com.myapp.UserInfo stored in UserInfo and the complete path com.myapp.TestActivity stored in Context are imported into import. The object user of the UserInfo type and the object context of the Context type are declared in model. In this way, the user and context can be directly invoked in the interface description files (layout-data-common and layout-data-uimode). In this application, files such as UserInfo and TestActivity are referred to as resource files. The resource file includes resources used to generate a UI of the application, and the resources may include a data structure, a view, a view property, and the like that are defined by the developers.

For details about the usage of import and model, refer to the syntactic and semantic rules in layout-data-common, layout-data-uimode, and styles.

Layout-data-common is used to describe a common UI. All types of electronic devices parse content in layout-data-common, and lay out the common UI based on the content in layout-data-common. Layout-data-uimode is used to describe a UI of a specified device. In an implementation, a difference between the UI of the specified device and the common UI is declared in layout-data-uimode. In another implementation, all conditions applicable to the UI of the specified device are declared in layout-data-uimode. The specified device may be a mobile phone, a watch, a head unit, a smart home device (for example, a smart television, a smart screen, or a smart speaker), a large screen, a notebook computer, a desktop computer, or the like. For example, a specific form of layout-data-uimode may include layout-data-phone (used for a mobile phone), layout-data-watch (used for a watch), layout-data-television (used for a television), and the like.

Styles are used to define customized parameters in an app. The developers can customize parameters in styles.

I. Layout Orchestration

All UIs in an app include views. UI layout orchestration is to orchestrate view properties on the UI.

1. Control

The customized UI engine 11 supports all native views of Android® and the extended views in the operating system, and further supports views customized by the developers in the app or integrated by using static packages. The view may specifically include a text view, such as a TextView view or an EditText view, or may include a button view, such as a Button view or an ImageButton view, or may include an image view, such as an Image view. This is not limited in this embodiment of this application.

For the native views of Android® and the extended views in the operating system, the view names can be directly invoked in layout-data-common or layout-data-uimode. For example, the native views of Android® may include TextView, EditText, and the like; and the extended views in the operating system may include HwButton and the like. The following is an example of declaring views. In this example, the native views TextView and EditText of Android® are declared.

```
{
  "Column(id:name)": {
    "TextView(text:@string/text_name)": { },
    "EditText(hint:@string/text_hint, text:$user.name)": { }
  }
}
```

For the views customized by the developers in the app or integrated by using static packages, complete package names of resource packages of the views need to be imported into import. In this way, the views can be invoked in layout-data-common or layout-data-uimode. The following is an example of declaring a customized view in the app. In this example, a complete package name com.myapp.widget.MyCircleView of a resource package of a MyCircleView view is imported into import, and then MyCircleView is directly invoked in layout-data-common.

```
{
  "import": {
    "MyCircleView": "com.myapp.widget.MyCircleView",
  },
  "layout-data-common": {
    "Column(layout_width:match_parent,)": {
      "MyCircleView(app.borderWidth:3dp)": { },
      ...
  }
}
```

In an implementation, the customized UI engine 11 supports the developers in specifying an alias for a view. The following is an example in which a complete package name com.myapp.widget.MyCircleView of a resource package of MyCircleView is imported into import, and a name of MyCircleView is specified as AliasName.

```
{
  "import": {
    "AliasName": "com.myapp.widget.MyCircleView",
  },
}
```

In an implementation, when a view is invoked in layout-data-common or layout-data-uimode, the view is declared in a form of ComponentName( ):{ }. For example, TextView( ):{ } indicates that a TextView is declared.

2. Control Property

Control properties supported by the customized UI engine 11 include a native property of Android®, and a visual property, a layout property, an interaction property, an animation property, and a software and hardware dependency property that are extended in the operating system.

When ComponentName( ):{ } is used to describe a view, a property and a property value of the view can be transferred in { } in an implementation, and a format is "property 1:property value 1, property 2:property value 2". The following is an example in which the TextView view is declared, a textSize property of TextView is transferred in { }, and a property value of textSize is @dimen/mySize.

```
{
  "TextView( )": {
    "textSize": "@dimen/mySize"
  },
}
```

In another implementation, a property and a property value of a view may be transferred in ( ). The following is an example in which the TextView view is declared, a text property of TextView is transferred in ( ), and a property value of text is @string/text_name.

```
{
  "TextView(text:@string/text_name)": { }
}
```

In an implementation, if a view property and a property value are transferred in both ( ) and { } for a same view, content in ( ) is ignored.

The property value of the view property may be assigned in any one of the following manners: being directly specified by using a string value; accessing a resource value defined in background data; accessing a classification parameter declared in background data; or accessing a value in a view model (ViewModel) object.

The customized UI engine 11 supports specifying a namespace (namespace) of a view property in namespace.propertyName mode. In an implementation, if no namespace is specified, it indicates that a namespace of Android® is specified by default. In an implementation, the customized UI engine 11 supports using namespace androidhwext to point to an extended resource package in the operating system, and using namespace app to point to a customized resource package in the app. The extended resource package in the operating system provides the customized UI programming capability in the operating system. The customized resource package in the app provides the customized view property in the app.

In an implementation, the developers may further define another namespace. The namespace defined by the developers is imported through import, and a package name of a resource package that defines a view property is provided. The following is an example in which the namespace myspace defined by the developers is imported, and a complete package name of a myspace resource package is com.myapp. After myspace is imported to import, a borderWidth property in myspace can be invoked in layout-data-common.

```
{
  "import": {
    "myspace": "com.myapp",
  },
  "layout-data-common": {
    "Column(layout_width:match_parent,)": {
      "MyCircleView(myspace.borderWidth:3dp)": { },
      ...
    }
}
```

II. Data & Interface Binding

The customized UI engine 11 supports bidirectional binding of elements on the UI to background data. A binding relationship between the elements (such as views and view groups) on the UI and the background data can be declared and specified in the interface description file (layout-data-common or layout-data-uimode). The MVVM framework 11*c* in the customized UI engine 11 may refresh the background data based on a UI change, or automatically refresh a corresponding UI based on a background data change.

For example, an element on the UI may be bound to a view model (ViewModel) object. ViewModel is imported into import and an object of a ViewModel type is declared in model. Then, the ViewModel object is invoked in layout-data-common or layout-data-uimode.

In an example, a property value of a view property on the UI is bound as a value of the ViewModel object. The following is an example in which a complete package name com.myapp.UserInfo of a resource package of UserInfo (UserInfo is a ViewModel) is introduced to import, an object user of the UserInfo type is declared in model, and then data in user is accessed in layout-data-common.

```
{
  "import": {
    "UserInfo": "com.myapp.UserInfo"
  },
  "model": {
    "user": "UserInfo",
  },
  "layout-data-common": {
    "Column( )": {
      "ImageView(id:photo)": {
        "imageUri": "$user.photo"
      },
      "TextView(text: $user.name)": { },
      "TextView(text: $user.age)": { },
      "CheckBox(checked: $user.agreed)": { },
      "TextView (text: submitted information, visible:$user::hasName)":
      { }
    }
  }
}
```

In an implementation, a variable value (field) in a ViewModel object (model) is accessed in $model.field mode. For example, $user.photo is a variable photo in an access user, and $user.name is a variable name in the access user. In an implementation, a return value of a function (function) in the ViewModel object (model) is accessed in $model::function mode. For example, $user::hasName is a return value of the hasName function in the access user.

In the preceding example, an imageUri property (image) of an ImageView view is bound to background data user.photo, and the text (text) property of the TextView view is bound to background data user.name, the text property of the TextView view is bound to background data user.age, a checked (checked) property of a CheckBox view is bound to background data user.agreed, and a visible (visible) property of the TextView view is bound to background data user::hasName. When the background data changes, the property value of the view property changes, and a display effect of the view on the UI changes.

In an implementation, visibility of the view may be obtained based on the background data, to implement a function of hiding a part of the UI. When a variable in the background data changes (visible to gone, or gone to visible), the view on the UI can be hidden or displayed accordingly. The following is an example in which visibility (visible) of a column of views (Column) is determined by a value of a variable user.visible.

```
{
  "layout-data-common": {
    "Column(visible:$user.visible)": {
      "EditText(hint:@string/text__hint, text:$user.name)": { }
    }
  }
}
```

In another example, a user input is received on the UI, and the user input is bound to a value of the ViewModel object. The following is an example in which a complete package name com.myapp.UserInfo of a resource package of UserInfo (UserInfo is a ViewModel) is introduced to import, an object user of the UserInfo type is declared in model, and then it is declared in layout-data-common to assign a user input value of the text (text) property of an EditText view to a variable name in user. "=" is used to assign a value to background data.

```
{
  "import": {
    "UserInfo": "com.myapp.UserInfo",
  },
  "model": {
    "user": "UserInfo",
  },
  "layout-data-common": {
    "Column( )": {
      "EditText(hint:@string/text__hint, text:= $user.name)": { }
    }
  }
}
```

III. Interaction Behavior Orchestration

The customized UI engine 11 supports declaring, in the interface description file, an execution action corresponding to a view response event. An event scope supported by a view is determined by event listening supported by the view. For example, if the button (Button) view supports setOnClickListener (setOnClickListener), an onClick (click) event can be bound to the view in the interface description file. The customized UI engine 11 performs bidirectional transparent transmission between the view and the background data on an event parameter and a return value of a response function in the background data. The following is an example. In layout-data-common, the Button view is declared to execute an action (the return value of the response function) defined in the background data context.buttonClick in response to the onClick event.

```
{
  "import": {
    "Context": "com.myapp.TestActivity"
  },
  "model": {
    "context": "Context",
  },
  "layout-data-common": {
    "LinearLayout( )": {
      "Button( )": {
        "onClick": "$context.buttonClick"
      }
    }
  }
}
```

The customized UI engine 11 supports the UI execution engine to load life cycle events of views, including onPreMount, onMount, onUnmount, onPreUpdate, onUpdate, and the like, where onPreMount indicates that the view is invoked before being mounted to the UI, onMount indicates that the view is invoked after being mounted to the UI, onUnmount indicates that the view is invoked after being removed from the UI, onPreUpdate indicates that the view is invoked before the UI is refreshed due to a data change, and onUpdate indicates that the view is invoked after the UI is refreshed due to a background data change.

In an implementation, whether an event is consumed is determined by the return value of the response function. Optionally, the customized UI engine 11 complies with a native interface definition of Android®, and transparently transmits a processing result in the background data to the view.

IV. Differentiation Description

1. The Customized UI Engine 11 Supports that a Property of a View Depends on a Configuration Parameter of an Electronic Device.

A variable of configuration parameters of the electronic device is defined in the operating system. The variable of configuration parameters of the electronic device may be declared in the interface description file. When the electronic device runs the interface description file, the configuration parameter of the electronic device is accessed, and the electronic device obtains a value of the configuration parameter based on software and hardware conditions of the electronic device. In this way, when different types of electronic devices run a same interface description file, different UIs are generated because software and hardware conditions and configuration parameters of the electronic devices are different.

In an implementation, a configuration parameter (config) of a current electronic device is accessed in $env.config mode.

For example, the configuration parameter of the electronic device may include content shown in Table 1.

TABLE 1

| | Parameter | Description | Name | Parameter type |
|---|---|---|---|---|
| Hardware dependency | Width | Screen resolution width | screen__width | int |
| | Height | Screen resolution height | screen__height | int |
| | Interaction mode | Touchscreen, button, pointer, or remote view | interaction__mode | finger, keyboard, pointer |
| | Side screen | | side__screen | boolean |
| | Cutout screen | | cutout | boolean |
| | Foldable screen | | fold__screen | boolean |
| | Camera | | camera__sensor | none, front, back, both |

TABLE 1-continued

| | Parameter | Description | Name | Parameter type |
|---|---|---|---|---|
| Software dependency | Dark mode | Dark mode | dark_mode | boolean |
| | Screen density | The value varies with the display mode | dpi | ldpi, mdpi, hdpi, xhdpi, xxhdpi, xxxhdpi |
| | Short side | Quantity of current DPs on the short side, which varies with the display mode | smallestWidth | int |
| | Layout orientation | Layout from right to left | layout_orientation | LTR, RTL |
| | Landscape mode and portrait mode | The screen is in landscape mode or portrait mode currently | orientation | land, port |

The following is an example. A property value of a dependOn property of a view can be assigned to a field in a configuration parameter to declare that a view property depends on a configuration parameter. In this example, visibility of a scan view (TextView) depends on camera hardware (camera_sensor) of the electronic device. It indicates that if the electronic device has a camera, the scan view is displayed; or if the electronic device does not have a camera, the scan view is not displayed.

```
{
  "layout-data-common": {
    "TextView(text: scan)": {
      "dependOn": $env.config.camera_sensor
    }
  }
}
```

2. Layout-Data-Uimode is Used to Describe a UI of a Specified Device.

The developers can declare the UI of the specified device in layout-data-uimode. A display effect of the UI of the specified device is different from that of the common UI.

In an implementation, all conditions applicable to the UI of the specified device are declared in layout-data-uimode. For example, refer to FIG. 16A to FIG. 16D. An interface description file 710 includes code blocks such as layout-data-common 711 and layout-data-watch 712. The layout-data-common 711 is used to describe a common UI applicable to various types of electronic devices, and the layout-data-watch 712 is used to describe a UI applicable to a watch. As shown in FIG. 16A to FIG. 16D, the layout-data-common 711 declares a property and a property value of each view in the common UI. A mobile phone reads the interface description file 710, parses and executes content in the layout-data-common 711, and generates a corresponding view based on the property and the property value of each view declared in the layout-data-common 711. For example, the mobile phone correspondingly generates an image view 721 based on a content block 7111 in the layout-data-common 711, correspondingly generates a view group 722 based on a content block 7112 in the layout-data-common 711, correspondingly generates a view group 723 based on a content block 7113 in the layout-data-common 711, correspondingly generates a button view 724 based on a content block 7114 in the layout-data-common 711, and correspondingly generates a view group 725 based on a content block 7115 in the layout-data-common 711. In this way, a UI 720 of the mobile phone is generated based on the content block 7111, the content block 7112, the content block 7113, the content block 7114, and the content block 7115.

The layout-data-watch 712 declares a property and a property value of a view on the UI applicable to the watch. The watch reads the interface description file 710. If determining that the layout-data-watch 712 used for the watch exists in the interface description file 710, the watch parses and executes content in the layout-data-watch 712, and generates a corresponding view based on a property and a property value of each view declared in the layout-data-watch 712. For example, the watch correspondingly generates an image view 731 based on a content block 7121 in the layout-data-watch 712, correspondingly generates a view group 732 based on a content block 7122 in the layout-data-watch 712, correspondingly generates a view group 733 based on a content block 7123 in the layout-data-watch 712, and correspondingly generates a button view 734 based on a content block 7124 in the layout-data-watch 712. In this way, a UI 730 of the watch is generated based on the content block 7121, the content block 7122, the content block 7123, and the content block 7124.

In this way, the watch, as a specified device, reads content in a second code segment (layout-data-watch 712), and an electronic device other than the watch reads content in a first code segment (layout-data-common 711). Different types of electronic devices may present different UI display effects by reading a same interface description file of a same UI. A set of interface description files may be developed to develop differentiated UIs for different types of electronic devices, to reduce development difficulty of developers.

In another implementation, a difference between the UI of the specified device and the common UI is declared in layout-data-uimode. For example, refer to FIG. 17A to FIG. 17D. An interface description file 810 includes code blocks such as layout-data-common 811 and layout-data-watch 812. The layout-data-common 811 is used to describe a common UI applicable to various types of electronic devices, and the layout-data-watch 812 is used to describe a difference between a UI of a watch and the common UI. As shown in FIG. 17A to FIG. 17D, the layout-data-common 811 declares a property and a property value of each view in the common UI. A mobile phone reads the interface description file 810, parses and executes content in the layout-data-common 811, and generates a corresponding view based on the property and the property value of each view declared in the layout-data-common 811. The mobile phone correspondingly generates an image view 721 based on a content block 8111 in the layout-data-common 811, correspondingly generates a view group 722 based on a content block 8112 in the layout-data-common 811, correspondingly generates a view group 723 based on a content block 8113 in the layout-data-common 811, correspondingly generates a button view 724 based on a content block 8114 in the layout-data-common 811, and correspondingly generates a view group 725 based on a content block 8115 in the layout-data-common 811. In this way, a UI 720 of the mobile phone is generated based on the content block 8111, the content block 8112, the content block 8113, the content block 8114, and the content block 8115.

The layout-data-watch 812 declares a property and a property value of a view that is on the UI of the watch and that is different from the common UI. The watch reads the interface description file 810, and parses and executes content in the layout-data-common 811. The watch determines that the layout-data-watch 812 used for the watch exists in the interface description file 810, and parses and executes content in the layout-data-watch 812. The watch generates a corresponding view based on a property and a property value of each view declared in the layout-data-common 811 and the layout-data-watch 812. As shown in FIG. 17A to FIG. 17D, the watch correspondingly generates an image view 731 based on a content block 8111 in the layout-data-common 811, correspondingly generates a view group 732 based on a content block 8112 in the layout-data-common 811, correspondingly generates a view group 733 based on a content block 8113 in the layout-data-common 811, and correspondingly generates a button view 734 based on a content block 8114 in the layout-data-common 811. According to the description of the layout-data-watch 812, a property value of a visible (visible) property of a generated view group corresponding to the content block 8115 in the layout-data-common 811 is set to gone (gone). In other words, the view group corresponding to the content block 8115 in the layout-data-common 811 is not displayed on the watch. As shown in FIG. 17A to FIG. 17D, the UI 730 of the watch includes views generated based on the content block 8111, the content block 8112, the content block 8113, and the content block 8114.

In this way, all types of electronic devices read content in the first code segment (layout-data-common 711), and the watch, as a specified device, further reads content in the second code segment (layout-data-watch 712). Different types of electronic devices may present different UI display effects by reading a same interface description file of a same UI. A set of interface description files may be developed to develop differentiated UIs for different types of electronic devices, to reduce development difficulty of developers.

3. Style

The customized UI engine 11 allows developers to customize parameters in style for a current interface description file. The following is an example. The developers define myTextStyle in style and can invoke the customized parameter in $style.myTextStyle mode in layout-data-common.

```
{
  "layout-data-common": {
    "Column( )": {
      ...
      "Button(style:$style.myTextStyle)": { },
    }
  },
  " style": {
    "myTextStyle": {
      "textSize": "24sp",
      "textcolor": "white"
    }
  }
}
```

A UI is developed by using the syntactic and semantic rules provided in this embodiment of this application. Syntax is simple and efficient, and a set of interface description files can be developed to be applicable to different types of electronic devices. This avoids separately developing a UI for different types of electronic devices, and reduces development costs.

The UI parsing engine 11*a* is configured to parse the interface description file, and convert content in the interface description file into a data format that matches the UI execution engine 11*b*. In some examples, the UI parsing engine 11*a* may further perform syntax check on content in the interface description file. If the syntax check on the interface description file succeeds, the UI parsing engine 11*a* parses the interface description file; or if the syntax check on the interface description file fails, the UI parsing engine 11*a* does not parse the interface description file.

Figure 18:
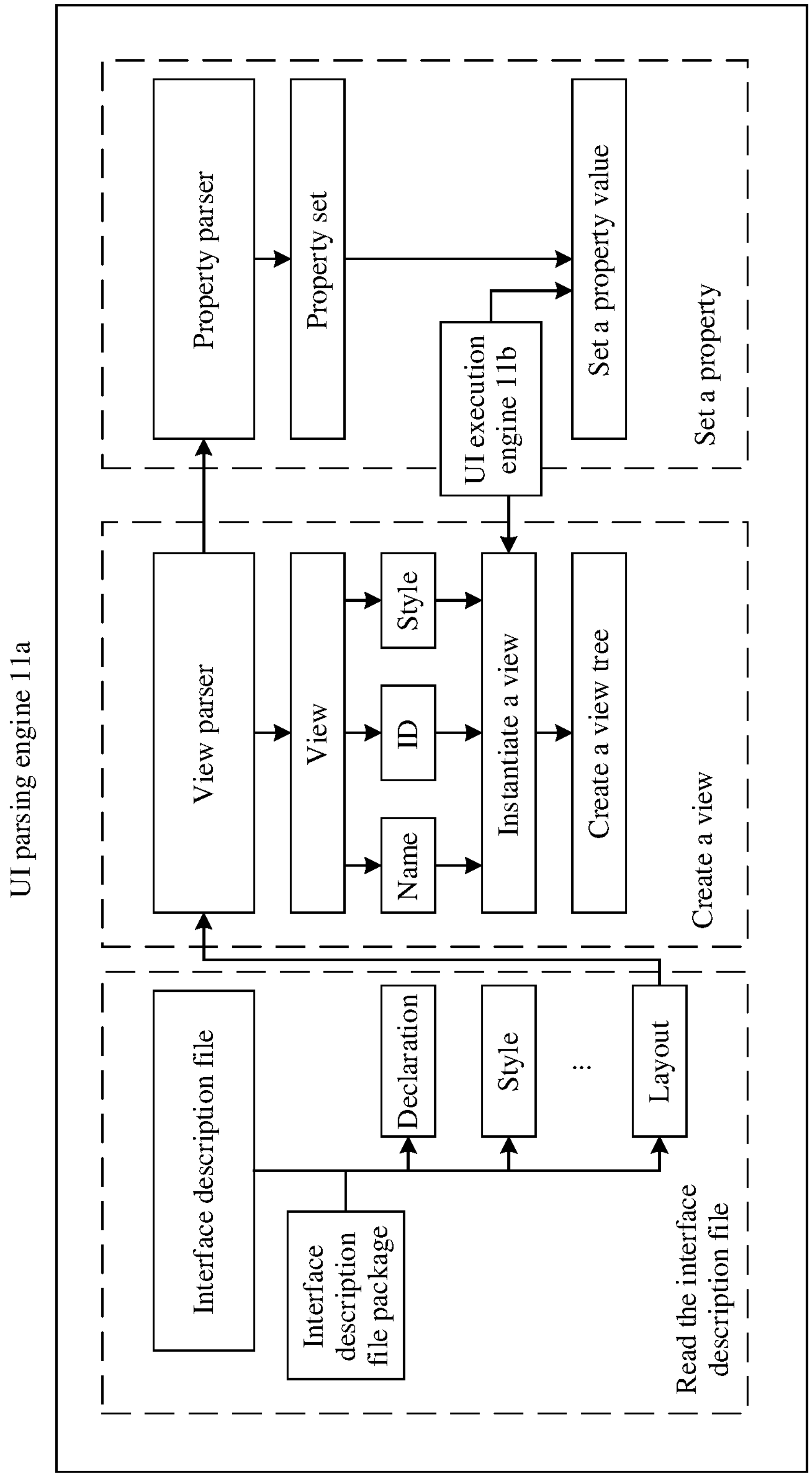
FIG. 18 is a schematic diagram of a scenario example of a user interface implementation method according to an embodiment of this application.

Refer to FIG. 18. In an example, the UI parsing engine 11*a* reads the interface description file, parses data in fields such as declaration (model), style (style), and layout (layout-data-common and layout-data-uimode) in the interface description file, and stores the data to a database after preprocessing the data. A view parser is used to parse data in the layout field, and the UI execution engine 11*b* is recursively invoked, based on a logical structure described in the layout, to instantiate the view, so as to form a view tree of the UI. A property parser is used to parse a property field of each view, and the UI execution engine 11*b* is invoked to set a property for each view, so as to complete UI drawing.

Figure 19A:
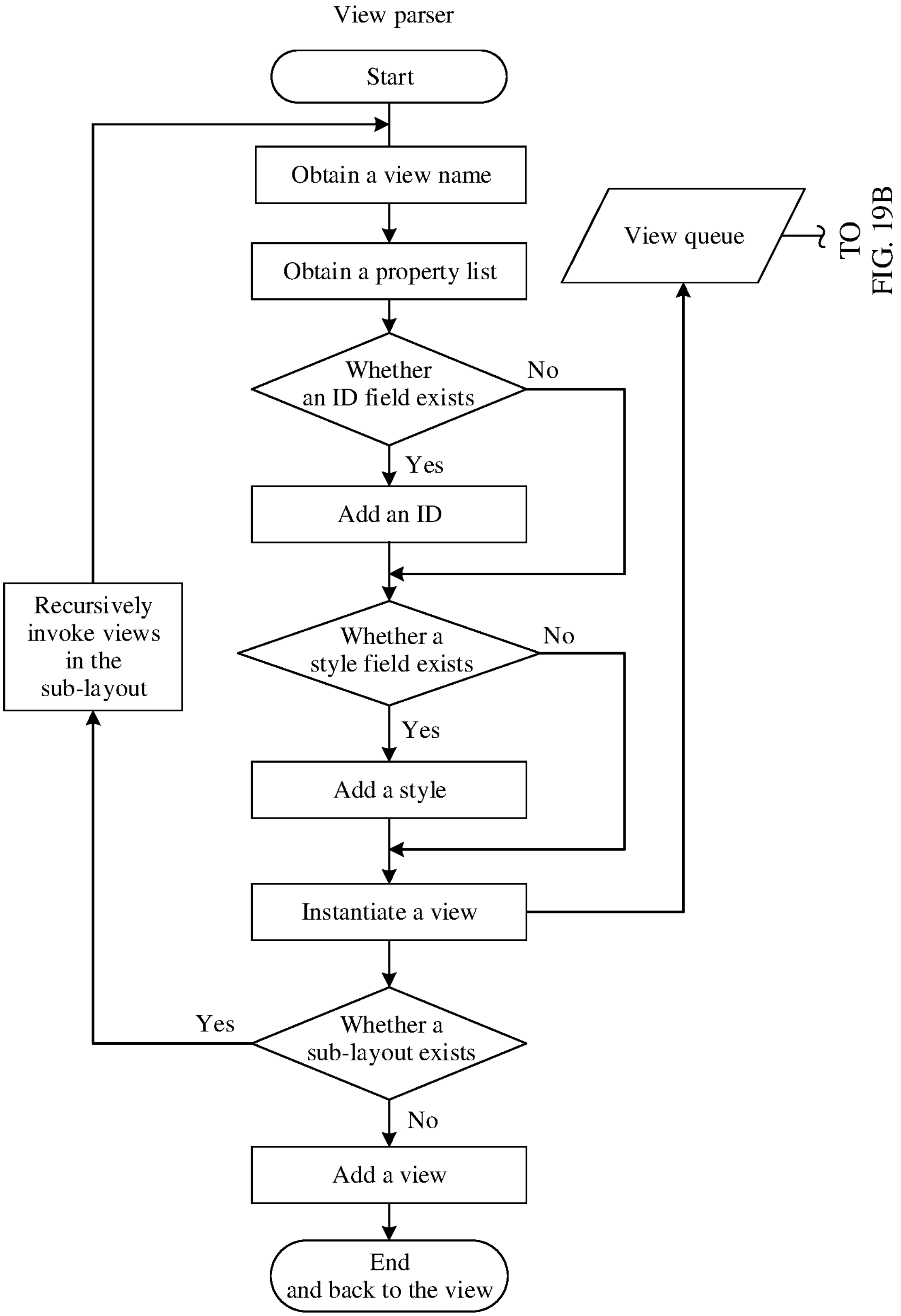
FIG. 19A and FIG. 19B are a schematic diagram of a scenario example of a user interface implementation method according to an embodiment of this application.
Figure 19B:
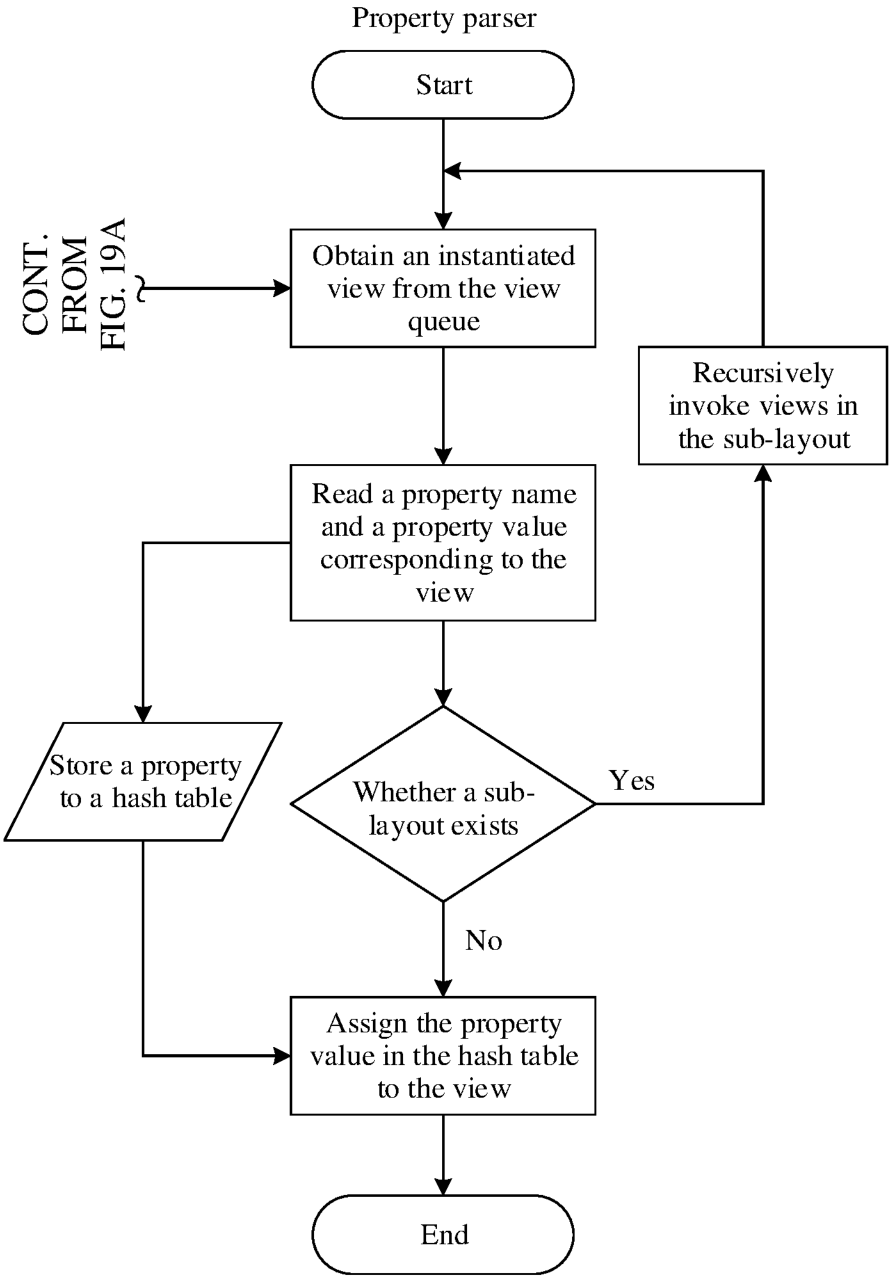

A working process of the view parser and the property parser is shown in FIG. 19A and FIG. 19B. The view parser gets a name of a view and gets a property list of the view. If a view ID (identity, ID) exists, add the view ID, or if a view style (style) exists, add the view style, to instantiate the view to form a view queue. If a sub-layout exists, recursively invoke views in the sub-layout. After parsing views in all layouts, add views and return generated views. The property parser obtains the instantiated view from the view queue, reads a property name and a property value that are corresponding to the view, and stores the property (including the property name and the property value) to a hash table. If a sub-layout exists, recursively invoke views in the sub-layout. After properties of all views are parsed, assign a property value of each view stored in the hash table to a corresponding view.

The UI execution engine 11*b* is configured to: build views (instantiated views and property settings) of the UI based on the data parsed by the UI parsing engine 11*a*, perform layout orchestration on the views, and generate an interface declared in the interface description file. The UI execution engine 11*b* may further implement mapping between a component event and user behavior, and execute, in response to the user behavior, an action corresponding to the user behavior defined in the interface description file.

Figure 20A:
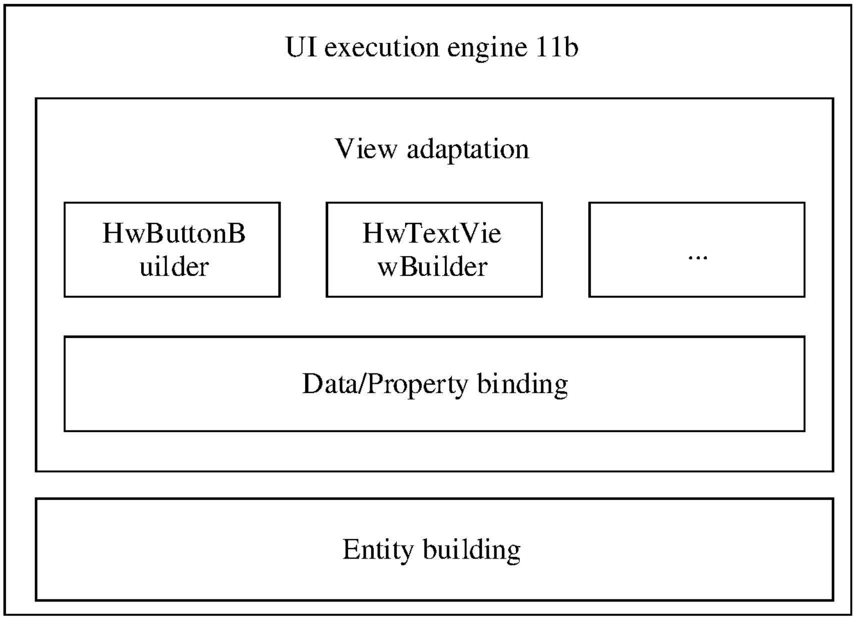
FIG. 20A is a schematic diagram of a scenario example of a user interface implementation method according to an embodiment of this application.

For example, refer to FIG. 20A. In the UI execution engine 11*b*, a Build (Builder) class is built for each view. The Builder class uses inheritance logic that is the same as that of Android®, so that a child view can inherit all properties and setting methods of a parent view, and a repeated definition is not needed. The Builder class contains an entity construction method of a corresponding view and a method for setting a visual property of the view, to instantiate the view and set the property. For a view customized by developers, a Builder class of the customized view may be provided in the UI execution engine 11*b*, so that access costs are low and the view is relatively friendly to the developers.

In some embodiments, for an Android® native view property declared in the interface description file, the UI execution engine 11*b* may perform property setting based on the declaration in the interface description file, to complete view instantiation, and the built view has the Android® native view property.

Figure 20B:
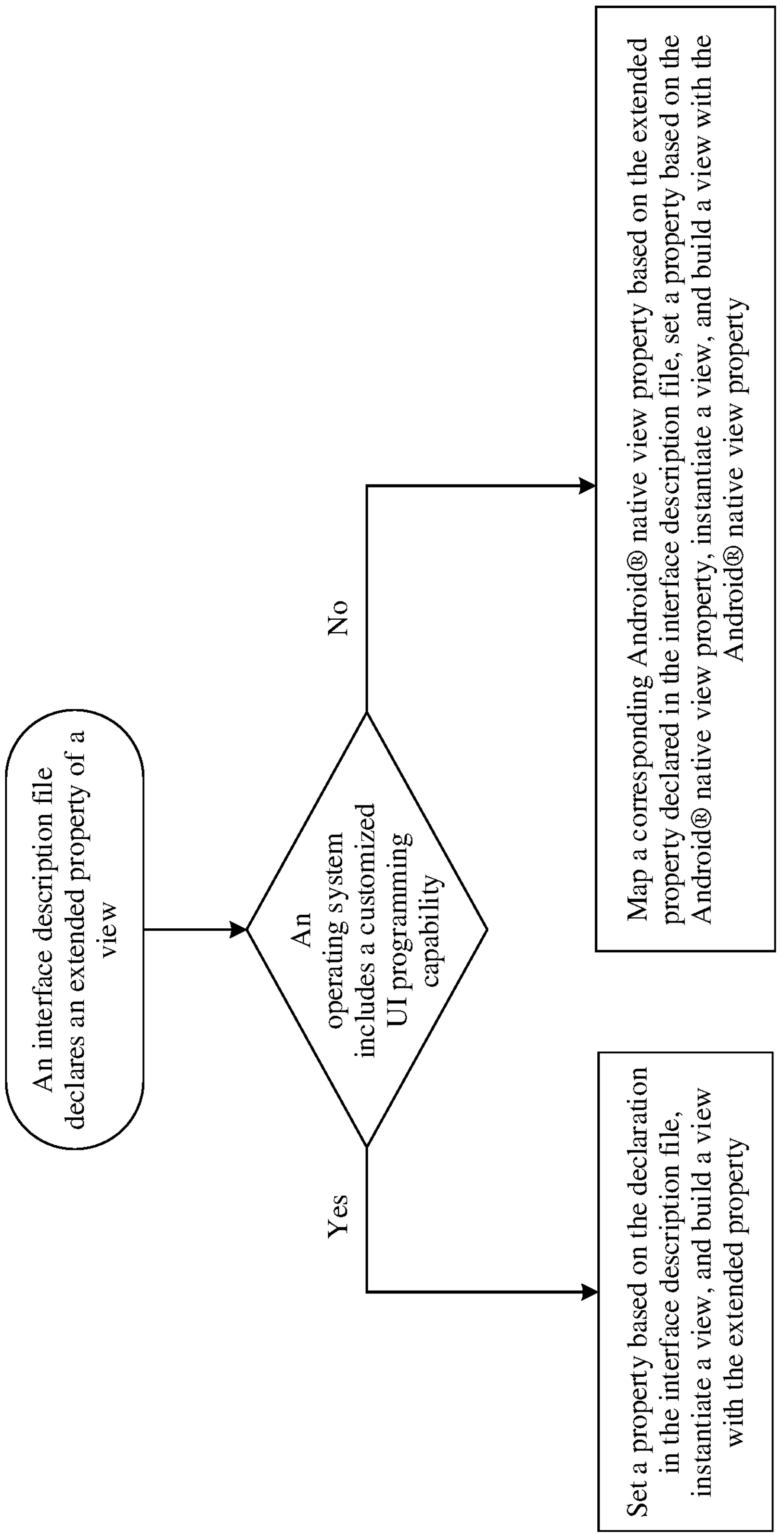
FIG. 20B is a schematic flowchart of a user interface implementation method according to an embodiment of this application.

Refer to FIG. 20B. For an extended property of a view declared in the interface description file, if it is determined that an operating system includes a customized UI programming capability, the UI execution engine 11*b* performs property setting based on the declaration in the interface description file, completes view instantiation, and builds a view having the extended property. If it is determined that the operating system does not include the customized UI programming capability, the UI execution engine 11*b* maps a corresponding Android® native view property based on the extended property declared in the interface description file, performs property setting based on the corresponding Android® native view property, completes view instantiation, and builds a view having the Android® native view property. The view does not have the extended property.

Figure 20C:
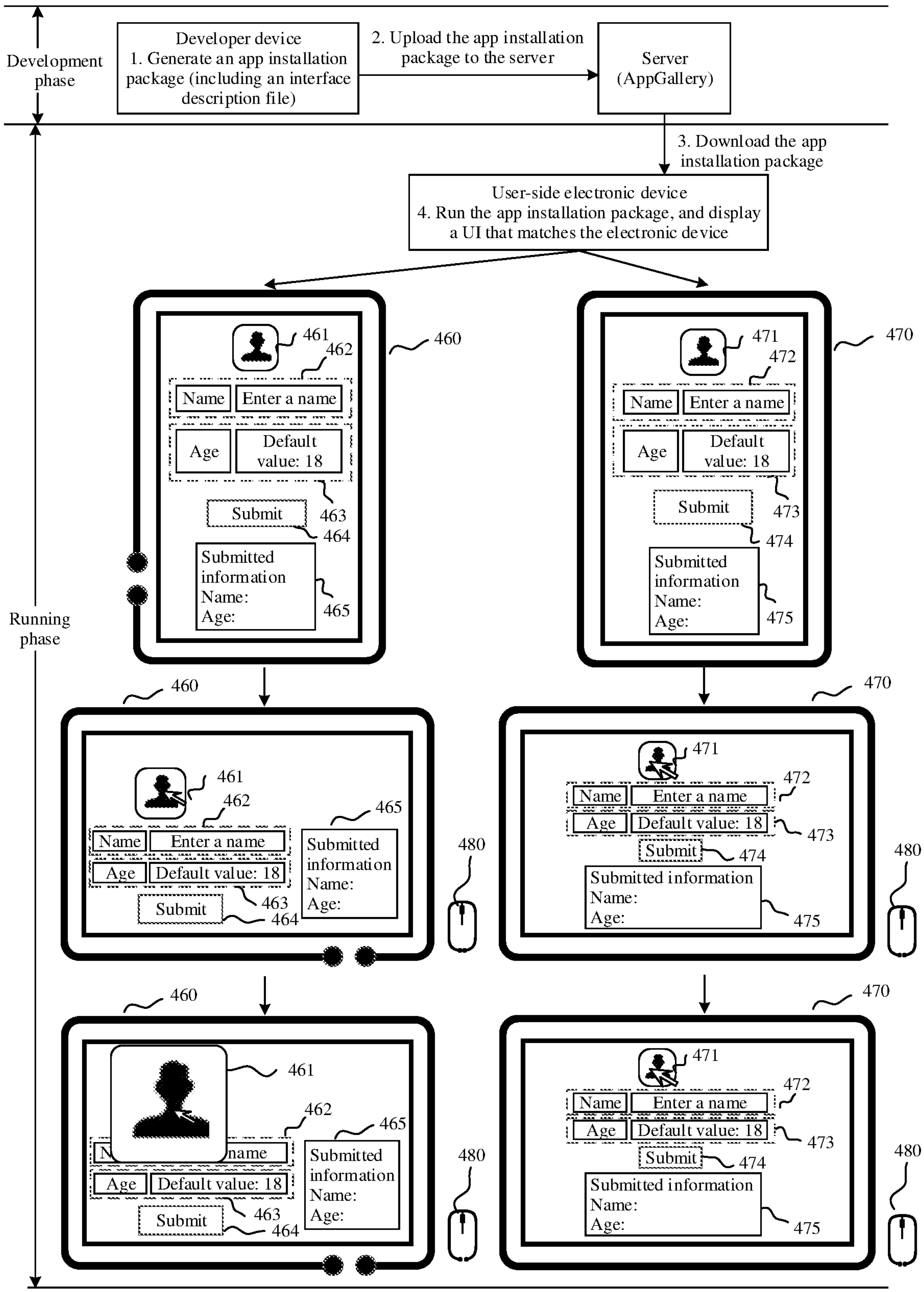
FIG. 20C is a schematic diagram of a user interface implementation method according to an embodiment of this application.

For example, refer to FIG. 20C. An app installation package is generated on a developer device, including the interface description file. The app installation package is uploaded to a server, and the app is released in an AppGallery provided by the server. A user may download the app installation package in the AppGallery by using a user-side electronic device (the electronic device 100). After running the app installation package, the user-side electronic device obtains the interface description file in the installation package. When running the app, the user-side electronic device displays, on the display based on the interface description file, a UI that matches the electronic device.

For example, the interface description file includes the following content:

```
{
  "layout-data-common": {
    "HwMagicLayout (id: layout)": {
      "imageview (id: imageview)": {
        "zoomEnable": true
      }
    }
  }
}
```

In an example, a tablet 460 is used as the user-side electronic device to run an app. An operating system of the tablet 460 includes a customized UI programming capability. On a UI of the tablet 460, a customized view group HwMagicLayout is successfully built, and the view group has an extended layout property in the operating system. For example, the extended layout property in the operating system may include layout properties such as automatic stretching, hiding, equalization, proportion, extension, or wrapping. The automatic stretching means that a height or width of a view is automatically zoomed in or zoomed out based on a window size, to adapt to the window size. Hiding is a capability of the view visible or gone in the layout. Equalization means that content in the view is evenly distributed in the layout. Proportion means that the view occupies a total layout size according to a specified percentage in a specified direction. Extension means that the view is extended and displayed on the UI based on a display size. Wrapping means that the content in the view is displayed in one or more lines in the layout. As shown in FIG. 20C, a UI layout of the tablet 460 has the extended layout property in the system. When the tablet 460 is in portrait display mode, a view 461, a view group 462, a view group 463, a view 464, and a view group 465 are vertically arranged in one column.

When the tablet 460 is in landscape display mode, the view 461, the view group 462, the view group 463, and the view 464 are vertically arranged in a first column, and the view group 465 is arranged in a second column. The UI layout of the tablet 460 is adaptively adjusted based on a size and a shape of a display window.

On the UI of the tablet 460, an interaction capability "zoomEnable" takes effect on the view 461 "imageview". When the tablet 460 is connected to a mouse 480, the view 461 may be zoomed in and displayed in response to a zoom-in operation performed by a user on the view 461 (for example, when a cursor corresponding to the mouse 480 is placed on the view 461, a scroll wheel of the mouse 480 is rotated upward).

In another example, a tablet 470 is used as the user-side electronic device to run an app. An operating system of the tablet 470 does not include a customized UI programming capability. A UI of the tablet 470 does not support a customized view group HwMagicLayout. A view on the UI has a native linear layout (LinearLayout) property of Android®. When the tablet 470 is in portrait display mode or landscape display mode, a view 471, a view group 472, a view group 473, a view 474, and a view group 475 are vertically arranged in one column. A UI layout of the tablet 470 is fixed, and cannot be adaptively adjusted based on a size and a shape of a display window.

On the UI of the tablet 470, an interaction capability "zoomEnable" cannot take effect on the view 471 "imageview". That is, when the tablet 470 is connected to the mouse 480, if a cursor corresponding to the mouse 480 is placed on the view 471, and a scroll wheel of the mouse 480 is rotated upward, a size of the view 471 remains unchanged.

In this way, an interface description file that conforms to a syntax rule in the syntactic and semantic library 11*d* can be successfully run in different operating systems. This implements running across operating system platforms and reduces development difficulty for the developers.

It should be noted that the UI execution engine 11*b* dynamically parses data when the electronic device runs the interface description file, and obtains a related parameter of the electronic device when the electronic device runs the interface description file. This prevents the developers from precompiling the interface description file in a development tool to generate a preset data file. In this way, UI development does not depend on a compilation environment, and development and running across development platforms can be implemented.

The MVVM framework 11*c* is configured to perform bidirectional binding between an element on the UI and background data. In the interface description file, a binding relationship between an element (such as a view or a view group) on the UI and the background data is declared and specified. Optionally, after simple data instances are set, the MVVM framework 11*c* may refresh the background data based on a UI change, and automatically refresh a corresponding UI based on a background data change. This helps the developers focus on UI design and orchestration, simplifies a UI development process, and greatly reduces development time for the developers to implement frontend and backend data interaction.

Figure 21:
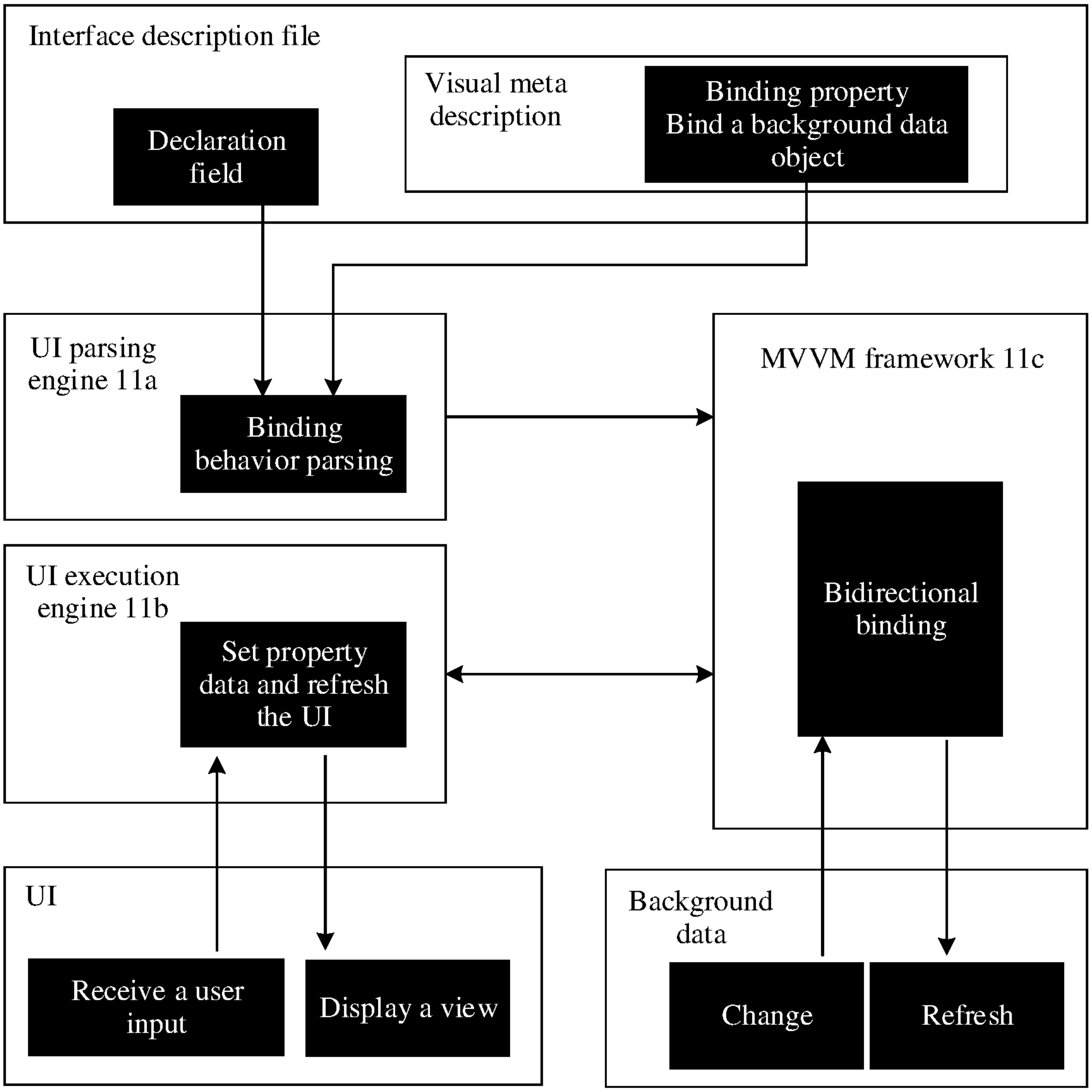
FIG. 21 is a schematic diagram of a scenario example of a user interface implementation method according to an embodiment of this application.

For example, refer to FIG. 21. Developers declare a view field in an interface description file, bind a property to the view, and bind a background data object. The UI parsing engine 11*a* parses binding behavior in the interface description file to obtain a correspondence between the view property and the background data object. The MVVM framework 11*c* is configured to implement bidirectional binding between a view and the background data. When the background data changes, the MVVM framework 11*c* maps the background data to data of a corresponding view property; and the UI execution engine 11*b* sets property data of the view, and refreshes the UI. When the property data of the view on the UI changes (for example, in response to a user input, data such as a shape and a text of the view changes), the MVVM framework 11*c* maps the property data of the view to the background data, and the background data is refreshed.

The UI rendering engine 11*e* is configured to render and arrange the interface generated by the UI execution engine 11*b*, and output display content to a display.

According to the user interface implementation method provided in this embodiment of this application, different types of electronic devices present different UI layouts by reading a same interface description file of a same UI. A set of interface description files that are applicable to various different types of electronic devices can be developed, to reduce development difficulty for the developers.

Figure 22:
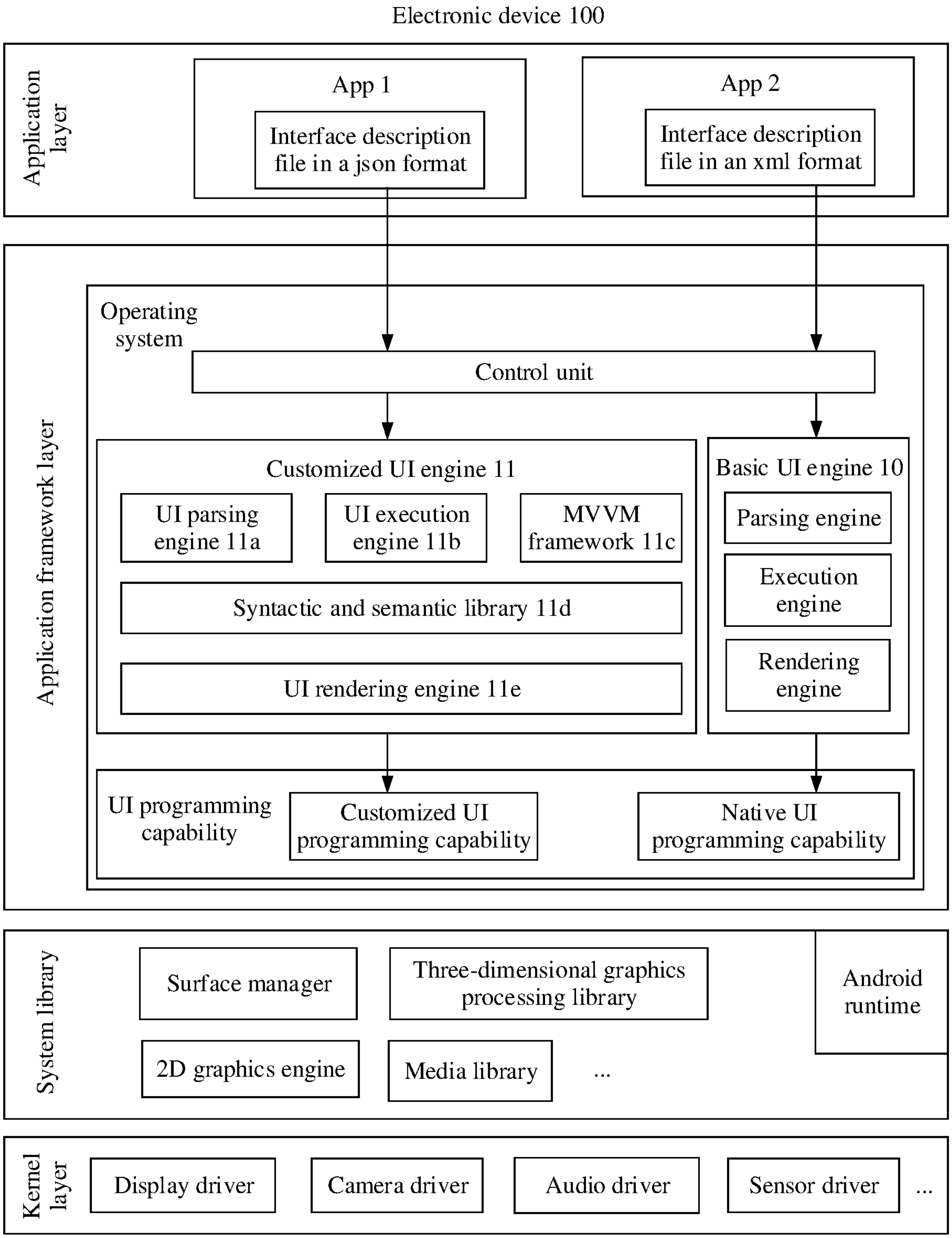
FIG. 22 is a schematic diagram of a user interface implementation method according to an embodiment of this application.

Refer to FIG. 22. In some embodiments, a software system of the electronic device 100 may include an application layer, an application framework layer, an Android runtime (Android runtime) and system library, and a kernel layer.

An interface description file of an application layer app 1 is in a json format, and an interface description file of an application layer app 2 is in an xml format.

An operating system of the application framework layer includes a control unit. When the electronic device 100 runs an app, the control unit obtains an interface description file of an app. For example, when the electronic device 100 runs the app 1, the control unit obtains the interface description file in the json format of the app 1. When the electronic device 100 runs the app 2, the control unit obtains the interface description file in the xml format of the app 2. The control unit distributes, based on a type of the interface description file, the interface description file to a basic UI engine 10 or the customized UI engine 11 for UI drawing. For example, the control unit obtains the interface description file in the json format of the app 1, and distributes the interface description file in the json format of the app 1 to the customized UI engine 11 for processing. For example, the control unit obtains the interface description file in the xml format of the app 2, and distributes the interface description file in the xml format of the app 2 to the basic UI engine 10 for processing. In an implementation, specified paths of the interface description file in the json format and the interface description file in the xml format in an application installation package are different. The control unit obtains the interface description file in the json format from a first specified path of an application installation package of the app 1, and obtains the interface description file in the xml format from a second specified path of an application installation package of the app 2. In another implementation, different tags are preset for the interface description file in the json format and the interface description file in the xml format, and the control unit determines the type of the interface description file based on the preset tags of the interface description file.

The customized UI engine 11 parses, executes, and renders the interface description file in the json format of the app 1, to generate a UI of the app 1. A view on the UI of the app 1 may support a native UI programming capability of a general-purpose OS (for example, Android®), and may further support a customized UI programming capability in an operating system of the electronic device 100.

The basic UI engine 10 parses, executes, and renders the interface description file in the xml format of the app 2, to generate a UI of the app 2. A view on the UI of the app 2 supports a native UI programming capability of a general-purpose OS (for example, Android®).

In this way, the electronic device 100 may run an app developed by using the interface description language in the json format, or may run an app developed by using the interface description language in the xml format, to implement forward compatibility of the operating system.

An embodiment of this application further provides a user interface implementation method, applied to a UI of an application widget.

Developers can develop widgets corresponding to apps. For example, a mobile phone can display a widget of an application on the notification bar, home screen, and leftmost screen. Generally, an application widget displayed on the notification bar is referred to as a customized notification bar, an application widget displayed on the home screen is referred to as a home screen widget, and an application widget displayed on the leftmost screen is referred to as a leftmost screen card. The customized notification bar, the home screen widget, and the leftmost screen card can present information in an application to a user more intuitively, and support an operation on the application without opening the application, so that the user can use the application conveniently. An increasing quantity of applications provide widgets for users.

Currently, there are few layout manners and view types that can be displayed on a user interface (user interface, UI) of an application widget, and diversified requirements of the user cannot be met. Embodiments of this application provide a user interface implementation method and an apparatus, to support display of various layout manners and view types on a UI of an application widget, thereby facilitating use of the application widget by a user and improving user experience.

Generally, developers use an interface description language to develop a UI of an application (Application, app) in an application development tool. The developers also use the interface description language to develop a UI of an application widget in the application development tool.

Figure 23:
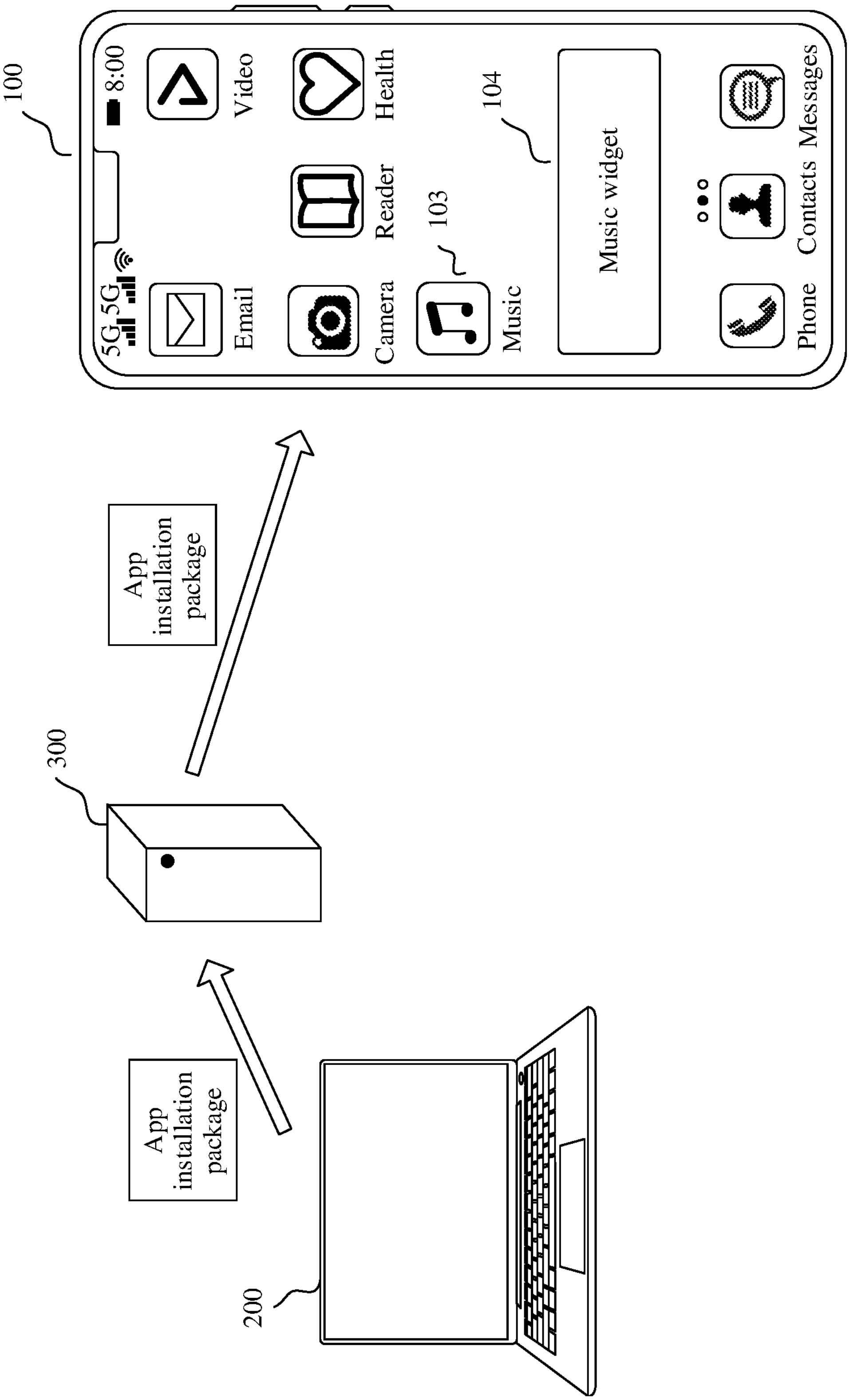
FIG. 23 is a schematic diagram of a scenario of a user interface implementation method according to an embodiment of this application.

Refer to FIG. 23. An application development tool (for example, Android Studio or DevEco Studio) is installed on an electronic device 200. The electronic device 200 in this application may also be referred to as a developer device. Developers develop a UI of an app in the application development tool to generate an interface description file. The interface description file in this application may also be referred to as a description file. The developers also develop a UI of an application widget in the application development tool, to form a widget interface description file. The developers pack the interface description file and the widget interface description file into an installation package of the app, and release the app in an AppGallery provided by the server 300. The AppGallery may provide an installation package of each app for a user to download. For example, the installation package may be an Android® application package (Android application package, APK) file.

It should be noted that, in an implementation, the widget interface description file is independent of the interface description file. In another implementation, the widget interface description file may be a part of the interface description file (for example, a code segment in the interface description file is used as the widget interface description file). This is not limited in embodiments of this application.

In the following embodiment, an example in which the widget interface description file is a separate file is used for description.

For example, a mobile phone is the electronic device 100. The user may download an installation package of an app from the AppGallery by using the mobile phone. The app installation package includes the interface description file and the widget interface description file. A music app is used as an example. After downloading an installation package of the music app, the mobile phone may install the music app on the mobile phone by running the installation package. In this way, the mobile phone also obtains the interface description file and the widget interface description file in the installation package.

For example, as shown in FIG. 23, after the music app is installed on the mobile phone, the home screen of the mobile phone includes a shortcut icon of the music app—a "Music" icon 103. The mobile phone may receive a tap operation performed by the user on the "Music" icon 103, and in response to the tap operation performed by the user on the "Music" icon 103, the mobile phone generates a UI of the music app based on the interface description file, and presents the UI of the music app on a display. The mobile phone may further display a widget (referred to as a music widget) of the music app on the home screen of the mobile phone according to a user setting. The mobile phone generates a UI of the music widget based on the widget interface description file, and displays a UI 104 of the music widget on the display.

It may be understood that, in some embodiments, developers may directly develop a UI of an app and a UI of an application widget on the electronic device 100, and run the app and the application widget on the electronic device 100. That is, the electronic device 200 and the electronic device 100 may be a same electronic device. This is not limited in embodiments of this application.

Generally, an element presented on the UI is referred to as a view (View), and the view can provide a specific operation function for the user or be used to display specific content. For example, native views of the Android® system include a text view (TextView), a text box (EditText), a button (Button), an image button (ImageButton), an image view (ImageView), and the like.

The Android system is used as an example. All UI elements in an application are formed by a view (View) and a view group (ViewGroup). A UI may include one or more views or view groups. The view is an element displayed on a display interface, and the view group is a layout container for storing the view (or view group). A new view or view group can be added to the view group, so that views are arranged based on a specific hierarchy and structure relationship. For example, developers may design a view or a view group on each UI in an app by using a layout such as a linear layout (LinearLayout), a table layout (TableLayout), a relative layout (RelativeLayout), a frame layout (FrameLayout), an absolute layout (AbsoluteLayout), or a grid layout (GridLayout), to generate a layout file of each UI, for example, an interface description file or a widget interface description file.

Currently, the Android® system supports limited layout manners and view types of an application in an application widget, and diversified requirements of the user cannot be met. An embodiment of this application provides a user interface implementation method, to support various layout manners and view types of an application in an application widget.

The user interface implementation method provided in this embodiment of this application not only supports application of a native linear layout (LinearLayout), frame layout (FrameLayout), relative layout (RelativeLayout), and grid layout (GridLayout) of an Android® system to an application widget, but also supports application of a native table layout (TableLayout) and absolute layout (AbsoluteLayout) of the Android® system to the application widget.

The user interface implementation method provided in this embodiment of this application not only supports application of a native button (Button), image view (ImageView), image button (ImageButton), progress bar (ProgressBar), text view (TextView), list view (ListView), grid view (GridView), stack view (StackView), view stub (ViewStub), adapter view flipper (AdapterViewFlipper), view flipper (ViewFlipper), analog clock (AnalogClock), and chronometer (Chronometer) of the Android® system to the application widget, but also supports application of a native text box (EditText), check box (CheckBox), picker (Picker), scroll view (ScrollView), radio button (RadioButton), rating bar (RatingBar), search box (SearchView), seekbar (SeekBar), and switch (Switch) of the Android® system to the application widget.

Figure 24A:
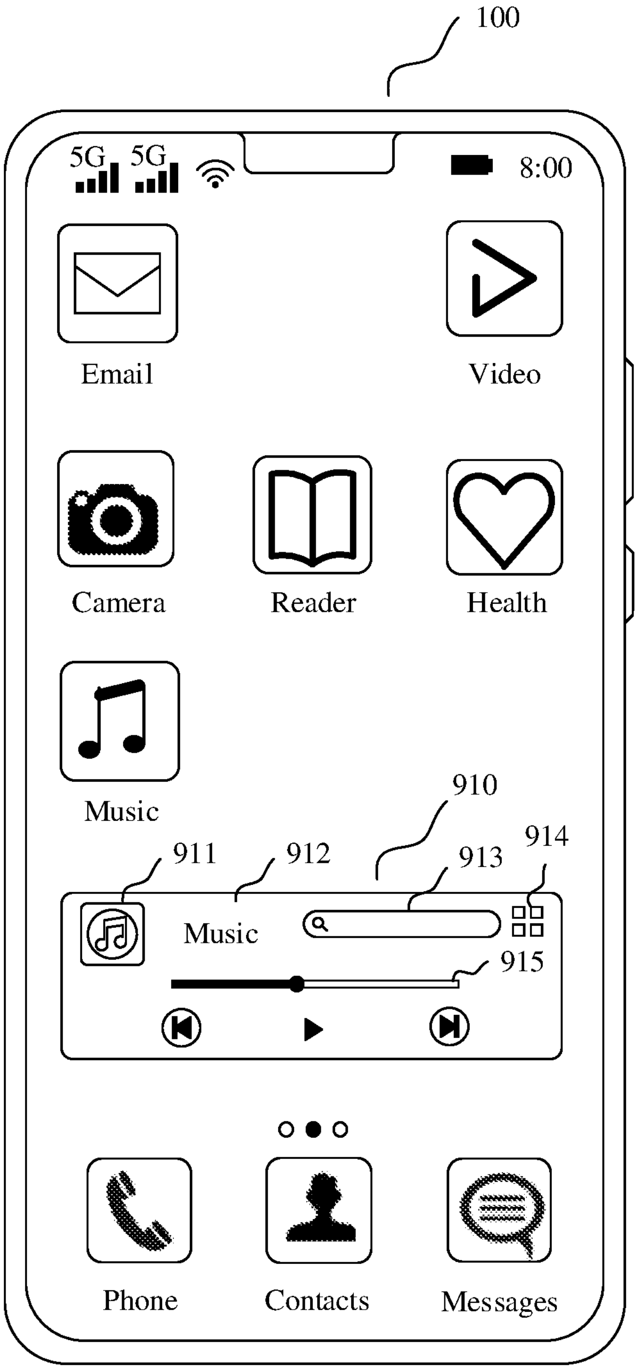
FIG. 24A is a schematic diagram of a scenario example of a user interface implementation method according to an embodiment of this application.

For example, a mobile phone is used as the electronic device 100, and a music app is used on the mobile phone. The mobile phone 100 may display a widget (referred to as a music widget) of the music app on the home screen. As shown in FIG. 24A, the mobile phone 100 displays a UI 910 of the music widget. The UI 910 includes: an image view 911, configured to display an image set by the app; a text view 912, configured to display a track name of played music; a search box 913, configured to receive an input of a user, and perform a search in response to an input text of the user; an image button 914, configured to switch a display style of the music widget; a seekbar 915, configured to adjust a progress of playing music based on a user operation; and another control.

Figure 24B:
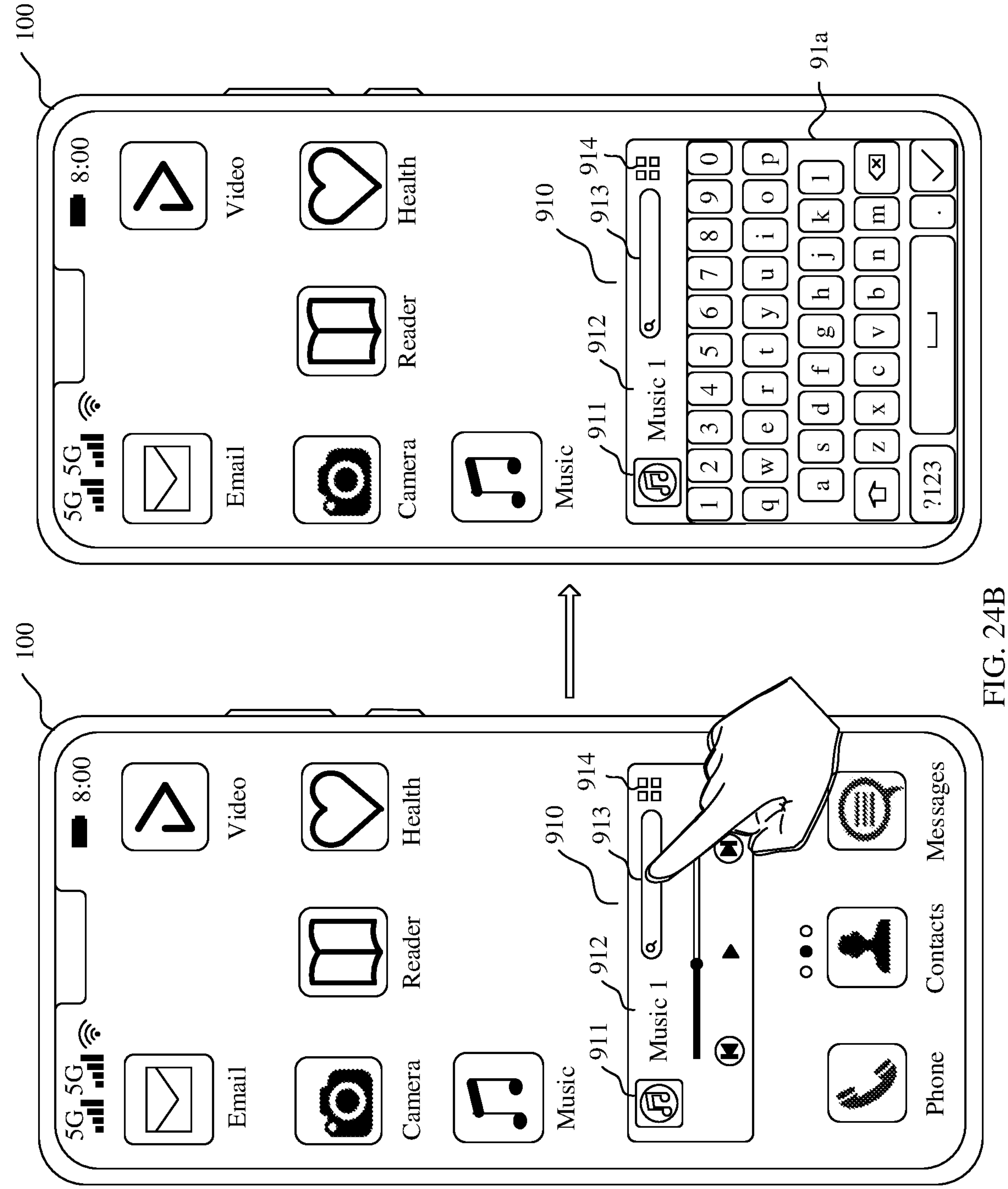
FIG. 24B is a schematic diagram of a scenario example of a user interface implementation method according to an embodiment of this application.

For example, as shown in FIG. 24B, the mobile phone 100 may receive a tap operation performed by the user on the search box 913, and display an enlarged search box 913 and a soft keyboard 91*a* on the home screen in response to the tap operation. The user may use the soft keyboard 91*a* to enter text for the search box 913. The mobile phone 100 performs a search based on the text entered to the search box 913.

Figure 24C:
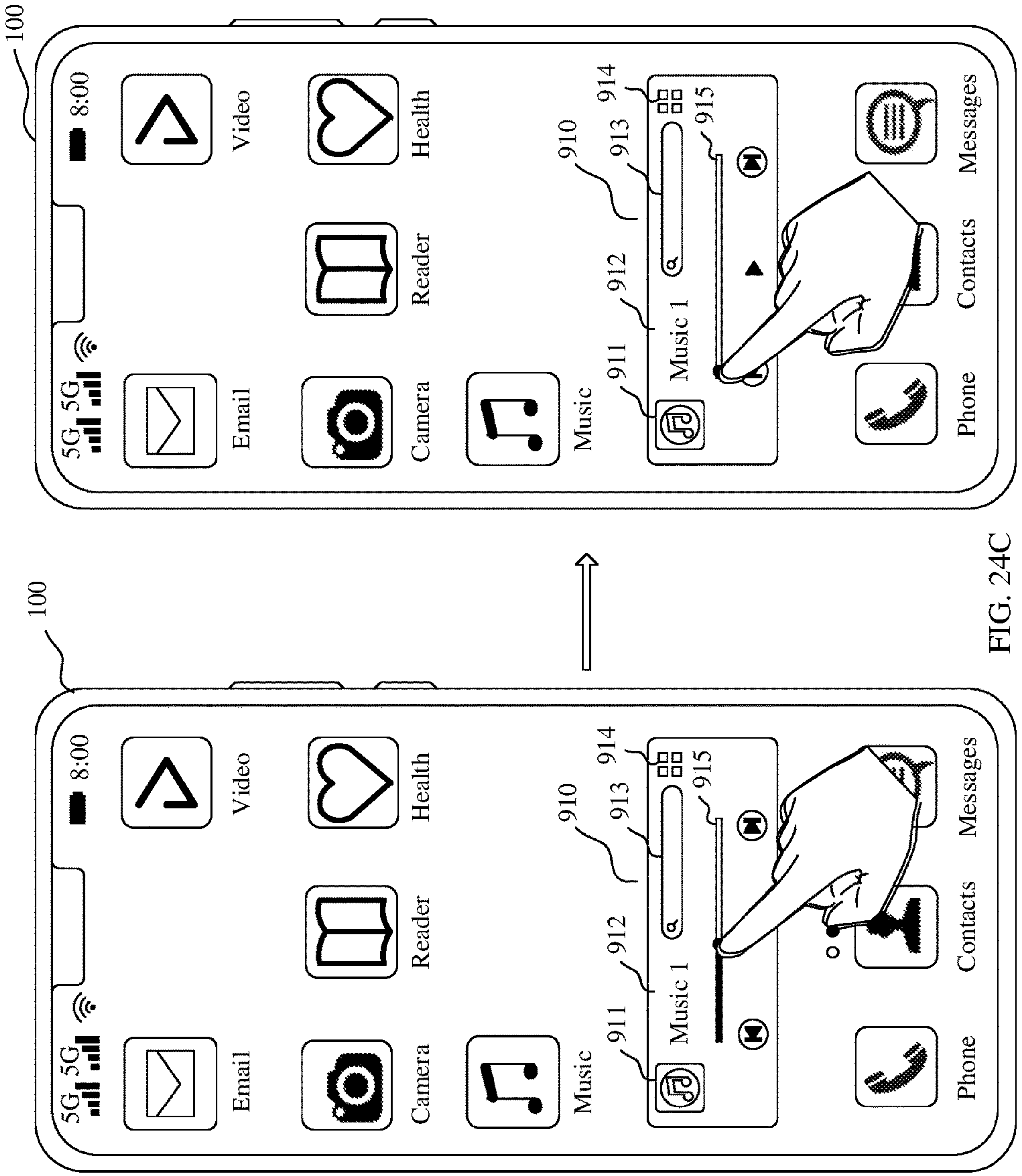
FIG. 24C is a schematic diagram of a scenario example of a user interface implementation method according to an embodiment of this application.

For example, as shown in FIG. 24C, the mobile phone 100 may receive a drag operation performed by the user on the seekbar 915, and adjust a music playing progress.

The user interface implementation method provided in this embodiment of this application further supports application of a customized UI programming capability in an operating system to an application widget, so that a view in the application widget has a visual property, a layout property, an interaction property, an animation property, and a software and hardware dependency property that are extended in the operating system. The layout property refers to a layout of each view on a UI, for example, a shape, a position, and a size of the view. The visual property refers to visual effects such as a color and grayscale of a view. The interaction property refers to a capability of providing a view response based on user behavior, for example, performing a search based on "confirm" behavior of a user. The animation property refers to displaying an animation effect on a view, for example, displaying a click-rebound animation on a view. The software and hardware dependency property refers to software and hardware parameters of a view dependency device. For example, the extended layout property in the operating system may include layout properties such as automatic stretching, hiding, equalization, proportion, extension, or wrapping. The automatic stretching means that a height or width of a view is automatically zoomed in or zoomed out based on a window size, to adapt to the window size. Hiding is a capability of the view visible or gone in the layout. Equalization means that content in the view is evenly distributed in the layout. Proportion means that the view occupies a total layout size according to a specified percentage in a specified direction. Extension means that the view is extended and displayed on the UI based on a display size. Wrapping means that the content in the view is displayed in one or more lines in the layout.

Figure 24D:
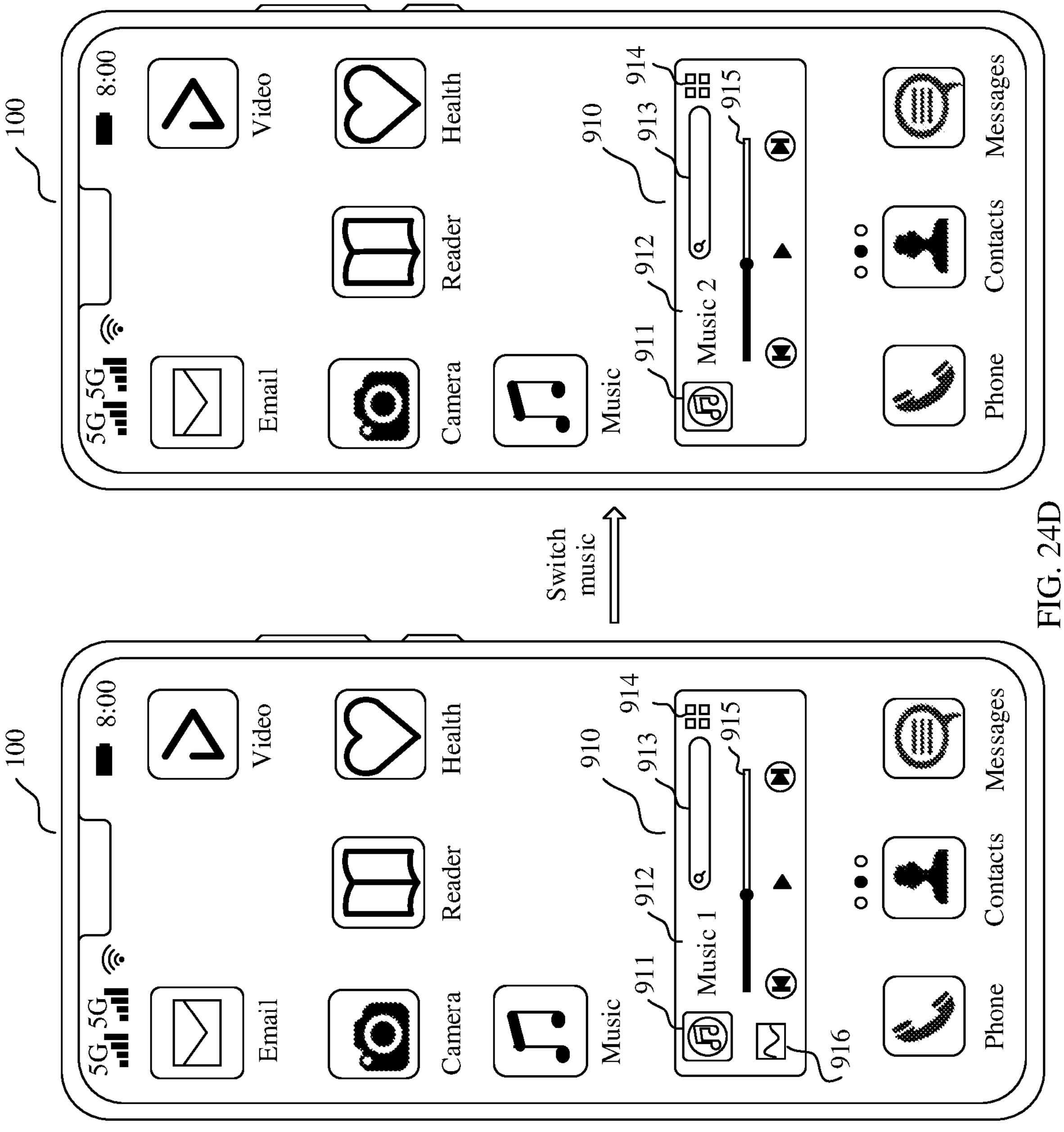
FIG. 24D is a schematic diagram of a scenario example of a user interface implementation method according to an embodiment of this application.

For example, as shown in FIG. 24D, the UI 910 of the music widget may include an image button 916, configured to display lyrics of music. The mobile phone may receive a tap operation performed by the user on the image button 916, and in response to the tap operation performed by the user on the image button 916, the mobile phone displays lyrics of currently played music. The image button 916 may be displayed or not displayed on the UI 910. Whether the image button 916 is displayed depends on whether the currently played music has lyrics. If the currently played music has corresponding lyrics, the image button 916 is displayed on the UI 910. If the currently played music does not have corresponding lyrics, the image button 916 is not displayed on the UI 910. For example, as shown in FIG. 24D, when the currently played music is music 1, the UI 910 includes the image button 916. When the currently played music is music 2, the UI 910 does not include the image button 916.

The user interface implementation method provided in this embodiment of this application further supports application of layout manners and view types that are defined by developers in an app to an application widget.

The developers can apply, based on a design purpose, native layout manners and view types of the Android® system, layout manners and view types defined in the operating system, and layout manners and view types defined in the app to the application widget, to facilitate use by the user.

Figure 25:
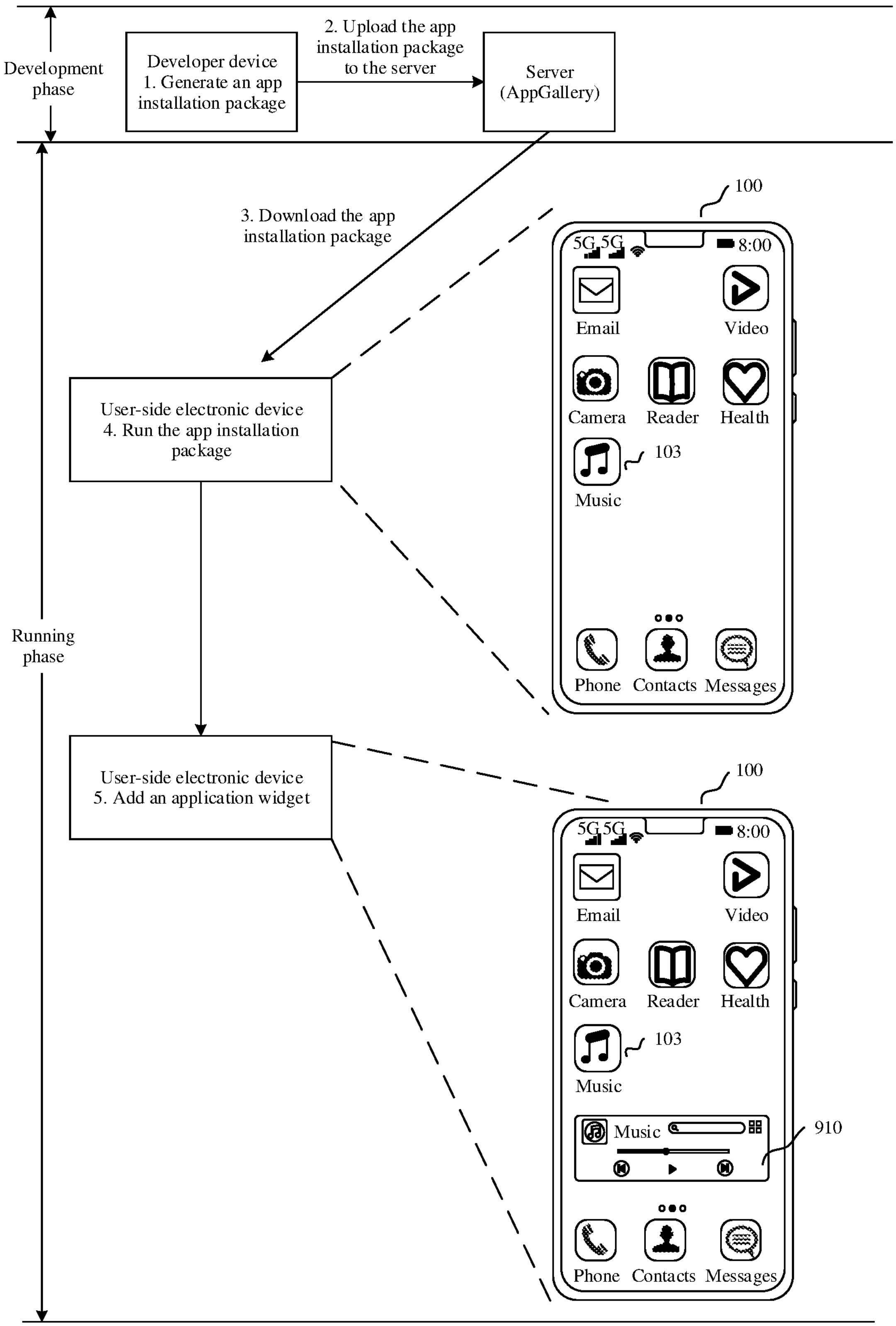
FIG. 25 is a schematic diagram of a user interface implementation method according to an embodiment of this application.

Refer to FIG. 25. In an implementation, in an app development phase, developers open a development tool (for example, DevEco Studio) in the electronic device 200 (developer device), use an interface description language in the development tool, perform interface description and interface behavior definition based on syntactic and semantic specifications of the interface description language, develop a UI, and generate an interface description file and a widget interface description file for release.

For example, the interface description file and the widget interface description file are in a json format. The developers can perform UI layout orchestration, data & interface binding, interaction behavior orchestration, and differentiation description in the interface description file and the widget interface description file. All UIs in the application and the application widget include views. UI layout orchestration is to orchestrate view properties on the UI. Data & interface binding is to declare and specify a binding relationship between an element (such as a view or a view group) on the UI and background data in the interface description file or the widget interface description file. Interaction behavior orchestration is to declare an execution action corresponding to a view response event in the interface description file or the widget interface description file. An event scope supported by a view is determined by event listening supported by the view. For example, if a button (Button) supports setOnClickListener (setOnClickListener), an onClick (click) event can be bound to the view in the interface description file. Differentiation description includes: arranging different code segments for different types of electronic devices, so that UIs of application widgets have different display effects on different types of electronic devices; obtaining values of configuration parameters based on software and hardware conditions of the electronic devices and applying the values to views; defining parameters applicable to apps, and the like.

For example, the user may declare, in the widget interface description file of the music app, the image view 911, the text view 912, the search box 913, the image button 914, the seekbar 915, and the image button 916 shown in FIG. 24A to FIG. 24D, and perform property orchestration on these views, so that the UI 910 of the music widget includes these views. These views can be native views of the Android® system, views defined in the operating system, or views defined in the music app.

The developers can also apply view properties defined in the operating system to these views in the widget interface description file, for example, apply the software dependency property defined in the operating system to the image button 916, and declare that a display property of the image button 916 depends on that music currently played by the app has lyrics.

The developers can also bind views to background data in the widget interface description file. For example, the seekbar 915 is bound to background data. The mobile phone receives a drag operation performed by the user on the seekbar 915, and updates a current music playing progress in the background data based on the drag operation performed by the user on the seekbar 915. If the current music playing progress in the background data changes, the seekbar 915 is updated.

The developers can also declare execution actions corresponding to these view response events in the widget interface description file. For example, the search box 913 is declared to perform a search action in response to a click event.

Then, an app installation package is generated on the developer device, including the interface description file and the widget interface description file. The app installation package is uploaded to a server, and the app is released in an AppGallery provided by the server. A user may download the app installation package in the AppGallery by using a user-side electronic device (the electronic device 100). After running the app installation package, a user-side electronic device obtains the interface description file and the widget interface description file in the installation package. For example, as shown in FIG. 25, after running the installation package of the music app, the mobile phone 100 displays the icon 103 of the music app on the home screen. The mobile phone 100 may receive a tap operation performed by the user on the icon 103, run the music app, and display a UI of the music app on the display based on the interface description file.

Further, the user-side electronic device adds the application widget to the notification bar, the home screen, or the leftmost screen according to a setting of the user. The user-side electronic device generates the UI of the application widget based on the widget interface description file, and displays the UI of the application widget on the notification bar, the home screen, or the leftmost screen. For example, as shown in FIG. 25, the mobile phone 100 displays the UI 910 of the music widget on the home screen.

Figure 26:
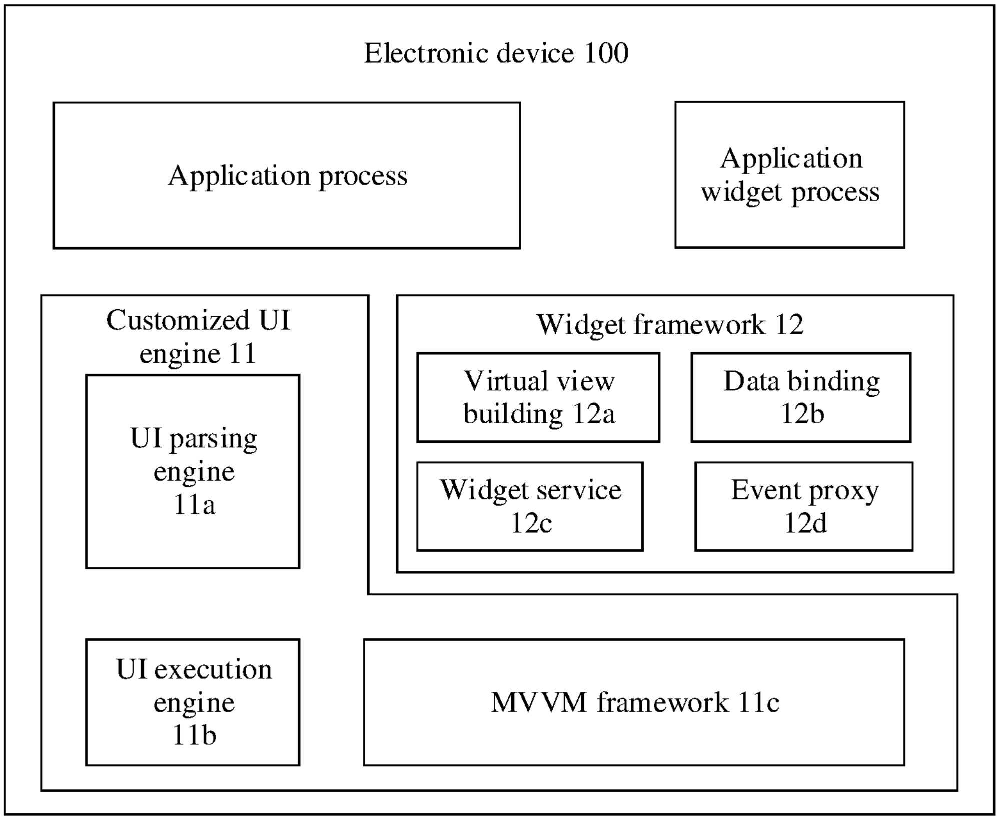
FIG. 26 is a schematic diagram of a user interface implementation method according to an embodiment of this application.

Refer to FIG. 26. An application widget process in the electronic device 100 runs independently of an application process. An application installed on the electronic device 100 runs by invoking an application process, and an application widget runs by invoking an application widget process. For example, if the application widget is set on the home screen, a home screen process is the application widget process. If the application widget is set on the leftmost screen, a leftmost screen display process is the application widget process. If the application widget is set in a specified application, a process of the specified application is the application widget process.

The electronic device 100 further includes units such as the customized UI engine 11 and a widget framework 12.

In some examples, the application process obtains an interface description file of an app, and invokes the customized UI engine 11 to parse and execute the interface description file of the app, to generate a UI of the app. The customized UI engine 11 may include the UI parsing engine 11*a*, the UI execution engine 11*b*, the MVVM (model-view-viewmodel) framework 11*c*, and the like. The UI parsing engine 11*a* is configured to parse the interface description file, and convert content in the interface description file into a data format that matches the UI execution engine 11*b*. In some examples, the UI parsing engine 11*a* may further perform syntax check on content in the interface description file. If the syntax check on the interface description file succeeds, the UI parsing engine 11*a* parses the interface description file; or if the syntax check on the interface description file fails, the UI parsing engine 11*a* does not parse the interface description file. The UI execution engine 11*b* is configured to: build views (instantiated views and property settings) of the UI based on the data parsed by the UI parsing engine 11*a*, perform layout orchestration on the views, and generate an interface declared in the interface description file. The UI execution engine 11*b* may further implement mapping between a component event and user behavior, and execute, in response to the user behavior, an action corresponding to the user behavior defined in the interface description file. The MVVM framework 11*c* is configured to perform bidirectional binding between elements in the UI and background data. In the interface description file, a binding relationship between an element (such as a view or a view group) on the UI and the background data is declared and specified. Optionally, after simple data instances are set, the MVVM framework 11*c* may refresh the background data based on a UI change, and automatically refresh a corresponding UI based on a background data change. This helps the developers focus on UI design and orchestration, simplifies a UI development process, and greatly reduces development time for the developers to implement frontend and backend data interaction.

In some examples, the application process obtains a widget interface description file, and invokes the widget framework 12 to process the widget interface description file, to form widget UI data used to display an application widget UI. The widget framework 12 includes modules such as virtual view building 12*a*, data binding 12*b*, widget service 12*c*, and event proxy 12*d*. The virtual view building 12*a* parses the view interface description file by invoking the UI parsing engine 11*a*, instantiates the parsed view interface description file, and invokes the UI execution engine 11*b* to build an interface, so as to build a view, a view group, and the like, and form the widget UI data. The widget UI data exists in the application process and is bound to background data (such as a view model (ViewModel)). The data binding 12*b* is configured to bind a property, an interaction event, and the like of a view or a view group built by the virtual view building 12*a* to the background data (for example, a view model (ViewModel) for processing service logic, including data processing logic related to a virtual object). The widget service 12*c* is configured to track and process a currently processed object and data (model) bound to the object in a process of generating the application widget UI; and is further configured to manage data transmission between the application process and the application widget process; and is further configured to manage a cross-process event proxy, and send and receive a cross-process event. The event proxy 12*d* is configured to process backhaul and response of an event in the application widget process. For example, a dedicated event transmission class (for example, HiAction) is defined in the event proxy 12*d*. The event transmission class supports implementation of a Parcelable interface, and may perform cross-process transmission (for example, invoke a native cross-process Binder mechanism of Android®). A series of events are stored in the event transmission class, and each event includes information such as a layout identifier, a view identifier, and an event type. When a user performs an operation on the application widget, the application widget process receives the operation and triggers an interaction event, that is, adds an event to HiAction. The application widget process transmits the added event to the application process. The application process performs a corresponding action in response to the event. The application process further invokes the MVVM framework for processing. If data or a view property changes, the widget UI data is updated, cross-process interface data and properties are updated, and a display interface of the application widget process is further updated. In an implementation, the application process further sends the widget interface description file to the application widget process. The application widget process invokes the widget framework 12 to process the widget interface description file to form widget UI data, and displays the widget UI data, that is, displays the application widget IU.

An application is installed on the electronic device, and the user may add an application widget corresponding to the application to the notification bar, the home screen, or the leftmost screen.

Figure 27A:
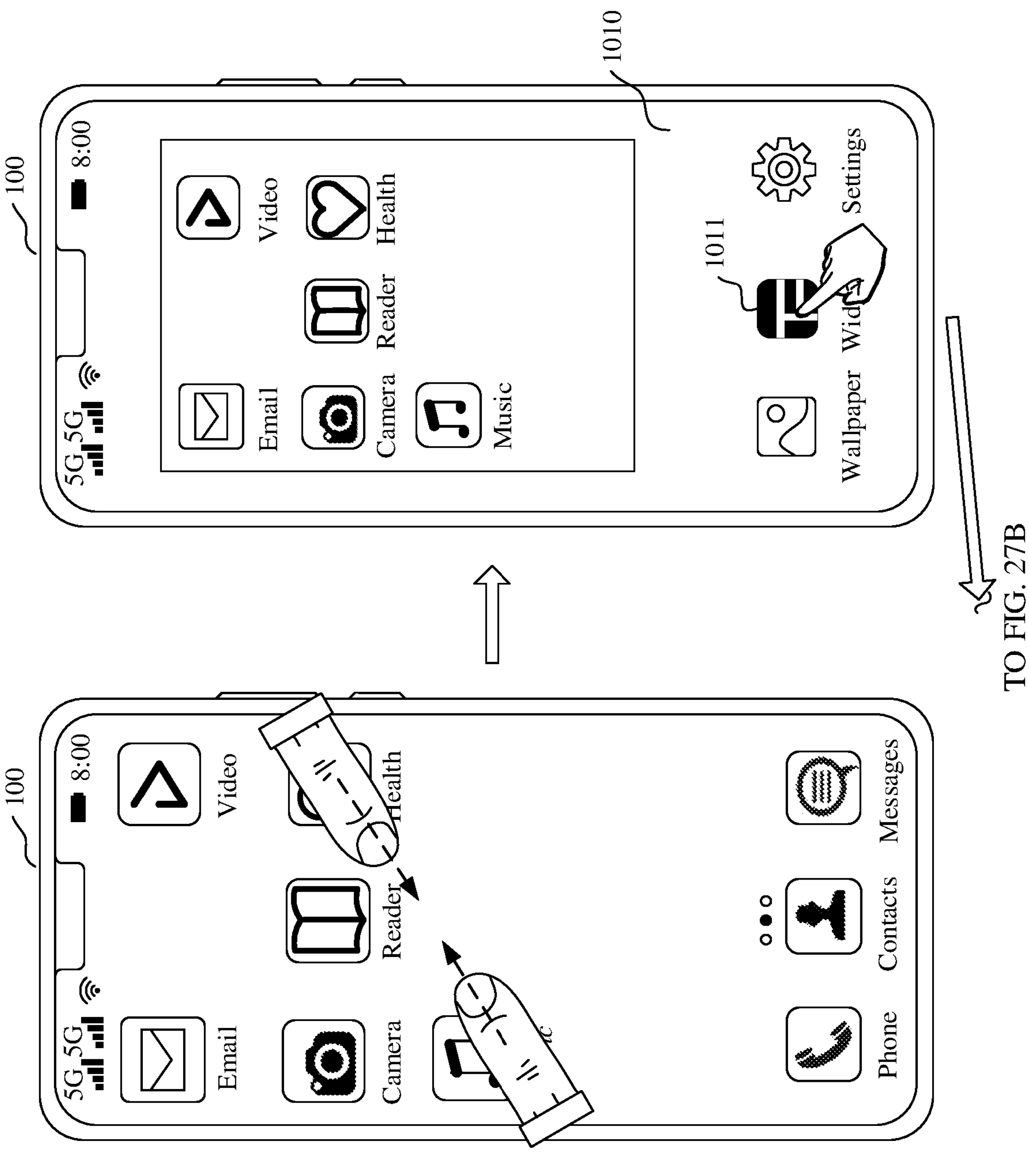
FIG. 27A and FIG. 27B are a schematic diagram of a scenario example of a user interface implementation method according to an embodiment of this application.
Figure 27B:
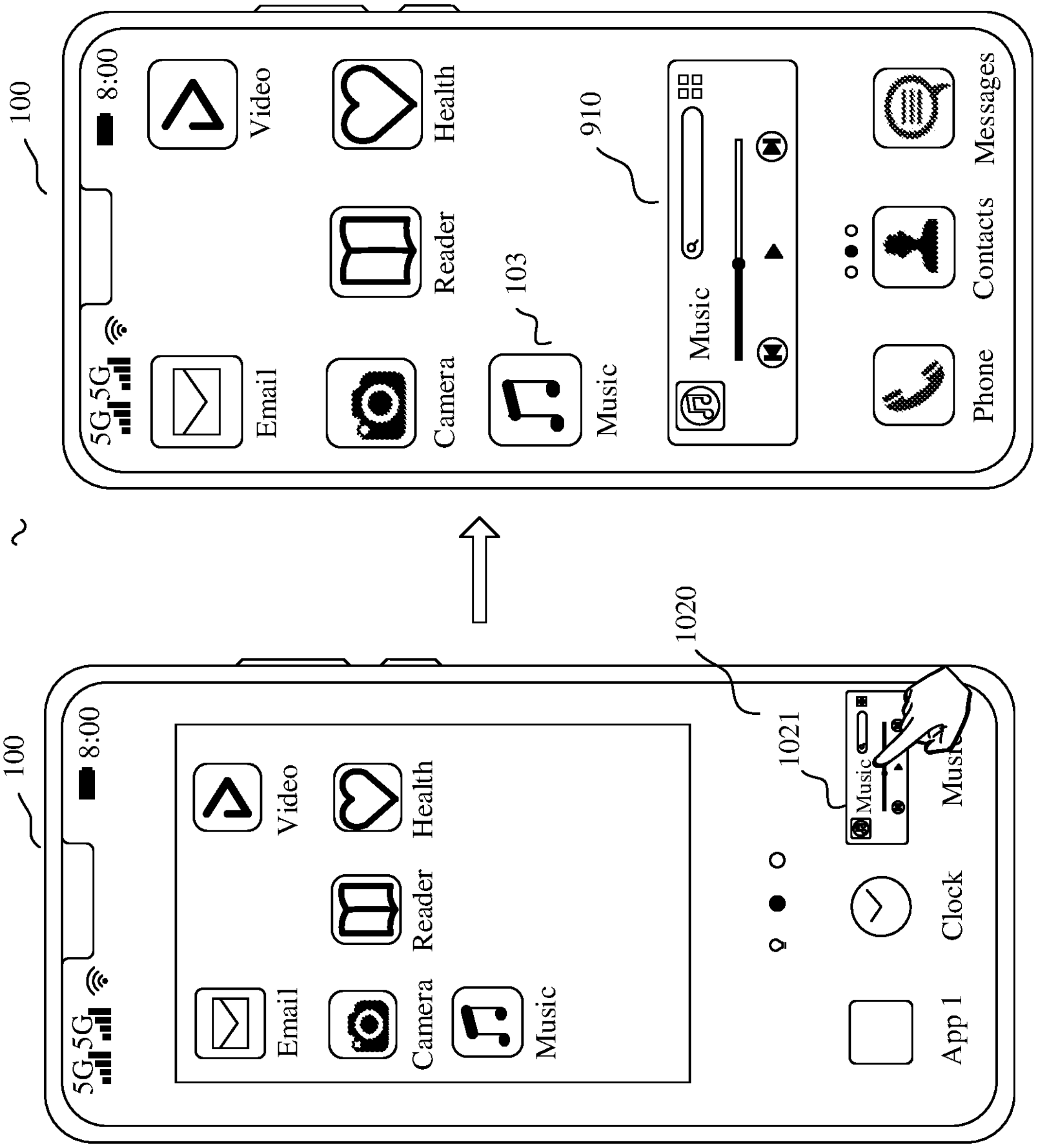

In some embodiments, the user does not open the application, and separately adds an application widget corresponding to the application. For example, refer to FIG. 27A and FIG. 27B. The mobile phone 100 receives a two-finger pinch operation of a user on the home screen. The mobile phone 100 displays a shortcut settings interface 1010 in response to the two-finger pinch operation on the home screen. The shortcut settings interface 1010 includes a "Window widget" option 1011, used to add a home screen widget to the home screen. The mobile phone 100 may display a home screen widget adding interface 1020 in response to a tap operation performed by the user on the "Window widget" option 1011. The home screen widget adding interface 1020 includes a "Music" option 1021, configured to add a music widget to the home screen. The mobile phone 100 receives a tap operation performed by the user on the "Music" option 1021, and in response to the tap operation performed by the user on the "Music" option 1021, a UI 910 of the "music widget" is displayed on the home screen of the mobile phone 100.

Figure 28:
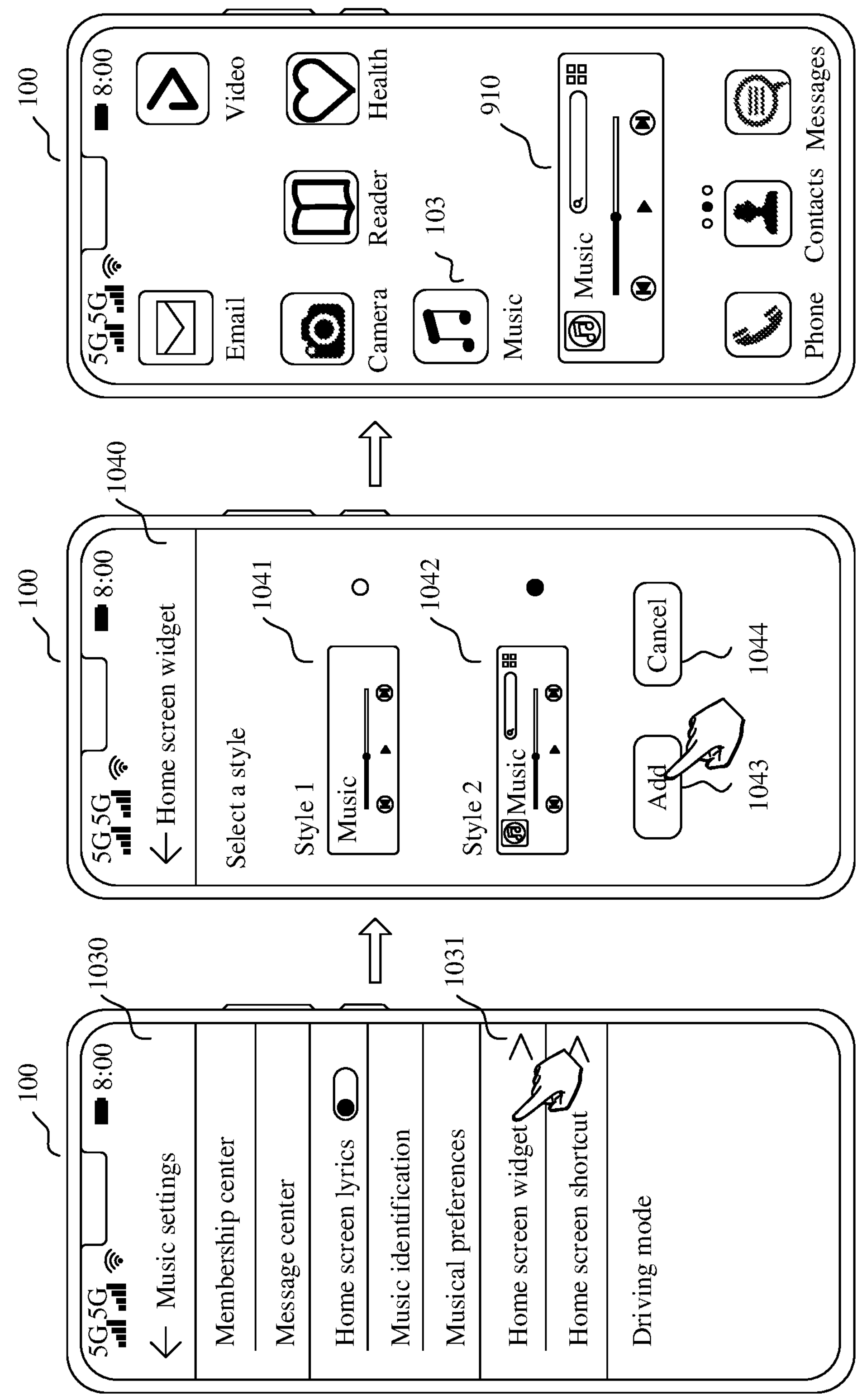
FIG. 28 is a schematic diagram of a scenario example of a user interface implementation method according to an embodiment of this application.

In some other embodiments, the user adds a corresponding application widget to the application. For example, as shown in FIG. 28, the user opens a "Music setting" interface 1030 of the "Music" application on the mobile phone 100. The "Music setting" interface 1030 includes a "Home screen widget" option 1031. The "Home screen widget" option 1031 is used to add the music widget to the home screen of the mobile phone. The mobile phone 100 receives a tap operation performed by the user on the "Home screen widget" option 1031, and in response to the tap operation performed by the user on the "Home screen widget" option 1031, the mobile phone 100 displays a "Home screen widget" interface 1040. The "Home screen widget" interface 1040 includes a "Style 1" option 1041 and a "Style 2" option 1042, and further includes an "Add" button 1043 and a "Cancel" button 1044. The user may tap the "Add" button 1043 to add the music widget to the home screen by using an interface corresponding to the "Style 1" option 1041 or the "Style 2" option 1042; or may tap the "Cancel" button 1044 to exit adding the music widget. For example, the mobile phone 100 receives a tap operation performed by the user on the "Add" button 1043, and adds, based on a selection of the user, the music widget to the home screen by using an interface corresponding to the "Style 2" option 1042. The UI 910 of the "music widget" is displayed on the home screen of the mobile phone 100.

Figure 29A:
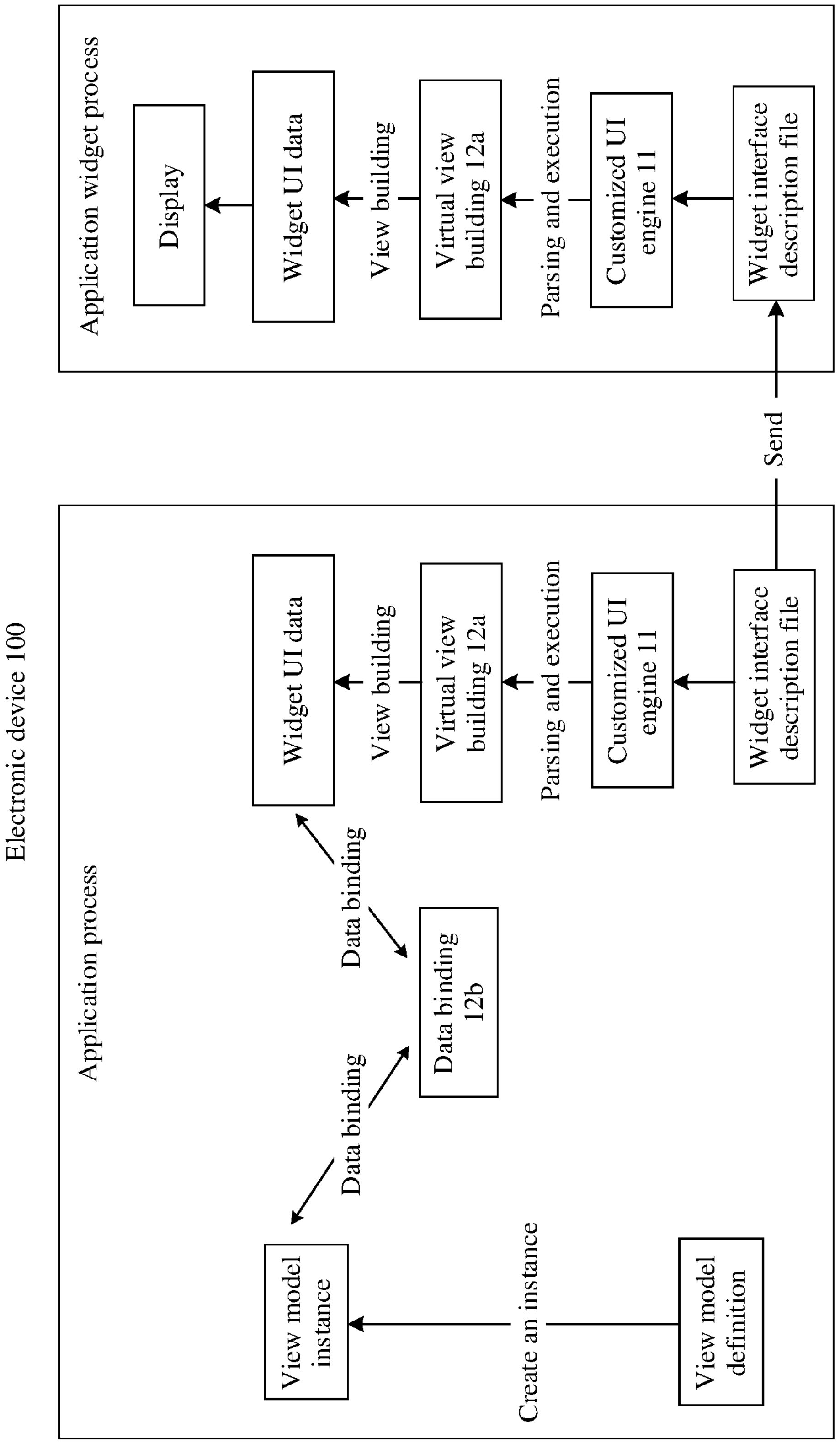
FIG. 29A is a schematic diagram of a user interface implementation method according to an embodiment of this application.

Refer to FIG. 29A. In an implementation, a user performs an operation of adding an application widget. An application widget process of the electronic device 100 receives an operation of adding an application widget by the user (for example, a tap operation of the user on the "Music" option 1021 in FIG. 27A and FIG. 27B), and the application widget process notifies an application process that the operation of adding an application widget by the user is received. If the application process is in a non-started state, the electronic device 100 starts the application process, so that the application process runs in the background. Alternatively, the application process of the electronic device 100 receives an operation of adding an application widget by the user (for example, a tap operation of the user on the "Add" button 1043 in FIG. 28), and the application process notifies the application widget process that the operation of adding an application widget by the user is received.

The application process obtains a widget interface description file from an application installation package. The application process invokes the customized UI engine 11 to parse and execute the widget interface description file, then invokes the virtual view building 12*a* to build a widget UI data view, generates a view, a view group, and the like based on a layout orchestration in the widget interface description file, and forms widget UI data (including information such as a widget and a widget layout).

It should be noted that the widget interface description file may be a file independent of an interface description file, or may be a code segment in the interface description file. Optionally, after obtaining the widget interface description file, the electronic device 100 may parse and execute only some code segments in the widget interface description file. For example, the user selects the music widget interface corresponding to the "Style 1" option 1041 in FIG. 28. After receiving a tap operation performed by the user on the "Add" button 1043, the mobile phone 100 parses and executes a code segment corresponding to the "Style 1" in the widget interface description file. The user selects the music widget interface corresponding to the "Style 2" option 1042 in FIG. 28. After receiving a tap operation performed by the user on the "Add" button 1043, the mobile phone 100 parses and executes a code segment corresponding to the "Style 2" in the widget interface description file.

Then, the data binding 12*b* invokes the MVVM framework 11*c* to perform data binding between the widget UI data and the background data (for example, the view model). In this way, if the background data changes, the corresponding widget UI data may be refreshed; or if the widget UI data changes, the corresponding background data may be refreshed.

Further, the application process sends the widget interface description file to the application widget process.

The application widget process invokes the customized UI engine 11 to parse and execute the widget interface description file, then invokes the virtual view building 12*a* to build a widget UI data view, generates a view, a view group, and the like based on a layout orchestration in the widget interface description file, forms widget UI data (including information such as a widget and a widget layout), and displays the widget UI data, that is, displays the application widget UI. Because a same code segment is used by the application process to generate the widget UI data and the application widget process to generate the application widget UI, views on the application widget UI are in a one-to-one correspondence with views in the widget UI data.

Figure 29B:
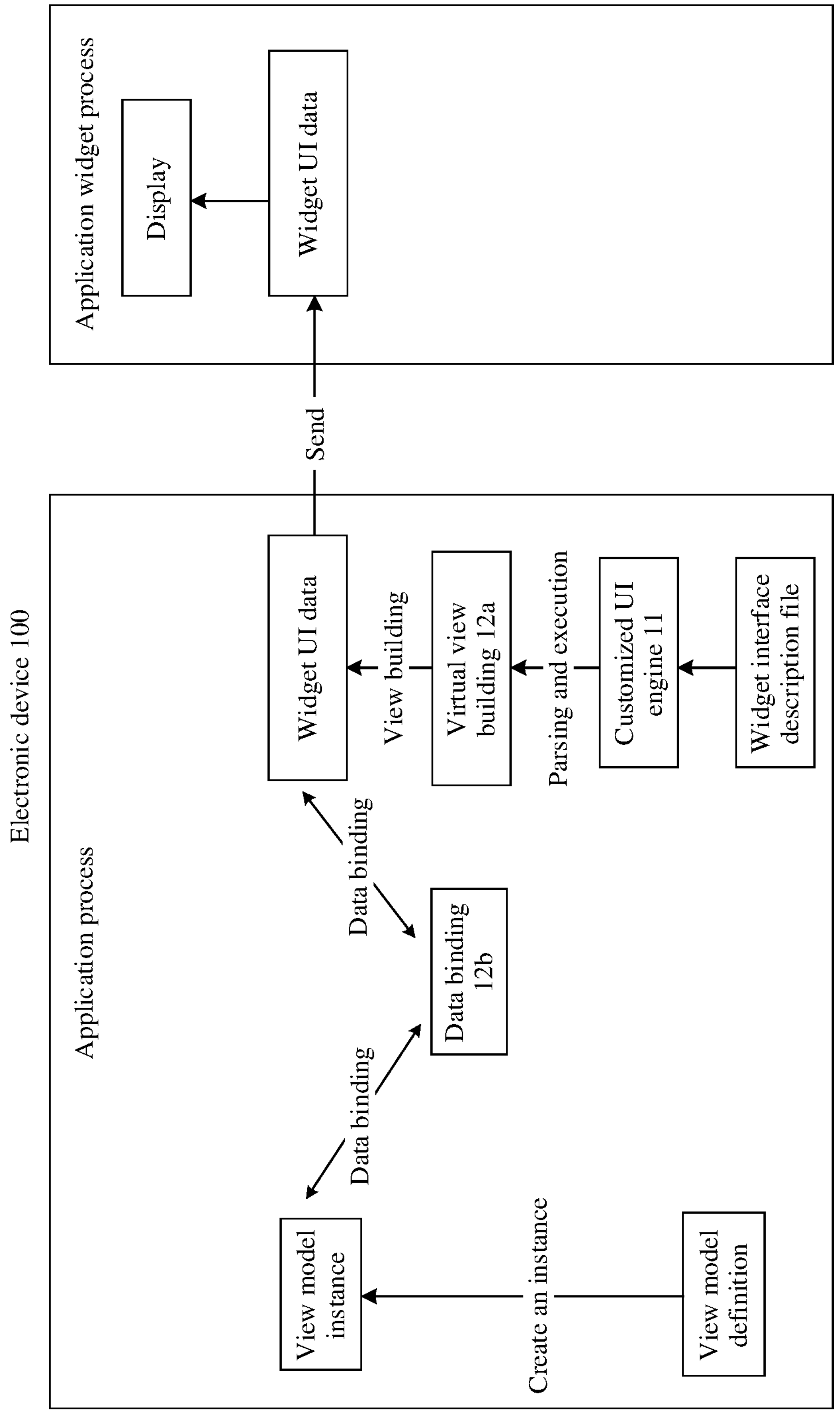
FIG. 29B is a schematic diagram of a user interface implementation method according to an embodiment of this application.

Optionally, as shown in FIG. 29B, the application process may also send the widget UI data to the application widget process after generating the widget UI data, and the application widget process displays the widget UI data, that is, displays the application widget UI. In this way, the views on the application widget UI are also in a one-to-one correspondence with the views in the widget UI data.

After an application widget is added to the notification bar, the home screen, or the leftmost screen, the user can perform an operation on the application widget UI. For example, the user may drag the seekbar 915 on the UI 910 of the music widget in FIG. 24A to adjust a playback progress of the music currently played on the music application.

Figure 29C:
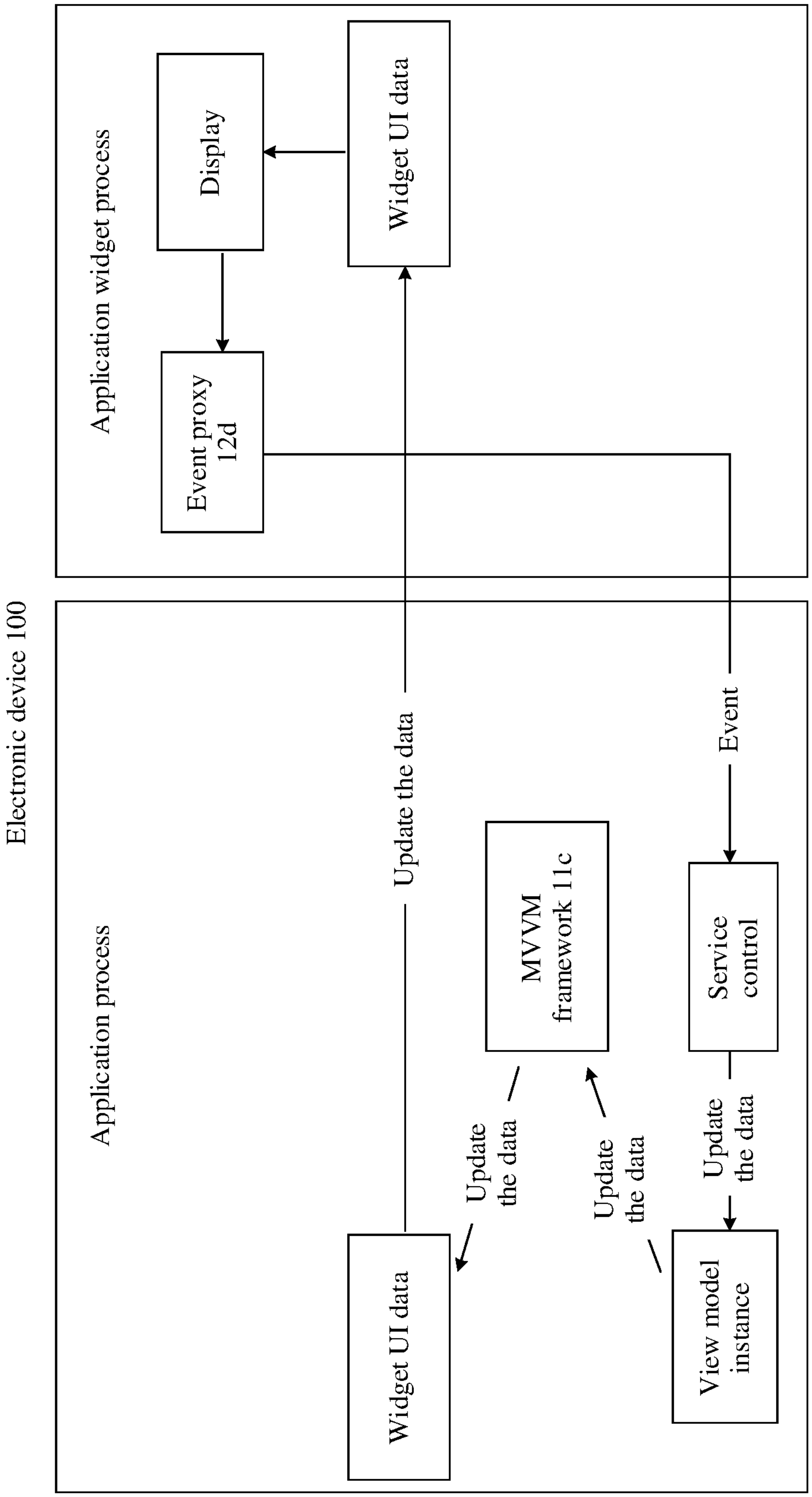
FIG. 29C is a schematic diagram of a user interface implementation method according to an embodiment of this application.

Refer to FIG. 29C. In an implementation, when the user performs an operation on the UI of the application widget, the application widget process receives the user operation, and transmits the user operation to the event proxy 12*d*. A dedicated event transmission class is defined in the event proxy 12*d*, and the event transmission class is used for cross-process transmission. A plurality of events are stored in the event transmission class, and each event includes information such as a layout identifier, a view identifier, and an event type. After receiving the user operation, the event proxy 12*d* generates an event corresponding to the operation in the event transmission class, and sends the event to the application process (if the application process is not started, the application process is started, so that the application process runs in the background). After receiving the event, the application process obtains a corresponding view based on the layout identifier and the view identifier, and executes corresponding service logic based on the event acting on the view. Because the views on the application widget UI are in a one-to-one correspondence with the views in the widget UI data, the application process further refreshes the background data based on the received event. The background data change triggers the widget UI data update. The application process may further send the updated widget UI data to the application widget process, and the application widget process displays the updated application widget UI based on the refreshed widget UI data.

Figure 29D:
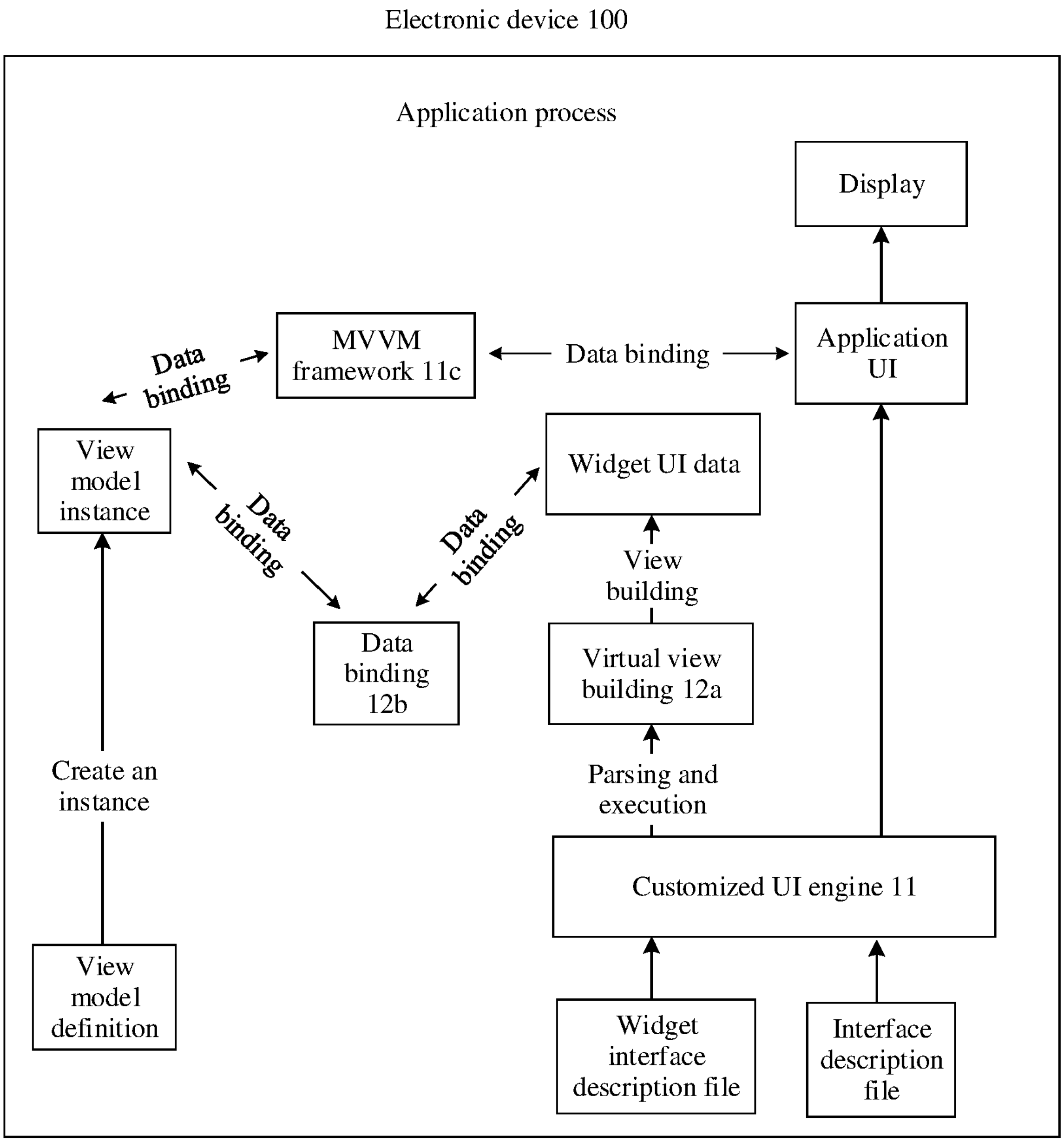
FIG. 29D is a schematic diagram of a user interface implementation method according to an embodiment of this application.

Refer to FIG. 29D. In some embodiments, an application process is started, and the application process obtains an interface description file. The application process invokes the customized UI engine 11 to parse and execute the interface description file, generate a UI of the application, and display the UI of the application. Then, the MVVM framework 11$c$ performs data binding between the UI of the application and background data (for example, a view model).

The application process receives an operation of adding an application widget by a user, and the application process obtains a widget interface description file from an application installation package. The application process invokes the customized UI engine 11 to parse and execute the widget interface description file, then invokes the virtual view building 12$a$ to build a widget UI data view, generates a view, a view group, and the like based on a layout orchestration in the widget interface description file, and forms widget UI data (including information such as a widget and a widget layout). Then, the data binding 12$b$ invokes the MVVM framework 11$c$ to perform data binding between the widget UI data and the background data (for example, the view model). Further, the application widget process displays the UI of the application widget based on the widget UI data.

In this way, a display of the electronic device 100 displays the UI of the application and the UI of the corresponding application widget.

Figure 30:
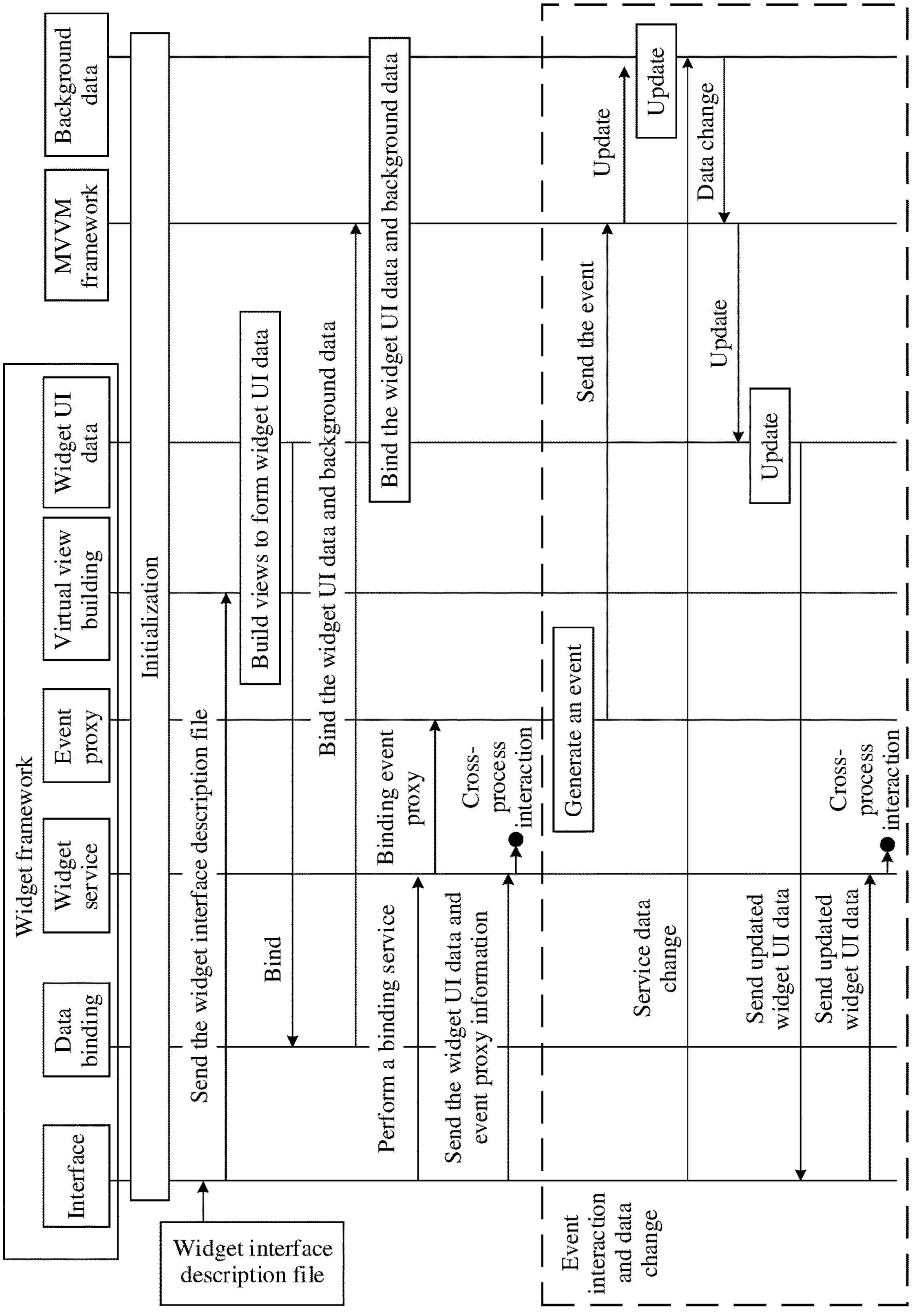
FIG. 30 is a schematic flowchart of a user interface implementation method according to an embodiment of this application.

In an example, FIG. 30 shows an example of a procedure of a user interface implementation method according to an embodiment of this application.

A user performs an operation of adding an application widget. An application widget process of the electronic device 100 receives an operation of adding an application widget by the user (for example, a tap operation of the user on the "Music" option 1021 in FIG. 27A and FIG. 27B), and the application widget process notifies an application process that the operation of adding an application widget by the user is received. If the application process is in a non-started state, the electronic device 100 starts the application process, so that the application process runs in the background. Alternatively, the application process of the electronic device 100 receives an operation of adding an application widget by the user (for example, a tap operation of the user on the "Add" button 1043 in FIG. 28), and the application process notifies the application widget process that the operation of adding an application widget by the user is received. Modules such as a widget framework, an MVVM framework, and background data are initialized. The widget framework obtains a widget interface description file from an application installation package and sends the file to a virtual view building module. The virtual view building module builds views based on the widget interface description file to form widget UI data. A data binding module invokes the MVVM framework to bind the widget UI data to background data. The application process invokes a widget service to perform a binding service. The widget service binds the widget UI data to an event proxy. Then, information such as the widget UI data and the event proxy of the widget UI data are sent across processes. In this way, after receiving the widget UI data and the event proxy information of the widget UI data, the application widget process may display the application widget UI based on the widget UI data.

After the application widget is added successfully, the user can perform an operation on the application widget UI. The application widget process receives the operation performed by the user on the application widget UI. The event proxy adds an event corresponding to the operation and sends the event to the application process. The application process executes service logic in response to the event, and invokes the MVVM framework to update the background data. When the service data of an application changes, the background data change causes the MVVM framework to update the widget UI data. The application process sends the updated widget UI data across processes. After receiving the updated widget UI data, the application widget process may display an updated application widget UI based on the updated widget UI data.

According to the user interface implementation method provided in this embodiment of this application, the application process generates the widget UI data based on the widget interface description file, and sends the widget interface description file or the widget UI data to the application widget process. The application widget process generates the application widget UI based on the widget interface description file or the widget UI data. Developers can declare native layout manners and view types of the Android® system in the widget interface description file, and can also declare customized view types and UI programming capabilities in an operating system, and layout manners and view types defined by the developers in an app. The operating system allows the application widget process to invoke the UI engine to parse and execute the widget interface description file and generate the application widget UI. In this way, various layout manners and view types can be displayed on the UI of the application widget, thereby facilitating use of the application widget by the user and improving user experience.

Figure 31:
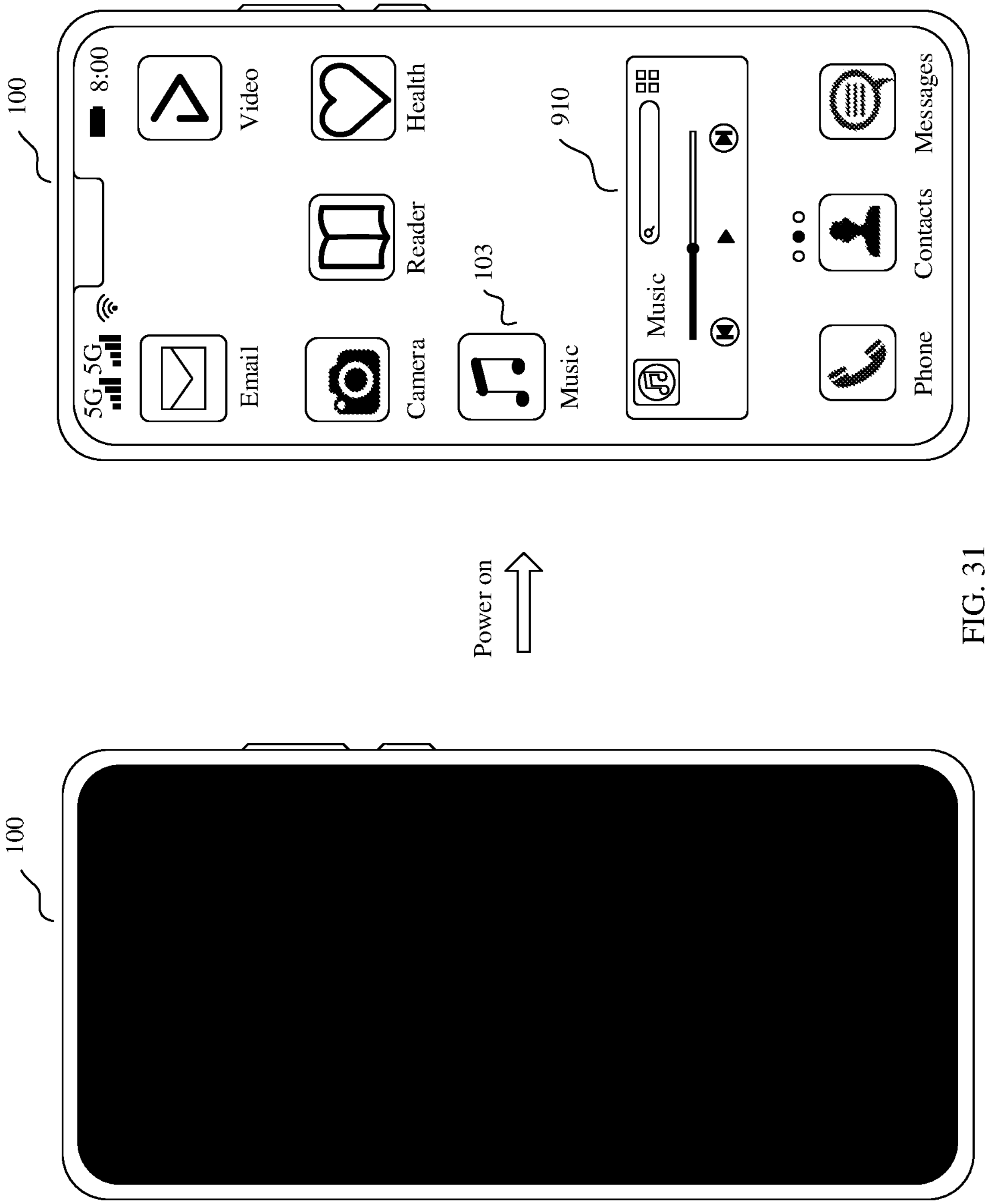
FIG. 31 is a schematic diagram of a scenario example of a user interface implementation method according to an embodiment of this application.

In some embodiments, after the application widget is added to the electronic device, the electronic device is powered off. After the electronic device is powered on again, the UI of the application widget is displayed. That is, after adding the application widget, the electronic device reloads the application widget UI. As shown in FIG. 31, the mobile phone 100 is powered on, and the UI 910 of the music widget is displayed on the home screen of the mobile phone 100.

Figure 32:
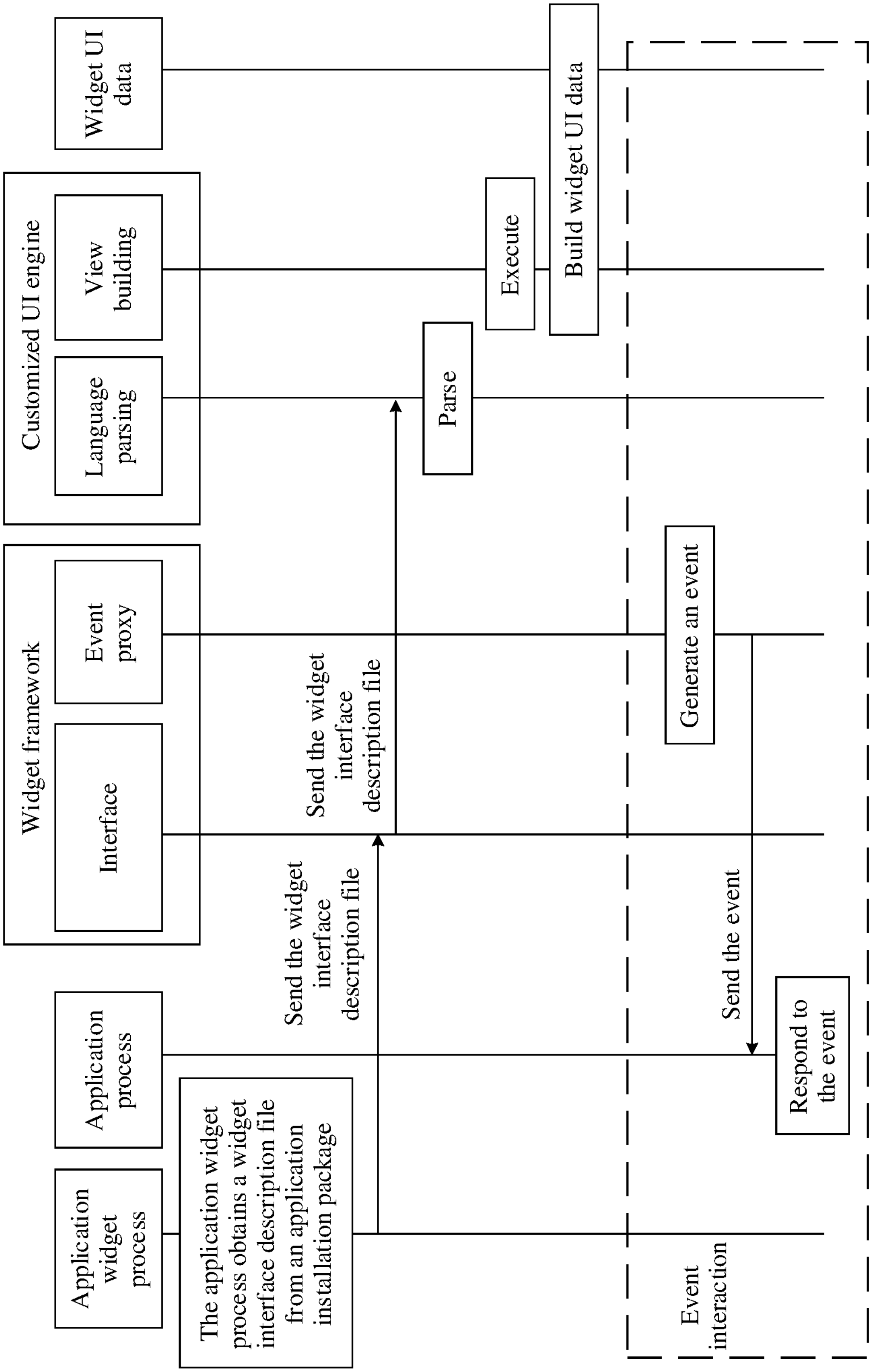
FIG. 32 is a schematic flowchart of a user interface implementation method according to an embodiment of this application.

In an example, FIG. 32 shows an example of a procedure of a method for reloading an application widget UI by an electronic device.

After the electronic device is powered on, an application widget process is started. The application widget process obtains a widget interface description file from an application installation package. The application widget process invokes a customized UI engine to parse and execute the widget interface description file, forms widget UI data, and displays an application widget UI based on the widget UI data.

After the application widget is reloaded successfully, a user can perform an operation on the application widget UI. The application widget process receives the operation performed by the user on the application widget UI. An event proxy adds an event corresponding to the operation and starts an application process, so that the application process runs in the background of a system. The event is sent to the application process. The application process executes corresponding service logic in response to the event, and invokes an MVVM framework to update background data. For a processing procedure of event interaction and a background data change, refer to related descriptions in FIG. 30. Details are not described herein again.

In this scenario, the application widget process generates, draws, and loads the application widget UI. Processes such as generating the widget UI data by the application process, binding the widget UI data and the background data, and establishing a correspondence between the widget UI data and the application widget UI data may not be executed.

According to the user interface implementation method provided in this embodiment of this application, the application process of the electronic device generates the widget UI data based on the widget interface description file, and binds the widget UI data to the background data. The application widget process also obtains the widget UI data based on the widget interface description file, and displays the widget UI data as the UI of the application widget. In this way, a correspondence is established between the UI of the application widget and the background data, and various layout manners and view types can be displayed on the UI of the application widget, thereby facilitating use of the application widget by the user and improving user experience.

An embodiment of this application further provides a user interface implementation method, used to present a UI when an app on an electronic device is projected to a playback device for playing.

With the rapid development of the Internet of Things (Internet of Things, IoT), both the type and quantity of IoT devices increase rapidly. A consumer may use a device such as a mobile phone or a tablet computer as a control device of an IoT device to control the IoT device, so that the control device and the IoT device work collaboratively. For example, when the user uses an app on the control device, the user may project the app to the IoT device for playing (the IoT device is referred to as a playback device). For example, because a screen size of a television is relatively large, better viewing experience can be brought to the user, and the user may project an app on the mobile phone to the television for playing. Because screen forms and sizes of IoT devices differ greatly, how to perform projection on IoT devices with screens of various forms and sizes to obtain a projection interface that matches the screen forms and sizes of the IoT devices is a problem that needs to be resolved.

Embodiments of this application provide a user interface implementation method and an apparatus, to support projection of various UIs on a control device to an IoT device for playing, thereby improving user experience. The control device is the user-side electronic device (the electronic device 100) in the foregoing embodiments.

Figure 33A:
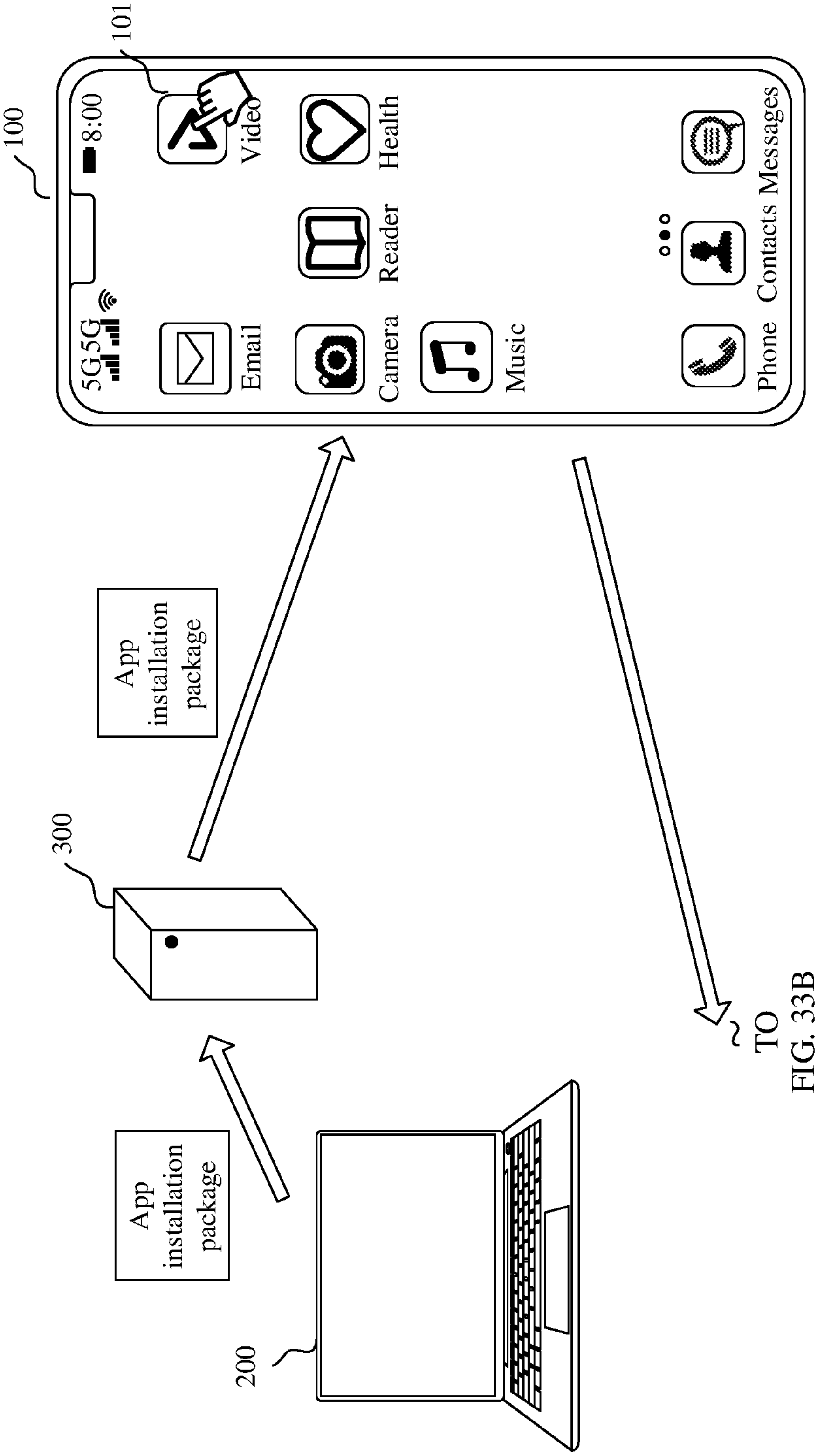
FIG. 33A to FIG. 33C are a schematic diagram of a scenario of a user interface implementation method according to an embodiment of this application.
Figure 33B:
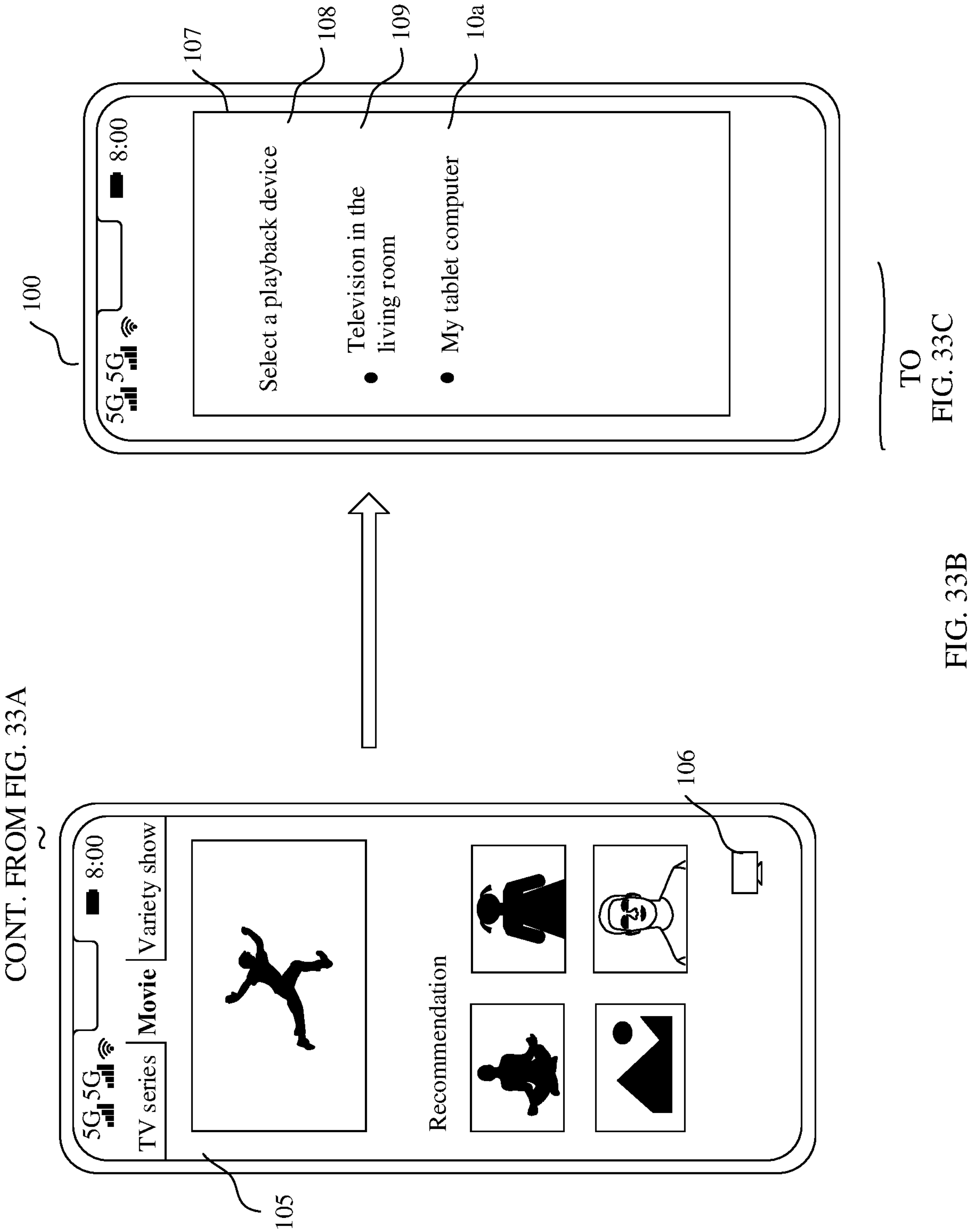
Figure 33C:
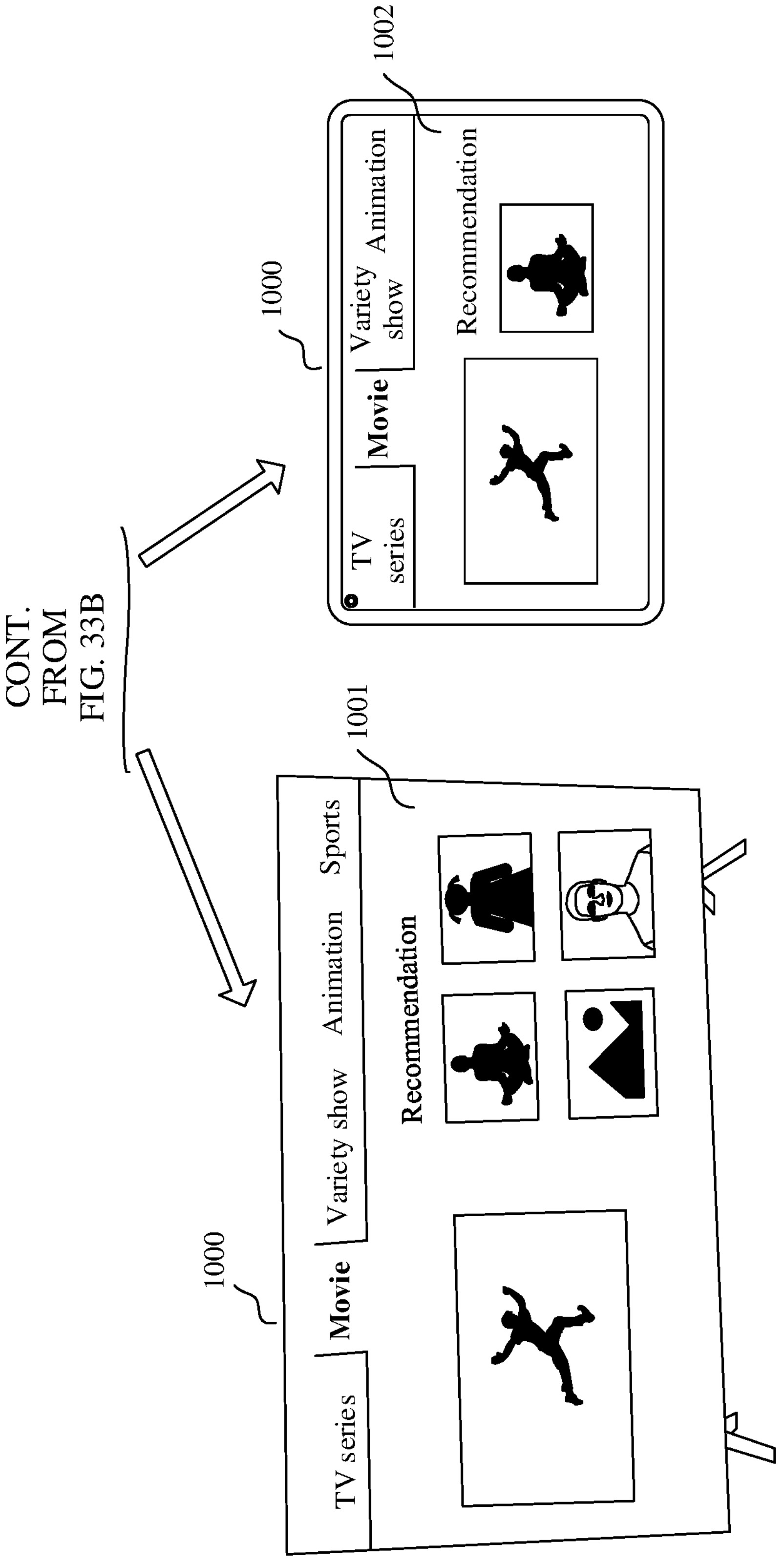

An embodiment of this application provides a user interface implementation method. Refer to FIG. 33A to FIG. 33C. An application development tool (for example, Android Studio or DevEco Studio) is installed on the electronic device 200. The electronic device 200 in this application may also be referred to as a developer device. Generally, developers use an interface description language to develop a UI of an app and a playback end UI in the application development tool. It may be understood that, in some embodiments, the developers may directly develop the UI of the app and the playback end UI on the control device 100, and run the app on the control device 100. That is, the electronic device 200 and the control device 100 may be a same electronic device. This is not limited in this embodiment of this application.

In some embodiments, the developers develop, in the application development tool, the UI of the app (that is, the UI displayed when the electronic device installs and runs the app), to form an interface description file. The interface description file in this application may also be referred to as a description file. The developers also develop an app UI (that is, a playback end UI) to be displayed on a playback end in the application development tool to form a playback end interface description file. The developers pack the interface description file and the playback end interface description file into an installation package of the app, and release the app in an AppGallery provided by the server 300. The AppGallery may provide an installation package of each app for a user to download. For example, the installation package may be an Android® application package (Android application package, APK) file.

For example, a mobile phone is the control device 100. A user may download an installation package of an app from the AppGallery by using the mobile phone. A video app is used as an example. After the mobile phone downloads an installation package of the video app, the video app may be installed on the mobile phone by running the installation package. In this way, the mobile phone also obtains the interface description file and the playback end interface description file in the installation package.

Optionally, in some embodiments, the interface description file may also be used as the playback end interface description file, that is, the interface description file and the playback end interface description file are a same file.

The mobile phone may present a UI of a corresponding app on a display based on the interface description file. For example, after the mobile phone downloads the installation package of the video app, the "Video" icon 101 is generated on the home screen. The user may tap the "Video" icon 101 to open the video app. In response to a tap operation performed by the user on the "Video" icon 101, the mobile phone runs the video app. An OS platform is installed on the mobile phone. The customized UI engine of the OS platform reads the interface description file, parses and executes the interface description language, and renders the UI of the video app based on the interface description in the interface description file. A display apparatus (for example, a display) of the mobile phone presents a UI 105 of the video app. Further, the interface description file may further include a definition of interface behavior. The mobile phone may perform, in response to an operation performed by the user on the UI 105, a corresponding interface action based on interface behavior defined in the interface description file, to implement the interface behavior. Generally, the OS platform has a corresponding programming language used to implement interface behavior, implement a dynamic change of the UI 105, and respond to the operation of the user on the UI 105. For example, Android® uses JAVA, and iOS® uses a swift programming language to implement interface behavior.

The mobile phone may further project each interface of the video app to a playback device 1000 for display. For example, a home screen or a playback screen of the video app is projected to the playback device 1000. The playback device 1000 renders a corresponding playback end UI based on an interface description that matches a device type and that is in the playback end interface description file. For example, still refer to FIG. 33A to FIG. 33C. The UI 105 of the video app includes a "projection" button 106. The "projection" button 106 is used to project an interface of an app running on the mobile phone to the playback device for display. The mobile phone receives a tap operation performed by the user on the "projection" button 106, and in response to the tap operation performed by the user on the "projection" button 106, the mobile phone displays a device selection interface 107. The device selection interface 107 includes prompt information 108, used to prompt the user to select a playback device for projection. The device selection interface 107 further includes a "Television in the living room" option 109 and a "My tablet computer" option 10*a*. The user may tap the "Television in the living room" option 109, to project the UI of the video app to the smart television for display. The mobile phone receives a tap operation performed by the user on the "Television in the living room" option 109, and in response to the tap operation performed by the user on the "Television in the living room" option 109, the mobile phone projects the UI of the video app to the smart television. The smart television displays a playback end UI 1001 corresponding to the UI 105. The user may also tap the "My tablet computer" option 10*a*, to project the UI of the video app to the tablet computer for display. The mobile phone receives a tap operation performed by the user on the "My tablet computer" option 10*a*, and in response to the tap operation performed by the user on the "My tablet computer" option 10*a*, the mobile phone projects the UI of the video app to the tablet computer. The tablet computer displays a playback end UI 1002 corresponding to the UI 105. Device types of the smart television and the tablet computer are different, and screen sizes and forms are also different. An interface layout of the playback end UI 1001 on the smart television is different from that of the playback end UI 1002 on the tablet computer. In other words, the playback end UI is differentially displayed on electronic devices of different device types.

The playback device 1000 may include a portable computer (such as a mobile phone), a smart home device (such as a smart television, a smart screen, a large screen, or a smart speaker), a handheld computer, a personal digital assistant (personal digital assistant, PDA), a wearable device (such as a smartwatch or a smart band), a tablet computer, a notebook computer, a netbook, an augmented reality (augmented reality, AR)/virtual reality (virtual reality, VR) device, a vehicle-mounted computer, or the like. This is not limited in this embodiment of this application. In an example, the playback device 1000 may include the structure shown in FIG. 2. Details are not described herein again. It may be understood that a structure shown in this embodiment of this application in FIG. 2 does not constitute a specific limitation on the playback device 1000. In some other embodiments of this application, the playback device 1000 may include more or fewer components than those shown in FIG. 2, or combine some components, or split some components, or have different component arrangements. The components shown in FIG. 2 may be implemented by using hardware, software, or a combination of software and hardware.

Figure 34:
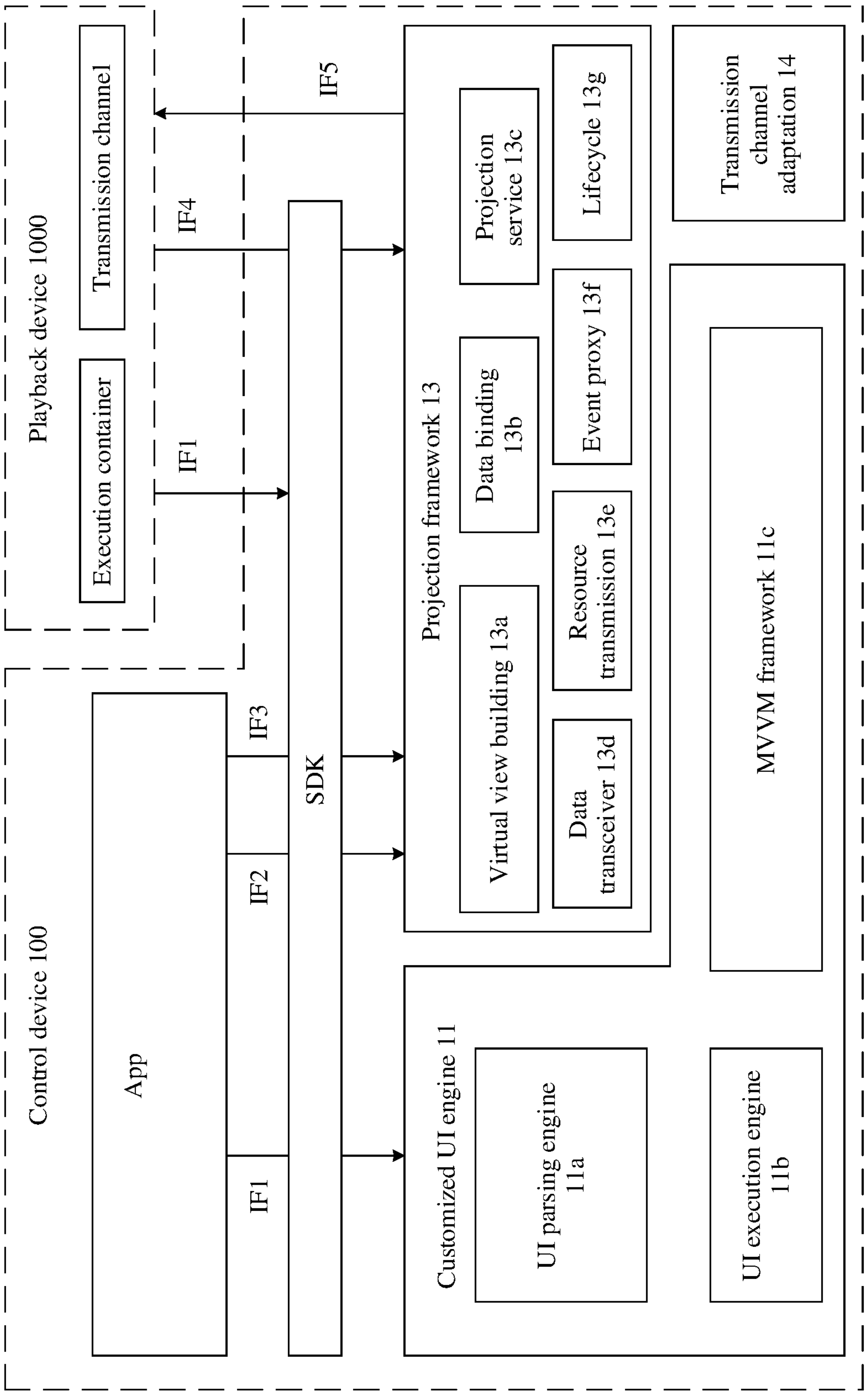
FIG. 34 is a schematic diagram of a user interface implementation method according to an embodiment of this application.

Refer to FIG. 34. The control device 100 includes units such as the customized UI engine 11, a projection framework 13, and a transmission channel adaptation 14. The customized UI engine 11 provides an IF1 interface, and the projection framework 13 provides IF2, IF3, IF4, and IF5 interfaces.

Table 2 describes the interfaces IF1 to IF5.

TABLE 2

| | Interface | Description | Input | Output |
|---|---|---|---|---|
| IF1 | inflate | Create an entity view (View) object | context, jsonFile, ViewModel | Entity view |
| IF2 | obtainDistributedView | Create a virtual view (DistributedView, DView) object that can be migrated | context, jsonfile, ViewModel | Virtual view |
| IF3 | send | Send the virtual view to a peer end | context, dview, targetInfo | resultCode |
| IF4 | reportEvent | Report an event (interaction or life cycle) to a projection framework for distributed processing | context, event | boolean |
| IF5 | onUpdateUi | Refresh a projection framework callback interface | context, jsonfile | void |

The customized UI engine 11 parses and executes an interface description file of an app, to generate a UI of the app. The customized UI engine 11 may include the UI parsing engine 11*a*, the UI execution engine 11*b*, the MVVM (model-view-viewmodel) framework 11*c*, and the like. The UI parsing engine 11*a* is configured to parse the interface description file, and convert content in the interface description file into a data format that matches the UI execution engine 11*b*. In some examples, the UI parsing engine 11*a* may further perform syntax check on content in the interface description file. If the syntax check on the interface description file succeeds, the UI parsing engine 11*a* parses the interface description file; or if the syntax check on the interface description file fails, the UI parsing engine 11*a* does not parse the interface description file. The UI execution engine 11*b* is configured to: build views (instantiated views and property settings) of the UI based on the data parsed by the UI parsing engine 11*a*, perform layout orchestration on the views, and generate an interface declared in the interface description file. The UI execution engine 11*b* may further implement mapping between a component event and user behavior, and execute, in response to the user behavior, an action corresponding to the user behavior defined in the interface description file. The MVVM framework 11*c* is configured to perform bidirectional binding between elements in the UI and background data. In the interface description file, a binding relationship between an element (such as a view or a view group) on the UI and the background data is declared and specified. Optionally, after simple data instances are set, the MVVM framework 11*c* may refresh the background data based on a UI change, and automatically refresh a corresponding UI based on a background data change. This helps the developers focus on UI design and orchestration, simplifies a UI development process, and greatly reduces development time for the developers to implement frontend and backend data interaction.

The transmission channel adaptation 14 is configured to adapt a data transmission channel between the control device 100 and the playback device 1000, for example, convert data of the control device 100 into a format applicable to the data transmission channel, so that the control device 100 can send the data to the playback device 1000 through the data transmission channel.

The projection framework 13 is configured to process the playback end interface description file, to form playback end UI data used to display the playback end UI. The projection framework 13 includes modules such as virtual view building 13*a*, data binding 13*b*, projection service 13*c*, data transceiver 13*d*, resource transmission 13*e*, event proxy 13*f*, and life cycle 13*g*. The virtual view building 13*a* invokes the UI parsing engine 11*a* and the UI execution engine 11*b* to build a view, a view group, and the like based on the playback end interface description file, to form playback end UI data. The playback end UI data exists in an app process and is bound to the background data. The data binding 13*b* is configured to bind a property, an interaction event, and the like of a view or a view group built by the virtual view building 13*a* to the background data (for example, a view model (ViewModel) for processing service logic). The projection service 13*c* is configured to track an object currently processed and data (model) bound to the object in a projection process, and is further configured to manage the data transmission channel between the control device 100 and the playback device 1000. The data transceiver 13*d* is used for data sending and receiving between the control device 100 and the playback device 1000. For example, an interface of a transceiver proxy may be defined to implement a default transceiver built in the control device 100. For another example, a transceiver applicable to an app may be customized in the app based on an interface specification. For example, if information is transmitted in a ContentProvider manner in an app, ContentProvider is used in a send( ) function in the data transceiver 13*d* to implement data sending and receiving. The resource transmission 13*e* is configured to transmit a data resource of a specific type (for example, data, an image, or a video whose data volume is greater than a specified value). The resource transmission 13*e* is configured to manage the data resource of the specific type, for example, sending, receiving, buffering, identifying, and progress control. The event proxy 13*f* is a channel for delivering an event to prevent the event from being blocked by data transmission. The life cycle 13*g* is configured to manage a life cycle of a combination between a running entity of the control device 100 and a running entity of the playback device 1000 in a projection process. For example, life cycles of the control device 100 and the playback device 1000 are shown in Table 3:

TABLE 3

| Status of the control device | Status of the playback device | Event to be sent | Response of the control device | Response of the playback device |
|---|---|---|---|---|
| Standalone running | Not running | The control device initiates a projection instruction | Keep the standalone running state and wait for receiving of the peer end | Request user authorization |
| Standalone running | Request authorization | The playback device sends authorization | Enter a server running state and start to push data to the playback device | Enter the running state |
| Standalone running | Request authorization | The playback device sends authorization rejection | Keep the standalone running state | Stop running |
| Standalone running | Request authorization | The control device closes an app | Disabled state | Stop running |
| Server running state | Running state | The playback device is disabled | Enter the standalone running state | Stop running |
| Server running state | Running state | The playback device runs the app in the background | Keep the server running state and suspend pushing data to the playback device | Background camping state |
| Server running state | Running state | The control device closes an app | Disabled state | Stop running |
| Server suspended state | Background camping | The playback device plays the app in the foreground | Enter the server running state and start to push data to the playback device | Enter the running state |
| Server suspended state | Background camping | The playback device is disabled | Enter the standalone running state | Stop running |

Figure 35A:
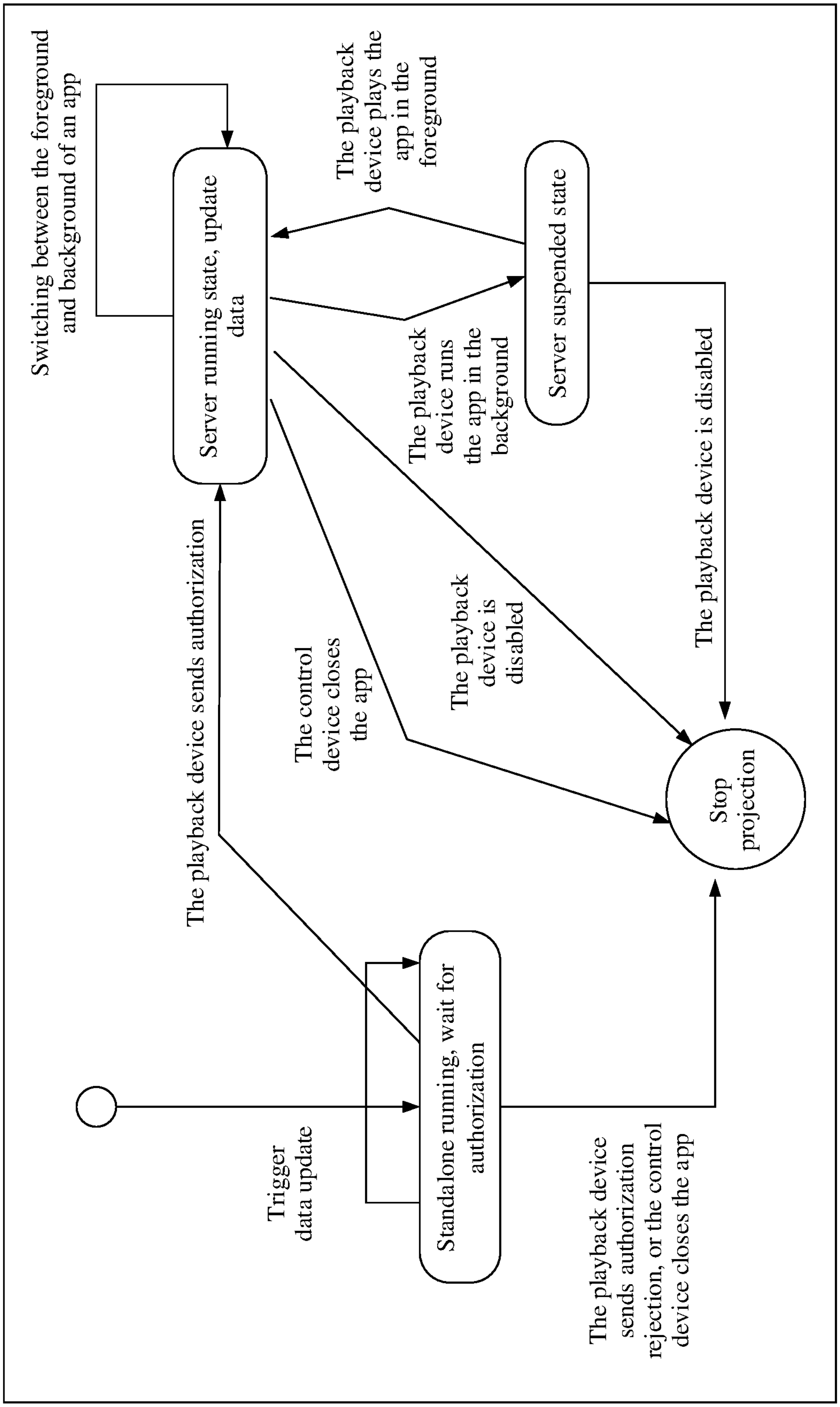
FIG. 35A is a schematic diagram of a user interface implementation method according to an embodiment of this application.

For example, as shown in FIG. 35A, when the control device 100 is in the standalone running state, the control device 100 triggers projection, and waits for user authorization for projection on the playback device. If the user approves the authorization, the playback device sends an authorization instruction to the control device, and the control device 100 enters the service running state. If the user rejects the authorization, the playback device sends an authorization rejection instruction to the control device, and the control device 100 stops projection. When the control device 100 is in the server running state, if the app switches to run in the background, the control device 100 stops pushing data to the playback device; or if the app switches to run in the foreground, the control device 100 starts to push data to the playback device. When the control device 100 is in the server running state, if the control device closes the app, or the playback device is disabled, projection is stopped. When the control device 100 is in the server running state, if the app of the playback device switches to run in the background, the control device 100 enters the server suspended state. When the control device 100 is in the server suspended state, if the app of the playback device switches to play in the foreground, the control device 100 enters the server running state. When the control device 100 is in the server suspended state, if the playback device is disabled, projection is stopped.

Figure 35B:
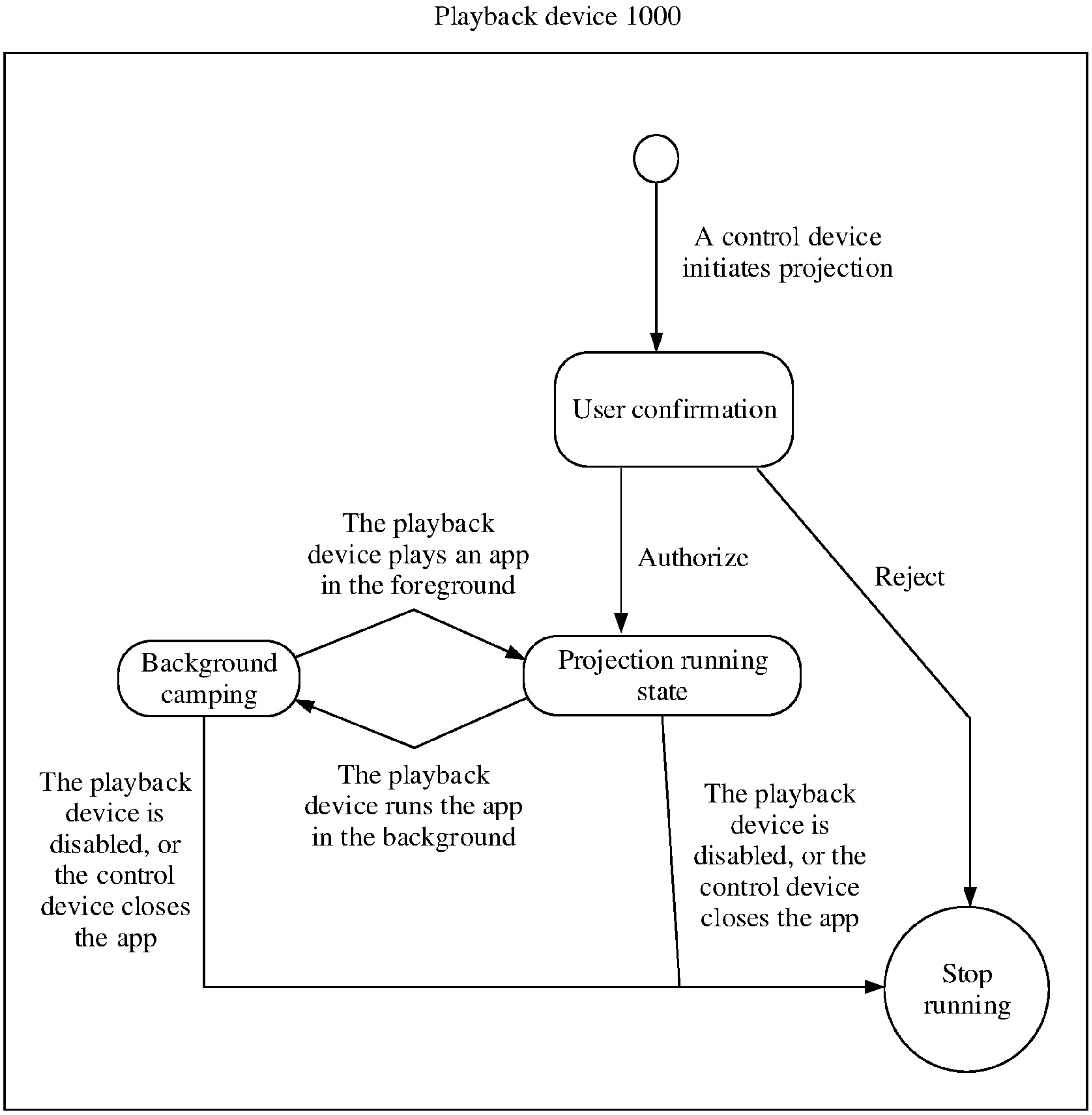
FIG. 35B is a schematic diagram of a user interface implementation method according to an embodiment of this application.

For example, as shown in FIG. 35B, the playback device 1000 receives a projection request initiated by the control device, and waits for the user to confirm authorization. If the user confirms the authorization, the playback device 1000 enters a projection running state; or if the user rejects the authorization, the playback device 1000 stops running. When the playback device 1000 is in the projection running state, if the app switches to run in the background, the playback device 1000 enters the background camping state. When the playback device 1000 is in the background camping state, if the app switches to play in the foreground, the playback device 1000 enters the projection running state. When the playback device 1000 is in the projection running state or the background camping state, if the playback device is disabled or the control device closes the app, the playback device stops running.

Figure 36:
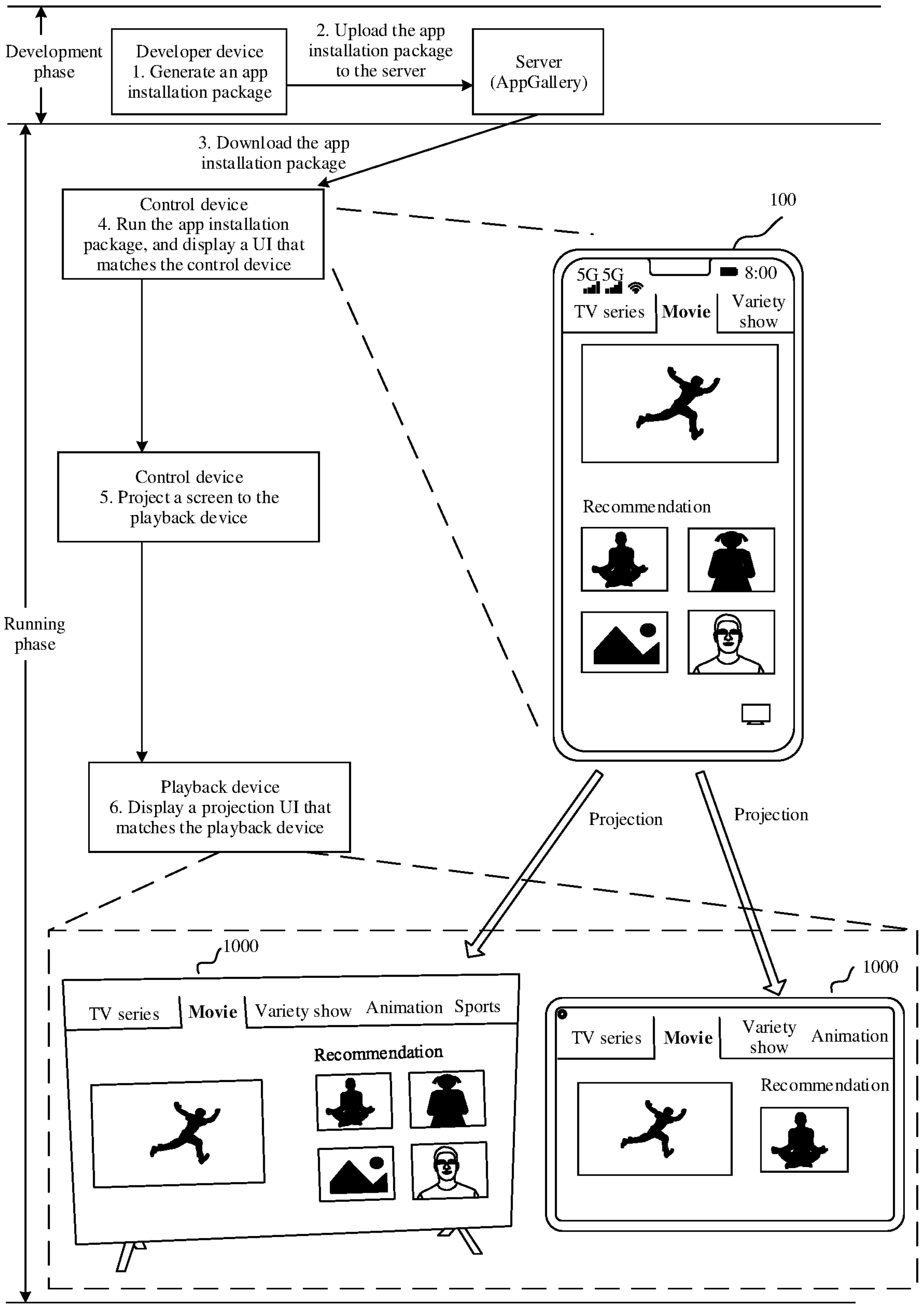
FIG. 36 is a schematic diagram of a user interface implementation method according to an embodiment of this application.

Refer to FIG. 36. In an app development phase, developers generate an installation package of an app on a developer device, including an interface description file and a playback end interface description file. The developers use an interface description language to develop the interface description file and the playback end interface description file on the developer device based on syntactic and semantic specifications of the interface description language, and add code to the interface description file and the playback end interface description file for UI development.

The developers can perform UI layout orchestration, data & interface binding, interaction behavior orchestration, differentiation description, and the like in the interface description file and the playback end interface description file.

All UIs in an app include views. UI layout orchestration is to orchestrate view properties on the UI. For example, views on the UI may include all native views of Android® and the extended views in an operating system, and views customized by the developers in the app or integrated by using static packages are also supported. The view may specifically include a text view, such as a TextView view or an EditText view, or may include a button view, such as a Button view or an ImageButton view, or may include an image view, such as an Image view. This is not limited in this embodiment of this application. View properties include a native property of Android®, and a visual property, a layout property, an interaction property, an animation property, and a software and hardware dependency property that are extended in the operating system. The visual property refers to visual effects such as a color and grayscale of a view. The interaction property refers to a capability of providing a view response based on user behavior, for example, performing a search based on "confirm" behavior of a user. The animation property refers to displaying an animation effect on a view, for example, displaying a click-rebound animation on a view. The software and hardware dependency property refers to software and hardware parameters of a view dependency device.

Data & interface binding is to declare and specify a binding relationship between an element (such as a view or a view group) on the UI and background data in the interface description file or the playback end interface description file.

Interaction behavior orchestration is to declare an execution action corresponding to a view response event in the interface description file or the playback end interface description file. An event scope supported by a view is determined by event listening supported by the view. For example, if the button (Button) view supports setOnClickListener (setOnClickListener), an onClick (click) event can be bound to the view in the interface description file.

Differentiation Description:

1. The developers may declare a variable of a configuration parameter of the electronic device in the interface description file or the playback end interface description file. When the electronic device runs the interface description file or the playback end interface description file, the configuration parameter of the electronic device is accessed, and the electronic device obtains a value of the configuration parameter based on software and hardware conditions of the electronic device. In this way, when different types of electronic devices run the interface description file or the playback end interface description file, different UIs are generated because software and hardware conditions and configuration parameters of the electronic devices are different.

2. The developers may customize parameters in the interface description file or the playback end interface description file. For example, the interface description file and the playback end interface description file are in a json format. The interface description file or the playback end interface description file may include parts such as style and layout-data-common. The developers define myTextStyle in style and can invoke the customized parameter in $style.myTextStyle mode in layout-data-common. The following is an example:

```
{
  "layout-data-common": {
    "Column( )": {
      ...
      "Button(style:$style.myTextStyle)": { },
    }
  },
  " style": {
    "myTextStyle": {
      "textSize": "24sp",
      "textcolor": "white"
    }
  }
}
```

3. The developers can orchestrate code for a specified device in the interface description file or the playback end interface description file. For example, the interface description file and the playback end interface description file are in a json format. The interface description file or the playback end interface description file may include the following structure:

```
{
  "layout-data-common": { },
  "layout-data-uimode": { },
}
```

The developers can declare a common playback end UI in layout-data-common. All types of playback devices parse content in layout-data-common, and lay out the common playback end UI based on the content in layout-data-common. Layout-data-uimode is used to describe a playback end UI of a specified device. In an implementation, a difference between the playback end UI of the specified device and the common playback end UI is declared in layout-data-uimode. The specified device parses and executes the content in layout-data-common and layout-data-uimode to generate the playback end UI of the specified device. In another implementation, all conditions applicable to the playback end UI of the specified device are declared in layout-data-uimode. The specified device lays out the playback end UI of the specified device based on the content in Layout-data-uimode. The specified device may be one of a mobile phone, a watch, a head unit, a smart home device (for example, a smart television, a smart screen, or a smart speaker), a large screen, a tablet computer, a notebook computer, a desktop computer, or the like. For example, a specific form of layout-data-uimode may include layout-data-phone (used for a mobile phone), layout-data-watch (used for a watch), layout-data-television (used for a smart television), layout-data-pad (used for a tablet computer), layout-data-car (used for a head unit), and the like. In this way, different types of playback devices may parse and execute code segments corresponding to the playback devices, and build playback end UIs, to display, on the different types of playback devices, playback end UIs that match the types of the playback devices.

The developers upload the app installation package generated on the developer device to a server, and the app is released in an AppGallery provided by the server. A user may download the app installation package in the AppGallery by using a user-side electronic device (the control device 100). After running the app installation package, the control device obtains the interface description file and the playback end interface description file in the installation package. When running the app, the control device displays, on the display based on the interface description file, a UI that matches the control device.

In a process in which the control device runs the app, an interface of the app may be further projected to the playback device for display. For example, the control device determines, based on a user input, the playback device that performs projection, and sends a projection instruction to the playback device. The projection instruction includes an identifier of the projection interface. The playback device receives the projection instruction, obtains a corresponding playback end interface description file based on the identifier of the projection interface, and forms, based on the playback end interface description file, a playback end UI that matches a device type of the playback end UI.

Figures 1, 37A:
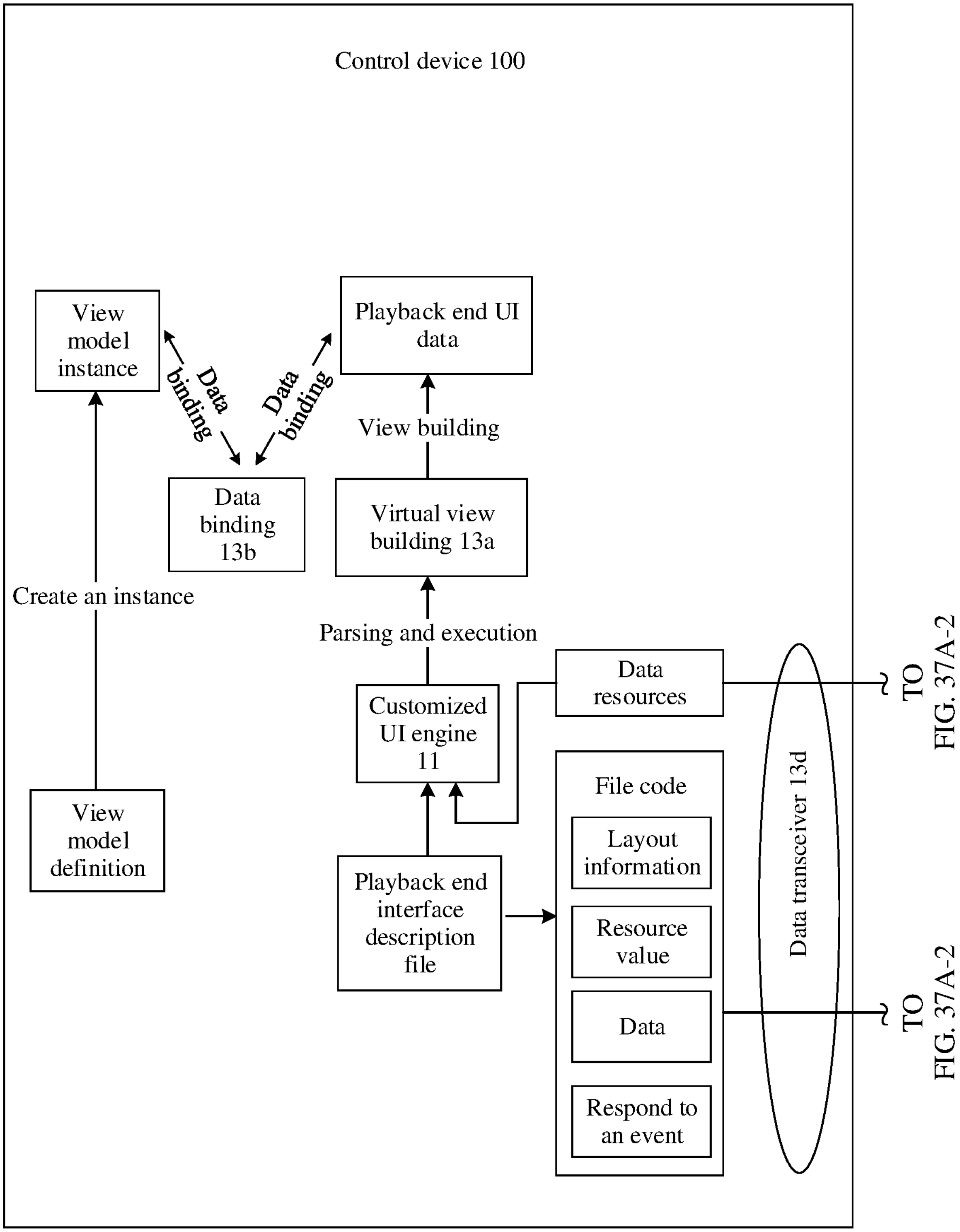
Figures 2, 37A:
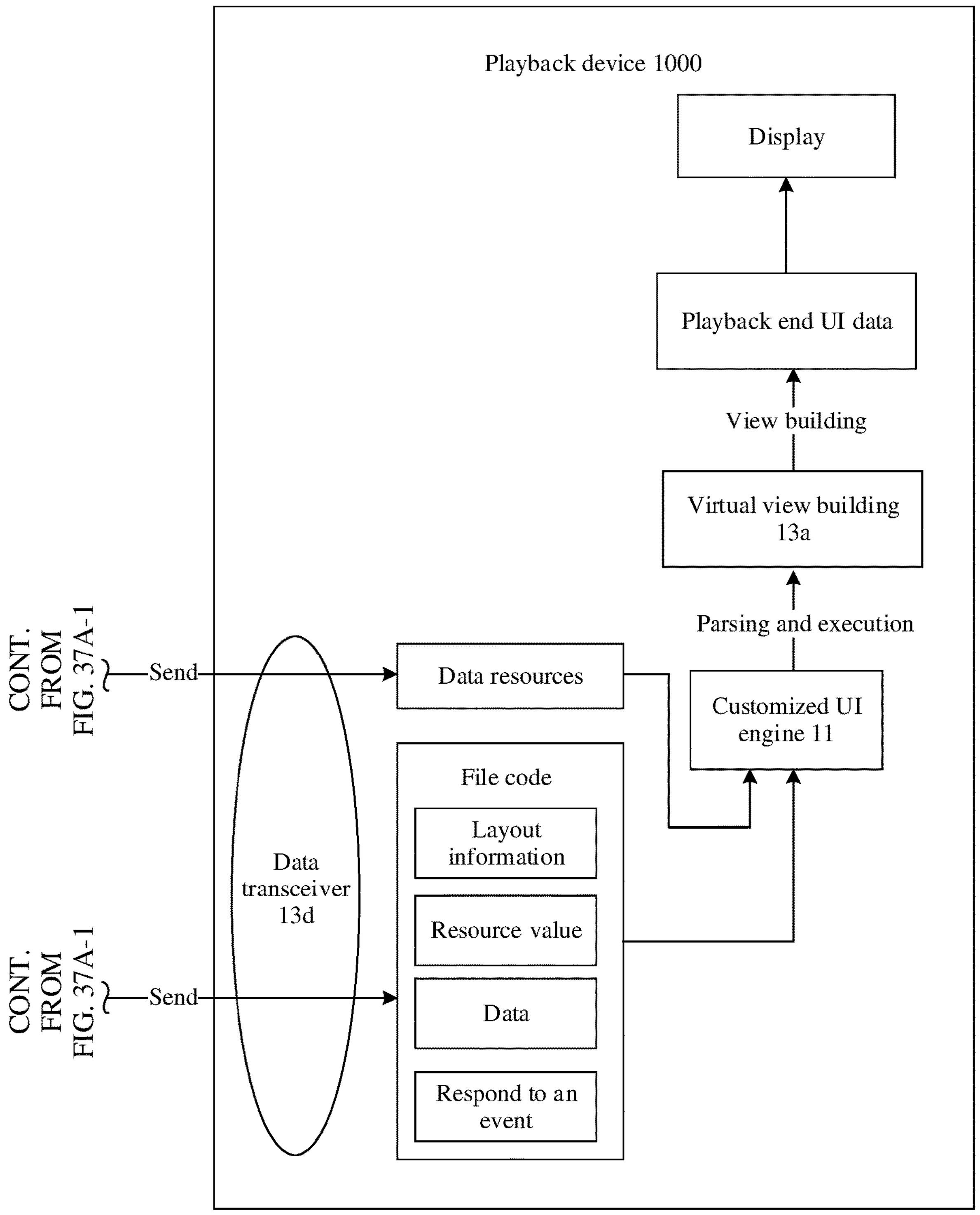

For example, refer to FIG. 37A-1 and FIG. 37A-2. The control device 100 receives a projection operation of the user (for example, the mobile phone receives a tap operation performed by the user on the "My tablet computer" option 10*a* in FIG. 33A to FIG. 33C), and obtains the playback end interface description file corresponding to a current interface from the app installation package. The control device 100 further determines, based on the user input, a device type of the playback device 1000 that performs projection (for example, if the mobile phone receives a tap operation performed by the user on the "Television in the living room" option 109 in FIG. 33A to FIG. 33C, the mobile phone determines that the playback device 1000 is a smart television; or if the mobile phone receives a tap operation performed by the user on the "My tablet computer" option 10*a* in FIG. 33A to FIG. 33C, the mobile phone determines that the playback device 1000 is a tablet computer).

The virtual view building 13*a* in the OS of the control device 100 invokes the customized UI engine 11 to parse and execute a code segment that is corresponding to the device type of the playback device 1000 and that is in the playback end interface description file, performs view building based on the code segment that is corresponding to the device type of the playback device 1000 and that is in the playback end interface description file, and generates a view, a view group, and the like based on a layout orchestration in the code segment, to form playback end UI data. For example, the playback device 1000 is a smart television, and the control device 100 parses and executes a code segment that is in the playback end interface description file and that is corresponding to the smart television, to form playback end UI data for projection to the smart television. The playback device 1000 is a tablet computer, and the control device 100 parses and executes a code segment that is in the playback end interface description file and that is corresponding to the tablet computer, to form playback end UI data for projection to the tablet computer. Then, the data binding 13*b* invokes the MVVM framework 11*c* to perform data binding between an object in the playback end UI data and background data (for example, a view model). In this way, if the background data changes, the corresponding playback end UI data may be refreshed; or if the playback end UI data changes, the corresponding background data is refreshed. Further, the control device 100 sends the playback end interface description file and a resource file (including data resources associated with the playback end interface description file) to the playback device 1000 by using the data transceiver 13*d*. In an implementation, the control device 100 encodes the playback end interface description file. After data such as layout information, a resource value, data, and a response event definition is encoded, the encoded data is transmitted to the playback device 1000 through a data transmission channel. A data resource of a specific type (for example, data, an image, or a video whose data volume is greater than a specified value) is transmitted to the playback device 1000 through a specific data transmission channel. Optionally, the data resource of the specific type may be transmitted to the playback device 1000 before the playback end interface description file is sent. In this way, a rate of transmitting the playback end interface description file to the playback device 1000 is increased, and a delay of displaying the playback end UI by the playback device 1000 is shortened. The control device 100 further initializes the event proxy 13*f*, and establishes an event transmission channel between the control device 100 and the playback device 1000, to transmit event information.

The playback device 1000 receives the playback end interface description file and the data resources by using the data transceiver 13*d*. The virtual view building 13*a* in the OS of the playback device 1000 invokes the customized UI engine 11 to parse and execute the code segment that is corresponding to the device type of the playback device 1000 and that is in the playback end interface description file, performs view building based on the code segment that is corresponding to the device type of the playback device 1000 and that is in the playback end interface description file, generates a view, a view group, and the like based on a layout orchestration in the code segment, to form playback end UI data (including information such as a view and a view layout), and displays the playback end UI data, that is, displays the playback end UI. Because a same code segment is used by the control device 100 to generate the playback end UI data and the playback device 1000 to generate the playback end UI data, views on the playback end UI generated by the playback device 1000 are in a one-to-one correspondence with views in the playback end UI data generated by the control device 100.

After the playback end UI is generated, the playback device 1000 displays, on the display, the playback end UI that matches a form and size of a screen of the playback device. For example, as shown in FIG. 36. When the smart television is used as the playback device, the smart television parses and executes a layout-data-television code segment in the playback end interface description file, to generate the playback end UI corresponding to the smart television. When the tablet computer is used as the playback device, the tablet computer parses and executes a layout-data-pad code segment in the playback end interface description file, to generate the playback end UI corresponding to the tablet computer.

Figure 37B:
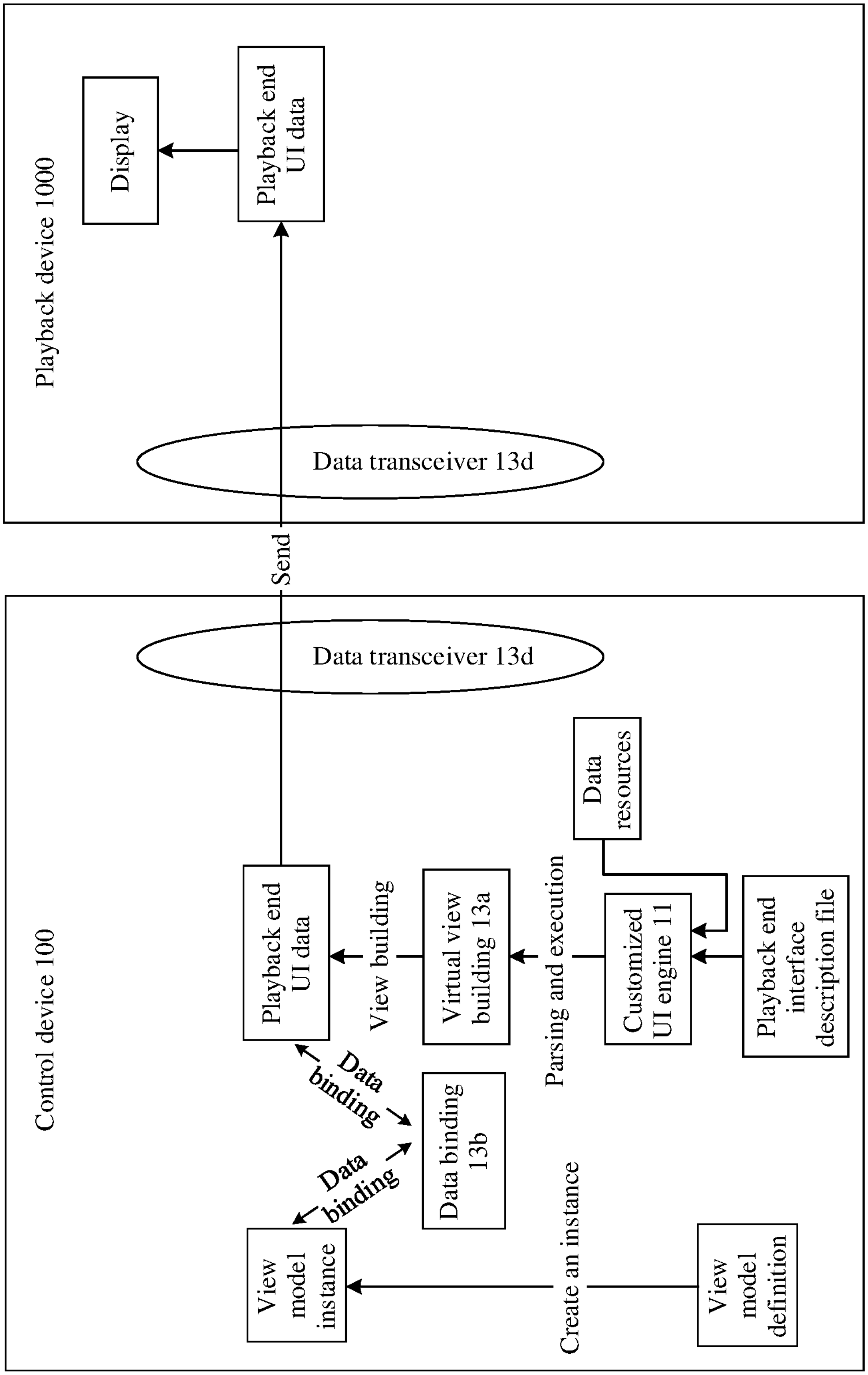
FIG. 37B is a schematic diagram of a user interface implementation method according to an embodiment of this application.

Optionally, in some embodiments, as shown in FIG. 37B, after the control device 100 performs view building based on the code segment that is corresponding to the device type of the playback device 1000 and that is in the playback end interface description file, and generates the playback end UI data based on a layout orchestration in the code segment, the control device 100 sends the generated playback end UI data to the playback device 1000. After receiving the playback end UI data, the playback device 1000 displays the playback end UI based on the playback end UI data.

According to the user interface implementation method provided in this embodiment of this application, the playback device generates, based on the code segment that is corresponding to the device type of the playback device and that is in the playback end interface description file, the playback end UI corresponding to the playback device. Playback end UIs displayed by playback devices of different types match shapes and sizes of screens of the playback devices. When developing an app, the developers can easily develop the playback end UI and define various types of views (including all native views of Android®, views extended in an operating system, and views customized by the developers in the app or integrated by using static packages) in the playback end interface description file of the app. Various types of views are supported, so that all types of apps support a projection function. In addition, the playback end UI supports more types of views, facilitating use by the user.

In an implementation, the virtual view building 13*a* in the OS of the control device 100 parses and executes a code segment that is corresponding to the device type of the playback device 1000 and that is in the playback end interface description file, and builds the playback end UI data based on the code segment that is corresponding to the device type of the playback device 1000 and that is in the playback end interface description file. The playback end UI data is not displayed on the display of the control device 100 (that is, the playback end UI data exists in an app process and is not sent to a display process). The control device 100 displays the UI generated based on the interface description file. After the interface of the control device 100 is projected to the playback device 1000, the user may perform another operation on the control device 100, and the playback device 1000 normally plays projected content.

Figures 1, 38A:
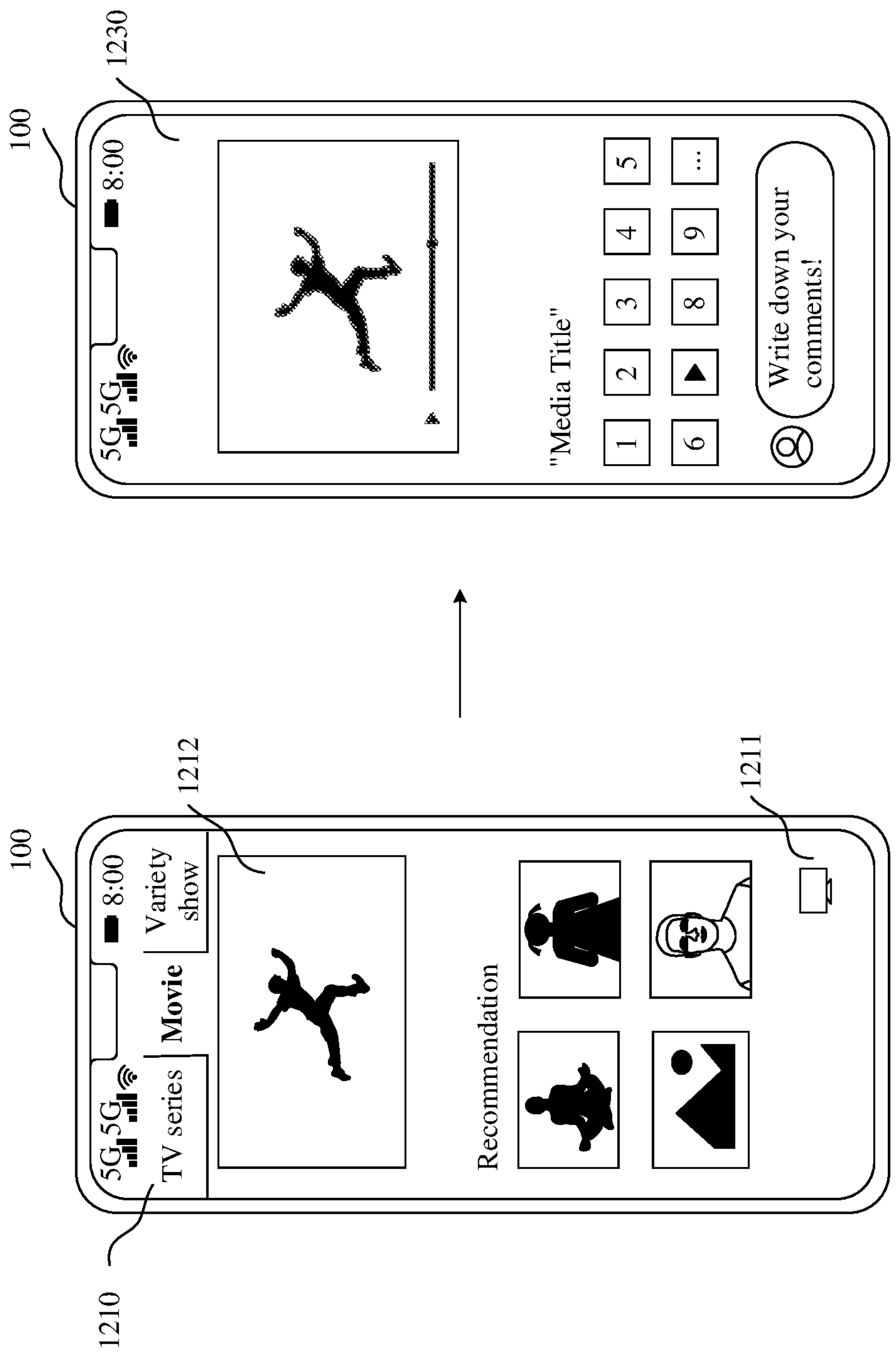
Figures 2, 38A:
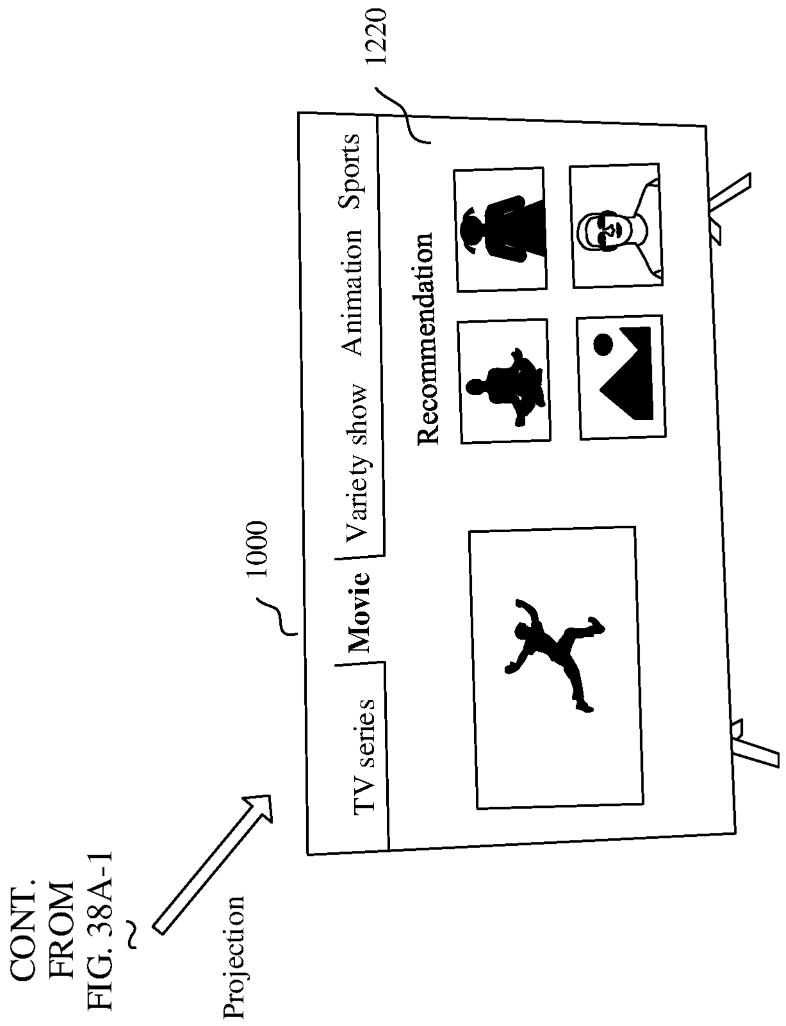

For example, as shown in FIG. 38A-1 and FIG. 38A-2, the mobile phone displays an interface 1210 of the "Video" app, and the interface 1210 includes a "projection" button 1211. The mobile phone receives a tap operation performed by the user on the "projection" button 1211, and determines the playback device based on an input of the user. The mobile phone projects the screen to a smart television based on the input of the user. As shown in FIG. 37A-1 and FIG. 37A-2 or FIG. 37B, the mobile phone generates the playback end UI data based on the playback end interface description file, and sends the playback end interface description file to the smart television. The smart television generates the playback end UI data based on the playback end interface description file, and displays the playback end UI based on the playback end UI data. Refer to FIG. 38A-1 and FIG. 38A-2. The smart television displays a playback end UI 1220.

After that, the user may continue to perform other operations on the mobile phone. For example, as shown in FIG. 38A-1 and FIG. 38A-2, the mobile phone receives a tap operation performed by the user on an image 1212, and displays an interface 1230 of the "Video" app in response to the tap operation performed by the user on the image 1212.

In this way, after projecting the screen to the playback device, the control device may continue to perform another function, and the playback device plays projection content independently. The control device and the playback device do not affect each other, to implement better collaboration between devices.

Figure 38B:
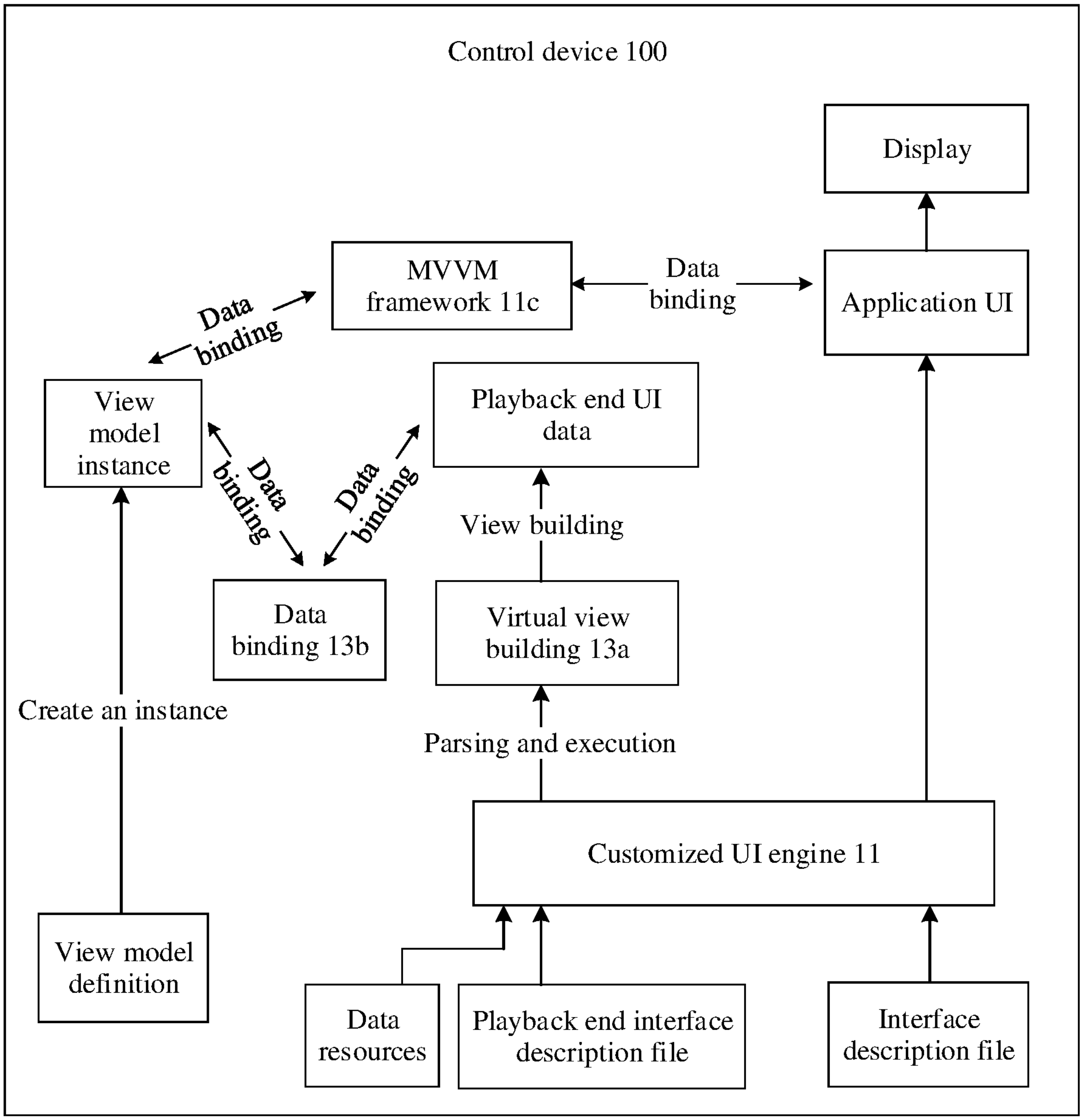
FIG. 38B is a schematic diagram of a scenario example of a user interface implementation method according to an embodiment of this application.

For example, as shown in FIG. 38B, the customized UI engine 11 in the OS of the control device 100 parses and executes an interface description file, generate a UI of an application, and display the UI of the application. The MVVM framework 11*c* performs data binding between the UI of the application and background data (for example, a view model).

The virtual view building 13*a* in the OS of the control device 100 invokes the customized UI engine 11 to parse and execute a code segment that is corresponding to the device type of the playback device 1000 and that is in the playback end interface description file, performs view building based on the code segment that is corresponding to the device type of the playback device 1000 and that is in the playback end interface description file, and generates a view, a view group, and the like based on a layout orchestration in the code segment, to form playback end UI data. Then, the data binding 13*b* invokes the MVVM framework 11*c* to perform data binding between an object in the playback end UI data and the background data (for example, the view model). Further, the control device 100 sends the playback end interface description file and a resource file (including data resources associated with the playback end interface description file) to the playback device 1000 by using the data transceiver 13*d*, or sends the playback end UI data to the playback device 1000. In this way, the playback device 1000 may display the player end UI based on the player end UI data.

In another implementation, the virtual view building 13*a* in the OS of the control device 100 parses and executes the code segment that is corresponding to the device type of the playback device 1000 and that is in the playback end interface description file, and builds the playback end UI data based on the code segment that is corresponding to the device type of the playback device 1000 and that is in the playback end interface description file. The app process sends the playback end UI data to the display process, and displays the playback end UI on the display of the control device 100. The control device 100 and the playback device 1000 display a playback end UI generated based on a same code segment.

Figures 1, 39A:
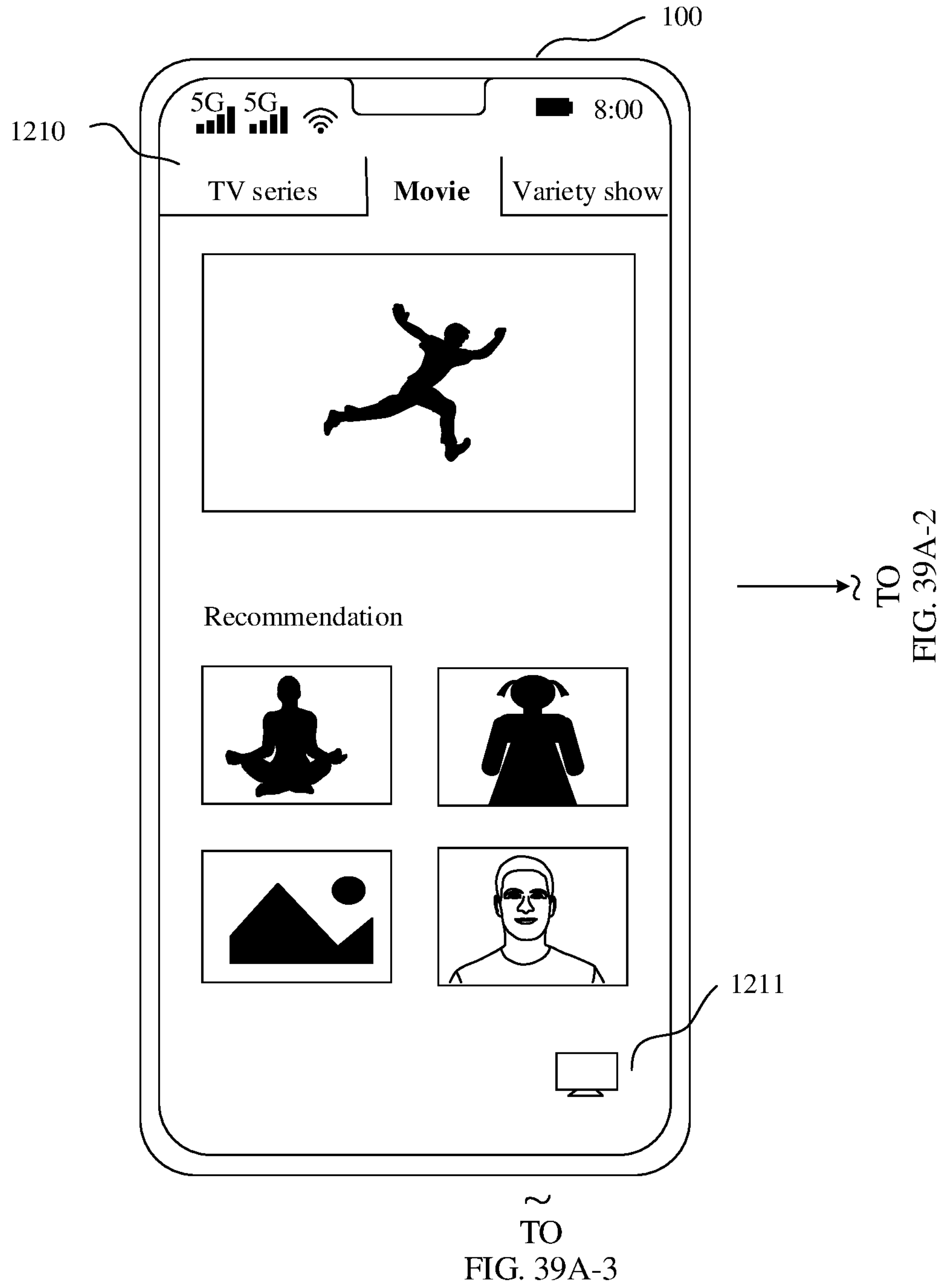
Figures 2, 39A:
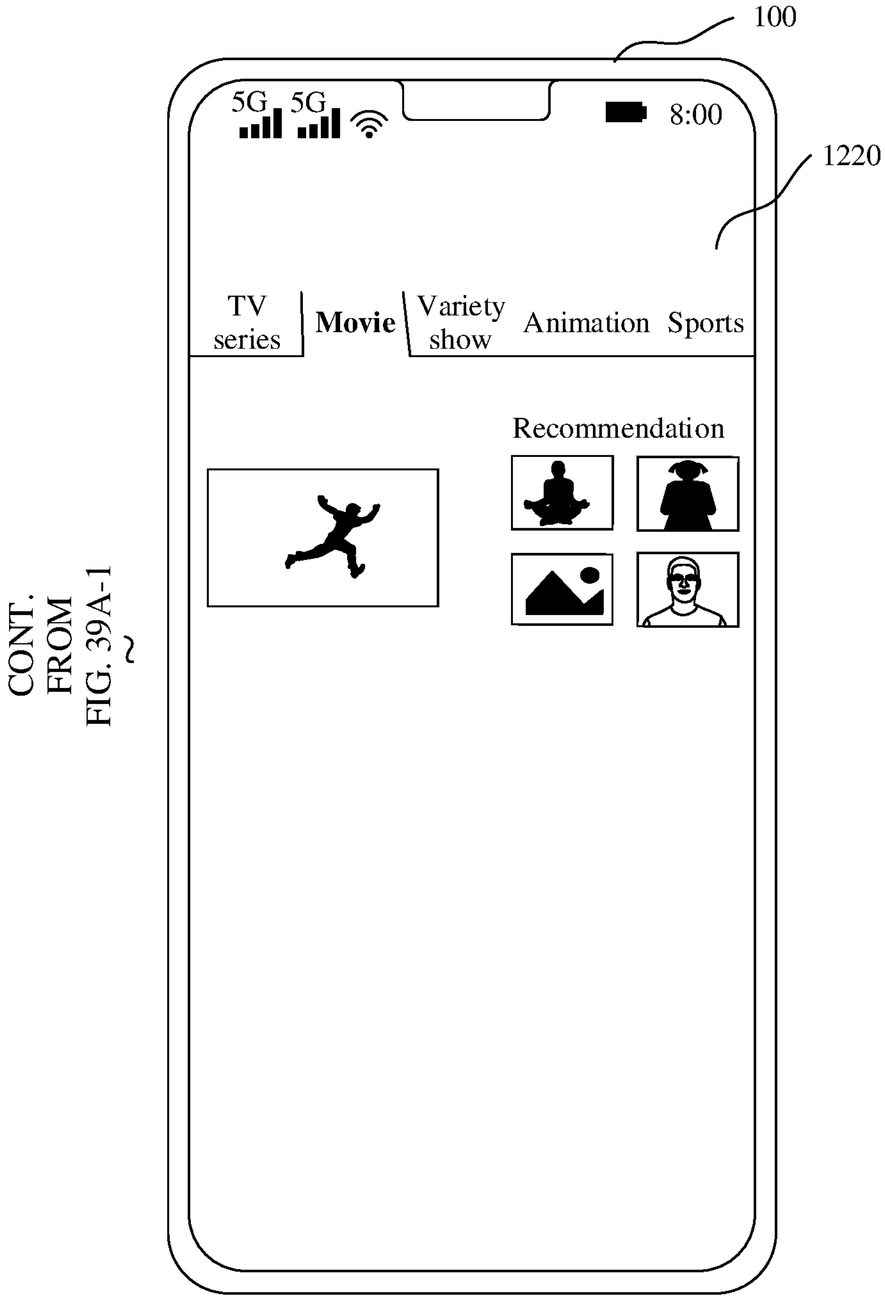
Figures 3, 39A:
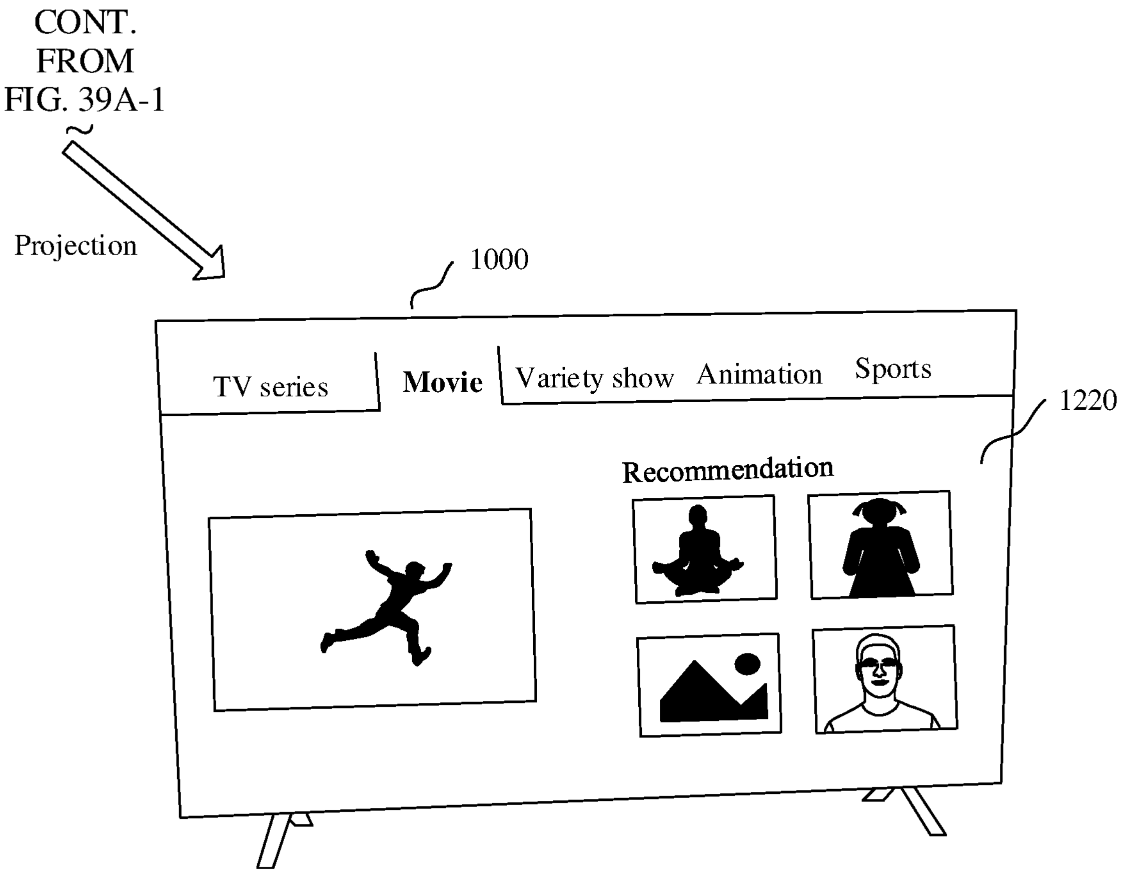
Figures 1, 39B:
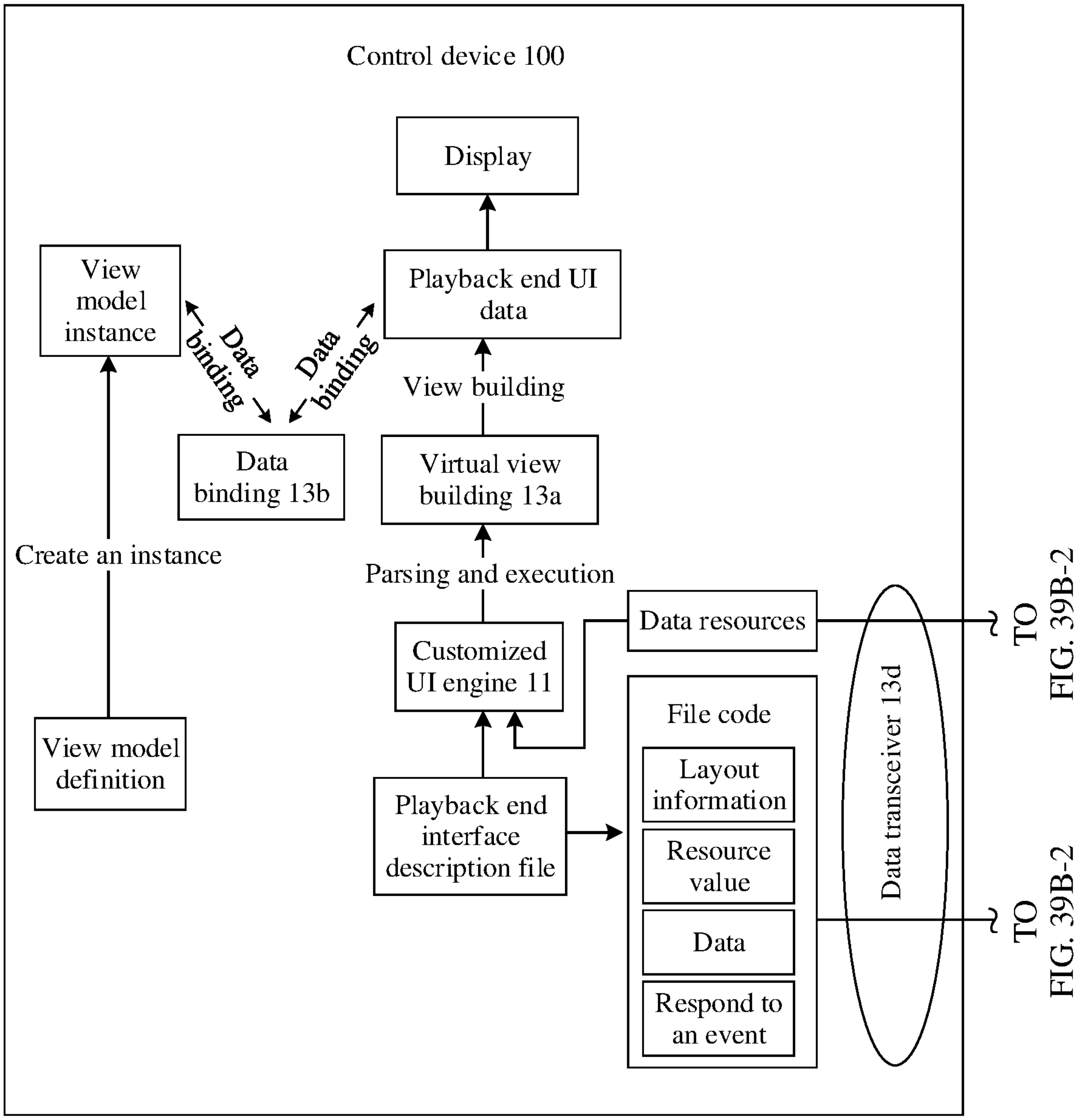
Figures 2, 39B:
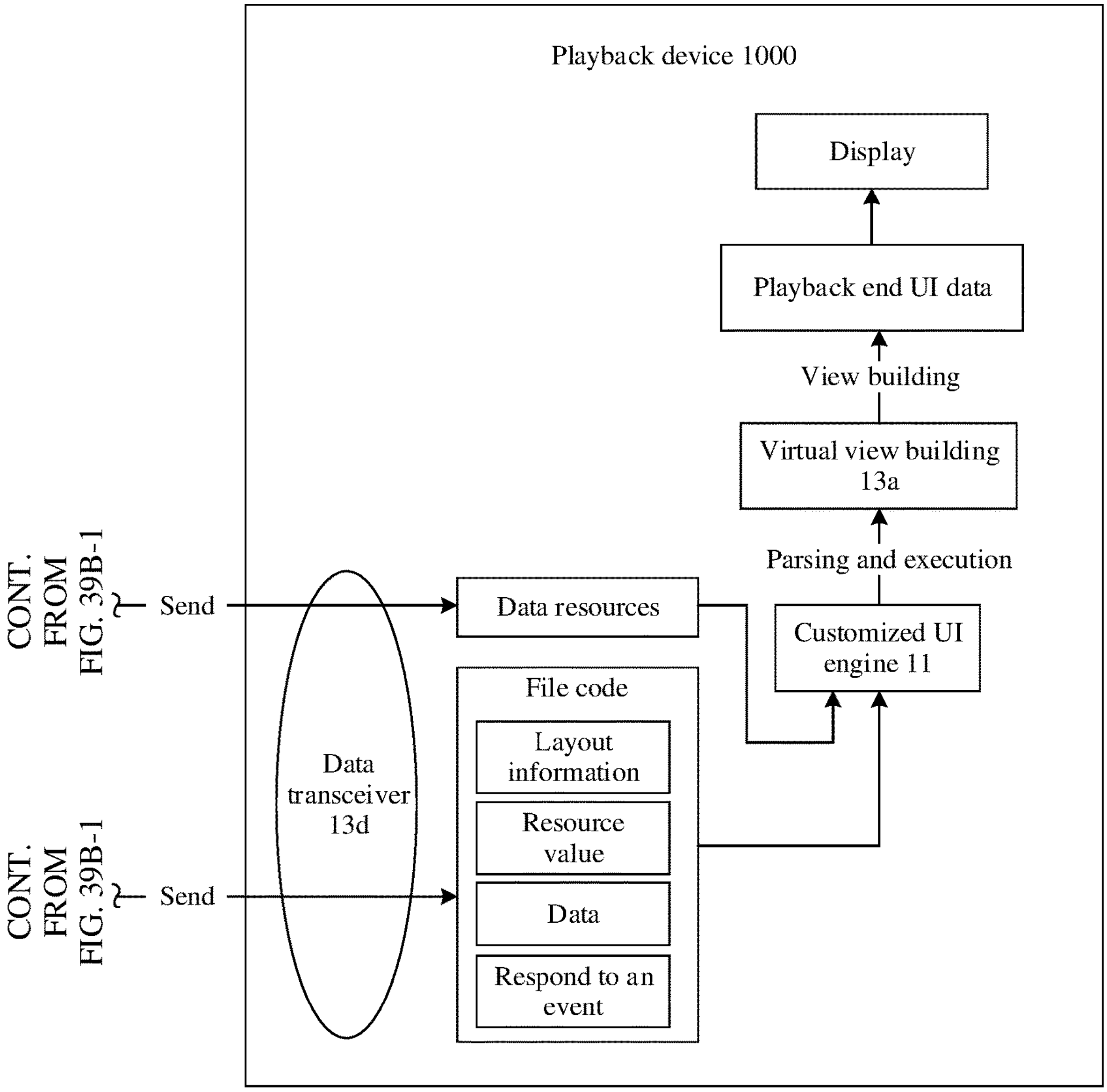

For example, as shown in FIG. 39A-1 to FIG. 39A-3, the mobile phone displays an interface 1210 of the "Video" app, and the interface 1210 includes a "projection" button 1211. The mobile phone receives a tap operation performed by the user on the "projection" button 1211, and determines the playback device based on an input of the user. The mobile phone projects the screen to a smart television based on the input of the user. As shown in FIG. 39B-1 and FIG. 39B-2, the mobile phone generates the playback end UI data based on the playback end interface description file, and displays the playback end UI based on the playback end UI data. The mobile phone further sends the playback end interface description file to the smart television. The smart television generates the playback end UI data based on the playback end interface description file, and displays the playback end UI based on the playback end UI data.

As shown in FIG. 39A-1 to FIG. 39A-3, after the mobile phone performs projection to the smart television, the mobile phone also displays the playback end UI, and both the mobile phone and the smart television display the playback end UI 1220.

In this way, the control device and the playback device synchronously play the playback end UI, so that mirror projection can be implemented, and the control device and the playback device work cooperatively.

In some embodiments, when the control device 100 receives an operation performed by the user on the playback end UI or service data changes, the data binding 13*b* invokes the MVVM framework 11*c* to update the playback end UI data. There is a one-to-one correspondence between views on the playback end UI and views in the playback end UI data. Therefore, the update of the playback end UI data triggers the update of the playback end UI. In this way, when the control device 100 receives a user operation or service data change, the playback end UI of the playback device 1000 may be synchronously updated.

Figure 40A:
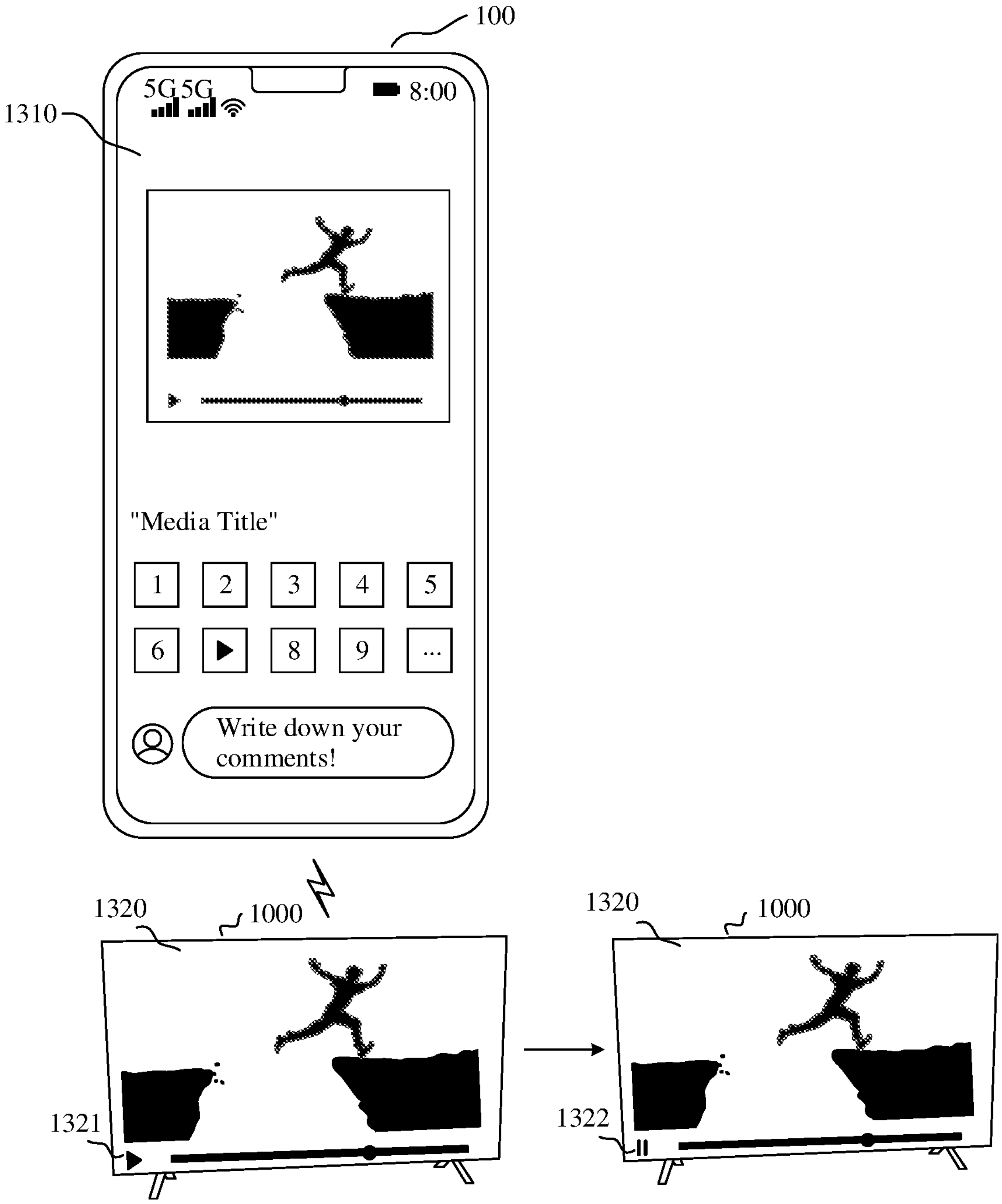
FIG. 40A is a schematic diagram of a scenario example of a user interface implementation method according to an embodiment of this application.

For example, refer to FIG. 40A. The mobile phone displays a UI 1310 of the "Video" app. The mobile phone projects the UI 1310 of the "Video" app to the smart television based on a user input. The smart television displays a playback end UI 1320 of the "Video" app, and the playback end UI 1320 includes a "play" button 1321.

The user may perform, on the smart television, an operation of starting playing a video (for example, the user selects the "play" button 1321 by using a remote control of the smart television, and taps the "play" button 1321). The smart television receives a click operation performed by the user on the "play" button 1321, plays the video in response to the click operation performed by the user on the "play" button 1321, and displays an updated UI 1320. The updated playback end UI 1320 includes a "pause" button 1322.

Figure 40B:
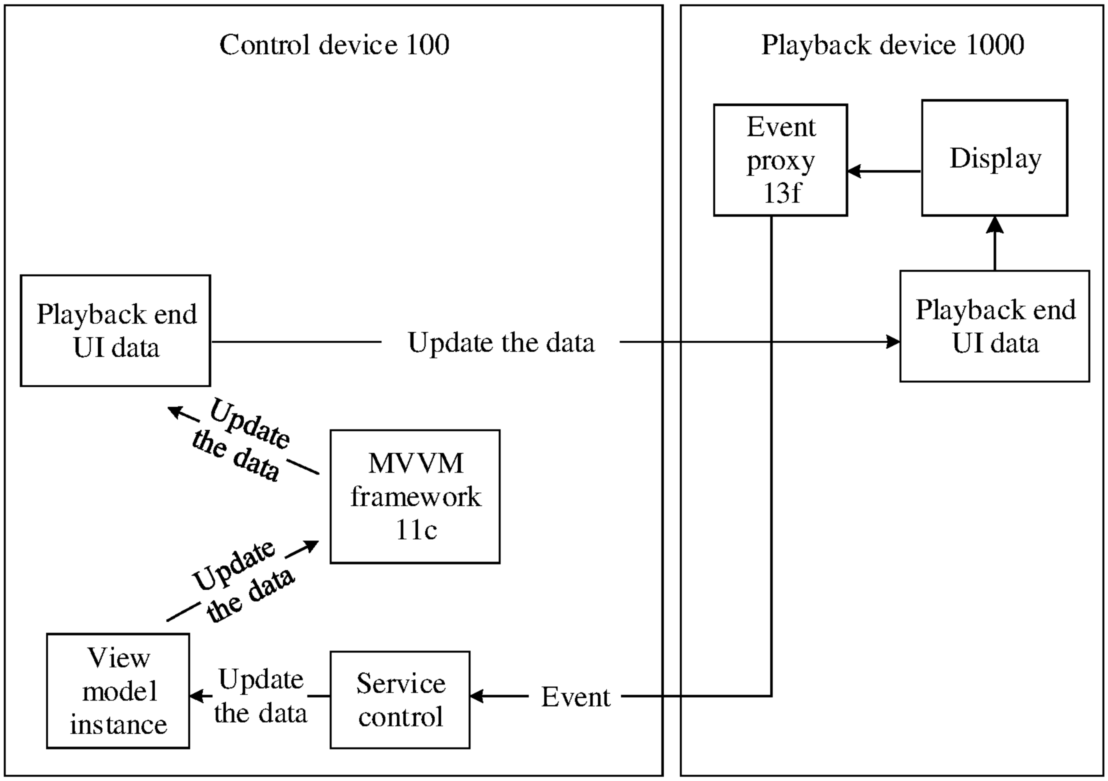
FIG. 40B is a schematic diagram of a user interface implementation method according to an embodiment of this application.

In an implementation, as shown in FIG. 40B, a dedicated event transmission class is defined in the event proxy 13*f*, and the event transmission class is used for cross-device transmission. A plurality of events are stored in the event transmission class, and each event includes information such as a layout identifier, a view identifier, and an event type. The playback device 1000 receives an operation performed by the user on the playback end UI, generates, in the event transmission class, an event corresponding to the operation, and transmits the event to the control device 100 by using an event transmission channel. After receiving the event, the control device 100 obtains a corresponding view based on a layout identifier and a view identifier, and executes corresponding service logic based on the event acting on the view. There is a one-to-one correspondence between views on the playback end UI and views in the playback end UI data. Therefore, the control device 100 further updates background data, and a background data change triggers update of the playback end UI data. The control device 100 sends updated playback end UI data to the playback device 1000, and the playback device 1000 displays the updated playback end UI based on the updated playback end UI data.

In this way, the user may control the app on the playback device, and the control device executes corresponding service logic, and updates the playback end UI on the playback device. In some examples, if the control device and the playback device display the playback end UI in a mirror manner, the UI on the control device may be further synchronously updated, to facilitate use by the user. In addition, for an operation performed by the user on the playback device, the control device executes related service logic, and the control device controls the playback device in a unified manner, thereby facilitating management. In addition, a case in which the playback device has relatively low performance and does not support complex service logic processing is avoided.

In some embodiments, the playback device 1000 receives a second operation performed by the user on the playback end UI. The playback device 1000 obtains an updated playback end interface description file from the control device 100, and generates an updated playback end UI.

Figures 1, 40C:
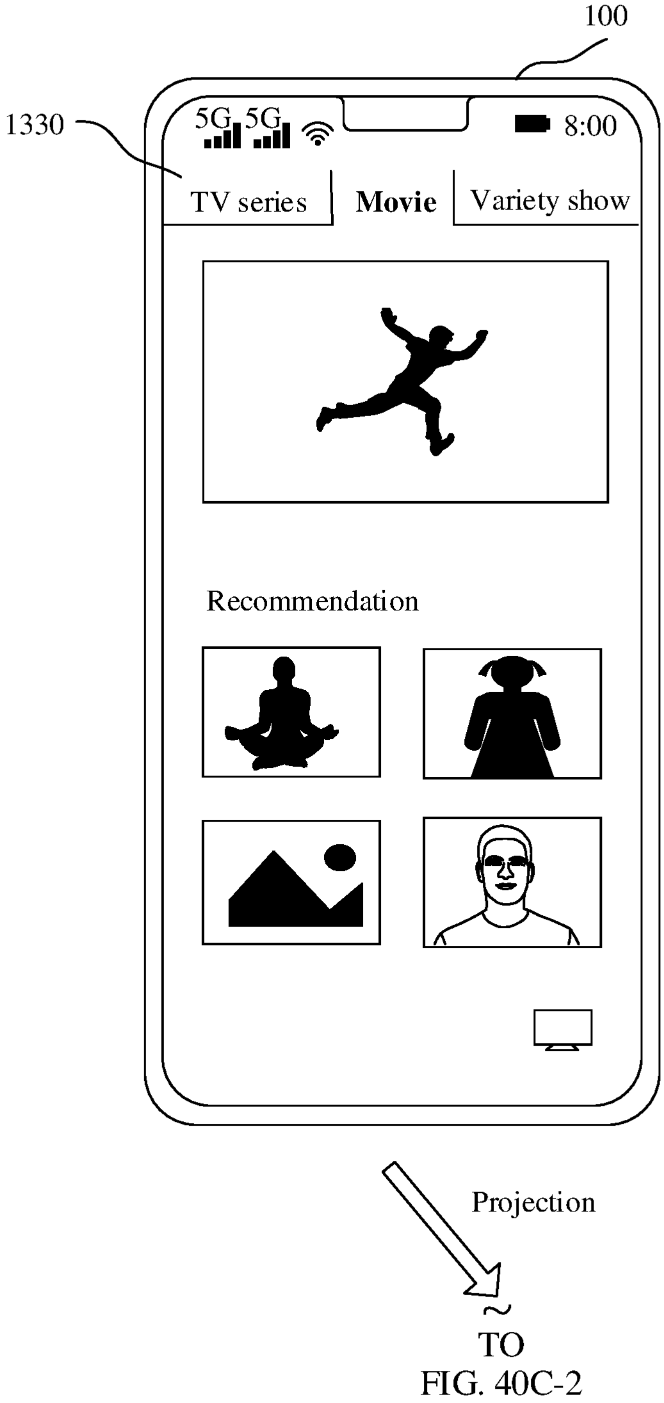
Figures 2, 40C:
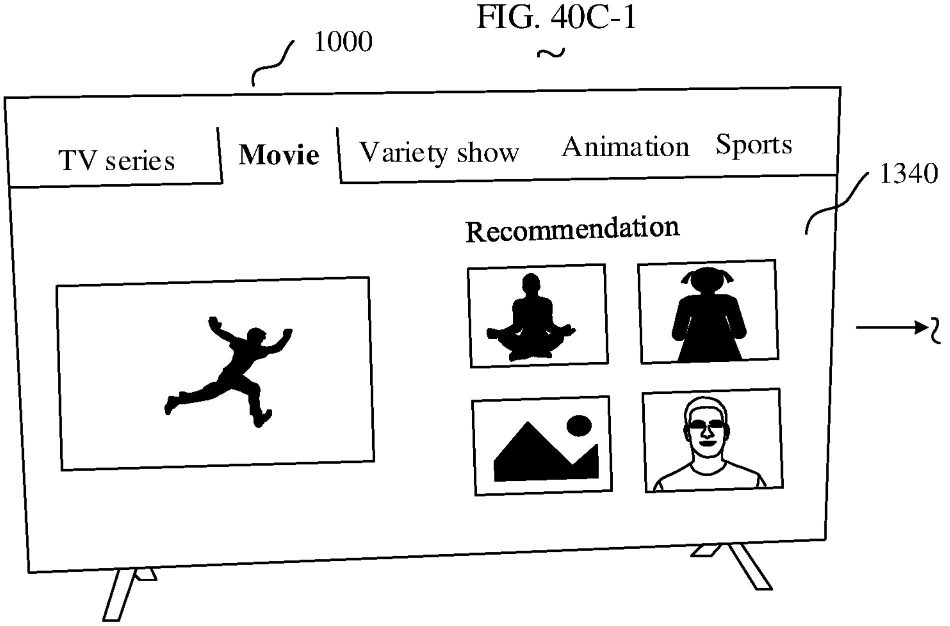
Figures 3, 40C:
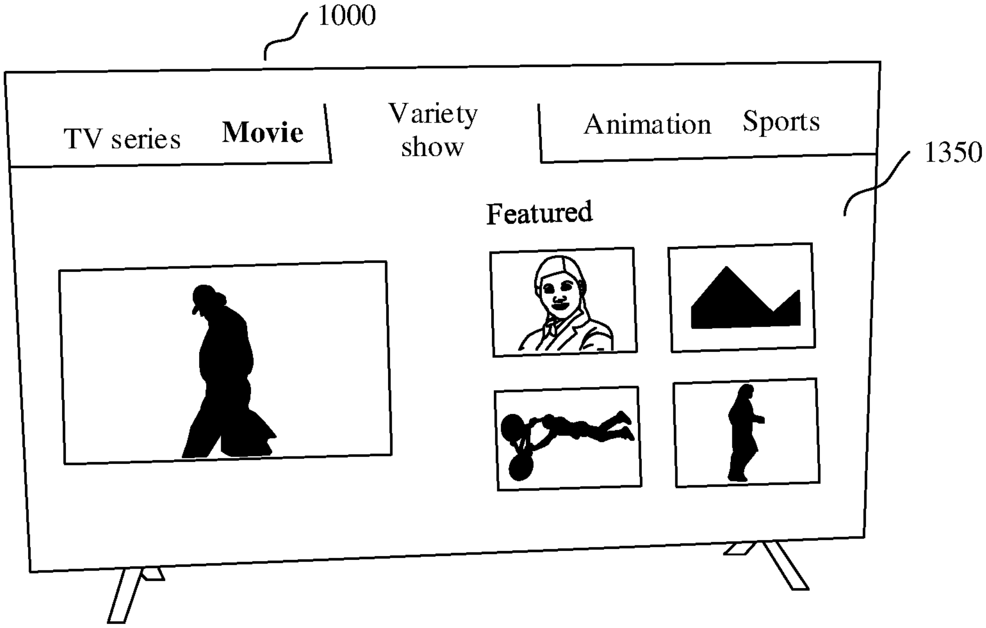

For example, as shown in FIG. 40C-1 to FIG. 40C-3, the mobile phone displays a UI 1330 of the "Video" app. The mobile phone projects the UI 1330 of the "Video" app to the smart television based on a user input. The smart television displays a playback end UI 1340 of the "Video" app. The smart television receives a second operation performed by the user on the playback end UI 1340 (for example, the user moves a focus on the playback end UI 1340 from "Movie" to "Variety show" by using a remote control). In response to the second operation performed by the user on the playback end UI 1340, the smart television displays an updated playback end UI, that is, a playback end UI 1350 of the "Video" app.

Figures 1, 40D:
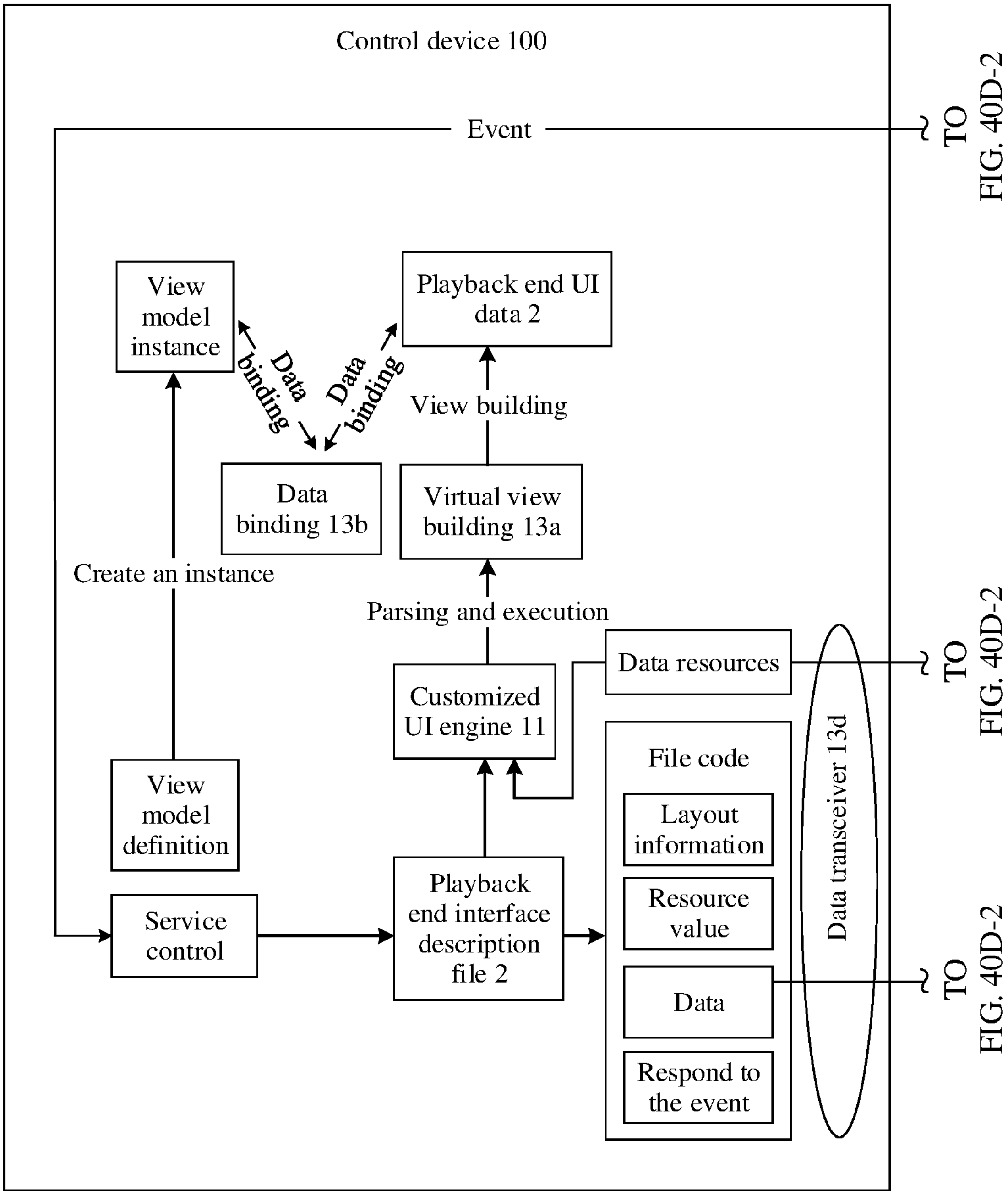
Figures 2, 40D:
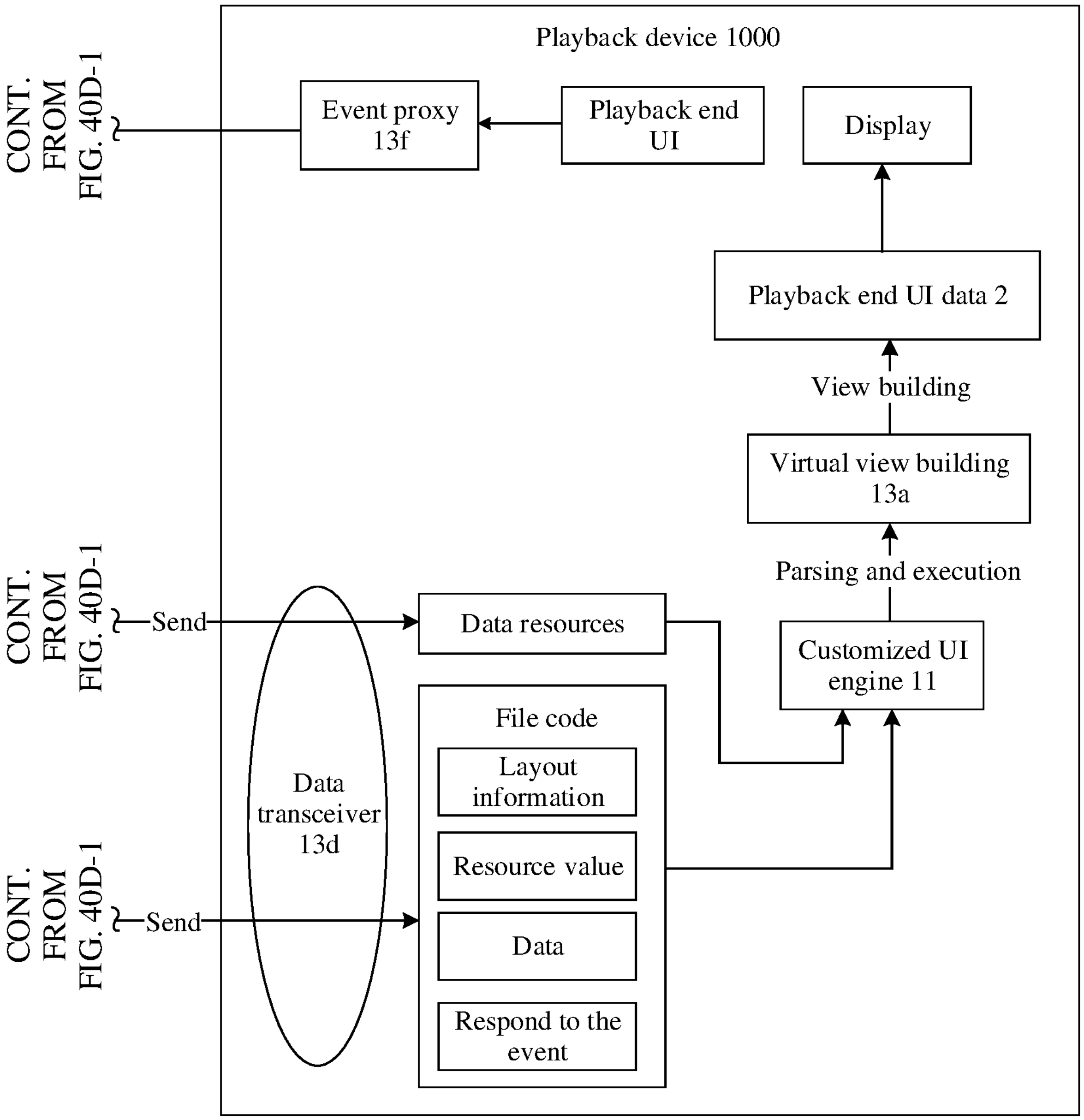

In an implementation, as shown in FIG. 40D-1 and FIG. 40D-2, the playback device 1000 receives the second operation performed by the user on the playback end UI, generates, in the event transmission class, an event corresponding to the second operation, and transmits the event to the control device 100 by using the event transmission channel. After receiving the event, the control device 100 obtains a corresponding view based on a layout identifier and a view identifier, and executes corresponding service logic based on the event acting on the view. The control device 100 determines to update the playback end UI to a playback end UI whose focus is "Variety show", and obtains a playback end interface description file 2 corresponding to the playback end UI whose focus is "Variety show". The virtual view building 13*a* in the OS of the control device 100 invokes the UI to parse and execute a code segment that is corresponding to the device type of the playback device 1000 and that is in the playback end interface description file 2, performs view building based on the code segment that is corresponding to the device type of the playback device 1000 and that is in the playback end interface description file 2, and generates a view, a view group, and the like based on a layout orchestration in the code segment, to form playback end UI data 2. Then, the data binding 13*b* invokes the MVVM framework 11*c* to perform data binding between an object in the playback end UI data 2 and the background data (for example, the view model). Further, the control device 100 sends the playback end interface description file 2 and a resource file (including data resources associated with the playback end interface description file 2) to the playback device 1000 by using the data transceiver 13*d*. In an implementation, the control device 100 encodes the playback end interface description file 2. After data such as layout information, a resource value, data, and a response event definition is encoded, the encoded data is transmitted to the playback device 1000 through a data transmission channel. A data resource of a specific type (for example, data, an image, or a video whose data volume is greater than a specified value) is transmitted to the playback device 1000 through a specific data transmission channel. The playback device 1000 receives the playback end interface description file 2 and the resource file of the data resources by using the data transceiver 13*d*. The virtual view building 13*a* in the OS of the playback device 1000 invokes the customized UI engine 11 to parse and execute the code segment that is corresponding to the device type of the playback device 1000 and that is in the playback end interface description file 2, performs view building based on the code segment that is corresponding to the device type of the playback device 1000 and that is in the playback end interface description file 2, generates a view, a view group, and the like based on a layout orchestration in the code segment, to form playback end UI data 2 (including information such as a view and a view layout), and displays the playback end UI data 2, that is, displays the updated playback end UI.

In this way, the user may directly perform an operation on the playback end UI on the playback device. The control device executes service logic corresponding to the operation, and sends, to the playback device, an updated playback end interface description file corresponding to the playback end UI. The playback device generates the updated playback end UI based on the updated playback end interface description file. Therefore, an operation can be directly performed on the playback end UI on the playback device, and the playback end UI can be successfully switched.

Figures 1, 41A:
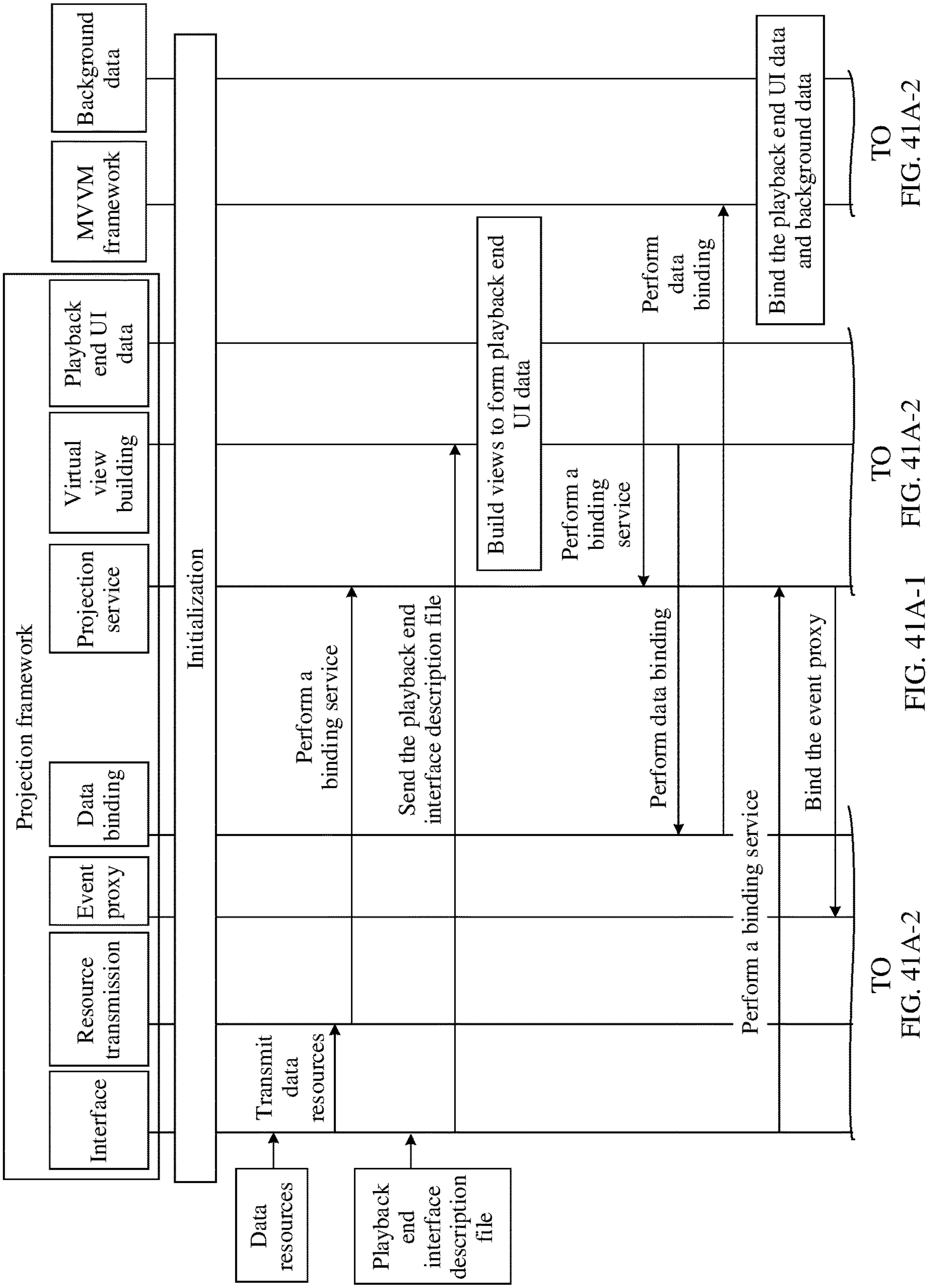
Figures 2, 41A:
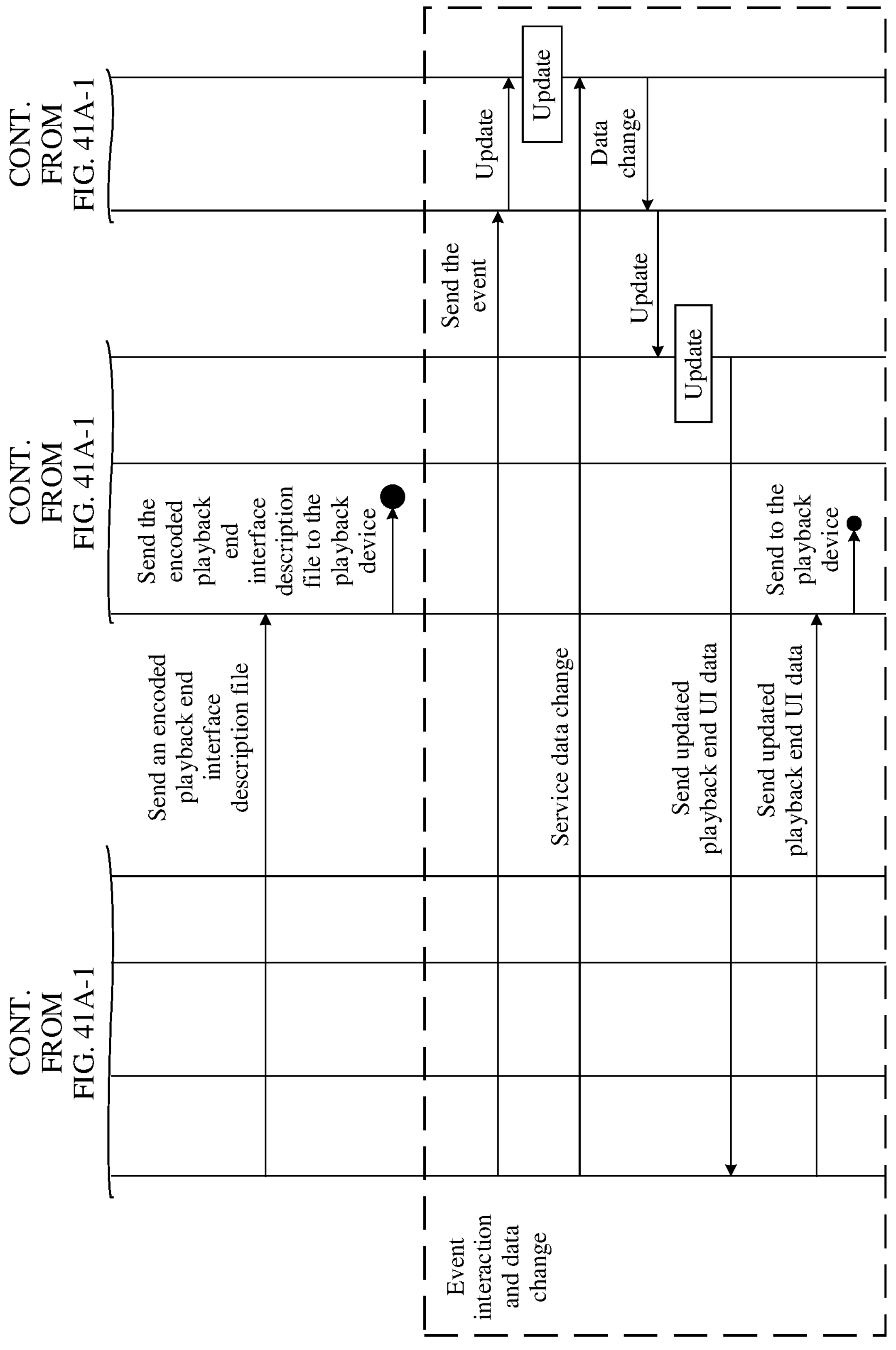

FIG. 41A-1 and FIG. 41A-2 show an example of a processing procedure of a control device in a user interface implementation method according to an embodiment of this application. After an app is installed on the control device, a projection framework, an MVVM framework, background data, and the like are initialized. Then, a resource transmission module transmits data resources related to the app, and binds the data resources to a projection service. The projection framework obtains a playback end interface description file from an application installation package and sends the file to a virtual view building module. The virtual view building module builds views based on the playback end interface description file to form playback end UI data, and binds the playback end UI data to the projection service. Then, the virtual view building module notifies the data binding module to bind the playback end UI data to background data. The data binding module invokes the MVVM framework to bind the playback end UI data to the background data. The projection service is also bound to an event proxy. Further, the playback end interface description file is sent to the playback device after being encoded. In this way, after receiving the encoded playback end interface description file, the playback device may generate and display a playback end UI based on the playback end interface description file.

The projection framework receives the event sent by the playback device, and sends the event to the MVVM framework. The MVVM framework updates the background data based on the event. When the service data of the app changes, a background data change causes the MVVM framework to update the playback end UI data. The control device sends the updated playback end UI data to the playback device. In this way, after receiving the updated playback end UI data, the playback device may display the updated playback end UI based on the updated playback end UI data.

Figure 41B:
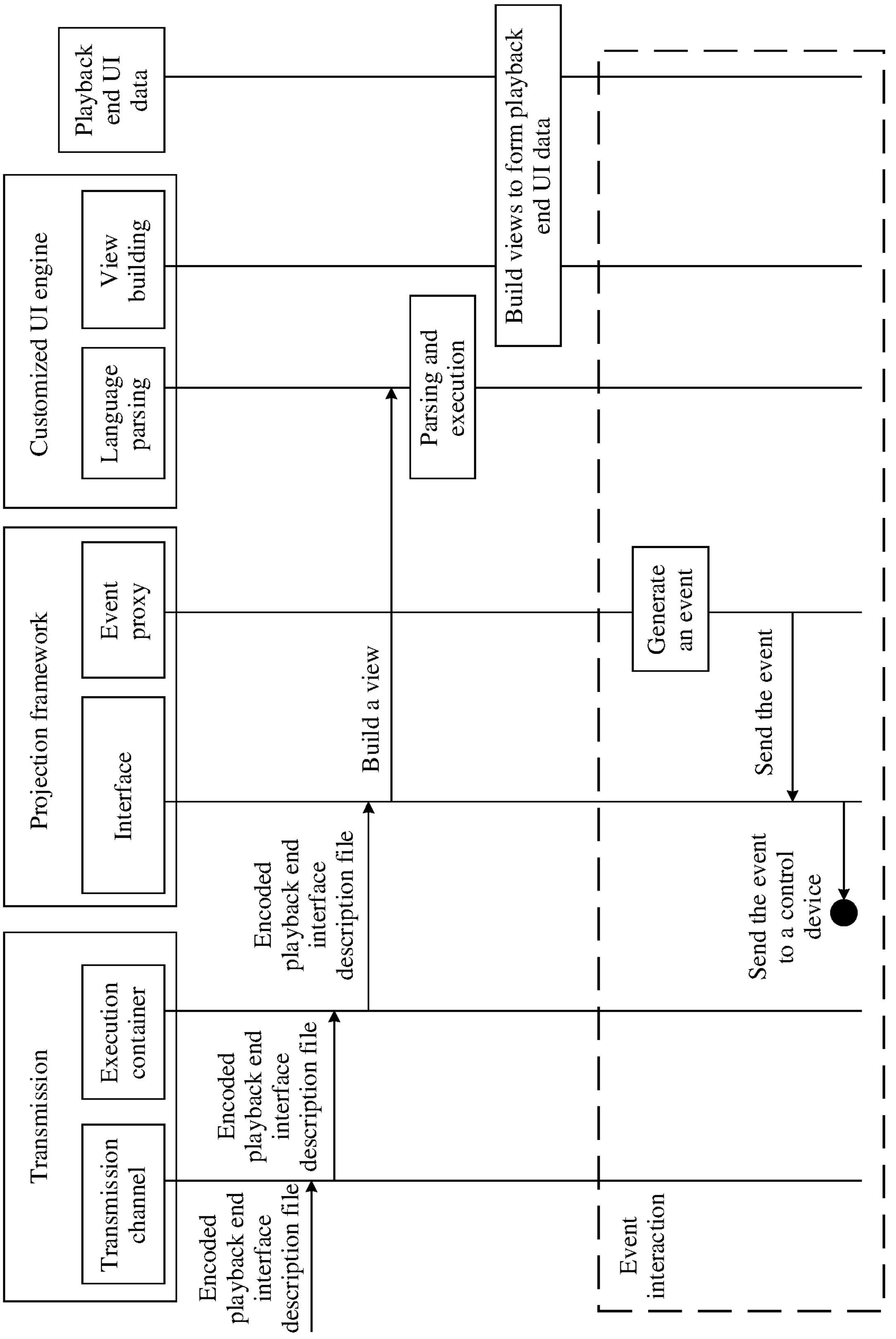
FIG. 41B is a schematic flowchart of a user interface implementation method according to an embodiment of this application.

FIG. 41B shows an example of a processing procedure of a playback device in a user interface implementation method according to an embodiment of this application. The playback device receives, through a transmission channel, an encoded playback end interface description file sent by the control device. A projection framework invokes a customized UI engine to parse and execute the playback end interface description file, generates playback end UI data, and displays a playback end UI based on the playback end UI data. An event proxy module receives an operation performed by a user on the playback end UI, generates a corresponding event, and transmits the event to the control device, so that the control device processes the event.

An embodiment of this application provides a user interface implementation method. In a process in which a control device runs an app, if a preset condition is met, the control device pushes preset information to a playback device for playing.

Figures 1, 42A:
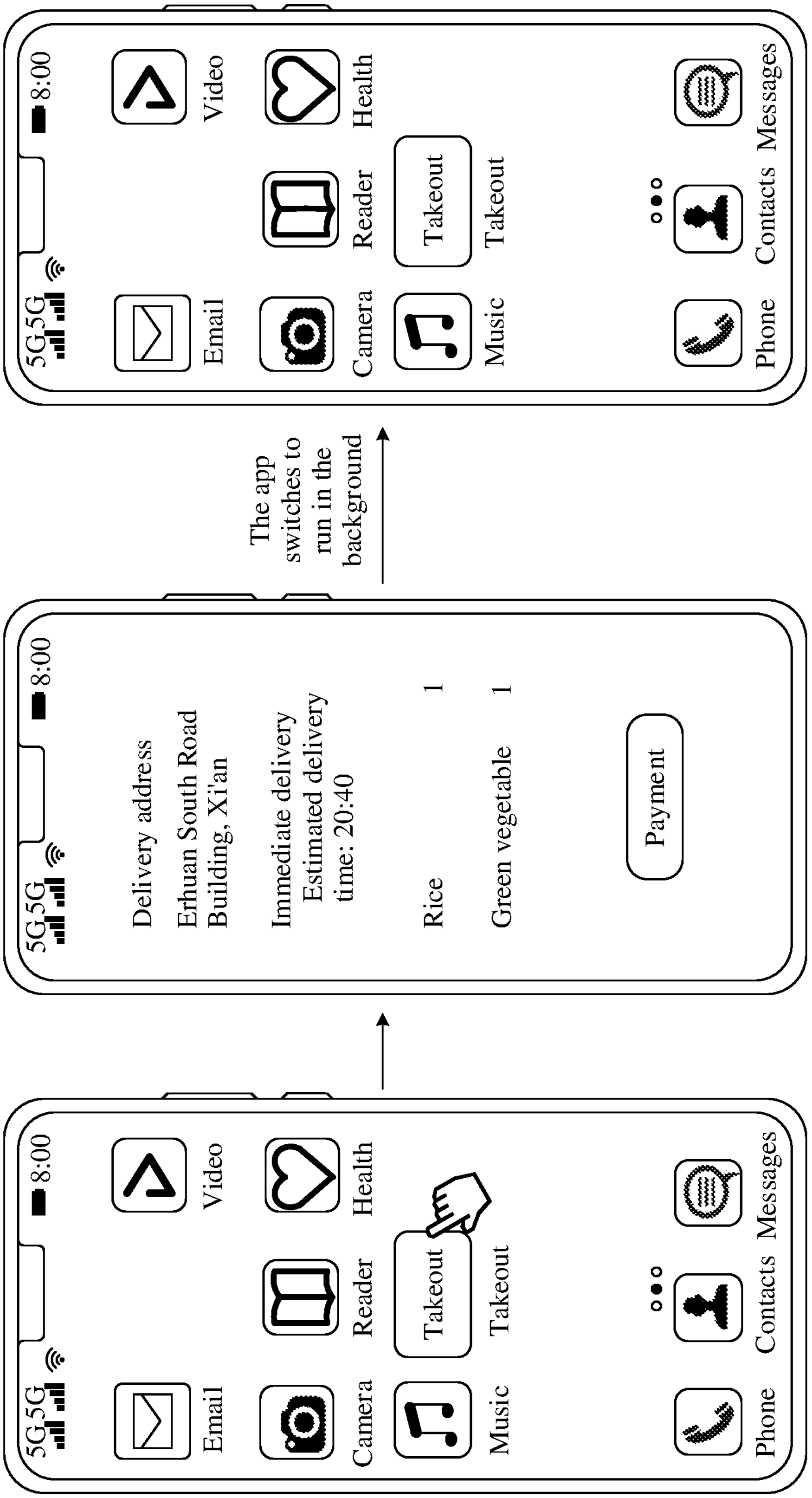
Figures 2, 42A:
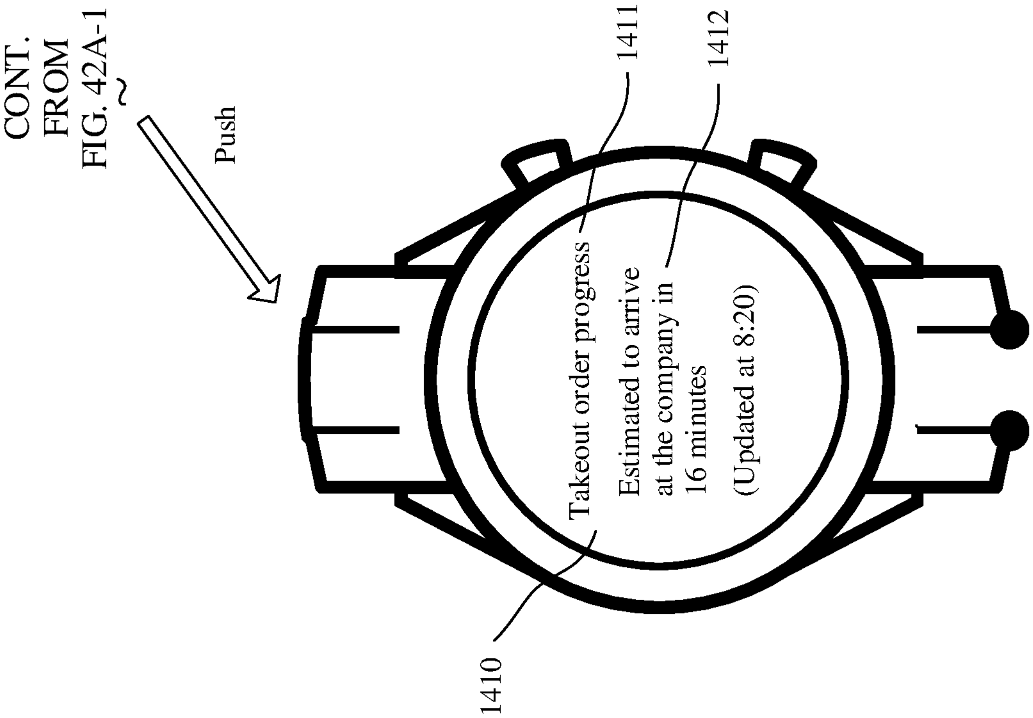

For example, a mobile phone is used as the control device, and a smartwatch is used as the playback device. For example, as shown in FIG. 42A-1 and FIG. 42A-2, the user opens a “Takeout” app on the mobile phone to order a meal, and places an order for payment. Optionally, the app switches to run in the background. When a preset condition is met (for example, the mobile phone determines that the takeout order is estimated to be delivered 20 minutes later; or for another example, the user performs a query operation on the smartwatch), the mobile phone pushes the preset information to the smartwatch for display. For example, as shown in FIG. 42A-1 and FIG. 42A-2, the smartwatch displays a playback end UI 1410, and the playback end UI 1410 includes a “Takeout order progress” view 1411 and prompt information 1412.

In an implementation, developers define, in a development phase, a playback end interface description file (or a code segment in the playback end interface description file) for pushing information to the playback end when the preset condition is met. It is defined in the playback end interface description file that the playback end UI of the smartwatch includes the view 1411 and the prompt information 1412. In a process in which the mobile phone runs the “Takeout” app (including switching the “Takeout” app to the background for running), the mobile phone determines that the preset condition is met, reads a specified code segment, generates playback end UI data based on the specified code segment, and sends the specified code segment (or the generated playback end UI data) to the smartwatch. The smartwatch generates the playback end UI 1410 based on the specified code segment (or the generated playback end UI data).

Figure 42B:
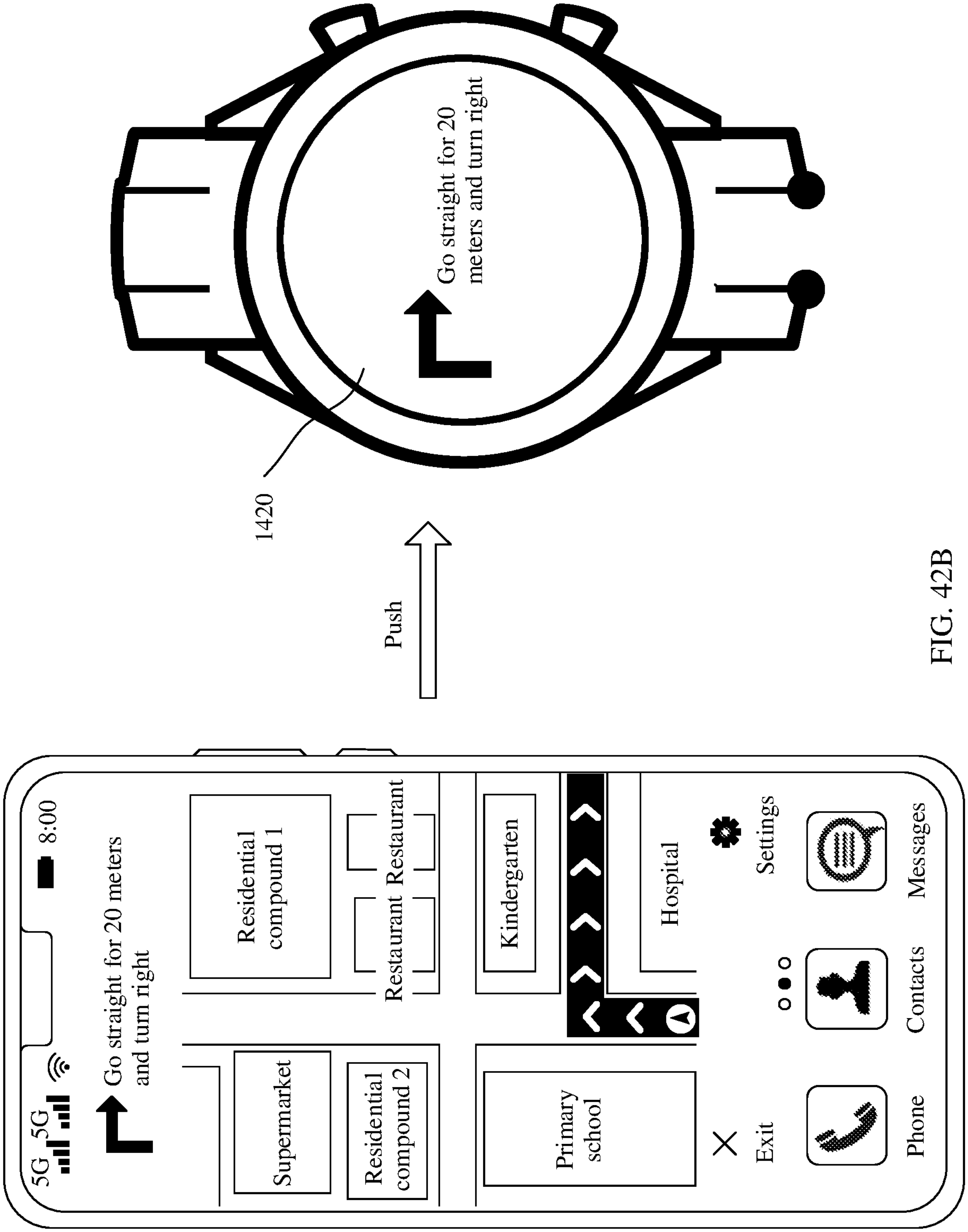
FIG. 42B is a schematic diagram of a scenario example of a user interface implementation method according to an embodiment of this application.

For example, as shown in FIG. 42B, the user performs navigation on the mobile phone by using a navigation app. When a preset condition is met (for example, a forward direction is changed), the mobile phone generates playback end UI data based on a specified code segment, and sends the specified code segment (or the generated playback end UI data) to the smartwatch. The smartwatch generates the playback end UI 1420 based on the specified code segment (or the generated playback end UI data).

Further, the smartwatch receives an operation performed by the user on the smartwatch, generates an event corresponding to the operation, and sends the event to the mobile phone for processing. The mobile phone processes service logic, performs a corresponding action, and updates the playback end UI data. The mobile phone further sends the updated playback end UI data to the smartwatch, and the smartwatch updates the playback end UI based on the updated playback end UI data.

According to the user interface implementation method provided in this embodiment of this application, when the preset condition is met, the control device automatically pushes some information of a running app to the playback device for playing. Playback devices of different types may read code segments corresponding to the device type, so that differentiated layout of playback end UIs of the devices can be conveniently implemented. In addition, the user may control the app on the playback device, and the control device performs service logic processing. In this way, use experience of the user can be improved, and a case in which the playback device has relatively low performance and does not support complex service logic processing can be avoided.

It may be understood that, to implement the foregoing functions, the electronic device includes corresponding hardware structures and/or software modules for performing the functions. A person skilled in the art should be easily aware that, in combination with units and algorithm steps of the examples described in embodiments disclosed in this specification, embodiments of this application may be implemented by hardware or a combination of hardware and computer software. Whether a function is performed by hardware or hardware driven by computer software depends on particular applications and design constraints of the technical solutions. A person skilled in the art may use different methods to implement the described functions for each particular application, but it should not be considered that the implementation goes beyond the scope of embodiments of this application.

In embodiments of this application, the electronic device may be divided into function modules based on the foregoing method examples. For example, each function module may be obtained through division based on each corresponding function, or two or more functions may be integrated into one processing module. The integrated module may be implemented in a form of hardware, or may be implemented in a form of a software function module. It should be noted that, in embodiments of this application, module division is an example, and is merely a logical function division. In actual implementation, another division manner may be used.

Figure 43:
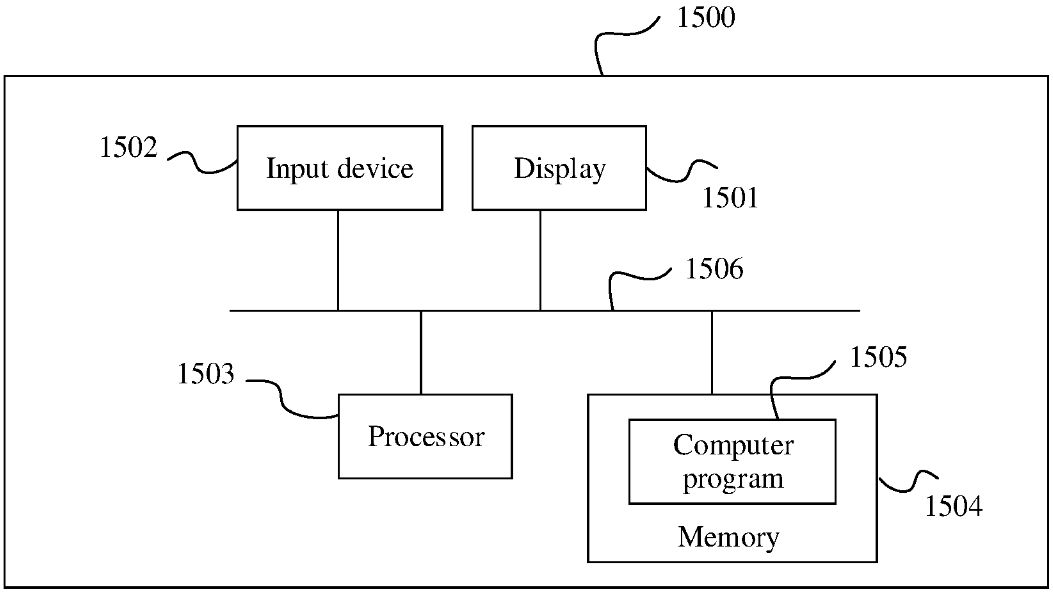
FIG. 43 is a schematic diagram of a structure composition of an electronic device according to an embodiment of this application.

As shown in FIG. 43, an embodiment of this application discloses an electronic device 1500. The electronic device may be an electronic device running the foregoing development tool, or an electronic device running an app in the foregoing embodiment, or an electronic device running an application widget in the foregoing embodiment. The electronic device may be the foregoing control device or playback device. The electronic device may specifically include: a display 1501, an input device 1502 (for example, a mouse, a keyboard, or a touchscreen), one or more processors 1503, a memory 1504, one or more application programs (not shown), and one or more computer programs 1505. The foregoing components may be connected through one or more communication buses 1506. The one or more computer programs 1505 are stored in the memory 1504 and are configured to be executed by the one or more processors 1503. The one or more computer programs 1505 include instructions, and the instructions may be used to perform related steps in the foregoing embodiments. In an example, the electronic device 1500 may be the electronic device 100 or the electronic device 200 in FIG. 1. In an example, the electronic device 1500 may be the developer device or the user-side electronic device in FIG. 14. In an example, the electronic device 1500 may be the electronic device 100 or the electronic device 200 in FIG. 23. In an example, the electronic device 1500 may be the control device 100, the electronic device 200, or the playback device 1000 in FIG. 33A to FIG. 33C.

An embodiment of this application further provides a computer-readable storage medium. The computer-readable storage medium stores computer program code. When a processor executes the computer program code, an electronic device performs the methods in the foregoing embodiments.

An embodiment of this application further provides a computer program product. When the computer program product runs on a computer, the computer is enabled to perform the methods in the foregoing embodiments.

The electronic device 1500, the computer-readable storage medium, or the computer program product provided in embodiments of this application is configured to perform the corresponding methods provided above. Therefore, for beneficial effects that can be achieved, refer to the beneficial effects of the corresponding methods provided above. Details are not described herein again.

The foregoing descriptions about implementations allow a person skilled in the art to clearly understand that, for the purpose of convenient and brief description, division of the foregoing function modules is taken as an example for illustration. In actual application, the foregoing functions may be allocated to different function modules for implementation based on a requirement, in other words, an inner structure of an apparatus is divided into different function modules to implement all or some of the functions described above.

In the several embodiments provided in this application, it should be understood that the disclosed apparatus and method may be implemented in other manners. For example, the described apparatus embodiment is merely an example. For example, the module or unit division is merely logical function division and may be other division in actual implementation. For example, a plurality of units or components may be combined or integrated into another apparatus, or some features may be ignored or not performed. In addition, the displayed or discussed mutual couplings or direct couplings or communication connections may be implemented through some interfaces. The indirect couplings or communication connections between the apparatuses or units may be implemented in electronic, mechanical, or other forms.

In addition, function units in embodiments of this application may be integrated into one processing unit, or each of the units may exist alone physically, or two or more units may be integrated into one unit. The integrated unit may be implemented in a form of hardware, or may be implemented in a form of a software function unit.

When the integrated unit is implemented in the form of a software function unit and sold or used as an independent product, the integrated unit may be stored in a readable storage medium. Based on such an understanding, the technical solutions of embodiments of this application essentially, or the part contributing to the conventional technology, or all or some of the technical solutions may be implemented in the form of a software product. The software product is stored in a storage medium and includes several instructions for instructing a device (which may be a single-chip microcomputer, a chip or the like) or a processor (processor) to perform all or some of the steps of the methods described in embodiments of this application. The foregoing storage medium includes any medium that can store program code, for example, a USB flash drive, a removable hard disk, a ROM, a magnetic disk, or an optical disc.

The foregoing descriptions are merely specific implementations of this application, but are not intended to limit the protection scope of this application. Any variation or replacement within the technical scope disclosed in this application shall fall within the protection scope of this application. Therefore, the protection scope of this application shall be subject to the protection scope of the claims.

What is claimed is:

1. A method, comprising:

separately downloading, by a first electronic device and a second electronic device, an application installation package of a first application from a server, wherein the application installation package comprises a description file and a resource file, the description file is used to perform interface description and interface behavior definition on a first user interface (UI) of the first application, and the resource file comprises resources used to generate a UI of the first application, and the description file includes first code corresponding to a device type of the first electronic device and second code corresponding to a device type of the second electronic device;

separately installing, by the first electronic device and the second electronic device, the application installation package;

reading, by the first electronic device, the first code in the description file based on the device type of the first electronic device, and generating, based on a definition of the first code, a first UI of the first electronic device by using the resources in the resource file; and reading, by the second electronic device, the second code in the description file based on the device type of the second electronic device, and generating, based on a definition of the second code, a second UI of the second electronic device by using the resources in the resource file; and wherein the device type of the first electronic device is different from the device type of the second electronic device.

2. The method according to claim 1, further comprising:

generating, by the first electronic device, a first view on the first UI of the first electronic device based on a definition of third code in the description file, wherein the first view on the first UI of the first electronic device has a customized view property of an operating system of the first electronic device, and the third code is a part or all of the first code; and generating, by a third electronic device, a first view on a third UI of the third electronic device based on the definition of the third code in the description file, wherein the first view on the third UI of the third electronic device has a view property of a general-purpose operating system.

3. A method, comprising:

downloading, by a first electronic device, an application installation package of a first application, wherein the application installation package comprises a description file and a resource file, the description file is used to perform interface description and interface behavior definition on a first user interface (UI) of the first application, and the resource file comprises resources used to generate a UI of the first application, and the description file includes first code corresponding to a device type of the first electronic device and second code corresponding to a device type of a second electronic device;

installing, by the first electronic device, the application installation package; and reading, by the first electronic device, the first code in the description file based on the device type of the first electronic device, and generating, based on a definition of the first code, the first UI of the first electronic device by using the resources in the resource file.

4. The method according to claim 3, further comprising:

generating, by the first electronic device, a first view on the first UI of the first electronic device based on a definition of third code in the description file, wherein the first view on the first UI of the first electronic device has a customized view property of an operating system of the first electronic device, and the third code is a part or all of the first code.

5. The method according to claim 4, wherein the operating system of the first electronic device comprises a custom UI programming capability, and the custom UI programming capability is used to provide the customized view property of the operating system of the first electronic device.

6. The method according to claim 5, wherein the customized view property comprises at least one of a visual property, a layout property, an interaction property, an animation property, or a software and hardware dependency property.

7. The method according to claim 6, wherein the layout property comprises at least one of stretching, hiding, wrapping, equalization, proportion, or extension.

8. The method according to claim 3, wherein the first UI of the first electronic device comprises a second view, and the second view has a view property of a general-purpose operating system.

9. The method according to claim 3, wherein the first UI of the first electronic device comprises a third view, and the third view has a customized view property of the first application.

10. The method according to claim 3, wherein the description file comprises fourth code, and the fourth code is used to define a correspondence between a view property of a fourth view on the first UI of the first electronic device and first data in an operating system of the first electronic device; and the method further comprises:

receiving, by the first electronic device, a first input of a user on the fourth view; and modifying a value of the first data based on the first input.

11. The method according to claim 10, wherein the view property of the fourth view on the first UI of the first electronic device varies with the first data in the operating system of the first electronic device.

12. A method, comprising:

displaying a development interface of a first application, wherein the development interface of the first application comprises a description file, and the description file is used to perform interface description and interface behavior definition on a first user interface (UI) of the first application;

in response to a first operation entered by a user, adding first code corresponding to a device type of a first electronic device to the description file;

in response to a second operation entered by the user, adding second code corresponding to a device type of a second electronic device to the description file, wherein the device type of the first electronic device is different from the device type of the second electronic device; and generating an application installation package of the first application based on the description file.

13. The method according to claim 12, wherein the application installation package of the first application further comprises a resource file, and the resource file comprises resources used to generate a UI of the first application.

14. The method according to claim 12, wherein the description file comprises: third code defining that a first view has a customized view property of an operating system of the first electronic device, and fourth code defining that a second view has a view property of a general-purpose operating system.

15. The method according to claim 14, wherein the customized view property of the operating system of the first electronic device comprises at least one of a visual property, a layout property, an interaction property, an animation property, or a software and hardware dependency property.

16. The method according to claim 15, wherein the layout property comprises at least one of stretching, hiding, wrapping, equalization, proportion, or extension.

17. An electronic device, comprising:

one or more processors;

a display; and a memory, wherein the memory stores one or more computer programs, the one or more computer programs comprise instructions, and when the instructions are executed by the electronic device, the electronic device is enabled to perform:

downloading an application installation package of a first application, wherein the application installation package comprises a description file and a resource file, the description file is used to perform interface description and interface behavior definition on a first user interface (UI) of the first application, and the resource file comprises resources used to generate a UI of the first application, and the description file includes first code corresponding to a first device type of the electronic device and second code corresponding to a second device type, and the first device type is different from the second device type;

installing the application installation package; and reading the first code in the description file based on the first device type of the electronic device, and generating, based on a definition of the first code, a first UI of the electronic device by using the resources in the resource file.

* * * * *